United States Patent [19]

Rhodes

[11] Patent Number: 5,413,804

[45] Date of Patent: May 9, 1995

[54] PROCESS FOR MAKING WHEY-DERIVED FAT SUBSTITUTE PRODUCT AND PRODUCTS THEREOF

[75] Inventor: Kenneth H. Rhodes, Diamond Bar, Calif.

[73] Assignee: Cacique, Inc., Pasadena, Calif.

[21] Appl. No.: 867,138

[22] Filed: Apr. 15, 1992

Related U.S. Application Data

[63] Continuation-in-part of Ser. No. 690,813, Apr. 23, 1991, abandoned.

[51] Int. Cl.$^6$ .................. A23C 21/00; A23L 1/48
[52] U.S. Cl. ....................... 426/583; 426/89; 426/99; 426/656; 426/688; 426/804
[58] Field of Search .......... 426/2, 99, 89, 302, 426/305, 311, 658, 656, 804, 657, 583

[56] References Cited

U.S. PATENT DOCUMENTS

| | | | |
|---|---|---|---|
| 4,010,337 | 4/1977 | Hsu | 426/99 |
| 4,021,582 | 5/1977 | Hsu | 426/99 |
| 4,734,287 | 3/1988 | Singer et al. | 426/41 |
| 4,804,548 | 2/1989 | Sharma | 426/99 |
| 4,855,156 | 8/1989 | Singer et al. | 426/565 |
| 4,911,546 | 3/1990 | Singer et al. | 426/658 |
| 4,923,981 | 5/1990 | Weibel | 426/602 |
| 4,961,953 | 10/1990 | Singer et al. | 426/656 |
| 4,983,403 | 1/1991 | Ardaillou | 426/2 |
| 4,985,270 | 1/1991 | Singer et al. | 426/515 |
| 5,011,701 | 4/1991 | Baer | 426/602 |
| 5,015,483 | 5/1991 | Haynes | 426/73 |
| 5,021,248 | 6/1991 | Stark | 426/96 |
| 5,096,730 | 3/1992 | Singer | 426/556 |
| 5,098,718 | 3/1992 | Ardaillon | 426/2 |
| 5,106,644 | 4/1992 | El-Nokaly | 426/603 |
| 5,112,626 | 5/1992 | Zibell | 426/302 |
| 5,120,561 | 6/1992 | Silva | 426/531 |
| 5,147,677 | 9/1992 | Ziegler | 426/99 |
| 5,164,210 | 11/1992 | Campbell | 426/302 |

FOREIGN PATENT DOCUMENTS

| | | |
|---|---|---|
| 0076549 | 4/1983 | European Pat. Off. . |
| 347237 | 12/1989 | European Pat. Off. . |
| 0380225 | 8/1990 | European Pat. Off. . |
| 400714 | 12/1990 | European Pat. Off. . |
| 412590 | 2/1991 | European Pat. Off. . |
| 0441494 | 8/1991 | European Pat. Off. . |
| WO86/1404 | 3/1986 | WIPO . |

OTHER PUBLICATIONS

Koide 1987 International Food Sci & Tech 22 707–723.
Kirby 1991 International Food Sci & Tech 26:437–449.

(List continued on next page.)

Primary Examiner—Carolyn Paden
Attorney, Agent, or Firm—Peter J. Georges

[57] ABSTRACT

Described are protein and/or carbohydrate based fat-replicating systems and methods of making same in which fat globule mimicking particles of protein or carbohydrate origin are modified by encapsulating same in a membrane which more closely replicates the characteristics of natural fat globules. The membrane is of liposome architecture formed by lipids, in particular, liposomal phospholipids. Liposome encapsulated food additives and the method of making and using same in both fatty products of natural and synthetic origin are described. Also described is a method for making a fat substitute from whey curd, suitably of diary whey origin. The whey may include a protein additive such as a caseinate. Also described are the fat substitute products produced in accordance with such methods. Such products are dispersions formed from whey curd or a curd comprised of whey and protein additive. A fat substitute derived from a comminuted curd comprised of whey protein-caseinate coprecipitate is described. The preferred method of curd formation described involves denaturing and curd formation using steam. In accordance with the invention, agglomerated protein in the curd is deagglomerated, suitably a chopper is used to comminute the curd and form a dispersion having substantially smooth emulsion like organoleptic character. Additives are incorporated into the dispersion to enhance the properties thereof.

124 Claims, 19 Drawing Sheets

OTHER PUBLICATIONS

Kirby 1987 International Food Sci & Tech 22:355–375.
The Mechanism of Vesicle Formation, Lasic, Biochem J. (1988) 256, 1–11 (printed in Great Britain).
Information available from Natterman Phospolipid GmbH (Rhone–Poulenc Group), regarding characteristics of phospholipids (date unknown, but information acknowledged as prior art), 20 pages in length and 3 pages excerpted from unknown textbook pp. 2236–2238, Acceleration of Cheese Ripening, Alkhalaf et al.
Natipide 11: New Easy Liposome System, Sonderdruck aus Seifen–Ole–Fette–Wachse, Heft 14/1990, Seiten 509–515.
Review of Cosmetic Application of Liposomes, Dr. K. J. Forster, Cosmetics and Toiletries Manufacture, 192–200.
Prepared Foods, Jan., 1986, p. 134.
Phospholipids as Liposomes, Strauss S. Hanser, 1986; Crowe et al., 1987, 1 page excerpt.
Hadout Micro fluidics Corporation, entitled Homogenizers and their Use and the Food Industry, 3 pages, (indicated but acknowledged as prior art).

MEDIAN = 5.70 μm
SP.AREA = 12337 cm$^2$/cm$^3$
% on DIA:10.0 μm = 87.9%
DIA on %:90.0% = 10.54 μm

DISTRIBUTION TABLE

| SEG. # | SIZE (MICRONS) | INTVL % | UNDER SIZE % | SEG. # | SIZE (MICRONS) | INTVL % | UNDER SIZE % |
|---|---|---|---|---|---|---|---|
| (01) | 200.0 | 0.0 | 100.0 | (29) | 4.47 | 8.5 | 32.8 |
| (02) | 174.6 | 0.0 | 100.0 | (30) | 3.90 | 6.5 | 24.3 |
| (03) | 152.4 | 0.0 | 100.0 | (31) | 3.41 | 5.0 | 17.8 |
| (04) | 133.1 | 0.0 | 100.0 | (32) | 2.98 | 4.3 | 12.8 |
| (05) | 116.2 | 0.0 | 100.0 | (33) | 2.60 | 3.6 | 8.5 |
| (06) | 101.4 | 0.0 | 100.0 | (34) | 2.27 | 2.5 | 4.9 |
| (07) | 88.58 | 0.0 | 100.0 | (35) | 1.98 | 1.5 | 2.4 |
| (08) | 77.34 | 0.0 | 100.0 | (36) | 1.73 | 0.7 | 0.9 |
| (09) | 67.52 | 0.0 | 100.0 | (37) | 1.51 | 0.2 | 0.2 |
| (10) | 58.95 | 0.0 | 100.0 | (38) | 1.32 | 0.0 | 0.0 |
| (11) | 51.47 | 0.0 | 100.0 | (39) | 1.15 | 0.0 | 0.0 |
| (12) | 44.94 | 0.0 | 100.0 | (40) | 1.00 | 0.0 | 0.0 |
| (13) | 39.23 | 0.0 | 100.0 | (41) | 0.88 | 0.0 | 0.0 |
| (14) | 34.25 | 0.0 | 100.0 | (42) | 0.77 | 0.0 | 0.0 |
| (15) | 29.91 | 0.0 | 100.0 | (43) | 0.67 | 0.0 | 0.0 |
| (16) | 26.11 | 0.0 | 100.0 | (44) | 0.58 | 0.0 | 0.0 |
| (17) | 22.80 | 0.2 | 100.0 | (45) | 0.51 | 0.0 | 0.0 |
| (18) | 19.90 | 0.5 | 99.8 | (46) | 0.45 | 0.0 | 0.0 |
| (19) | 17.38 | 1.0 | 99.3 | (47) | 0.39 | 0.0 | 0.0 |
| (20) | 15.17 | 1.9 | 98.3 | (48) | 0.34 | 0.0 | 0.0 |
| (21) | 13.25 | 3.1 | 96.4 | (49) | 0.30 | 0.0 | 0.0 |
| (22) | 11.56 | 4.9 | 93.3 | (50) | 0.26 | 0.0 | 0.0 |
| (23) | 10.10 | 7.1 | 88.5 | (51) | 0.23 | 0.0 | 0.0 |
| (24) | 8.82 | 8.9 | 81.3 | (52) | 0.20 | 0.0 | 0.0 |
| (25) | 7.70 | 10.2 | 72.4 | (53) | 0.17 | 0.0 | 0.0 |
| (26) | 6.72 | 10.1 | 62.2 | (54) | 0.15 | 0.0 | 0.0 |
| (27) | 5.87 | 9.7 | 52.1 | (55) | 0.13 | 0.0 | 0.0 |
| (28) | 5.12 | 9.6 | 42.4 | (56) | 0.11 | 0.0 | 0.0 |

MEDIAN = 5.72 μm
SP.AREA = 12294 cm$^2$/cm$^3$
% on DIA:10.0 μm = 87.6%
DIA on %:90.0% = 10.61 μm

DISTRIBUTION TABLE

| SEG. # | SIZE (MICRONS) | INTVL % | UNDER SIZE % | SEG. # | SIZE (MICRONS) | INTVL % | UNDER SIZE % |
|---|---|---|---|---|---|---|---|
| (01) | 200.0 | 0.0 | 100.0 | (29) | 4.47 | 6.5 | 32.6 |
| (02) | 174.6 | 0.0 | 100.0 | (30) | 3.90 | 6.4 | 24.1 |
| (03) | 152.4 | 0.0 | 100.0 | (31) | 3.41 | 4.9 | 17.7 |
| (04) | 133.1 | 0.0 | 100.0 | (32) | 2.98 | 4.3 | 12.7 |
| (05) | 116.2 | 0.0 | 100.0 | (33) | 2.60 | 3.6 | 8.5 |
| (06) | 101.4 | 0.0 | 100.0 | (34) | 2.27 | 2.5 | 4.9 |
| (07) | 88.58 | 0.0 | 100.0 | (35) | 1.98 | 1.5 | 2.4 |
| (08) | 77.34 | 0.0 | 100.0 | (36) | 1.73 | 0.7 | 0.9 |
| (09) | 67.52 | 0.0 | 100.0 | (37) | 1.51 | 0.2 | 0.2 |
| (10) | 58.95 | 0.0 | 100.0 | (38) | 1.32 | 0.0 | 0.0 |
| (11) | 51.47 | 0.0 | 100.0 | (39) | 1.15 | 0.0 | 0.0 |
| (12) | 44.94 | 0.0 | 100.0 | (40) | 1.00 | 0.0 | 0.0 |
| (13) | 39.23 | 0.0 | 100.0 | (41) | 0.88 | 0.0 | 0.0 |
| (14) | 34.25 | 0.0 | 100.0 | (42) | 0.77 | 0.0 | 0.0 |
| (15) | 29.91 | 0.0 | 100.0 | (43) | 0.67 | 0.0 | 0.0 |
| (16) | 26.11 | 0.0 | 100.0 | (44) | 0.58 | 0.0 | 0.0 |
| (17) | 22.80 | 0.2 | 100.0 | (45) | 0.51 | 0.0 | 0.0 |
| (18) | 19.90 | 0.5 | 99.8 | (46) | 0.45 | 0.0 | 0.0 |
| (19) | 17.38 | 1.0 | 99.3 | (47) | 0.39 | 0.0 | 0.0 |
| (20) | 15.17 | 2.0 | 98.2 | (48) | 0.34 | 0.0 | 0.0 |
| (21) | 13.25 | 3.1 | 96.3 | (49) | 0.30 | 0.0 | 0.0 |
| (22) | 11.56 | 4.9 | 93.1 | (50) | 0.26 | 0.0 | 0.0 |
| (23) | 10.10 | 7.2 | 88.2 | (51) | 0.23 | 0.0 | 0.0 |
| (24) | 8.82 | 9.0 | 81.0 | (52) | 0.20 | 0.0 | 0.0 |
| (25) | 7.70 | 10.2 | 72.1 | (53) | 0.17 | 0.0 | 0.0 |
| (26) | 6.72 | 10.1 | 61.9 | (54) | 0.15 | 0.0 | 0.0 |
| (27) | 5.87 | 9.6 | 51.8 | (55) | 0.13 | 0.0 | 0.0 |
| (28) | 5.12 | 9.6 | 42.2 | (56) | 0.11 | 0.0 | 0.0 |

MEDIAN = 5.83 μm
SP.AREA = 12179 cm²/cm³
% on DIA:10.0 μm = 85.2%
DIA on %:90.0% = 11.25 μm

DISTRIBUTION TABLE

| SEG. # | SIZE (MICRONS) | INTVL % | UNDER SIZE % | SEG. # | SIZE (MICRONS) | INTVL % | UNDER SIZE % |
|---|---|---|---|---|---|---|---|
| (01) | 200.0 | 0.0 | 100.0 | (29) | 4.47 | 8.1 | 32.1 |
| (02) | 174.6 | 0.0 | 100.0 | (30) | 3.90 | 6.2 | 24.0 |
| (03) | 152.4 | 0.0 | 100.0 | (31) | 3.41 | 4.8 | 17.8 |
| (04) | 133.1 | 0.0 | 100.0 | (32) | 2.98 | 4.2 | 13.0 |
| (05) | 116.2 | 0.0 | 100.0 | (33) | 2.60 | 3.6 | 8.8 |
| (06) | 101.4 | 0.0 | 100.0 | (34) | 2.27 | 2.6 | 5.2 |
| (07) | 88.58 | 0.0 | 100.0 | (35) | 1.98 | 1.8 | 2.7 |
| (08) | 77.34 | 0.0 | 100.0 | (36) | 1.73 | 0.8 | 1.0 |
| (09) | 67.52 | 0.0 | 100.0 | (37) | 1.51 | 0.3 | 0.3 |
| (10) | 58.95 | 0.0 | 100.0 | (38) | 1.32 | 0.0 | 0.0 |
| (11) | 51.47 | 0.0 | 100.0 | (39) | 1.15 | 0.0 | 0.0 |
| (12) | 44.94 | 0.0 | 100.0 | (40) | 1.00 | 0.0 | 0.0 |
| (13) | 39.23 | 0.0 | 100.0 | (41) | 0.88 | 0.0 | 0.0 |
| (14) | 34.25 | 0.0 | 100.0 | (42) | 0.77 | 0.0 | 0.0 |
| (15) | 29.91 | 0.0 | 100.0 | (43) | 0.67 | 0.0 | 0.0 |
| (16) | 26.11 | 0.2 | 100.0 | (44) | 0.58 | 0.0 | 0.0 |
| (17) | 22.80 | 0.4 | 99.8 | (45) | 0.51 | 0.0 | 0.0 |
| (18) | 19.90 | 0.8 | 99.4 | (46) | 0.45 | 0.0 | 0.0 |
| (19) | 17.38 | 1.4 | 98.5 | (47) | 0.39 | 0.0 | 0.0 |
| (20) | 15.17 | 2.5 | 97.1 | (48) | 0.34 | 0.0 | 0.0 |
| (21) | 13.25 | 3.6 | 94.6 | (49) | 0.30 | 0.0 | 0.0 |
| (22) | 11.56 | 5.2 | 91.1 | (50) | 0.26 | 0.0 | 0.0 |
| (23) | 10.10 | 7.3 | 85.8 | (51) | 0.23 | 0.0 | 0.0 |
| (24) | 8.82 | 8.8 | 78.6 | (52) | 0.20 | 0.0 | 0.0 |
| (25) | 7.70 | 9.8 | 69.8 | (53) | 0.17 | 0.0 | 0.0 |
| (26) | 6.72 | 9.6 | 60.1 | (54) | 0.15 | 0.0 | 0.0 |
| (27) | 5.87 | 9.1 | 50.4 | (55) | 0.13 | 0.0 | 0.0 |
| (28) | 5.12 | 9.2 | 41.3 | (56) | 0.11 | 0.0 | 0.0 |

MEDIAN = 8.90 μm
SP.AREA = 8597 cm²/cm³
% on DIA:10.0 μm = 58.2%
DIA on %:90.0% = 17.33 μm

DISTRIBUTION TABLE

| SEG. # | SIZE (MICRONS) | INTVL % | UNDER SIZE % | SEG. # | SIZE (MICRONS) | INTVL % | UNDER SIZE % |
|---|---|---|---|---|---|---|---|
| (01) | 200.0 | 0.0 | 100.0 | (29) | 4.47 | 4.2 | 15.3 |
| (02) | 174.6 | 0.0 | 100.0 | (30) | 3.90 | 3.0 | 11.1 |
| (03) | 152.4 | 0.0 | 100.0 | (31) | 3.41 | 2.2 | 8.1 |
| (04) | 133.1 | 0.0 | 100.0 | (32) | 2.98 | 1.9 | 5.9 |
| (05) | 116.2 | 0.0 | 100.0 | (33) | 2.60 | 1.7 | 4.1 |
| (06) | 101.4 | 0.0 | 100.0 | (34) | 2.27 | 1.2 | 2.4 |
| (07) | 88.58 | 0.0 | 100.0 | (35) | 1.98 | 0.7 | 1.2 |
| (08) | 77.34 | 0.0 | 100.0 | (36) | 1.73 | 0.3 | 0.4 |
| (09) | 67.52 | 0.0 | 100.0 | (37) | 1.51 | 0.1 | 0.1 |
| (10) | 58.95 | 0.0 | 100.0 | (38) | 1.32 | 0.0 | 0.0 |
| (11) | 51.47 | 0.0 | 100.0 | (39) | 1.15 | 0.0 | 0.0 |
| (12) | 44.94 | 0.0 | 100.0 | (40) | 1.00 | 0.0 | 0.0 |
| (13) | 39.23 | 0.1 | 100.0 | (41) | 0.88 | 0.0 | 0.0 |
| (14) | 34.25 | 0.3 | 99.9 | (42) | 0.77 | 0.0 | 0.0 |
| (15) | 29.91 | 0.8 | 99.5 | (43) | 0.67 | 0.0 | 0.0 |
| (16) | 26.11 | 1.5 | 98.8 | (44) | 0.58 | 0.0 | 0.0 |
| (17) | 22.80 | 2.8 | 97.2 | (45) | 0.51 | 0.0 | 0.0 |
| (18) | 19.90 | 4.3 | 94.4 | (46) | 0.45 | 0.0 | 0.0 |
| (19) | 17.38 | 5.9 | 90.1 | (47) | 0.39 | 0.0 | 0.0 |
| (20) | 15.17 | 7.5 | 84.3 | (48) | 0.34 | 0.0 | 0.0 |
| (21) | 13.25 | 8.5 | 76.7 | (49) | 0.30 | 0.0 | 0.0 |
| (22) | 11.56 | 9.2 | 68.2 | (50) | 0.26 | 0.0 | 0.0 |
| (23) | 10.10 | 9.6 | 59.0 | (51) | 0.23 | 0.0 | 0.0 |
| (24) | 8.82 | 9.1 | 49.3 | (52) | 0.20 | 0.0 | 0.0 |
| (25) | 7.70 | 8.0 | 40.2 | (53) | 0.17 | 0.0 | 0.0 |
| (26) | 6.72 | 6.4 | 32.2 | (54) | 0.15 | 0.0 | 0.0 |
| (27) | 5.87 | 6.4 | 25.7 | (55) | 0.13 | 0.0 | 0.0 |
| (28) | 5.12 | 5.0 | 20.3 | (56) | 0.11 | 0.0 | 0.0 |

MEDIAN = 6.09 μm
SP.AREA = 12105 cm²/cm³
% on DIA:10.0 μm = 81.8%
DIA on %:90.0% = 12.10 μm

DISTRIBUTION TABLE

| SEG. # | SIZE (MICRONS) | INTVL % | UNDER SIZE % | SEG. # | SIZE (MICRONS) | INTVL % | UNDER SIZE % |
|---|---|---|---|---|---|---|---|
| (01) | 200.0 | 0.0 | 100.0 | (29) | 4.47 | 7.3 | 31.1 |
| (02) | 174.6 | 0.0 | 100.0 | (30) | 3.90 | 5.6 | 23.7 |
| (03) | 152.4 | 0.0 | 100.0 | (31) | 3.41 | 4.3 | 18.2 |
| (04) | 133.1 | 0.0 | 100.0 | (32) | 2.98 | 3.8 | 13.8 |
| (05) | 116.2 | 0.0 | 100.0 | (33) | 2.60 | 3.5 | 10.0 |
| (06) | 101.4 | 0.0 | 100.0 | (34) | 2.27 | 2.8 | 6.5 |
| (07) | 88.58 | 0.0 | 100.0 | (35) | 1.98 | 2.0 | 3.6 |
| (08) | 77.34 | 0.0 | 100.0 | (36) | 1.73 | 1.0 | 1.6 |
| (09) | 67.52 | 0.0 | 100.0 | (37) | 1.51 | 0.4 | 0.6 |
| (10) | 58.95 | 0.0 | 100.0 | (38) | 1.32 | 0.2 | 0.2 |
| (11) | 51.47 | 0.0 | 100.0 | (39) | 1.15 | 0.0 | 0.0 |
| (12) | 44.94 | 0.0 | 100.0 | (40) | 1.00 | 0.0 | 0.0 |
| (13) | 39.23 | 0.0 | 100.0 | (41) | 0.88 | 0.0 | 0.0 |
| (14) | 34.25 | 0.0 | 100.0 | (42) | 0.77 | 0.0 | 0.0 |
| (15) | 29.91 | 0.0 | 100.0 | (43) | 0.67 | 0.0 | 0.0 |
| (16) | 26.11 | 0.2 | 100.0 | (44) | 0.58 | 0.0 | 0.0 |
| (17) | 22.80 | 0.6 | 99.8 | (45) | 0.51 | 0.0 | 0.0 |
| (18) | 19.90 | 1.1 | 99.2 | (46) | 0.45 | 0.0 | 0.0 |
| (19) | 17.38 | 1.9 | 98.1 | (47) | 0.39 | 0.0 | 0.0 |
| (20) | 15.17 | 3.2 | 96.2 | (48) | 0.34 | 0.0 | 0.0 |
| (21) | 13.25 | 4.5 | 93.0 | (49) | 0.30 | 0.0 | 0.0 |
| (22) | 11.56 | 6.1 | 88.5 | (50) | 0.26 | 0.0 | 0.0 |
| (23) | 10.10 | 7.8 | 82.4 | (51) | 0.23 | 0.0 | 0.0 |
| (24) | 8.82 | 8.8 | 74.6 | (52) | 0.20 | 0.0 | 0.0 |
| (25) | 7.70 | 9.3 | 65.7 | (53) | 0.17 | 0.0 | 0.0 |
| (26) | 6.72 | 8.8 | 56.4 | (54) | 0.15 | 0.0 | 0.0 |
| (27) | 5.87 | 8.3 | 47.6 | (55) | 0.13 | 0.0 | 0.0 |

MEDIAN = 8.80 μm
SP.AREA = 8664 cm²/cm³
% on DIA:10.0 μm = 57.6%
DIA on %:90.0% = 20.56 μm

DISTRIBUTION TABLE

| SEG. # | SIZE (MICRONS) | INTVL % | UNDER SIZE % | SEG. # | SIZE (MICRONS) | INTVL % | UNDER SIZE % |
|---|---|---|---|---|---|---|---|
| (01) | 200.0 | 0.0 | 100.0 | (29) | 4.47 | 4.7 | 17.1 |
| (02) | 174.6 | 0.0 | 100.0 | (30) | 3.90 | 3.4 | 12.5 |
| (03) | 152.4 | 0.0 | 100.0 | (31) | 3.41 | 2.6 | 9.1 |
| (04) | 133.1 | 0.0 | 100.0 | (32) | 2.98 | 2.2 | 6.5 |
| (05) | 116.2 | 0.0 | 100.0 | (33) | 2.60 | 1.9 | 4.3 |
| (06) | 101.4 | 0.0 | 100.0 | (34) | 2.27 | 1.3 | 2.4 |
| (07) | 88.58 | 0.0 | 100.0 | (35) | 1.98 | 0.7 | 1.1 |
| (08) | 77.34 | 0.0 | 100.0 | (36) | 1.73 | 0.3 | 0.4 |
| (09) | 67.52 | 0.0 | 100.0 | (37) | 1.51 | 0.1 | 0.1 |
| (10) | 58.95 | 0.0 | 100.0 | (38) | 1.32 | 0.0 | 0.0 |
| (11) | 51.47 | 0.2 | 100.0 | (39) | 1.15 | 0.0 | 0.0 |
| (12) | 44.94 | 0.3 | 99.8 | (40) | 1.00 | 0.0 | 0.0 |
| (13) | 39.23 | 0.7 | 99.5 | (41) | 0.88 | 0.0 | 0.0 |
| (14) | 34.25 | 1.2 | 98.8 | (42) | 0.77 | 0.0 | 0.0 |
| (15) | 29.91 | 1.9 | 97.6 | (43) | 0.67 | 0.0 | 0.0 |
| (16) | 26.11 | 2.8 | 95.7 | (44) | 0.58 | 0.0 | 0.0 |
| (17) | 22.80 | 3.8 | 92.9 | (45) | 0.51 | 0.0 | 0.0 |
| (18) | 19.90 | 4.7 | 89.1 | (46) | 0.45 | 0.0 | 0.0 |
| (19) | 17.38 | 5.5 | 84.4 | (47) | 0.39 | 0.0 | 0.0 |
| (20) | 15.17 | 6.4 | 78.9 | (48) | 0.34 | 0.0 | 0.0 |
| (21) | 13.25 | 6.9 | 72.5 | (49) | 0.30 | 0.0 | 0.0 |
| (22) | 11.56 | 7.5 | 65.7 | (50) | 0.26 | 0.0 | 0.0 |
| (23) | 10.10 | 8.0 | 58.2 | (51) | 0.23 | 0.0 | 0.0 |
| (24) | 8.82 | 8.0 | 50.2 | (52) | 0.20 | 0.0 | 0.0 |
| (25) | 7.70 | 7.5 | 42.1 | (53) | 0.17 | 0.0 | 0.0 |
| (26) | 6.72 | 6.4 | 34.6 | (54) | 0.15 | 0.0 | 0.0 |
| (27) | 5.87 | 5.6 | 28.2 | (55) | 0.13 | 0.0 | 0.0 |
| (28) | 5.12 | 5.4 | 22.5 | (56) | 0.11 | 0.0 | 0.0 |

MEDIAN = 6.26 μm
SP.AREA = 11328 cm²/cm³
% on DIA:10.0 μm = 82.5%
DIA on %:90.0% = 11.89 μm

DISTRIBUTION TABLE

| SEG. # | SIZE (MICRONS) | INTVL % | UNDER SIZE % | SEG. # | SIZE (MICRONS) | INTVL % | UNDER SIZE % |
|---|---|---|---|---|---|---|---|
| (01) | 200.0 | 0.0 | 100.0 | (29) | 4.47 | 7.6 | 27.7 |
| (02) | 174.6 | 0.0 | 100.0 | (30) | 3.90 | 5.6 | 20.1 |
| (03) | 152.4 | 0.0 | 100.0 | (31) | 3.41 | 4.3 | 14.5 |
| (04) | 133.1 | 0.0 | 100.0 | (32) | 2.98 | 3.6 | 10.2 |
| (05) | 116.2 | 0.0 | 100.0 | (33) | 2.60 | 3.0 | 6.6 |
| (06) | 101.4 | 0.0 | 100.0 | (34) | 2.27 | 2.0 | 3.6 |
| (07) | 88.58 | 0.0 | 100.0 | (35) | 1.98 | 1.1 | 1.7 |
| (08) | 77.34 | 0.0 | 100.0 | (36) | 1.73 | 0.4 | 0.6 |
| (09) | 67.52 | 0.0 | 100.0 | (37) | 1.51 | 0.1 | 0.1 |
| (10) | 58.95 | 0.0 | 100.0 | (38) | 1.32 | 0.0 | 0.0 |
| (11) | 51.47 | 0.0 | 100.0 | (39) | 1.15 | 0.0 | 0.0 |
| (12) | 44.94 | 0.0 | 100.0 | (40) | 1.00 | 0.0 | 0.0 |
| (13) | 39.23 | 0.0 | 100.0 | (41) | 0.88 | 0.0 | 0.0 |
| (14) | 34.25 | 0.0 | 100.0 | (42) | 0.77 | 0.0 | 0.0 |
| (15) | 29.91 | 0.1 | 100.0 | (43) | 0.67 | 0.0 | 0.0 |
| (16) | 26.11 | 0.2 | 99.9 | (44) | 0.58 | 0.0 | 0.0 |
| (17) | 22.80 | 0.5 | 99.7 | (45) | 0.51 | 0.0 | 0.0 |
| (18) | 19.90 | 1.0 | 99.1 | (46) | 0.45 | 0.0 | 0.0 |
| (19) | 17.38 | 1.8 | 98.1 | (47) | 0.39 | 0.0 | 0.0 |
| (20) | 15.17 | 3.0 | 96.3 | (48) | 0.34 | 0.0 | 0.0 |
| (21) | 13.25 | 4.2 | 93.4 | (49) | 0.30 | 0.0 | 0.0 |
| (22) | 11.56 | 6.0 | 89.1 | (50) | 0.26 | 0.0 | 0.0 |
| (23) | 10.10 | 8.1 | 83.1 | (51) | 0.23 | 0.0 | 0.0 |
| (24) | 8.82 | 9.6 | 75.0 | (52) | 0.20 | 0.0 | 0.0 |
| (25) | 7.70 | 10.3 | 65.4 | (53) | 0.17 | 0.0 | 0.0 |
| (26) | 6.72 | 9.7 | 55.1 | (54) | 0.15 | 0.0 | 0.0 |
| (27) | 5.87 | 8.9 | 45.4 | (55) | 0.13 | 0.0 | 0.0 |
| (28) | 5.12 | 8.7 | 36.4 | (56) | 0.11 | 0.0 | 0.0 |

MEDIAN = 10.82 μm
SP.AREA = 7028 cm$^2$/cm$^3$
% on DIA:10.0 μm = 44.8%
DIA on %:90.0% = 21.29 μm

DISTRIBUTION TABLE

| SEG. # | SIZE (MICRONS) | INTVL % | UNDER SIZE % | SEG. # | SIZE (MICRONS) | INTVL % | UNDER SIZE % |
|---|---|---|---|---|---|---|---|
| (01) | 200.0 | 0.0 | 100.0 | (29) | 4.47 | 3.1 | 9.9 |
| (02) | 174.6 | 0.0 | 100.0 | (30) | 3.90 | 2.2 | 6.9 |
| (03) | 152.4 | 0.0 | 100.0 | (31) | 3.41 | 1.6 | 4.6 |
| (04) | 133.1 | 0.0 | 100.0 | (32) | 2.98 | 1.3 | 3.0 |
| (05) | 116.2 | 0.0 | 100.0 | (33) | 2.60 | 1.0 | 1.7 |
| (06) | 101.4 | 0.0 | 100.0 | (34) | 2.27 | 0.5 | 0.7 |
| (07) | 88.58 | 0.0 | 100.0 | (35) | 1.98 | 0.2 | 0.2 |
| (08) | 77.34 | 0.0 | 100.0 | (36) | 1.73 | 0.0 | 0.0 |
| (09) | 67.52 | 0.0 | 100.0 | (37) | 1.51 | 0.0 | 0.0 |
| (10) | 58.95 | 0.0 | 100.0 | (38) | 1.32 | 0.0 | 0.0 |
| (11) | 51.47 | 0.0 | 100.0 | (39) | 1.15 | 0.0 | 0.0 |
| (12) | 44.94 | 0.2 | 100.0 | (40) | 1.00 | 0.0 | 0.0 |
| (13) | 39.23 | 0.4 | 99.8 | (41) | 0.88 | 0.0 | 0.0 |
| (14) | 34.25 | 1.0 | 99.4 | (42) | 0.77 | 0.0 | 0.0 |
| (15) | 29.91 | 2.1 | 98.4 | (43) | 0.67 | 0.0 | 0.0 |
| (16) | 26.11 | 3.5 | 96.3 | (44) | 0.58 | 0.0 | 0.0 |
| (17) | 22.80 | 5.4 | 92.7 | (45) | 0.51 | 0.0 | 0.0 |
| (18) | 19.90 | 7.0 | 87.3 | (46) | 0.45 | 0.0 | 0.0 |
| (19) | 17.38 | 8.1 | 80.4 | (47) | 0.39 | 0.0 | 0.0 |
| (20) | 15.17 | 9.0 | 72.2 | (48) | 0.34 | 0.0 | 0.0 |
| (21) | 13.25 | 9.0 | 63.3 | (49) | 0.30 | 0.0 | 0.0 |
| (22) | 11.56 | 8.8 | 54.3 | (50) | 0.26 | 0.0 | 0.0 |
| (23) | 10.10 | 8.5 | 45.5 | (51) | 0.23 | 0.0 | 0.0 |
| (24) | 8.82 | 7.8 | 37.0 | (52) | 0.20 | 0.0 | 0.0 |
| (25) | 7.70 | 6.5 | 29.2 | (53) | 0.17 | 0.0 | 0.0 |
| (26) | 6.72 | 5.0 | 22.7 | (54) | 0.15 | 0.0 | 0.0 |
| (27) | 5.87 | 4.0 | 17.7 | (55) | 0.13 | 0.0 | 0.0 |
| (28) | 5.12 | 3.7 | 13.6 | (56) | 0.11 | 0.0 | 0.0 |

MEDIAN = 6.87 μm
SP.AREA = 10491 cm²/cm³
% on DIA:10.0 μm = 75.6%
DIA on %:90.0% = 13.88 μm

DISTRIBUTION TABLE

| SEG. # | SIZE (MICRONS) | INTVL % | UNDER SIZE % | SEG. # | SIZE (MICRONS) | INTVL % | UNDER SIZE % |
|---|---|---|---|---|---|---|---|
| (01) | 200.0 | 0.0 | 100.0 | (29) | 4.47 | 6.5 | 23.8 |
| (02) | 174.6 | 0.0 | 100.0 | (30) | 3.90 | 4.9 | 17.3 |
| (03) | 152.4 | 0.0 | 100.0 | (31) | 3.41 | 3.7 | 12.4 |
| (04) | 133.1 | 0.0 | 100.0 | (32) | 2.98 | 3.1 | 8.7 |
| (05) | 116.2 | 0.0 | 100.0 | (33) | 2.60 | 2.5 | 5.6 |
| (06) | 101.4 | 0.0 | 100.0 | (34) | 2.27 | 1.6 | 3.1 |
| (07) | 88.58 | 0.0 | 100.0 | (35) | 1.98 | 0.9 | 1.4 |
| (08) | 77.34 | 0.0 | 100.0 | (36) | 1.73 | 0.4 | 0.5 |
| (09) | 67.52 | 0.0 | 100.0 | (37) | 1.51 | 0.1 | 0.1 |
| (10) | 58.95 | 0.0 | 100.0 | (38) | 1.32 | 0.0 | 0.0 |
| (11) | 51.47 | 0.0 | 100.0 | (39) | 1.15 | 0.0 | 0.0 |
| (12) | 44.94 | 0.0 | 100.0 | (40) | 1.00 | 0.0 | 0.0 |
| (13) | 39.23 | 0.0 | 100.0 | (41) | 0.88 | 0.0 | 0.0 |
| (14) | 34.25 | 0.2 | 100.0 | (42) | 0.77 | 0.0 | 0.0 |
| (15) | 29.91 | 0.3 | 99.9 | (43) | 0.67 | 0.0 | 0.0 |
| (16) | 26.11 | 0.7 | 99.5 | (44) | 0.58 | 0.0 | 0.0 |
| (17) | 22.80 | 1.2 | 98.8 | (45) | 0.51 | 0.0 | 0.0 |
| (18) | 19.90 | 2.0 | 97.6 | (46) | 0.45 | 0.0 | 0.0 |
| (19) | 17.38 | 2.9 | 95.6 | (47) | 0.39 | 0.0 | 0.0 |
| (20) | 15.17 | 4.2 | 92.8 | (48) | 0.34 | 0.0 | 0.0 |
| (21) | 13.25 | 5.4 | 88.6 | (49) | 0.30 | 0.0 | 0.0 |
| (22) | 11.56 | 6.9 | 83.2 | (50) | 0.26 | 0.0 | 0.0 |
| (23) | 10.10 | 8.6 | 76.3 | (51) | 0.23 | 0.0 | 0.0 |
| (24) | 8.82 | 9.5 | 67.7 | (52) | 0.20 | 0.0 | 0.0 |
| (25) | 7.70 | 9.8 | 58.1 | (53) | 0.17 | 0.0 | 0.0 |
| (26) | 6.72 | 8.9 | 48.4 | (54) | 0.15 | 0.0 | 0.0 |
| (27) | 5.87 | 8.0 | 39.5 | (55) | 0.13 | 0.0 | 0.0 |
| (28) | 5.12 | 7.6 | 31.5 | (56) | 0.11 | 0.0 | 0.0 |

MEDIAN = 6.55 μm
SP.AREA = 10973 cm²/cm³
% on DIA:10.0 μm = 81.7%
DIA on %:90.0% = 11.79 μm

DISTRIBUTION TABLE

| SEG. # | SIZE (MICRONS) | INTVL % | UNDER SIZE % | SEG. # | SIZE (MICRONS) | INTVL % | UNDER SIZE % |
|---|---|---|---|---|---|---|---|
| (01) | 200.0 | 0.0 | 100.0 | (29) | 4.47 | 6.9 | 25.0 |
| (02) | 174.6 | 0.0 | 100.0 | (30) | 3.90 | 5.1 | 18.1 |
| (03) | 152.4 | 0.0 | 100.0 | (31) | 3.41 | 3.8 | 13.0 |
| (04) | 133.1 | 0.0 | 100.0 | (32) | 2.98 | 3.2 | 9.2 |
| (05) | 116.2 | 0.0 | 100.0 | (33) | 2.60 | 2.6 | 6.0 |
| (06) | 101.4 | 0.0 | 100.0 | (34) | 2.27 | 1.7 | 3.4 |
| (07) | 88.58 | 0.0 | 100.0 | (35) | 1.98 | 1.0 | 1.7 |
| (08) | 77.34 | 0.0 | 100.0 | (36) | 1.73 | 0.5 | 0.6 |
| (09) | 67.52 | 0.0 | 100.0 | (37) | 1.51 | 0.2 | 0.2 |
| (10) | 58.95 | 0.0 | 100.0 | (38) | 1.32 | 0.0 | 0.0 |
| (11) | 51.47 | 0.0 | 100.0 | (39) | 1.15 | 0.0 | 0.0 |
| (12) | 44.94 | 0.0 | 100.0 | (40) | 1.00 | 0.0 | 0.0 |
| (13) | 39.23 | 0.0 | 100.0 | (41) | 0.88 | 0.0 | 0.0 |
| (14) | 34.25 | 0.0 | 100.0 | (42) | 0.77 | 0.0 | 0.0 |
| (15) | 29.91 | 0.0 | 100.0 | (43) | 0.67 | 0.0 | 0.0 |
| (16) | 26.11 | 0.1 | 100.0 | (44) | 0.58 | 0.0 | 0.0 |
| (17) | 22.80 | 0.3 | 99.9 | (45) | 0.51 | 0.0 | 0.0 |
| (18) | 19.90 | 0.8 | 99.5 | (46) | 0.45 | 0.0 | 0.0 |
| (19) | 17.38 | 1.6 | 98.7 | (47) | 0.39 | 0.0 | 0.0 |
| (20) | 15.17 | 3.1 | 97.1 | (48) | 0.34 | 0.0 | 0.0 |
| (21) | 13.25 | 4.7 | 94.0 | (49) | 0.30 | 0.0 | 0.0 |
| (22) | 11.56 | 6.9 | 89.3 | (50) | 0.26 | 0.0 | 0.0 |
| (23) | 10.10 | 9.2 | 82.4 | (51) | 0.23 | 0.0 | 0.0 |
| (24) | 8.82 | 10.5 | 73.3 | (52) | 0.20 | 0.0 | 0.0 |
| (25) | 7.70 | 10.9 | 62.8 | (53) | 0.17 | 0.0 | 0.0 |
| (26) | 6.72 | 9.9 | 51.9 | (54) | 0.15 | 0.0 | 0.0 |
| (27) | 5.87 | 8.8 | 42.0 | (55) | 0.13 | 0.0 | 0.0 |
| (28) | 5.12 | 8.2 | 33.2 | (56) | 0.11 | 0.0 | 0.0 |

# PROCESS FOR MAKING WHEY-DERIVED FAT SUBSTITUTE PRODUCT AND PRODUCTS THEREOF

RELATED U.S. APPLICATION DATA

This is a continuation-in-part of U.S. patent application Ser. No. 07/690,813, filed Apr.23, 1991, now abandoned.

FIELD OF THE INVENTION

The present invention relates generally to protein and/or carbohydrate based fat-replicating systems, to fat substitute products derived from whey, in particular dairy wheys, and to food products incorporating such fat substitute products.

BACKGROUND OF THE INVENTION

The utility of recovering human nutritional value from whey has long been appreciated in the art. In U.S. Pat. No. 2,695,235, a process is described for preparing an artificial egg white from whey. A more recent utilization of whey for production of egg white substitutes is found in U.S. Pat. No. 4,029,825. More recently whey has been used as a source for making fat substitutes. Fat substitute products produced by the controlled heat denaturation of whey protein under high shear conditions are disclosed in U.S. Pat. Nos. 4,734,287; 4,855,156; 4,911,946; 4,961,953 and 4,985,270. Heat denatured whey protein has also been used as a component of a dispersed phase fat spread (See European Patent 0 076 549). The present invention relates to an alternative procedure for obtaining a fat substitute product emulating the mouthfeel of water-in-fat and fat-in-water emulsions without the need of oil additives or the requirement to control heat denaturation under high shear conditions.

SUMMARY OF THE INVENTION

It is a general object of the present invention to provide a fat substitute product using whey as the protein source. The whey suitably is a whey protein concentrate. The whey protein can include other protein additives such as caseinate. In addition to caseinate, other suitable protein sources include egg white and egg white isolates, protein isolates from meats, soy protein and isolates thereof. As a general rule, any protein or isolate thereof that will coagulate and precipitate with heat, acid, or any other safe food additive utilized in this invention. Another object of the invention is to provide a method of making the fat substitute product in a facile manner and converting the maximum content of whey protein to a fat substitute product.

Yet another object is to provide non-fat food products using the fat substitute product of the present invention as a substitute for fat-containing ingredients in the recipes of said food products.

These and other objects of the invention will be apparent from the description of the invention that follows.

An important attribute of the present invention is that organoleptically, no or very little difference can be detected between dispersed deagglomerated whey curd particles of the present invention and the dispersed fat globules of dairy products and other fat-containing foods.

The present invention in one of its aspects relates to a method of forming a dispersion of denatured protein particles that have a substantially smooth, emulsion like organoleptic character and can be used as a fat substitute. The method comprises heating a whey, suitably a dairy whey to denature the whey protein in the whey, and then acidifying the heated whey to form a curd. The curd is then separated from the whey. The agglomerated denatured whey protein is deagglomerated to form a dispersion of denatured whey protein particles in an aqueous phase formed during deagglomeration. The aqueous phase is comprised of an aqueous serum released by the curd during deagglomeration. The composition of the aqueous serum believed to be the sugars, soluble salts, and the protein that did not precipitate and is the same chemical composition as the whey from which the precipitated curd is recovered. The use of the aqueous serum component as the major portion of the dispersant (suspending medium) is believed to be an important feature of the present invention. The aqueous serum component of the curd is believed to create an environment for forming and maintaining the integrity of the whey curd-derived dispersoids that, in the dispersion of the present invention, provide the desired substantially smooth, emulsion like organoleptic character.

The fat substitute product of the present invention is substantially fat-free; that is, fat-free except for incidental presence of fat that may be present as a carry-over of the whey starting material or the additives. In other words, according to the present invention, any fat present is incidental to and not a requisite for the substantially smooth, emulsion-like organoleptic character of the whey-derived fat substitute product of the present invention.

Another aspect of the present invention relates to forming a dispersion of denatured protein particles that have a substantially smooth, emulsion like organoleptic character by introducing steam into a whey, suitably a dairy whey, to heat and denature protein in the dairy whey. The dairy whey is preferably a whey protein concentrate which may contain a protein additive. The preferred additive is caseinate. Steam is entrained in the dairy whey to form a steam-entrained whey that is pH adjusted to form a curd comprised of an agglomerated denatured whey protein of high water content. This curd is separated from its whey. The curd is deagglomerated to form a dispersion of denatured whey protein particles in a continuous aqueous phase comprised of an aqueous component released by the curd during deagglomeration.

The dispersed particles of denatured whey protein may be coated with a membrane-forming agent, preferably a phospholipid. The preferred phospholipid is lecithin fractions. Most preferably, the lecithin fractions used comprise phosphatidyl choline, phosphatidyl ethanolamine and phosphatidyl inositol, in the proper ratios to provide an imitation of the same species found in the natural food product. The phospholipid coating formed on the dispersed particles of denatured whey protein may further comprise a surface-active agent, preferably a surface active agent which imparts amphoteric charges. The membrane-forming agent and surface-active agent may be introduced together into the dispersion of denatured whey protein particles to form a membrane comprised of a membrane-forming agent and the surface active agent on the particles. Most preferably, the membrane-forming agent comprises a lecithin fraction with a high content of phosphatidyl choline and the surface-active agent comprises another lecithin fraction with the ability to impart amphoteric charges to the particles. The composition of the phospholipid fractions can be altered create a inner membrane best suited to the environmental conditions of the dispersion. A structure builder also may be introduced into the continuous aqueous phase of the dispersion, preferably, a microcrystalline cellulose. Also, a stabilizer may be incorporated into the continuous aqueous phase. The stabilizer is preferably a thixotropic agent, most preferably a hydrocolloid, with xanthan gum or pectin being the hydrocolloids of choice.

It is yet another aspect of the present invention to make a fat substitute by heating a whey protein concentrate to denature the whey protein, pH adjusting the heated whey protein concentrate to produce a curd comprising agglomerated denatured whey protein and then comminuting the curd using a high shear force to form a dispersion of denatured whey protein particles in a continuous aqueous phase formed during comminution of the curd. The dispersion formed emulates the mouthfeel of fat-in-water and water-in-fat emulsions. The stability of the dispersion may be enhanced by adding lecithin fractions while applying a high shear force to the dispersion; the stability of the lecithin fractions-containing dispersion may be further enhanced by adding microcrystalline cellulose while applying a high shear force to the dispersion; and, the stability can be even further enhanced by adding caseinate to create a bilayer lipoprotein membrane and then a stabilizer to further enhance stability while applying a high shear force.

It has been yet another discovery and is one of the important aspects of the present invention that dispersing microcrystalline cellulose and facilitating the incorporation of dispersed microcrystalline cellulose into the fat substitute can be achieved at great advantage by first encapsulating the individual cellulose microcrystals ("needles") in a phospholipid membrane or liposome.

In accordance with the preferred procedure of the present invention, a phospholipid is first introduced into an aqueous medium and liposomes formed therefrom with high sheer. The amount of liposome-forming phospholipid introduced must be in a ratio with an aqueous medium to create the appropriate liposome size. A high ratio of phospholipids to aqueous medium will result in liposomes of a small size. On the other hand, if too low a ratio of phospholipids to aqueous medium is used, liposomes will no longer be formed. The thickness of the vesicular wall of the liposomes can be controlled by the ratio and the application of subsequent sheer force. It has been observed that, if the amount of the liposome-forming agent falls in the range of from about 40% by weight to about 60% by weight of the amount of additive, e.g., microcrystalline cellulose, the advantages of envelopment can be best achieved. The optimal quantity of membrane-former will vary from additive to additive and also varies among the membrane-forming compositions selected from the lecithin fractions. The compostion of the membrane is determined by the selection of the lectihin fractions. Thus, the ratio of phosphatidyl choline, phosphatidyl ethanolamine and phosphatidyl inositol, can be controlled by the selection of individual lecthin fractions. Each lecthin fraction has a specific content of the above phophatides, thus, the mixture fo lecthin fractions will determine the nature and behavior of the encapsulating membrane. As new lecthin fractions become available, it can be seen that improved properties will ensue.

To determine if there is adequate membrane-former present and if the quantity of liposomes are sufficient, the additive (microcrystalline cellulose)in dispersion, when observed under a polarized microscope, appears to be uniformly distributed without substantial presence of clumped/entangled additive particles/crystals.

If inadequate membrane-former is used, it will be readily apparent by the continued difficulty in achieving uniform dispersion of the additive. Although adding excessive membrane forming agents may adversely effect functional characteristics in the final food product, the problem can be easily solved by adjusting the amount of liposome added or by changing the characteristics of the liposome by changing its compostion.

High sheen (most preferably resulting from mixing-/agitation under vacuum and/or application of heat) is a visual indication of liposome formation. The liposomes are suitably formed first in an aqueous base and then further dispersed in additional water. When microcrystalline cellulose is required, it may be added, suitably to the additional water. Mixing is continued until a high sheen is observed. A dispersion of microcrystalline cellulose is affirmed when the individual microcrystals, when observed under polarized light, are uniformly dispersed in the continuous liquid phase.

In the absence of phospholipid addition, adequate dispersal of microcrystalline cellulose requires the use of a two stage homogenizer at 2,000 psi in the first stage and 500 psi in the second stage.

It has also been discovered that the use of phospholipids in incorporating hydrocolloids (including the extremely difficult to disperse composition, pectin) in an aqueous continuous phase facilitates dispersion and hydration. When pectin is used as an additive, it is highly preferable to achieve uniform dispersal and hydration prior to addition and incorporation into the proteinaceous dispersions of the present invention that have a high calcium ion content. If heat is applied before the complete hydration of pectin or gelatin, the hydrocolloid will not perform its intended function and the resulting composition will display rough and grainy texture.

The present invention also relates to substantially fat-free fat substitutes comprised of deagglomerated whey curd having a substantially smooth, emulsion like organoleptic character made according to the method of the present invention. The curd of origin is preferably a dairy whey curd, most preferably formed from dairy whey protein concentrate that may contain a protein additive such as a caseinate. When the protein additive to the dairy whey is a caseinate, a dairy whey protein and casein coprecipitate is formed. Any other protein which will coprecipitate with whey protein and/or caseinate may be used as an additive protein. The fat substitute is preferably comprised of membrane-coated denatured whey protein particles dispersed in an aqueous serum phase released by the curd during deagglomeration in which the membrane is preferably of phospholipid origin, most preferably formed from lecithin fractions. The phospholipid distribution pattern comprises lecithin fractions having contents of phosphatides of choline, ethanolamine, and inositol with glycolipids which will envelop or encapsulate the precipitated and comminuted protein particle. The amphoteric charges should closely approximate the opposite amphoteric charges on the surface and interior of the denatured protein particle. Thus, the protein encapsulated particle will now display added repulsion forces.

Thus, colloidal stability is imparted to the system. Further, the exposed outward membrane surface should have the correct amphoteric charges in zones on the surface to facilitate further encapsulation by other proteins that will create a bilayer membrane. The bilayer membrane will provide additional stability to the colloidal dispersion and thus, closely duplicate the properties of natural occurring fat globules. The fat substitute may contain additives to enhance the stability of same, such additives suitably being introduced in accordance with the method of the present invention as herein described.

One way of looking at the present invention is that the invention resides in replicating the architecture of fat globules using a proteinaceous or carbohydrate core rather than the naturally occurring fatty core. This core can contain all of the physical characteristics such as crystalline structures that mimic the crystalline structures formed in natural fats. The core can also have the same properties of deformation that add richness to the mouthfeel of so many desirable foods.

The liposome membrane enveloping the dispersoids (proteinaceous, carbohydrate and/or other) of the present invention may be synthesized to correspond to and replicate the attributes of the fat globule membrane of all naturally occurring animal and vegetable fats. Phospholipids are found in all natural fat systems be it in globule form and dispersed in serum or entrapped in a matrix of protein or carbohydrate. The duplication of this naturally occurring membrane imparts to this invention a fat substitute technology that allows the close approximation of the lubricity, mouthfeel, body, and texture of fat containing food, natural or formulated.

The modification of the membrane of the present invention by homogenization provides the highest order of replication of fat globule architecture. The homogenization step can occur with the liposome itself, the liposome enveloped additive mixture, and at any step after the liposome or additive mixture has been added to the chopper or any combination thereof.

The proteinaceous particles of the present invention are perhaps best described by reference to identifiable features and attributes rather than measurements of what at best are particle size artifacts. In fact, due to the nature of the lipoprotein bilayer membrane surrounding the particle, it may be difficult to actually determine particle size without creating an artifact that is not representative of the orginal enrobed particle size.

The proteinaceous fat-replicating dispersion of the present invention is comprised of a proteinaceous dispersoid and a continuous aqueous serum phase. The dispersoid is encapsulated with a phospholipid-protein (lipoprotein) membrane that closely approximates the functionality of fat as it occurs in natural food environments. Optionally, the serum phase can contain structure building and/or stabilizing constituents.

The dispersoid component of the preferred embodiment of the present invention is comprised of denatured whey protein particles having a serum entrained in a sponge-like architecture. The interstices/pores of the sponge contain the aqueous serum that is the non-coagulable portion of the whey protein concentrate and/or other protein mixture of particle origin. The aqueous serum is of the same chemical composition as that of the aqueous phase that is expelled during comminution. The dispersoids of this invention are of a size, distribution, and character that provide a substantially smooth, lubricating, fat-like organoleptic tactile sensation in the mouth.

The protein particles are preferably enveloped in a membrane, suitably a bilayer phospholipid-protein (a high density lipoprotein) membrane. The exposed membrane surface most preferably has affixed thereto additive elements which retard/moderate reagglomeration. Reagglomeration is retarded by charge-inducing additive(s) or additive(s) imposing structural impediments to reagglomeration. Molecular structures termed hairs can protrude into the aqueous serum and provide further steric repulsion forces.

The improved attributes of envelopment and membrane modification are universal for both particles derived by whey curd comminution in accordance with the present invention as well as particles of the type described in U.S. Pat. No. 4,734,287 and other protein dispersoids forming fat-substitute dispersions based on proteinaceous particles.

Also encompassed by the present invention are food products, in which the fat substitute of the present invention is used in the recipe to impart the attributes of fat-containing ingredients. Among the food products contemplated are cheeses, such as ricotta, fat free cheesecake, bakery fillings, cream style dressings, mayonnaise, sour cream, and spreadable cheese, to name but a few.

The fat substitute of the present invention also finds application in food bases, where it can be used for partial or total replacement of fat in such food bases, e.g., low fat ricotta, icing bases, butter-like spreads, and the like. The present invention also relates to substantially fat-free light cream and whipped topping comprised of deagglomerated washed whey curd that has a substantially smooth, emulsion like organoleptic character.

The embodiment of the invention relating to enrobement of dispersoids forming fat-replicating dispersion has broad application. The marked improvement in dispersion stability extends to the universe of dispersoids that can be used in fat-replicating dispersions and includes dispersoids of proteinaceous, carbohydrate, or hydrocolloid origin. Thus, insoluble particles of architecture, size and distribution to impart, in dispersion, the requisite mouthfeel of a fat-substitute can universally benefit by enrobement in accordance with the present invention. This, because the membrane formed in accordance with the present invention imparts fat globule membrane-type attributes notwithstanding variations in particle origin.

The embodiment of the present invention, relating to enrobement, finds application in connection with facilitating dispersion and enhancing the properties of additives to both natural and synthetic (fat-replicating) fat systems.

BRIEF DESCRIPTION OF DRAWINGS

FIG. 15 illustrates schematically the sponge-like architecture of a comminuted whey curd particle.

FIG. 16 illustrates schematically the membrane-enrobed particle of FIG. 15.

FIG. 17 illustrates schematically the membrane-enrobed particle of FIG. 16 in a microcrystalline methylcellulose-containing system where the crystals are present in the serum-containing interstices of the particle, the membrane and also in the continuous aqueous phase in which the particle is suspended/dispersed.

FIG. 18 illustrates schematically the polylayer architecture of the phospholipid enrobed particle of FIG. 17 in which the exposed phospholipid surface is covered with a coat of caseinate protein which forms a second layer thereon.

FIG. 19 illustrates schematically the polylayer membrane configuration of FIG. 17 wherein the exposed surface is further modified to form a surface with hairy projections (fibrils).

DETAILED DESCRIPTION OF THE INVENTION

Figure 1:
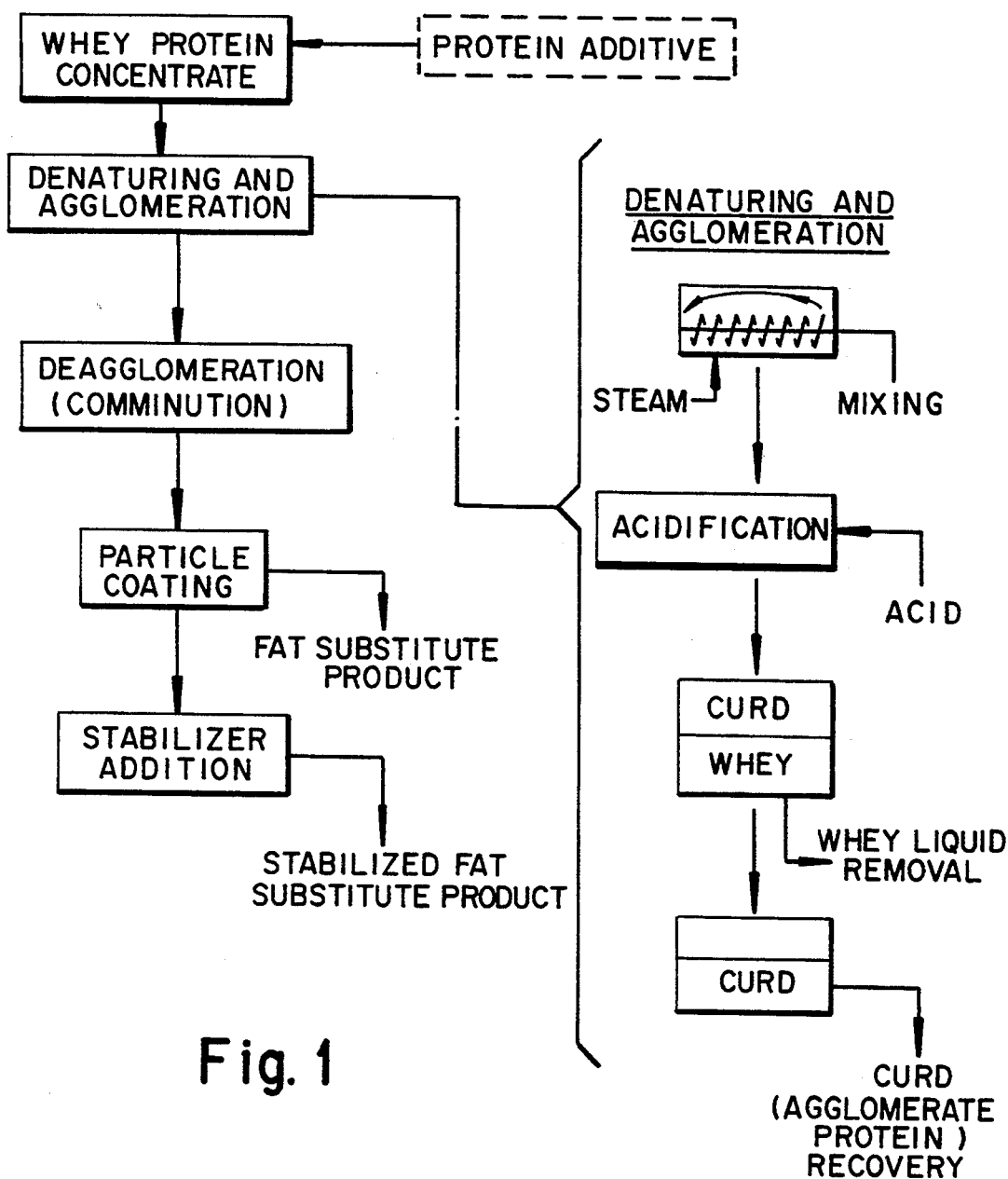
FIG. 1 represents a flow diagram illustrating the preferred method of the invention using whey protein concentrate as the protein source.

The present invention relates, in one of its aspects, to a process for making a fat substitute from whey by heating whey, suitably a dairy whey, most preferably in the form of a whey protein concentrate to denature the whey protein.

Whey protein used in the present invention may be obtained directly from cheese making whey without intervening processing such as ultrafiltration or the whey used in the present invention can be reconstituted dehydrated whey protein concentrate. For example, CAL PRO 50, a powdered whey protein concentrate containing 50% or more whey protein sold by CAL PRO, Corona, Calif., can be reconstituted and used alone or to fortify fresh whey and/or fresh whey protein concentrate.

It is preferred, where fresh whey is used, that the fines in the whey used in the process of the present invention be rapidly removed after separation of whey from curd. This is typically achieved using fine savers which operate utilizing sieve separation. This minimizes both hydrolysis of protein comprising the fines and the release of fat bound therein. Removal of fines also prevents membrane fowling downstream in whey treatment and an increase in the fat content of the final fat substitute.

Optionally the whey can contain a protein additive such as caseinate. When caseinate is added, a coprecipitate forms. The heated whey is pH adjusted and/or acidified to produce a curd comprised of agglomerated denatured whey protein and/or casein and retained serum. The curd is comminuted to form a dispersion of denatured whey protein particles in a continuous aqueous phase of serum released by the curd during comminution. The resulting dispersion emulates the mouthfeel of fat-in-water and water-in-fat emulsions. The achievement of protein curd particle dispersion emulating the mouthfeel of fat-in-water and water-in-fat emulsions is done so that a very efficient recovery and utilization of the protein content of the whey protein is achieved. The procedure involves an efficient recovery of protein from the whey by agglomeration of denatured protein to form a curd followed by recovery of substantially all the agglomerated protein by deagglomerating and comminuting such whey protein precipitate (breaking down the curd) and suspending and dispersing the deagglomerated denatured proteinaceous particles throughout a continuous aqueous phase comprised of the serum retained in the curd and released during deagglomeration.

To enhance stability, the particles in the dispersion are coated with a membrane-forming phospholipid composition having amphoteric charges and then a protein or other membrane forming compound to create a bilayer membrane to produce a stable dispersion of coated denatured whey protein particles. To further enhance stability, structure building agents and viscosity building agent(s) are added to the dispersion to inhibit reagglomeration of the polylayer coated whey protein particles.

The membrane-forming agent is preferably a phospholipid, most preferably a lecithin fraction with a high content of the phosphatides of choline, ethanolamine, and inositol with glycolipids, in a composition that closely duplicates the natural fat membrane that the fat substitute of this invention is duplicating. One of the distinguishing characteristics of this invention is that the enveloping membrane can be tailored to fit the final application environment. The membrane phospholipid is of such composition that it will encapsulate the protein particle by binding its amphoteric charges with those on the particle surface. Further, it will increase the repulsion of the particles in that state. Finally, it will aid in the formation of the second layer of protein or any other membrane forming material, such as a hydrocolloid, by matching its amphoteric charges with those of the second membrane layer. The formation of the second layer implies that a polylayer membrane is formed and if the second layer is a thick proteinous composition, then it would be termed high density lipoprotein.

The structure building agent is preferably a cellulose that has been chemically and physically altered such that the properties it imparts are moisture absorption and a lattice-like structure. Typically, natural fats form crystalline structures in nature and many of the processing techniques in the food industry take advantage of this property. In example, the churning of butter and the ability of cocoa butter to quickly coat chocolate covered candy. The resistance to deformity by these crystalline fat structures imparts to a given food its different mouthfeel. The difference in the crystalline structure of pure cocoa butter and a combination of cocoa butter and butterfat imparts totally different perceptions to the flavor, the melt, and total perception of dark chocolate versus milk chocolate. Thus, microcrystalline cellulose provides resistance to deformation of the particle and the amount employed will determine this important characteristic. Microcrystalline cellulose also imparts a lattice-work structure in the aqueous serum phase that prevents reagglomeration of the membrane coated particles and the moisture absorption further adds repulsion forces and aids in body and texture to the finished product. The addition of body and texture occurs without the deleterious effects produced by hydrocolloid overstabilization such as flavor masking, gummy texture, and heavy body.

The stabilizer is suitably a viscosity increasing or gelling agent. The stabilizer may be selected from any of the many well known hydrocolloids (hydrocolloid gums) also referred to as thickening agents in the food art such as xanthan gum, locust bean gum, carrageenan, gelatins, starch, carboxymethylcellulose and others. Mixtures of stabilizer such as xanthan gum, gelatin, and carrageenan may be used. Xanthan gum see other discription or pectin alone or in combination with other thickeners are the thickeners of choice.

Hydrocolloids can also contribute additional benefits to the fat substitute technology of this invention. Some hydrocolloids form complexes with milk and other proteins. The complex formed by Kappa carrageenan and casein is a weak gel that can be easily deformed and reformed again and has wide application in suspending cocoa in chocolate milk. Carboxymethylcellulose and xanthan gums form complexes with the whey proteins. Locust bean gum reacts with casein to form a precipitate at a pH below 5.2. Thus, the incorporation of hydrocolloids with the whey protein concentrate and/or casein or other proteins form additional complexes that have greater or less deformation characteristics. This phenomena will impart to the precipitated particle additional resistance to deformation with respect to mouthfeel. Thus, the characteristics of a sharp melting point fat such as cocoa butter or tallow can be duplicated. The sharp melting points of these fats is due to the large content of highly saturated triglycerides. Thus, by adding hydrocolloids and increasing the molecular weight of the coprecipitate, the particles will closely mimic the effects of hydrogenation or the saturated fatty acid composition of natural fats. Another means of strengthening and thereby increasing the resistance to deformation, is to react more of the —S—S— bonds by raising the pH of the whey protein concentrate mixture during the heating process and then lowering the pH to effect precipitation. It is believed that the foam-like or sponge-like structure is thickened and strengthened to provide additional resistance to deformation.

In the present invention, comminution is effected by a high shear force, preferably using an array of rotating knives, with a chopper (also called a bowl chopper) being the comminution device of choice.

The thickened dispersion may be cooled to further inhibit reagglomeration, most preferably to a temperature of about 40° F. or below.

Cooling is suitably achieved after packaging. The thickened (stabilized) dispersion may be encased in plastic or other suitable material and after that the encased thickened dispersion may be cooled by heat exchange through the casing in a liquid medium such as a salt brine.

In its most preferred embodiment, the present invention relates to a specific method of obtaining, in high yield, a dispersion of solid and highly denatured protein particles from heat denatured whey proteins and /or whey protein-casein coprecipitates. The resulting dispersion has a substantially smooth organoleptic character; that is, the dispersion mimics or imparts the mouthfeel of oil-in-water and water-in-oil emulsions.

The preferred embodiment involves introducing steam into a dairy whey to heat denature protein in the dairy whey and to entrain at least a portion of the steam in the curd matrix. The dairy whey used as protein source preferably is in the form of a whey protein concentrate. Optionally, a protein additive such as casein can be added to the dairy whey or whey protein concentrate to create a whey protein-caseinate coprecipitate curd. The resulting steam entrained diary whey is acidified to form a curd of agglomerated denatured whey protein. The curd has a high level moisture content, generally between from about 60 percent by weight to about 80 percent by weight of moisture based on total weight of curd. The moisture is both in a bound and imbibed state. The curd is separated from its whey or serum. The curd is then comminuted by suitable mechanical means such as a rotating blade array used in choppers—a widely used apparatus for meat processing. Comminution of the curd forms a dispersion of particles of denatured whey protein in the serum released from the curd during comminution. The serum forms the continuous aqueous phase of the dispersion. Comminution is continued until the dispersion acquires a substantially smooth, emulsion like, organoleptic character.

The curd contains water as its major component. Most of the water is retained or imbibed in the curd during curd formation and a smaller amount of water is bound to the denatured protein. In the embodiment of the invention, where steam is introduced directly into the whey, the curd generally has a density less than the density of the whey from which it separates so that as curd is formed, it rises to the top of the whey or the whey protein concentrate. In the indirect heat method, the curd approximates the density of the serum or is slightly greater than the serum density; thus, the curd must be kept in motion by agitation until it is separated from the curd. It has been observed that the drained curd typically contains water present in an amount of from about 65 weight percent to about 80 weight percent based on the weight of the curd after separation from the whey. Lower and higher water content within the above range can be controlled by the whey composition, cook temperature, and, when present, the type of additive(s) involved. What is important is that the curd is hard enough to produce the stable particles required to achieve the fat-like mouthfeel. It has been found that obtaining a curd of required "hardness" is typically a trial and error procedure. The "hardness" or texture qualities of the curd can be defined as the curd's ability to retain serum after the whey has been separated from it. If the curd is "soft", then it can be compressed very easily in the hand and the free serum can be easily expelled. When high shear forces are applied to a curd that is weak or soft, it disintegrates into a weak gelatinous gel. Thus, the curd formed according to the present inventions should have a sufficiently hard texture to be worked or polished under high shear forces. Generally, for the typical whey protein concentrate derived from enzymatic cheese making procedures such as the mozzarella whey of Example 1 herein, formation of the undesirable soft curd occurs when the pH of the whey or whey protein concentrate has lowered to below 6.0 to 5.8. The most probable explanation is that the proteolytic enzymes (rennet) used to coagulate the milk in the cheese making process and the proteolytic enzymes produced by the cultures become less specific as the pH decreases. Thus, hydrolysis of polypeptide polymer primary structure occurs and the lower weight molecular protein residues in the whey lose the ability to denature in the correct manner of this invention. The lactic acid content of the whey or whey protein concentrate also serves to hydrolyse or "break down" the proteins.

It has also been found that the curd can actually be too "hard". This excessive hardness was observed when cooking temperatures between 195 degrees F. to 205 degrees F. were used for casein-containing whey protein concentrate of the type produced in Example 1 herein. The curd became too hard to comminute and polish in a practical time span. Another phenomenon regarding hardness that was observed was that the addition of more casein to the whey protein—thereby decreasing the whey protein to casein ratio, tends to "soften" the curd. If the casein content of the coprecipitate is increased, the curd becomes softer. In this case, higher cook temperatures can be employed to produce strengthened foam or sponge-like structures that provide for increased resistance to deformation of the particle. The procedure duplicates the mouthfeel of high melting point fats.

The temperatures selected for curd formation are dependent on the characteristics of the whey being used. For example, where the level of casein content in the whey protein concentrate is increased, the cook temperature selected is lowered. As the whey protein concentrate ages, the cooking temperature selected is typically lower than where fresh whey protein concentrate is used. As the ion balance (e.g., Ca Ph, Mg) changes—this is typically a seasonal change in milk composition or based on type of cheese from which the whey is produced, the optimal temperatures selected will vary. As salt content is decreased (ionic strength), the temperature is increased. Additionally, calcium chloride or other salts such as phosphates can be employed to increase the ionic strength and enhance precipitation. Caution must be exercised, however, as the use of a too high ionic strength will cause a dry, mealy curd that results in a chalky mouthfeel or shattered particles. The use of sodium citrate will increase the moisture and the volumisity of the particle, but excessive use will cause reduced yield, soft curd, or no precipitation at all.

Most important is the time temperature relationship, that is, where a high temperature is selected, e.g., above about 205 degrees F., then the cook time is shortened. Cook time here is defined as the time from when the heat is first applied to the time that the whey is completely drained from the curd and it begins to cool. In areas where the final fat substitute is to be used in high pH products such as ice cream or in bakery creme fillings and toppings, cold water can be added to the whey while it is being drained. The curd can actually be washed in cold water to firm it up for the comminution process and to create variations in the properties of the finished fat substitute.

Further regarding the elevated temperatures of curd formation, it has been noted that where the curd is allowed to sit for extended periods of time prior to comminution, both the step of comminution and the resultant fat-replicating proteinaceous dispersion are adversely affected. E.g., where the curd has been left sitting for two to three hours after being withdrawn at 185 degrees, the comminution does not work as well and the product does not conform to the desired proteinaceous particle with the typical lubricity, slip, and plastic texture of the fat substitute when it is comminuted from fresh made curd.

Hardness is also affected by the cooking pH. If the cooking pH is raised by the addition of a neutralizing agent such as sodium carbonate or potassium hydroxide, then the curd usually becomes firm; that is, "hard". It is believed that the addition of calcium chloride increases the calcium ion concentration and thus, further dehydration and denaturation of the protein occurs at a faster rate at a given temperature. It has been observed that the degree of denaturation determines the heat stability of the final products that contain the fat substitute of the present invention. As hardness of the protein increases, comminution or deagglomeration requires a longer period of time. This is because polishing and manipulation of the curd requires more force as hardness increases. Comminution time can be reduced by the application of vacuum and heat during the comminution process. It is believed that deagglomeration of the curd (particle formation) is facilitated because, under vacuum conditions, the amount of air incorporated into the forming dispersion is decreased. As the particle size continues to decrease, the viscosity increases. Thus, this increasing viscosity further increases the air content at an increasing rate. As the viscosity increases further due to more air entrainment, the knifes are moving though air instead of particles and the serum phase. The efficiency of the deagglomeration process is reduced. Accordingly, deagglomeration under vacuum may be used to advantage.

It has further been observed that the temperature at which the deagglomeration process occurs also has a direct bearing upon efficiency of deagglomeration. The incorporation of air tends to cool the deagglomerated mass since the air is at ambient room temperature. One way of countering the lowering of temperature during deagglomeration is to add heat during this step. To accomplish this purpose, a chopper is used that is suitably equipped with steam injection nozzles on the bottom of the bowl. Steam injected through these nozzles will heat the bowl and the product therein. Following one embodiment of the present invention, the application of both vacuum and heat, will allow the reduction of the comminution/deagglomeration process by as much as 75 percent. Increased deagglomeration efficiency allows the cook temperature of the denaturing step to be raised and harder curd to be accommodated in the dispersion forming step. Thus, in applications where a heat stable fat substitute is required (e.g. in applications where the fat substitute is a constituent of a cooked or baked product), using higher cook temperatures will make a highly denatured whey protein-casein coprecipitate that will withstand baking or cooking temperatures without reagglomeration occurring or the losses of the shape of the spherical particle. The smooth, round protein particle is maintained or the resistance to baking temperature is increased by a higher level of denaturation of the curd used to manufacture the fat substitute.

Deagglomeration can occur at atmospheric, subatmospheric and superatmospheric pressures. Subatmospheric pressures may be used to advantage to prevent the buildup of entrained air in the curd during deagglomeration and dispersion formation. Moreover, where deagglomeration is achieved by using high shear forces, in particular, when the use of a bowl chopper is utilized, optimal comminution temperature can be achieved by either heating and/or cooling the curd particles and the serum in the liquid phase. Such temperature may suitably be achieved and/or maintained by heating the curd receptacle, the chopper bowl in the case of the chopper, by steam heating and/or water cooling, as the case may be. In some cases such as the ice cream base or after the addition of microcrystalline cellulose, heat is generated by the comminution/deagglomeration process and water has to be applied to the bottom of the chopper to maintain the optimum temperature. In most cases, steam has to be applied to the bowl to maintain temperature as the heat generated by comminution forces is less than the cooling effect of the vacuum.

Higher cook temperatures produce curd with a lower moisture content. This phenomenon also will result in a firmer and harder curd particle. As the whey is expelled from the curd during deagglomeration, the matrix is tighter and less water is bound and/or imbibed. The resulting particle has a higher density.

Comminution to obtain a dispersion possessing the required fat mimicking properties requires consideration of the moisture content of the curd. It has been observed that as serum content of the precipitated curd approaches 80 percent, the serum that is imbibed will release easily into the liquid phase and will create a larger continuous phase relative to the dispersed phase. The viscosity of the deagglomerated particles made from high moisture curd is substantially less than that made from low moisture curd. The number of particles per cubic volume will decrease and the final product will not have the desired fat like characteristics. The rate of the deagglomeration process increases (the time period for deagglomeration is decreased); yet, the resulting products made from the high moisture curd will be of "weak" or "slight" body. The body of said product can be increased by the addition of hydrocolloid gums. A point is reached, however, where the final product becomes unsatisfactory since the resulting body and texture will be perceived of as gummy or sticky upon the palate. This is in contrast to the lubricity and plasticity of fat. The curd moisture content, therefore, should be controlled with the final product considerations in mind. Thus, curd for the manufacture of mayonnaise should be high in moisture and soft in body whereas a Fat Free Bakers Cheese should be made from a hard curd (provided by a high degree of denaturation) to enhance the heat stability of the fat substitute component in the Bakers Cheese. Deagglomeration under vacuum conditions provides an additional means of controlling the moisture content of the fat substitute of the present invention. Since the deagglomeration of the curd occurs under vacuum, the temperature of deagglomeration and the inches of vacuum will determine the moisture content of the fat substitute. As the vacuum pressure is lowered, the temperature of the vaporization point of the imbibed water is lowered. The vaporization of the imbibed water will cool the temperature of the product being deagglomerated. Where deagglomeration is effected using a chopper, heating the bowl from the bottom by the application of live steam onto the bowl containing the dispersion further enhances the rate of vaporization. Maintaining a higher temperature further improves the rate of comminution. If the moisture content falls below the requirement, additional serum or water can be added back the vacuum chopper.

Accordingly, the factors that control the body, texture, and moisture content of the fat substitute are a result of the following factors:

1. The initial pH of the whey or whey protein concentrate.
2. The degree of protein hydrolysis of the whey protein.
3. The pH of the whey protein and/or casein during cooking.
4. The cook temperature and the length of time.
5. The whey protein to casein ratio.
6. The product temperature of the deagglomerated particles during processing.
7. The degree of the vacuum treatment during the deagglomeration processing.
8. The addition of hydrocolloid to the whey protein premix.
9. The cooking temperature and time held at a pH higher than 6.0.
10. The length of time between cooking and comminution.

In the steam heated denaturing and curd forming embodiment of the invention, the volume of dairy whey after steam entrapment is greater than the volume of dairy whey prior to steam entrapment. Besides, in the case where a dairy whey protein concentrate with casein addition is used to form the coprecipitate curd, the volume of the steam entrained whey has been observed to be between from about 15% to about 20% greater than the volume of the dairy whey-casein mixture prior to steam entrainment. Regardless of the whey used, volume increases on the order of 10% by volume or greater are the most desirable. This volume increase is due both to heat and the entrapment of the steam vapor phase in the denatured curd as it is formed. The use of steam vapor serves to denature the entire curd mass uniformly; however, this can be accomplished with indirect vessels by heating the whey protein concentrate slowly with good agitation and the employment of a holding period.

The dispersed particles of denatured whey protein that are formed by comminution are further treated to envelop or enrobe the same with a membrane-forming agent, suitably a phospholipid such as lecithin fractions, most preferably a lecithin fraction with the phosphatides of choline, ethanolamine, inositol and glycolipids. The formulation of the liposomes with the lecithin fraction should closely approximate the composition of the phospholipid of natural analogue if it is known. In the case of dairy products, the composition is known. However, the liposomes used in the duplication of butterfat lacked sphingomyelin because it is not commercially available. The formulations used in the examples using Alcolec® lecithin fractions were developed by trial and error. The envelopment process or membrane formation is suitably conducted as the second step in the bowl chopper. The chopper is capable of high knife speed moving through the deagglomerated particles at this stage. This insures vigorous agitation that mixes the phospholipid liposome encapsulated microcrystalline cellulose throughout the two phases. It is believed that the turbulence and flow behind each blade and on the side of each blade as it passes through the curd during comminution and deagglomeration not only reduces proteinaceous particle size, but further smooths or polishes the particle by the addition of the phospholipid at this point. The addition usually occurs after the first ten minutes of comminution begins, although this is not always the case depending upon the hardness of the curd. The eddies created behind each blade as it moves through the particles and the liquid serum phase is believed to produce changes in local pressure and violence in the eddie flow patterns. Restriction of product movement by utilizing a hood cover above the knives and a baffle behind the knifes creates additional localized pressure changes that reduce the size of the eddies behind the knife blade(s). It is believed that the reduction in size of the eddies continues to reduce the size of the proteinaceous particles and envelopes the particles with liposome vesicles previously formed, suitably in a STEPHAN cooker, as described hereafter. The tremendous stress forces remove the microcrystalline cellulose crystals from the center of the liposome phospholipid vesicle and impel them into both the inside of the particle and onto the outside of the membrane as it formed from the liposomes. The cellulose crystals may, in fact, further the efficiency of this process by rupturing the vesicle due to the vast changes in pressure as the bowl rotates. The design of the hood and the baffle creates high pressures and variances in this pressure as the bowl continues to rotate placing the fat substitute in process in and out of the hood and knife action. This change in pressure causes massive collisions between the liposomes and the protein particles. As in Oswald ripening, the small particles in a colloidal dispersion are sacrificed or victimized by the large particles. The smaller liposome vesicles are victimized by the large protein particles. The flow patterns or eddies accelerate this action. The ability of an individual chopper to reduce size, polish and condition the particle, and to then coat the particle with a phospholipid membrane are dependent on hood design and blade configuration and size. The forces generated in the chopper provide a facile means of enveloping the particles therein created.

Although not wishing to be bound, it is believed that the coated particle is substantially enveloped or encapsulated, herein also referred to as enrobed. The phospholipid membrane is believed to place amphoteric charges upon the membrane surface. This charged surface upon the protein particles will create a steric repulsion thereby preventing reagglomeration of the comminuted denatured coprecipitate protein particles. Stability of the dispersion is further substantially enhanced by the addition of caseinate or whey protein to the aqueous phase. This addition to the liquid phase during chopping will place an additional coating or membrane layer on the particle. This second layer upon the first denotes the membrane as polylayer. The casein in the form of sodium or potassium caseinate will form a smooth coating whereas if calcium caseinate of non fat milk solids are used, the coating will be rough and have a hairy surface. This additional layer provides additional repulsion force via steric and hairy fibrils protruding into the aqueous phase.

The next optional step is the incorporation of a viscosity builder into the continuous aqueous phase of the dispersion to inhibit reagglomeration of the polylayer membrane encapsulated denatured whey protein particles. The thickeners or viscosity builders used with greatest success have been pectin and/or xanthan gum. The pectin and/or xanthan gum content can vary widely, herein again depending to great degree on the whey and/or additives used as a source for the protein particles. Xanthan gum content of from about 0.1 percent to about 1.5 weight percent based on final weight of the stabilized dispersion has been found preferable. It is believed that pectin and/or xanthan gum also enhances or stabilizes the membrane formation. Fermented milk products, konjac powder, carrageenan and carboxymethyl cellulose have been used with success and are among the preferred stabilizers either alone, in combination with each other or with additional stabilizers.

In another preferred embodiment of the invention, whey is first concentrated via spiral ultrafiltration membranes so that total solids of about 13% or greater are achieved. This total solids content results in a protein content of 30% to 40% or greater as a percentage of the total solids. The whey protein concentrate is in liquid form. Whey protein concentrate is preferred. The volume to be heated is less as the concentration increases. It is further understood that dry whey protein concentrate with various degrees of modification could be used to fortify the concentrate or to alter the resulting curd properties. Also, dry whey protein concentrate could be fully reconstituted and used as the whey starting material of the invention. In addition, whey itself at a protein content of 0.75% to 1.25% could be used without any modification. This would require less equipment, ie, membranes, however, vast quanities of whey would have to be heated.

The whey protein concentrate is pumped into a cooker and mixed with a source of casein. The source of casein can be either nonfat milk solids or another source of casein such as sodium or calcium caseinate. The mixture is then heated to about 185° F. or greater depending upon the final desired product. The heat source is injected culinary steam. When the proper temperature is reached, the heated mixture is acidified with an edible acid. The preferred acids are acetic, citric, lactic acid or combinations thereof. The choice depends upon the degree of chelation desired. A fluffy hard curd forms that is less dense than the whey. This solid curd portion rises to the top of the liquid whey in the cooker. The whey (lactose) fraction is drained off from an outlet at the bottom of the cooker. The curd layer floats on the whey and then settles to the cooker bottom as the whey is drained off and the whey level lowers in the cooker. The curd can now be used as is or washed to further remove lactose and milk salts. If the curd is washed, the curd should cure for a period of time before the washing step is commenced. Problems in yield have been experienced when the washing step is started too early. An alternative method of washing the curd is to add cold water to the whey-curd mixture before all of the whey is drained off the curd and then repeat the washing steps until the liquid is clear. The washing step is the procedure of choice only when a very delicate flavored final product is desired without a slight acid flavor and odor. An example would be a light cream, whipped topping, or as an ingredient in non fat milk to improve the mouthfeel or richness.

The curd is transferred from the cooker to false bottom carts by the action of the spiral augers moving towards the opened doors.

An alternative method of precipitating the curd is outlined in Example 14 and Example 30. The whey protein and the caseinate are premixed and then pumped to a multiwall indirect steam heated processing vessel. The whey is pH adjusted with calcium chloride to pH 6.8 to 6.9 and then heated to 185 degrees F. to 200 degrees F. The whey protein concentrate-caseinate mixture is kept under low agitation during this process (60 RPM). The pH is then adjusted to pH 5.3 to 5.8 depending upon the caseinate to whey protein ratio. High temperatures are used when the content of whey protein is high relative to caseinate whereas the temperature is at the low end of the range when the caseinate content is high. The optimal pH for precipitation when the caseinate content is high is closer to 5.8 whereas when the caseinate content is low, the optimum pH is close to 5.4. Vinegar (acetic acid) or lactic acid/citric acid combination is used and diluted with water. The water/acid combination is slowly added to the processing vessel and a precipitate is formed. The curd-whey slurry is pumped to a fine saver and the curd is separated from the whey via a fine saver. An alternative means of separating the whey form the curd is to utilize a de-whey belt.

The curd is suitably gravity fed into a mixing blender and then discharged into the false bottomed kitchen carts via augers. A third alternative is explained in Example 30. In this example, the use of direct steam injection and jacket indirect heating is accomplished.

The curd is further drained and weighed into the chopper. The chopper suitably utilizes a multiple knife axial array of knives. The knives are highly polished and have very sharp blade edges. The curd is then reduced in particle size in the chopper until it begins to take on a sheen and the product obtains a mouthfeel like heavy cream. At this point, the solids content of the deagglomerated mass is approximately 25%. In another cooker that includes a means of mixing by high shear, a base is prepared containing the lecithin fractions or isolates and water heated suitably to 120 degrees F. This mixture appears like cream and comprises liposomes created by application of high shear to the lecithin/water mixture. The liposomes may then be heated, suitably to about 180 degrees F. with or without the addition of a structure builder such as microcrystalline cellulose. This mixture is then added to the chopper and the phospholipid complex forms a membrane around each protein particle. The action of the membrane formation creates an amphiphilic phase interface between the protein particle surfaces and the continuous aqueous serum phase. The protein particles then repel each other preventing reagglomeration. This adds stability to the system in that the protein particles naturally tend to reagglomerate or return to the coagulated state. The system is further stabilized by the addition of microcrystalline cellulose as an option which serves to further hydrate the particles to provide additional stability, to provide a crystalline structure within the protein particle that imitates the age crystal formation in natural fats, and to stabilize the continuous aqueous phase without adding high viscosity. Further stability can be furnished by the addition of casein as a second or polylayer membrane former. The casein or other milk protein will form this layer during the intense mixing and homogenizing action of the chopper. An additional fourth optional step is the addition of hydrophilic gums, cellulose gels, silica gels, gelatin, pectin, and/or other hydrocolloid gums that have been mixed and heated in an aqueous medium, suitably to about 180 degrees F. in a cooker with suitable steam injection ports and a blade mixer. The blade suitably is in the bottom of the cooker and exerts shear at the rate of 3000 RPM on the stabilizer so that it is fully hydrated and smooth. The gums and additional protein, when added to the dispersion of coated (membrane encased) protein particles in the chopper and mixed with it by further chopping, act to stabilize or thicken the water phase so that the protein particles do not migrate and reagglomerate. The stabilized product is then suitably stuffed into casings and dropped into cold brine. This is the preferred way to cool the product as agitation during cooling accelerates the reagglomeration process when the fat substitute is still at a high temperature. Reagglomeration is denoted by the appearance of rough, gritty texture and an aftertaste.

The dispersion formed from the whey protein and casein mixture may be considered a "coprecipitate" of the aforesaid proteins. The "precipitate" actually is a curd which floats on the surface of the whey of origin mixture when either whey, whey protein, and/or other protein additives are added and cooked in a direct steam injected cooker. In processing vessels heated with no direct steam injection, the curd is the same or more dense than the whey and thus, the slurry of whey and curd precipitate must be agitated so the curd remains suspended. The "coprecipitate" is formed by heat at the high pH in which the individual protein components cross-link or interact with one another. It is well known in the literature that kappa- casein and beta- lactalbumin interact with one another at temperatures above 180 degrees F. The conditions outlined previously set forth the factors that control the proper "hardness" of the agglomerated protein such that it will provide the comminuted curd with the desired mouthfeel. The curd is considered "soft" when it is first withdrawn from the cooker. It hardens as the temperature decreases and/or time passes. It has been observed that although comminuting—suitably utilizing a chopper (typically used for meat comminution)—of the curd provides a dispersion of protein particles in the aqueous component of the curd, such dispersion is not long lived. The longest period of time that the product will remain smooth and cream-like is 5 to 7 days. The addition of phospholipids extends the shelf life for another 10 to 14 days. The addition of microcrystalline cellulose will extend shelf life to 18 to 24 days or longer. The addition of casein as the polylayer will extend shelf life to 30 to 45 days or longer. The addition of hydrophilic gums (hydrocolloid gums) extends the shelf life for another 45 to 60 days or longer before the smooth character breaks down. The further addition and incorporation of other ingredients such as dehydrated cheese cultures and non fat milk solids using the comminuting means or other means of vigorous mixing provides lasting stability. The employment of ultra homogenization to the intermediate steps within the process or at the end of the process to the finished compounded formula will provide homogeneity that will last as long as the shelf life bacteriologically. Cheesecake base has remained at 40 degrees F. for 90 days and the base was baked into a finished product with no apparent defects in body and texture other than a slight gummy texture which many commercial cheesecakes display also.

Although other high shear mechanical comminuting means are contemplated by the present invention, it has been found that choppers (typically used for comminution of meats) provide the comminution/deagglomeration device of choice. A chopper uses a rotating bowl which passes its contents through a series of axially oriented sharp cutting knives. It has been found that the chopper can be used to comminute and polish the protein particles forming a dispersion of particles in the aqueous portion of the curd having the mouthfeel of oil-in-water and water-in-oil emulsions. The chopper also can be used (1) to membrane coat the dispersed particles; (2) to disperse fully the colloidal and non-colloidal particles to build structure; (3) to incorporate hydrocolloid stabilizers in the continuous aqueous liquid phase of the dispersion; (4) to incorporate non fat milk and cheese culture to provide additional structure and stability; (5) to incorporate other additives such as microbiological inhibitors into the dispersion; and, (6) to incorporate flavoring materials and color. A remarkable feature of the present invention, and this preferred embodiment in particular, is that the method of the present invention allows for the incorporation of any ingredient at any stage of the process. This means that the producer can incorporate the surface active or membrane-forming constituents at the most opportune time and multilayered particles can be formed. Ingredients can be added directly to the chopper that are normally very difficult to disperse in food systems. An example are the hydrophilic colloids. The process of the present invention also allows for the incorporation into the dispersion of substances that are difficult to dissolve or hydrate. And, last but not least, using a chopper allows for the formation of liposomes and the creation of cellulose gels without the use of high pressure homogenization. Further, finished products such as cheesecake base and spreadable cheese can be made completely in the chopper.

The chopper used in the present invention which comminutes the curd and forms the protein particle dispersion also is particularly well suited to effect envelopment or microencapsulation of the protein particles with the liposome additive of the present invention. Although liposome formation could be effected in situ, the preferred procedure to be followed in accordance with the present invention is to form liposomes prior to introduction of same into the chopper. This is suitably accomplished in a Stephan cooker or vacuum chopper following the procedure described and exemplified herein. The particle size of the liposome can be further reduced by subjecting the vesicle and its suspension to ultra homogenization.

The liposome enrobement/encapsulation/envelope, in accordance with the present invention, further allows for the incorporation of very difficult to disperse ingredients into simple formulations. The liposome suspensions of Examples 26 and 41 illustrate how two very difficult ingredients can be placed inside a vesicle or liposome so that they can easily be dispersed into items such as process cheese or as a "seeding" agent in the original whey protein—caseinate mixture or in whole milk ricotta to provide for additional yield. The use of the liposome moieties of the present invention in process cheese facilitates changes in how the fat agglomerates together when the cheese is sliced. A small amount of fat melts and agglomerates on the surface of process cheese when it is sliced. The vacuum applied to the package to insure shelf life compacts or places pressure on the slices so that they stick together and in severe cases, it is very difficult to find the distinct separation between the slices. The use of lecithin fraction liposome added directly to the cheese has been noted to prevent the slices from sticking together. Adding lecithin to the surface of cheese for this purpose is not new in the art. Dispersing lecithin fractions in the form of liposomes in the cheese block prior to slicing is. The functionality of the present invention of the liposomes provides the double advantage of enhancing additive attributes while decreasing the amount of additive required. When microcrystalline cellulose encapsulation was used, the slices not only separated with ease, but the melt down spread was restricted or short. This is a positive means of easily controlling the melt of process cheese as the liposomes serve to not only distribute the phospholipid fractions throughout the melted cheese mass, but to distribute enrobed crystals of cellulose throughout the cheese mass. This improves the short melt characteristic. When membrane-enrobed fumed silica was distributed thoughout processed cheese, the slice release properties improved further still. It is believed that the lubricating properties of silica, per se, provide this enhanced characteristic. The fumed silica made the process cheese melt like mozzarella. The cheese displayed string texture upon melt and chicken-breast texture when the pieces were pulled apart. Thus, by the employment of one of the two ingredients—microcrystalline cellulose to shorten the melt or fumed silica to lengthen it, process cheese melt characteristics can be easily controlled. Normally, control of these characteristics is accomplished by the melting salt type and amount and the age of the cheese used to make the process cheese. Melting salt adversely affect the flavor of process cheese. The string characteristics of natural mozzarella can thus be improved upon by the simple addition of the fumed silica to the finishing table, the de-whey belt curd, the enclosed finishing vat, or the cooker.

THE THEORETICAL UNDERPINNING OF THE INVENTION

Although not wishing to be bound, it is believed, based on observations made in developing and testing the fat substitute and products made therefrom that the theoretical underpinning of the present invention is as set forth below.

The differences in proteins that occur in nature are a result of DNA codons that specify the arrangement of the 19 primary and one cyclic amino acids. The amino acid residues are the monomer building blocks of proteins. The individual amino acid sequence is determined by the gene template. Further modification or tailoring occurs after synthesis due to the action of enzymes and the like.

In bovine milk, protein exists as the caseins and the whey proteins. The caseins are defined as the proteins precipitated by rennet action or acid at the isoelectric point of pH 4.6. The caseins are divided into four groups, the Alpha $^{s1}$ caseins, the Alpha $^{s2}$ caseins, the Beta caseins, and the Kappa caseins. The caseins represent 72 to 79 percent of the total protein of milk depending upon the species, environmental conditions, and feeding. The whey proteins are the proteins remaining in the serum after the caseins are precipitated by acid at pH 4.6 or by rennet. The major classes are Beta lactoglobulin, the Alpha lactalbumin, the serum albumins, and the immunoglobulin. Other remains of the caseins and minor proteins such as the membrane proteins are also classified as the whey proteins. Of importance to this novel invention are the physical and chemical properties and reactions of the caseins, the lactoglobulin, the lactalbumin, serum proteins, and other natural or modified proteins that will provide the same functional characteristics of the present invention.

All proteins exist in nature as peptide linked amino acid residues. The link results from the interaction of the amino group with the carboxyl group of the next amino acid. The structure resulting from this polypeptide or polymer of linked amino acids is called the primary structure. Proteins will differ from each other in both the proportions and the sequence of the amino acid residues contained therein. Besides the peptide linkages between the amino acids, there exists cross-linkages between the amino acids that are termed disulfide bridges.

The second level of architecture is the secondary structure. This level of architecture is a result of the rotation of the bond angles. The bond angle forms the typical helix coil and pleated sheet conformations that proteins exhibit. The electrostatic attraction of these steric relationships are regular and periodic along the polypeptide chain.

When electrostatic attraction occurs along the residues far apart on the linear chain, the architecture is called a tertiary structure. This attraction is primarily hydrogen, ionic, and hydrophobic bonding. The polypeptide chains become compactly coiled and folded. The hydrophobic bonds become buried inside the globular structures typical of the whey proteins.

When sub-units of polypeptide chains occur, the association of the protein is termed quaternary structure.

The stability and dispersion of the proteins in the continuous aqueous phase of the present invention, it is believed, depends upon the conformation and architecture of the individual protein when it is hydrated in the continuous serum phase. The various exposed groups determine the relative hydrophilic properties and thus, the degree of dispersion in the continuous aqueous phase of the present invention. A large portion of the surface area (up to 80 percent) of the denatured protein is exposed in the unfolded denatured state and is hydrophobic in nature. This hydrophobic characteristic is buried in the folded protein, thus, the protein globule is hydrophilic and termed soluble. The ionized groups are exposed and thus, the globular surfaces repel each other. The result is that the native whey protein will remain dispersed in the aqueous phase as a stable colloidal dispersion. In accordance with one embodiment of the present invention, a amphiphilic phospholipid is placed on the hydrophobic surface and the denatured protein particle becomes encapsulated.

The definition of denaturation of proteins as used herein contemplates the unfolding and uncoiling of the secondary and tertiary structure of the whey proteins or the whey protein-casein coprecipitate, where coprecipitate is used. The achievement of the changes the protein architecture is preferably such that it becomes permanent, irreversible, and as total as the cooking and physical comminution process will allow.

Denaturation is the result of the disruption of the nonvalent bonds along the polypeptide chain by a physical and/or chemical treatment or both. In the case of this invention, it is both. The chemical structure of the covalent polypeptide bonds of the primary structure are left in the native state. The destruction of the nonvalent bonds results in an entirely new architecture. This new architecture exposes the hydrophobic groups and thus, the entire electrostatic and steric nature of the chain begins to change. The denaturation of the proteins are reversible at this point. If the denaturation process is allowed to continue further, the side chain groups are exposed and become subject to chemical reaction. The denaturation of the proteins are reversible at this point. If the denaturation process is allowed to continue, the side chain groups are exposed and become subject to chemical reaction. Once this chemical reaction occurs, the denaturation process becomes irreversible.

It is believed that the increase in the reactivity of the thiol groups due to heat and pH change is of particular value to this invention. It is believed that the thiol groups undergo oxidation to "—S—S—" AND "—SO$_3$H" groups. The "—S—S—" linkages actually shift and intermolecular bonds form. The isomerization of the peptide bonds occurs with further splitting of the disulfides. At this point, denaturation becomes permanent and irreversible.

It is believed that the curd formation according to the present invention destroys the secondary and tertiary structure and architecture of the native proteins. The result is an increase in the permanence of the specific optical rotation with the ensuing decrease in solubility and aggregation of the denatured protein. In the case of the proteins utilized in this invention, the formation of curd occurs and the whey is easily separated therefrom. The curd is then comminuted and deagglomerated by mechanical means in the application of high shear force. The denatured whey protein curd is reduced to particles that, it is believed, become globular in nature. This globular denatured protein particle is very stable. This particle moves across the tactile sensory organs in the mouth in the same manner as a fat globule. The senses are "fooled" into believing this particle is a fat globule. Thus, when the particle is incorporated into food products, a fat-like organoleptic character is imparted. It is believed that the core protein of the particle, denatured as described above, possesses the degree of denaturation which provides stability at elevated temperatures such as those required for baking, as well as the other attributes which replicate fat globule properties.

Furthermore, as one skilled in the art can discern, any protein or combination of proteins that occur in nature or a modified form thereof, and will provide the preceding functionality, would be useful in this invention.

The deagglomeration/comminution process creates smaller precipitate particles thereby increasing the surface area of the dispersed phase. This increase in surface area results in an increase in free energy. Hence, the free energy exerts a force upon the dispersed particles by resisting the increase in surface area. This force is two dimensional and is known as interfacial or surface tension. The interfacial tension acts upon the protein particles to drive them back together again (reagglomeration).

Substances that will neutralize or adsorb the free energy are dissolved in the aqueous phase. The substances migrate or move to specific adsorption sites at the interface between the two or more phases. Substances that adsorb or accumulate at interfaces in colloidal dispersions are termed surfactants or surface active agents. The amount of accumulation or absorption at the surface is a function of the concentration of the surfactant, however, the reduction of interfacial tension many times is not a function of concentration of surfactant and is a little understood phenomena. Some substances dissolved in the solute or aqueous phase tend to migrate away from the interface and are termed negative absorbers and the interfacial tension increases with increased concentration. Most salts and some sugars in aqueous solution increase interfacial tension and hence, will cause precipitation of colloidal dispersions if the concentration is adequate.

The amount or concentration of the lecithin fractions (phospholipids) at the interface is dependant upon the concentration of negative adsorbers in the dispersion phase and how much is required at the surface to adequately off set the free energy created by the size of the increased surface area in the comminution step. Thus, extent of the particle size reduction and the salt concentration of the final dispersed phase determines the amount of surfactants added to the chopper.

It is believed that the inside of the liposome is hydrophobic (water aversion) as is the coprecipitate particle. When the liposome envelops the protein particle, the other plane of the amphiphilic membrane faces towards the outside. Since by definition, an amphiphilic membrane has both a hydrophobic and hydrophilic side, the hydrophilic side faces the outside of the particle. Thus, the envelopment of the particle by the amphiphilic membrane creates equilibrium between the two phases. The lecithin fractions are adsorbed at the interface of the particle and the aqueous phase thereby reducing interfacial tension. This action reduces free energy created by the increase in surface area as a result of the reduction in particle size by the comminution/deagglomeration process.

At this point, the protein particle is spherical which is caused by the forces exerted in the deagglomeration/comminution of the curd. The flow characteristics (eddies) leaving the trailing edges of the rotating knife blades reduce the particle size and the swirling, violent action causes rapid migration and absorption of the phospholipids at the interface. Once this has occurred, the pressure at the concave side (inside) of the spherical particle is greater than at the convex side (outside). This overpressure on the inside of the spherical particle is termed Laplace pressure and will resist deformation.. The resistance to deformation is because a local pressure towards the inside at any local point on the outside surface of the particle will cause an increase in the pressure at that point from the inside. Thus, it is believed that the precipitated particles will reach an equilibrium with the dispersed phase and roll over and around each other which tends to mimic natural oil in water emulsions such as cream. The tactile senses in the mouth will interpret or discern this phenomenon in the same manner as they do when fat placed in the mouth.

Since the protein particle or carbohydrate size is significantly larger than the microcrystalline cellulose particle, and the particle resembles a sponge holding water, cellulose crystals migrate into the inside of protein particle and to the surface of the particle. The contact angle at which the crystals absorb onto and penetrate through and into the surface of the protein particle is dependent upon the rate of adsorption of the lecithin fraction (phospholipid) membrane. Since the microcrystalline cellulose is of a different density than that of the other two phases, contact angles between it and the other phases are determined by the interfacial tensions of the aqueous phase, the microcrystalline cellulose, and the protein carbohydrate particle. This implies that as the interfacial tension between the three phases is lowered by the lecithin fractions or phospholytides, there is an increase both in the rate and amount of absorption of the microcrystalline crystals. If a crystal is removed from the interface between the protein particle and the liquid phase, then the interfacial energy would increase. As the interfacial energy increases, then the Van der Waals forces increases since the protein particles are of like composition. If the interfacial energy and the Van der Waals forces are sufficient to overcome Brownian movement, the particles will then collide and reagglomerate.

However, as the contact angle increases due to the adsorption of the lecithin fractions, the amount of energy required to remove the lecithin fractions and the microcrystalline cellulose crystals from inside or from the surface of the protein particle increases to many times its kinetic energy. Thus, the adsorbtion and absorption of the lecithin fractions and the microcrystalline cellulose crystals on and in the protein particle may become irreversible. Since the microcrystalline cellulose crystals are rigid and non-flexible, the contact angle at the interface between the protein particle and the aqueous phase is large and perpendicular. It is believed that the microcrystalline cellulose crystals stick out into the aqueous phase from the protein particles thereby preventing particle contact and reagglomeration. Thus, colloidal stability is enhanced.

As is suggested by the previous discussion and as is believed, the physical and chemical composition of the above-discussed system is complex and not uniform. When the lecithin fractions and microcrystalline cellulose are not evenly nor uniformly distributed on the surface of the protein particle, then interfacial gradients occur. The interfacial gradients cause instability since the lecithin will move over the surface towards areas of high interfacial tension. This movement will drag aqueous liquid with it along with the microcrystalline cellulose crystals. Homogenization or the application of vigorous steaming (action in the chopper) at the particle surface interface, it is believed, creates a more uniform distribution of the lecithin fractions on the surface. Thus, it is believed that homogenization leads to stability of the dispersion by uniformly spreading the lecithin fractions on the surface of the particle. The resistance to reagglomeration is enhanced by altering the interaction forces between the interfaces and the particles.

It is further believed that, as the interfacial tension of the microcrystalline cellulose is lowered at the serum-particle interface, absorption of serum and hydration rapidly occur. When the free energy of the mixture of microcrystalline cellulose and the protein particles becomes lower than that of their respective dry molecules and that of the solute serum, the protein particles and the microcrystalline cellulose become thermodynamically stable. When hydration and affinity with serum occurs between the crystals and the particles, repulsion develops when the distance between crystals and particles reaches a few water molecules. This is because the water of hydration extends and increases conformation of the particle and thus, causes changes in the charges between different parts of the individual particles. The like-charges upon the surface of the particles provide electrostatic repulsion forces between the protein or carbohydrate particles and hence, resistance to reagglomeration.

The hydration of the protein particle and its lattice work structure (spongy architecture) allows for changes in conformation or entropy. The protein particle possess conformational flexibility whereby it can assume numerous configurations in the aqueous or serum phase. Hence, the protein particle displays superior stability and resistance to reagglomeration at this stage and the membrane has a monolayer structure at the interface of the protein molecule and aqueous serum phase.

The protein or carbohydrate particle after the adsorption of the monolayer membrane also displays electrical charges due to the addition of ions and ionic charged groups. This is due to the different charged areas on the phospholipid molecules due to their amphiphilic nature. The entire particle then acquires an electrical charge and has electrostatical potential. This electrostatical potential causes an increase in the repulsive forces between like charged protein particles and it is proportional to the amount of phospholipid that can be adsorbed on the surface. The repulsive forces prevent the protein particles from approaching each other. The size of the surface area of the particle determines the quantity of phospholipid membrane in relationship to the mass of the particle. A large particle would have a smaller ratio of phospholipid to protein, thus, the electrostatic potential of the entire particle would be less than a smaller particle with a larger surface area and a higher ratio of phospholipid to protein. Since the particle is electrostatically charged, its repulsion forces can be affected by pH.

The aqueous serum phase surrounding the surface membrane of the protein or carbohydrate particle contains ions. It is believed that the positively charged ions will accumulate locally forming a diffuse or double layer around the phospholipid membrane separated by water molecules. The thickness of this double layer is dependent upon the electrostatic potential of the particle or the mass of the adsorbed phospholipid. The thickness of the double layer determines the distance at which the repulsion forces separate the protein particles. This distance between the membrane and the positively charged ion is dependent upon the ionic strength of the aqueous phase. Thus, as pH decreases and ionic strength increases, the amount of the phospholipid fractions must be increased to insure repulsion and, if the ionic strength increases sufficiently, then the positive ions can associate with the groups on the membrane and neutralize the charge on the particle. This results in decreased surface potential and reagglomeration. As can be readily seen, use of a fat substitute exhibiting the colloidal properties recited requires attention to the surface potential of the final food formulation in which it is employed.

The distance between the charged areas of the protein particle membrane surface is also a result of ionic strength. It is proportional to the thickness of the diffuse double layer. The separate charged areas can be distinguished and attract each other forming internal salt bridges. The salt bridges affect the conformation and the size of the protein particle. Thus, when ionic strength is increased, the particle is reduced in size and becomes rigid and the tendency to reagglomerate into large groups of particles is increased.

The measurement of ionic strength is easily determined with a pH meter; however, the measurement of surface potential in a highly complex system as this is not that easy. The new instruments that measure zeta potential determine how particles move in an electric field slipping along the water molecules in the distance between the membrane and the ionic field of the aqueous phase. However, since the distance or thickness between the membrane and ionic field is unknown in a complex system such as this, the determination of the zeta potential is difficult, if not, impossible. Thus, the zeta potential is always less than the surface potential, but the correlation between the two is difficult due to the number and complexity of the final food formulations.

The employment of this phenomena can also control the perceived fat tactile sensation in the mouth. Increasing the surface potential will allow the particles to slide over each other easily which will denote fat of a liquid nature whereas lowering the surface potential will cause slight flocculation and the water between the particles will not flow as easily. The protein particles will not slide as easily against each other and will be perceived as fat of high molecular weight. Solid fats typically display greater resistance to deformation in the mouth.

The DLVO theory will adequately predict the stability of colloid dispersions as it considers the combined effects of electrostatic repulsion and the Van der Waals forces of attraction. To determine the electromotive force of repulsion, the zeta potential and the particle size has to be known. The determination of zeta potential has been discussed along with the changes in conformity and rigidity of the particle. Since the protein particle is primarily composed of the aqueous serum phase surrounded by a sponge like or lattice work of protein, particle size determination is difficult to measure. It is for this reason that the Hamaker constant is difficult to determine since it depends upon the difference in polarity between the dispersed particle and the aqueous or continuous phase. Further, the determination of the Hamaker constant for the total particle would be difficult since the phospholipid membrane has a different polarity than the particle. The Hamaker constant is required for the determination of the electromotive force of attraction. Thus, due to the varied composition and the existence of various densities that will change with ionic strength, it is very difficult to determine particle size, viscosity, zeta potential, or predict the stability of the dispersion via the DLVO theory. This is not to say that quality control systems cannot be determined for a given process based upon the foregoing procedures to produce consistency from batch to batch, but one has to realize that the data is not representative of the actual occurrences or events.

In the last additional step to the chopper, a source of milk protein may be added. The protein suitably is casein in cases wherein the pH remains above 4.7 and viscosity is of concern. If viscosity or flocculation is not of concern (e.g., a sour cream non fat substitute), casein is still the choice. If viscosity or flocculation is of concern, then whey protein concentrate is the optimal additive. Casein may be added in the form of non fat milk solids or sodium/potassium caseinate. In the case of non fat solids, salt (sodium chloride) has to be present to provide enough ionic strength during the heating step. The increase in heat and ionic strength cause colloidal calcium phosphate to be removed from the calcium casein micelles. The reduction in calcium phosphate from the micelles of non fat milk powder causes the casein to spread over the lipoprotein membrane in the same manner as sodium caseinate. Calcium caseinate and non fat milk solids will give higher protein loads on the membrane surface area. If a natural cheese is to be manufactured, the choice would be whey protein and/or sodium caseinate as the calcium caseinate and non fat milk solids would precipitate upon the addition of rennet, calcium chloride, or acid to below pH 4.7. On the other hand, whey protein and sodium caseinate would be entrapped. The addition of milk proteins, in particular caseinate, forms an additional membrane like coating enveloping the protein particle. Proteins, and in particular, milk proteins have both hydrophilic and hydrophobic parts (they are amphiphilic). These parts align with the hydrophilic and hydrophobic areas of the lecithin membrane. Hence, the proteins can be termed surfactants or surface active agents. The proteins adsorb at the interface and begin to change conformation. This implies that the long spiral chains unfold and become stretched over the surface. Some of the moieties and segments may penetrate the sponge-like structure of the particle and become absorbed. The other moiety of the chain may protrude out into the continuous or aqueous phase. As with any surfactant layer previously discussed, time and velocity are required for the surfactant to become fully adsorbed upon the surface and for equilibrium to exist between the three phases (microcrystalline cellulose, continuous and dispersed phase). The rate of arrival of the casein at the interface surface can be accelerated by the application of hyper homogenization.

After adsorption, the milk protein chains and micelles can protrude from the surface. Thus, the precipitated whey protein particle now takes on the characteristics of sodium caseinate and/or calcium caseinate micelles and/or fat globules as they exist in milk. Any other protein that would form micelles or enrobe phospholipids in the same manner as the milk proteins would prove useful in this invention. Thus, it is believed the protein particles now acquire the mechanisms that keep natural fats with bi-layers or poly-layers in dispersion or suspension in an aqueous phase. It is futher believed that the heat applied during the final step in many of the Examples creates modified proteins because of Maillard reactions with lactose or other sugars and dextrins. These Maillard reaction products may provide the same affinity for the phospholipid membrane as the glycoproteins do in natural fat emulsions or dispersions. Thus, this final membrane structure can be termed a lipoprotein. If the lipomembrane is thick enough or has become loaded with protein, then it could be termed high density lipoprotein (HDL).

If, as is believed, the protrusions extending from the dispersoids of the present invention into the aqueous phase display the same characteristics or function in the same manner as protein protrusions do in nature, then they serve as repulsion agents. The suggested mechanism is that as the whey protein enveloped particles approach each other, the protrusions or chains interpenetrate and become compressed. The conformation of the protein changes and energy is released in the form of steric repulsion. This is analogous to a spring being compressed and released. Further repulsion can be exhibited by hydration of the chains that cause repulsion due to further conformational deformities seeking equilibrium. Furthermore, if the membrane protein has been subjected to heat in the presence of hydrocolloids, as in several of the Examples, then reactions between the proteins and the hydrocolloids may cause the protrusions to carry charges. If so, they may cause their own motion upon being brought in close proximity. Many models of natural fat term these protrusions "hairs". The degree to which they protrude and their repulsion activity is termed "hairiness."

WHEY PROTEIN CONCENTRATE

Dairy whey is the liquid serum remaining after the butterfat and the rennet and/or acid coagulable proteins are removed from milk by a cheesemaking process. Among the numerous dairy whey sources suitable for the present invention are wheys which do not contain high levels of proteolytic enzymes, e.g., whey from cottage cheese production which is acid set and wheys derived from production of rennet-formed cheese.

During the production of cheese, casein is precipitated from the milk by one of two methods. The first involves the culturing of milk with acid producing microorganisms or adding acid to lower the pH to about 4.7 whereupon the casein proteins precipitate from the milk to form the curd that will ultimately be processed to cheese. In the alternative process, the precipitation of the casein is accomplished using a rennet enzyme rather than acid. The "acid casein" is used in the production of soft cheeses such as cottage cheese, while the "rennet casein" or "para-casein" is used in the manufacture of cheeses such as cheddar or mozzarella. Acid is also added to milk to produce the caseinate isolates such as sodium and calcium caseinate.

Dairy whey comprises lactalbumin and lactoglobulin proteins. Lactalbumin makes up 2% to 5% of the total skim milk protein and is believed to function in milk as a proteinaceous surfactant stabilizer of the fat particles. Lactoglobulin makes up another 7% to 12% of the total skim milk protein and is closely associated with the casein protein in whole milk. Whey derived from the acid precipitation process mentioned above is referred to as acid or sour whey and generally has a pH of about 4.3 to 4.6. Whey derived from the enzymatic precipitation process, also mentioned above, is called sweet whey and generally has a pH of from about 5.9 to about 6.5 As derived from the cheese making process, whey generally is an aqueous medium comprising 90% or more water.

Whey protein concentrate is the result of ultrafiltration of the whey in which the protein content is raised from an average of 13 percent of the dry solids to 30 to 80 percent of solids based upon dry matter. The whey passes under pressure across a semi permeable membrane by which the lower molecular weight lactose, soluble salts, water, lactic acid, and lower molecular weight protein will permeate through the membrane and the heavy molecular weight proteins and insoluble mineral salts are retained. Therefore, the whey protein concentrate is termed in the art as "retentate" and the lactose fraction is termed "permeate". Since the membrane must operate in a balanced fashion, the permeate composition will always remain approximately the same on both sides of the membrane. The protein and insoluble salt composition is a result of the size of pore diameter (diatoms) in the membrane. The smaller the pore size, the more likely retained protein (retentate) will have a higher percentage of lower molecular weight protein. The protein percentage or content of the retentate is dependent upon the pressure employed on the retention side of the membrane. If water is added to the retentate and further processed through membranes, it is termed difiltration. It can be readily discerned, the addition of water to the system lowers the solubles such as lactose and and salts thus concentrating or increasing the ratio of the retentates to the permeates. The fat substitute of this invention made from a difiltration whey protein concentrate would have less lactose, salt, and acid than the fat substitute made with the normal ultrafiltration process. Thus, the protein particle made with the difiltration whey protein concentrate would have different properties than with regular whey protein concentrate.

The utilization of whey protein concentrate in this invention as a source of whey protein is the preferred method as it eliminates the heating of vast quantities of whey.

SUBSEQUENT TREATMENTS OF STABILIZED FAT SUBSTITUTE FOR SPECIFIC APPLICATIONS

Where the fat substitute is to be used in compositions such as ice cream, mayonnaise or cream cheese, the stability of the stabilized fat substitute can be further enhanced by homogenization. Enhancement by homogenization appears to occur universally across the gamut of homogenization procedures used in homogenization of naturally occurring fatty products as well as at the elevated conditions of ultra homogenization.

Homogenization has been performed using an array of different homogenization devices, namely, APV GAULIN CD-30, APV Rannie 12.51 H, Niro Soave NS 2006 and Microfluidics M110 homogenizers. All of the foregoing homogenizers can be considered ultra homogenizers in that they can achieve pressures above 10,000 pounds per square inch. The preferred practice is to use two stages whereby the second stage serves to create back pressure in the cavity between the two stages. In accordance with this preferred procedure, from about 10 to about 15 percent of the first stage pressure is preferably applied to the second stage; i.e., if 10,000 PSI is applied to the first stage, then 1,000 to 1,500 would be applied to the second stage.

The stability of the stabilized fat substitute has been further enhanced by homogenization using an APV GAULIN two stage homogenizer at an inlet temperature of 120° F. and outlet temperature of 165° F., with a pressure of up to 6,000 psi on the first stage and up to 2,500 psi for the second stage. The homogenized stabilized fat substitute was thereafter used in preparing a fat free soft spreadable cheese, a fat free mayonnaise, a fat free bakers cheese, and the like. A fat free ice cream mix was prepared in the same manner.

Although evaluation of preliminary research results suggested that homogenization was not indicated for certain fat substitute foodstuffs of the present invention, it has since been found that homogenization will universally enhance the stability of both fat substitute, per se, food base made therefrom, as well as finished food products. Stability, as herein used, denotes the ability of the fat substitute and products made therefrom to maintain original body, texture, lubricity, plasticity, and other characteristics such as fat like mouthfeel. In fact, one aspect of the present invention resides in the discovery that homogenization lengthens the freeze-thaw cycle of products made with fat substitute of the present invention. As an example, finished cheesecake made with cheesecake base of the present invention will remain firm and slice clean for up to six months when the cheesecake is made with base that has been homogenized. Frozen cheesecake made with unhomogenized base will develop a sticky, gummy mouthfeel after two or three months under normal conditions occurring in frozen food distribution channels. Referring again to the characteristics imparted by the homogenization of cheesecake base, it has also been found that cheesecake made with homogenized base will incorporate air during the creaming and whipping steps much faster, on the order to 2× to 3× times as fast, than cheesecake made from base without homogenization. The homogenization allows for the cheesecake batter to reach the correct specific gravity in a shorter length of whipping time than the batter made from unhomogenized base. Moreover, it has been observed that the air cell structure in the finished cheesecake made from homogenized base has smaller foam cells than the cheesecake made from unhomogenized base. In a large plant environment, the fast whipping time is highly advantageous where production conditions are precisely controlled. The fact that the homogenized base whips faster needs to be taken into account in small bakery shops in that the creaming and whipping steps become critical, i.e., the batter can incorporate too much air in a very short time.

The homogenization step of the present invention can be operated across a range of pressures and conditions used in the processing of dairy and other food products. Operating the homogenization step by implementation of high pressure stuffing using an infeed pump has shown excellent results. It is believed that the unexpected improvement in stability enhancement may be as a result of subjecting the product of the invention to the shear created by the bevel seat of the by-pass valve that is typically used in in-line homogenizing systems. The product returning to the infeed hopper using the aforesaid procedure has been observed to have a distinct improvement in sheen.

The typical homogenizing pressure used in the dairy industry ranges from about 1,000 to about 5,000 PSI. The products of this invention, when homogenized at these pressures whether single or multiple passes are used and/or whether single or multiple stages are employed, generally show an improvement in stability. The same is true where elevated levels of pressure above about 5,000 psi are used. Moreover, homogenization at hyper homogenization conditions has been found to remarkably enhance stability.

Hyper homogenization is defined as homogenization using pressures of about 10,000 psi or more. Homogenization at such high pressure levels is presently in use in the biotechnology industry. Hyper homogenization is used extensively to disrupt cells contained in the ultrafiltration rententate. The design of these units now allows for the processing of heavy, viscous products as long as the input of stuffing pressure is high enough to fill the cylinders on the intake stroke and the valve is designed to close and open under the conditions of high pressure and in the presence of a viscous product.

Although the comminution step of the present invention is described by reference to devices and blade arrays typically used in the meat industry, other methods of comminution are contemplated, provided only that the involved apparatuses are capable of working the hardened protein of the curd. Likewise, although subsequent treatment by homogenization is believed to impart the preferred enrobed particle membrane architecture, other methods of achieving the "homogeneous" surface are also contemplated.

Referring now to the operation of the chopper blade arrays, it is believed that the turbulence and flow behind each blade and on the side of each blade as it passes through the curd during comminution and deagglomeration not only reduces proteinaceous particle size, but smooths or polishes the particle. The eddies created behind each blade as it moves through the curd mass is believed to produce changes in local pressure and violence of the eddie flow patterns. Restriction of product movement by utilizing a hood cover above the knives and a baffle behind the knives creates additional localized pressure changes that reduce the size of the eddy behind the knife blade(s). It is believed that this reduction in size of the eddy reduces the size of the proteinaceous particles being formed by comminution. The efficiency of the chopper can be adjusted advantageously by modifying the chopper hood and the placement of restriction devices in the hood. The design of the hood creates the pressure and hence, the flow pattern out of the hood. The flow pattern or eddies determine both the size and the ability of one chopper design to preform more efficiently over another. The characteristic of the chopper to reduce size, polish and condition the particle, and to then coat the particle with a phospholipid membrane are dependent on hood shape, baffle size, and the hood configuration, blade configuration and size. The selection of the above can be adjusted for a particular curd and quantity to be processed. The forces generated in the chopper provide a facile means of enveloping the particles therein created. The enveloping liposomes may be suitably generated in a separate mixing device, such as a Stephan cooker, which is the device of choice herein adopted for liposome production.

The process of homogenization is to add further colloidal stability to the final product or to insure that the outer layer of the membrane is in place. The process of forcing the product through the small valve opening increases the velocity and creates intense turbulence in the flow. The small eddies smooth and polish the protein particle and place the phospholipid membrane in contact with the casein membrane protein. Since several hours, if not days, are required for the product to reach equilibrium when produced in the chopper, the homogenization process creates this equilibrium in a matter of minutes if not seconds. The intense velocity of the streaming carries the protein to the surface of the particle through convection and this force will cause substantially thicker protein membrane. The higher the pressure and the resulting temperature, the thicker the protein membrane will become. The thickness of the protein layer can be controlled by adding surfactants before the homogenizing process that will displace the casein at the surface of the protein particle. Examples are adding an over abundance of lecithin fractions, using sweet cream buttermilk in place of non fat powder, adding monoglycerides or other synthetic surfactants, and the free fatty acids in the enzymatic modified cheese. The process of heating the non fat milk solids to 180 degrees F. reacts the whey protein with the caseinate and the result is an even thicker protein membrane. The higher the temperature in the Stephan cooker, the thicker the protein layer will become.

It is believed that the protein particle withstands disruption and therefore, the particle size is reduced slightly, if at all. When the finished homogenized product is compared with the same product withdrawn out of the chopper with an optical microscope, the particles appear to be the same size. This is same size that was determined via the Horiba laser particle analyzer. The analysis showed the protein particles had a mean average of 4 to 8 microns. Although optical measurements are not as accurate as the laser, they did show that the particles did have approximately the same approximate size before and after homogenization. The most unusual occurrence observed, however, was that the homogenized particles were flocculated or closely approximated each other. This was not the case with the sample that was not homogenized. Normally, samples prepared for the Horiba instrumentation are diluted with water on the order of 1000:1. The homogenized samples would not break apart in the water as the non homogenized samples did. The non homogenized sample gave the same results as previously, for example, 5 to 6 microns as the mean particle size. However, the homogenized sample showed 75 microns in diameter for the same dilution with the same amount and time of applied sonication. Observation under the optical microscope showed continued clumping or flocculation. The reason it was termed flocculation is that none of the particle cores were touching. If the particle cores were actually touching, the term would then be coalescence or aggregation. The sample was subject to continued sonication with continued analysis with the Horiba laser. As the loose flocculation broke up, the particle size as determined by the laser instrument continued to become smaller. When the sonication finally separated the particles as observed with the optical microscope, the Horiba laser determined the mean diameter to be 2.5 microns. Observed under the microscope, the particles appeared to be at least half the size of the particles as observed originally before sonication. Thus, the homogenized particles prepared sufficiently by sonication for analysis by the Horiba laser were an artifact of how they existed in the original dispersion. It is believed that the process of preparation by sonication at a 1000:1 dilution causes severe osmotic pressure upon the unprotected protein particle. Since it has a lattice work (spongy) structure, typically containing about 2 parts of solute to one part of protein lattice work or sponge-like interior, the high level of sonication disrupted the size and structure of the particle. The solids content of the original solute was 45 percent, thus, the dilution in water at close to 0 percent solids and the application of sonication caused extreme osmotic pressure and partial collapse of the lattice work structure sponge-like interior. Thus, the Horiba Laser saw an artifact of what actually existed in the original matrix.

In other patents and the art, Singer et al U.S. Pat. No. 4,961,953 and Unilever EP 0 412 590 A1, the inventors specifically refer to particles under 2.0 microns with no more than 2% of the particles exceeding 3.0 microns. The precipitated particle of this invention and its characteristics make it extremely difficult to determine the actual particle size as it occurs or exists as a fat substitute and even more so in the final product. This is because all present analysis procedures create artifacts. With a protein particle that displays a unique sponge-like architecture, the difficulty is extreme. Most proteins exist as random coils and may contain 20 percent to 50 percent bound water. Bound water is defined as water bound by forces that create a crystal or ice like structure. This water is very difficult to eliminate from the protein particle. Secondly, proteins and in particular, denatured whey proteins or precipitates, hold up to 2.5 times their weight as held or imbibed water. This water is held physically like a sponge within the sponge-like architecture and structure once a precipitate is formed. Thus, the volume of the precipitated protein particle is very difficult to determine. If the particles are centrifuged at 25,000 RPM for 25 minutes, then a large percentage of the imbibed water will be expelled from the particles. Thus, determining the number of particles per unit of volume by multiplying the decant protein product of ultracentrifuging by the particle size distribution does not, insofar as the present invention is concerned, offer an accurate means of measurement of of the number of particles per volume unit.

Perhaps the most valid means of measuring or discussing colloidal stability is determining the surface weighted average which relates to the total volume of dispersed material as it compares to its total surface area. From this result, the average mean free distance between particles can be determined. The distance between the particles and how they react to each other has more to do with the colloid stability and the tactile perception of fat than particle size or the resulting distribution of said. To even determine the above, the assumption has to be made that all particles are of the same density which is not the case. The weight ratio of the phospholipid membrane to the protein sponge-like core different for a large particle as opposed to a small one. Thus, the density of a small particle is vastly different from a large particle due to the increased ratio of the phospholipid membrane to protein core in the same particle.

The same discussion can be applied to voluminosity. The precipitated curd in the chopper before the addition of the liposomes has a voluminosity of 5 to 6 ml per gram of protein. The drained curd at this point contains water (actually solute containing lactose and salts) which is either bound or imbibed. If assumptions are made that all of the phospholipids, microcrystalline cellulose, and most of the casein is added to the particle and the changes in specific gravity accounted, then the voluminosity of the particle due to the hairy layer could double. Thus, the voluminosity could increase to as much as 10 to 12 ml per gram of protein. The protein particle size at this point would be changed rather dramatically from when it started the comminution and membrane forming process. After the addition of sugars, maltodextrins, acids, and the like to the chopper, the effect of ionic and osmotic forces changes the particle voluminosity further. Thus, the particle size is changed and affected in many modes in this environment.

If careful statistical analysis is done on fat particle size distributions occurring naturally in various systems (particularly milk fat) or to the data presented in prior fat substitute art, it is found that 75% to 85% of the fat or fat substitute particles are smaller than one micron in diameter. Thus, most naturally occurring fat systems (globule forms) contain vast numbers of small globules that represent only a small fraction of the total weight of the fat content. Most, if not all, of this data was determined on instruments that were able to discern 0.1 microns. The new laser instrumentation will discern particle size down to 0.01 microns and thus, the particle size distribution would move further towards a smaller mean average.

Probably the largest body of data concerning fat globule characteristics is studies relating to naturally occurring butterfat. In unhomogenized milk containing 3.5 percent butterfat by weight, the number of fat globules approximates $15 \times 10^9 \cdot ml^{-1}$ with 75 percent below 1 micron diameter and a mean average diameter of 0.8 microns. The large number of small globules is difficult to determine as is evidenced by studies on skim milk separation which suggests a far greater number of small globules. The large number of small globules always makes the mean average difficult to determine. Thus, the standard deviation or the width of the size distribution for individual cows is only 0.4 while mixed milk from many cows only broadens or increases the standard deviation to 0.45. This implies consistency while the data shows that wide variations occur in the number of globules, the quantity of fat, and the average mean diameter. This means that different size diameters can be made to coincide by merely altering the scales or the level of discrimination.

The major concern to both the organoleptic and the colloidal chemist is the volume surface average diameter which relates the total fat volume to its total surface area. In the case of a fat substitute, it would be the surface weighted average or the total volume of dispersed protein particles to its relative surface area. In non-homogenized cows' milk, the average is about 3.4 microns. This is a significantly higher number than the mean average particle size of 0.8 microns. If the same data is analyzed logarithmically with the weight of the fat considered, then:

1. Eighty percent (80%) of the fat globules contain only five percent (5%) of the fat by weight. (It is believed that they do not contribute to the sensation of fat in milk and other fat systems as well.)
2. Twenty percent (20%) of the fat globules contain ninety five percent of the fat by weight. (It is believed they contribute the sensation of fat in milk and other fat systems as well.)

It has been widely known that unhomogenized milk with the same fat content by weight and volume will be perceived by tactile senses to be "richer" than homogenized milk of the same fat content. It can be readily seen that homogenization lowers the mean particle size and thus, moves a greater number of particles and a larger portion of the fat volume or weight to a level that cannot be perceived by the human tactile senses in the mouth as fat. It is also widely known that skim milk contains a vast number of small fat globules, yet it contains less than 0.12% fat via ether extraction. Further, a vast majority of humans can differentiate between skim milk at 0.12%, low fat at 1%, low fat at 2%, and whole milk at 3.25%, or ice milk at 3.5% butterfat versus ice cream at 10% butterfat and premium ice cream at 16% butterfat.

The organoleptic technologist must consider the perceived area of fat globule size as by the human senses. Thus, particle size and its determination has little to do with fat perception other than to be of interest as a quality assurance tool. Unhomogenized milk that has been allowed to rest without agitation will develop a solid cream layer and if enough time goes by, a cream plug or thick layer will develop. Fat globules with sizes in the range of 20 to 30 microns thus occur. Thus, flocculation and coalescence has occurred denoting instability; nevertheless, the cream layer will taste "rich", "pleasing", and "fatty". The skim or serum portion underneath the cream layer is perceived as having no fat content, yet it contains vast numbers of small globules, perhaps a number equal to or greater than the number of globules in cream layer if coalescence has occurred.

It is obvious that other factors play a major role in how a human perceives richness contributed by fat in food. Of prime concern to the organoleptic technologist attempting to mimic butterfat is the 20% particle distribution that makes up 95% of the fat content. The physical and colloidal state of butterfat in various dairy products differs rather dramatically. In milk and cream that has been homogenized, the globules exist as a very stable dispersion or emulsion and will remain so for days upon end with no apparent coalescence or agglomeration. In sour cream and yogurt products that have been subjected to a far higher temperature treatments and a far higher homogenization pressures, the globules exist in an agglomerated state. Yet, the perceived fat content of soured or acidified dairy products is higher than the unagglomerated fat globules in milk. The high heat and homogenization treatment of sour cream base places a much thicker layer of casein on the fat globule and an increase in the hairiness of the globule. The finished sour cream always tastes richer than the base from which it is made. This condition is due to the action of the pH or the acid upon the outer casein membrane. There is a dramatic increase in viscosity due to the agglomeration of the fat globules as the fluid between them now moves very slowly. The casein hairs can actual react with one another and form a loose network of aggregated globules. Thus, there is an increased resistance to flow past one another by the fat globules. The viscosity and an apparent increase in fat content is observed versus the base from which the sour cream was made. The higher the heat treatment and the more homogenization (two stages and 2 or more times), the thicker and richer the body and texture that is achieved in sour cream. Thus, the apparent richness or fat content in cultured products is a function of how the fat globules slip by each other and how they resist deformation in the human mouth. The more resistance to flow or the manner by which the globules roll by each other and the amount and type of deformation establishes how the tactile senses determine the quantity and the quality of the fat content.

In ice cream, a completely different set of conditions occur with respect to fat content. A replacement surfactant is added to the ice cream mix before pasteurization and homogenization. The surfactant replaces or has a greater affinity for the interface of the fat globules with the serum. The replacement of the natural milk phospholipid membrane with mono or diglycerides, Tweens, or egg yolk phospholipids cause the degradation of the stability of the fat globule dispersion. Hence, colloidal stability degenerates and coalescence and agglomeration occur. The fat globules become "sticky" as the soft fat inside the globule sticks to other exposed fat from another fat globule. The fat globules under intense agitation and the reduction in temperature agglomerate around the entrained air as it is incorporated into the mix. The "art" in making excellent ice cream is to create just enough destabilization to create just the right amount of lamellae formation of all of the fat around the incorporated air. If the correct amount of destabilization has occurred, the product will appear rich and have an excellent "eat". This is because the fat content appears to be greater than before the air incorporation. The fat globule formation around each air lamellae gives the impression that the fat content as a weight percentage is higher than it actually is. This is because the fat globules now surround an air lamellae and the tactile senses in mouth percieve it as one large fat globule.

In butter, the fat exists in a completely different colloidal dispersion. The solid fat is in the continuous phase and the liquid is in the dispersed phase. This changes completely the perceived tactile sensation in the human mouth. In the process of manufacturing high quality butter as made in Denmark, the cream is high temperature pasteurized at 185 degrees F., then allowed to culture at 65 degrees F., then cooled to 55 degrees F. and allowed to set for 10 hours, and then cooled to 45 degrees F. The cream is then churned and the revolving churn deforms the fat globule and pushes part of the liquid fat to the outside of the fat globule. The streaming caused by the rotating action of the churn washes part of the phospholipid membrane off the globules and they then begin the agglomerate. The ratio of liquid fat to solid fat/fat crystals is very important in producing the proper texture in the finished butter. It is believed that the fat crystal deforms the fat globule allowing further puncturing the phospholipid membrane and allowing more liquid fat into the three phase dispersion which then acts to break the surface tension of the air bubble. The foam breaks and agglomeration of the coalesced globules begins so that granulation of the gobules now occurs. This collision of the granules is the working process which creates butter body and texture that has not been duplicated by margarine or butter produced in the continuous churn. The melting, spreading, and mouthfeel of this type of butter is a result of the development of the crystalline fat forms. Butterfat, because of its content of fatty acids that have melting points from $-8$ degrees F. to 170 degrees F., displays a wide range melting point of 75 degrees to 85 degrees F. Thus, the mouth perceives a vast array of deformations due to soft or liquid fat with a dispersion of the solid crystals within it. The body and texture characteristics of a butter can be altered by the churning temperature, the size of the crystal formations, and the working processes. In the case of this invention, the microcrystalline cellulose crystal provides the same function as crytalized fat needles.

Thus, stability of the protein dispersoid particles and the delay of onset of grainy texture (believed to be the result of protein particle agglomeration/coalescence) is enhanced by altering the continuous dispersion phase, such as by addition of stabilizers and/or structure builders, and is further enhanced by enveloping the protein dispersoid with a membrane-forming agent and is even further enhanced by treating the thus enveloped dispersoid to achieve a surface which more closely replicates the surface of fat globules.

It is an aspect of the present invention to enhance the fat replicating attributes of a fat-substitute, protein-based dispersion comprising protein dispersoids in a continuous aqueous phase by forming a membrane on said dispersoids which replicates the membrane on fat particles.

It is a yet further aspect of the present invention to treat the enveloped protein dispersoids, suitably by homogenization in a manner such that the membrane surface of the dispersoid is further modified to replicate the properties of fat globules in homogenized fat-based systems.

The aspects of the present invention could accordingly be classified using the following categories:

methods of forming proteinaceous, carbohydrate, or hydrocolloid particles from denatured curd, which particles are of size such that a fat-mimicking dispersion is formed (and the dispersion thus formed);

methods of improving stability of fat-mimicking proteinaceous, carbohydrate, or hydrocolloid dispersions (regardless of origin) by modifying the properties of the continuous liquid phase of the dispersion, by adding stabilizers and/or structure builders (and the stabilized dispersion thus formed);

methods of enhancing the fat-globule replicating properties of proteinaceous, carbohydrate, or hydrocolloid dispersoids by enveloping same with a membrane-forming composition replicating the membrane of naturally occurring fat-globules (and the resulting enveloped dispersoid and dispersions comprising same);

methods of further treating enveloped dispersoids to replicate the surface architecture of fat globules (and the resulting treated enveloped dispersoids and dispersions comprising same).

Of particular note regarding the wide-ranging utility of the liposomes formed and utilized in the formation of the fat-replicating proteinaceous, carbohydrate, or hydrocolloid based dispersed particles is the fact that such liposomes are of advantage in formation of the preferred fat-globule replicating dispersoids of the present invention. Such liposomes also have been found to enhance the incorporation of additives into the continuous liquid phase of the dispersion of the present invention. In other liquid mediums, including milk, liposomes can be used to encapsulate enzyme(s) added to induce accelerated ageing, lactose hydrolyzing, and fat lipolyses. The application of liposomes for the introduction of enzymes into cheese, milk or curd reduces the amount of enzymes required. Proteolytic enzymes are particularly expensive and difficult to work with in a cheese manufacturing environment. The proteolytic enzymes cause allergic reactions and sensitivity to the enzyme(s) which develops readily in humans. Modern cheese plants use air to convey curd and some of the enzymes become air borne. Thus, plant personnel will develop allergies to these enzymes. The liposome enveloped enzyme eliminates the problem of air borne contamination since the enzyme can now be applied to the curd on finishing tables, vats, belts, mills, etc. without the enzyme becoming air borne. It has been found that the enzyme requirement to achieve the desired proteolysis in the same given time period is 50 percent or less. This is a significant reduction in the cost of accelerated ripened cheese. If the casein or protein coating is applied to the outside of the membrane, then the liposome vesicle will behave like a casein micelle or fat globule and precipretate out with the curd. If the enzyme is encapsulated in the lecithin fraction liposome with a casein outer bilayer and then rapidly frozen and further freeze dried, the enzyme system will have a long shelf life. The powdered protease liposome can then be simply mixed with milk and added to the cheese milk in the cheese vat.

The methodology of liposome production for the encapsulation of enzymes is the same as that for particle envelopment with a few precautions. The lecithin fractions are first pasteurized to eliminate any pathogens and then cooled to below 80 degrees F. Sterilized or pasteurized water is used to dissolve the enzymes and care must be exercised so that the enzymes are not left in the water for longer than ten to fifteen minutes. If animal tissue enzymes are used, twenty to thirty minutes in water is required to leach the enzymes from the tissue. If other enzymes are to be used, they can be added later. When the enzymes and water mixture have conditioned for the correct time period, the water-enzyme mixture is added slowly to the lecithin fraction phospholipid in a high sheer environment such as a Stephen cooker. Cooling water is maintained on the outside jacket so that the temperature remains below 85 degrees F. If the liposomes are to be homogenized, then the liposome encapsulated enzymes are cooled so that the output temperature is maintained below 85 degrees F. The use of the Microfluidics M110 homogenizer affords the possibility of cooling the liposome encapsulated enzyme system during homogenization. The reason for the temperature control is that the enzymes used in accelerated ripening are inactivated at temperatures close to 100 degrees F. At this point, the liposome encapsulated enzymes can be added directly to cheese curd on finishing tables or to enzyme modified cheese base to make enzyme modified cheese.

In the process of this invention, enzyme modified cheese is made using a meat chopper and the liposome encapsulated enzymes. Cheese is high temperature pasteurized at 190 degrees F. with additional microbial inhibitors added. This high temperature not only kills most of the bacteria, but it further inactivates any inherit enzymes that are present in the cheese from the original milk or starter culture. Therefore, the cheese is as enzyme and bacteriologically free as possible. The cheese is added to a chopper equipped with carbon dioxide cooling and the temperature is lowered to approximately 40 degrees F. under vacuum. Additional pasteurized water is added to the cooling cheese as it is pulled into the chopper by the vacuum. Enough water is added to adjust the moisture content to 55 to 60 percent $H_2O$. When the temperature has reached 40 degrees F., the liposome encapsulated enzymes are added to the cheese. The cheese containing a high level of enzymes is discharged from the chopper and packed into casings. The casings are stored for 10 to 20 days at 60 degrees F. or until the proper flavor has developed. The enzyme modified cheese at the end of the short ageing period is then pasteurized again to inactivate the enzymes and packed in casings or 5 gallon pails and cooled immediately.

Achievement of a uniform dispersion of microcrystalline cellulose or any other hydrocolloids in an aqueous continuous liquid phase is very difficult to achieve and requires extensive energy to separate and prevent agglomeration. It has been discovered that uniform and stable distribution of microcrystalline cellulose and a wide variety of difficult to disperse additives can be achieved wherein a membrane-forming vesicle such as lecithin derived phospholipid fractions are used. Thus, in accordance with the present invention, facile dispersions of difficult dispersoids can be easily accomplished in aqueous phases or polar liquids. Hydrocolloids that have been slurried in water, propylene glycol, and corn syrup/water solutions and then encapsulated in the phospholipid liposome have been xanthan gum, carrageen, carboxymethylcellulose, methylcellulose, oat fiber, microcrystalline cellulose, oatrim, fumed silica, alginate, konjac flour, pectin, agar, gum arabic and flocced cellulose. Some of these mixtures could be homogenized at high pressures and freeze dried or low temperature dried in a fluidized bed or foam mat. The benefit would be a readily dispersible hydrocolloids/surfactant mixture that would have wide applications in the convenience foods and processing applications where high shear is impractical or will destroy the food or its functionality. An additional benefit was that it removed the chalky, grainy mouthfeel from the fiber which has application in making fiber supplements pleasing and appealing.

Though not essential to the present invention, the advantages achieved in connection with incorporation and/or stabilization of additives such as structure builders and in particular microcrystalline cellulose suggests that use of liposomes to envelop both proteinaceous, carbohydrate, or hydrocolloid dispersoids and one or more of the additives present is particularly preferred.

An interesting attribute of utilizing liposome enveloped additives such as microcrystalline cellulose in fat-replicating and/or fat-based solid food products, e.g., typical fat-containing cheese products, is that such products, when sliced and reformed into a block, display a substantially reduced tendency of coalescence. The coalescence of the cheese slices is observed where a cheese block or cylinder is presliced. The addition of phospholipid liposome, or enveloped microcrystalline cellulose or fumed silica not only curtails adhesion of the cheese slices, but will also affect the melt characteristics. Microcrystalline cellulose shortens the melt or texture which is normally controlled by breaking down the paracasein chain with phosphate salts which results in the "classic" process cheese flavor. Thus, with this invention, a process cheese can be made with more of the natural cheese flavor and texture. The phospholipid enveloped fumed silica provides a melt much akin to the texture of mozzarella. The texture stretches and strings in the same manner. When structure builders and in particular, enveloped microcrystalline cellulose or fumed silica are distributed in a presliced cheese, the need for individual slice wrapping is eliminated.

Thus, it is yet another aspect of the present invention to use an enveloped microcrystalline cellulose additive or its equivalent to prevent the slices in presliced fat-based or fat-replicate based products from coalescing during storage. Cheeses such as American cheese, processed cheese spread, processed cheese food, etc., are candidates of particular importance. The additive may be incorporated at any stage of the cheese making process, preferably before the cooking process. The amount of microcrystalline cellulose may vary, suitably ranging from about 0.05 percent to as high as about 0.50 percent in processed cheese spread. The content of fumed silica likewise can vary from about 0.02 percent to about 0.25 percent. For best results, the content of lecithin fractions should normally not exceed 0.25 percent.

MEMBRANE FORMATION AND SURFACE-ACTIVE AGENTS

It is widely known to those skilled in the dairy art that phospholipids play an important part in the emulsification of butterfat in naturally occurring milk and dairy systems. The churning of butter from cream is dependent upon the butter churn washing off the phospholipid membrane from the fat globule. The physical churning action then causes the fat globules to aggregate into granules. These granules are further washed with water to remove both the remaining phospholipid and the non fat milk solids as the churning action continues. The result is a very smooth textured product, namely, butter.

Since phospholipids are the surface active-agents and membrane formers in natural products such as milk and are a component of all living cells performing membrane transfers, phospholipids were evaluated in creating a stable dispersion of protein in the present invention and in this regard lecithin fractions were specifically evaluated. The major problem encountered was finding the most satisfactory lecithin fraction system. Most lecithin is derived from soybeans and in a minor case, from rice. Lecithin derived from soybeans is vastly different in composition from that found in milk. Lecithin is a complex mixture of phospholipids; namely, phosphatidylcholine, phosphatidylethanolamine, phosphatidyl-inositol, phosphatidic acid, and glycolipids. Most of the refined lecithins contain soybean oil as part of the composition that is unsatisfactory for use in a fat free food product. The lecithin fractions that have been found particularly useful in the present invention are those that are widely used in the pharmaceutical and cosmetic industries, since one can blend the fractions to produce the desired functionality, namely, membrane or liposome formation and placing steric charges on the protein particles.

The synthetic and natural surface active agents are classified by as (1) nonionic, (2) anionic, (3) cationic, and (4) amphoteric. Amphoteric or amphiphilic surface active agents possess all three of the preceding characteristics (1), (2) and (3). It is believed that lecithin and its fractions in particular, are amphoteric because of its complex composition of the various phospholipids. The new technology allows for the separation and concentration of the individual phospholipid fractions such that, if they are combined together with water under high shear, they will form liposomes. The liposomes will form high strength membranes around particles and will then place amphoteric charges upon the surface of the particle. The particles will then tend to sterically repel each other and thus, resist reagglomeration.

The other common characteristic of surface active agents is that they all are polar (hydrophilic-water loving) and non-polar (hydrophobic-water hating). It is this characteristic that makes them excellent emulsifiers or colloidal dispersion stabilizers. Part of the molecule penetrates the water phase and part of the molecule penetrates the oil phase. The relative size of the polar and non-polar portions of the molecule will determine the type and quality of the emulsion produced. It the case of fat substitutes made from denatured and dispersed fully hydrated protein particles, the blended phospholipids intermingle with the polar and non-polar protein polymers. As discussed previously, the theory of this invention is based upon the rearrangement of the protein polymers which results in the exposure of the hydrophobic portions that results in precipitation and aggregation of the curd. The natural state of the denatured protein is to remain aggregated. The addition of the lecithin fractions, it is believed, results in intermingling and aligning with the protein polymer thereby creating a new physical complex that resists reagglomeration and aggregation. Thus, the particle remains in a dispersion with a stable film barrier or membrane.

It has been found that the fat substitute of the present invention also displays increased richness; that is, an improved emulsion-like character after the lecithin fractions are added to the chopper. There is a reduction in the apparent viscosity of the dispersion and both characteristics are probably a result of a reduction in the particle-media friction at the interface of the two. This reduction in interfacial tension serves to enhance the fat like character by adding additional lubricity and to enhance the stability of this invention by imparting repulsion.

Referring to the proteinaceous particles displayed in FIG. 15 through FIG. 19, these are schematic drawings presented to depict particle states beginning with formation in the chopper and ending after treatment in a homogenizer.

Figure 15:
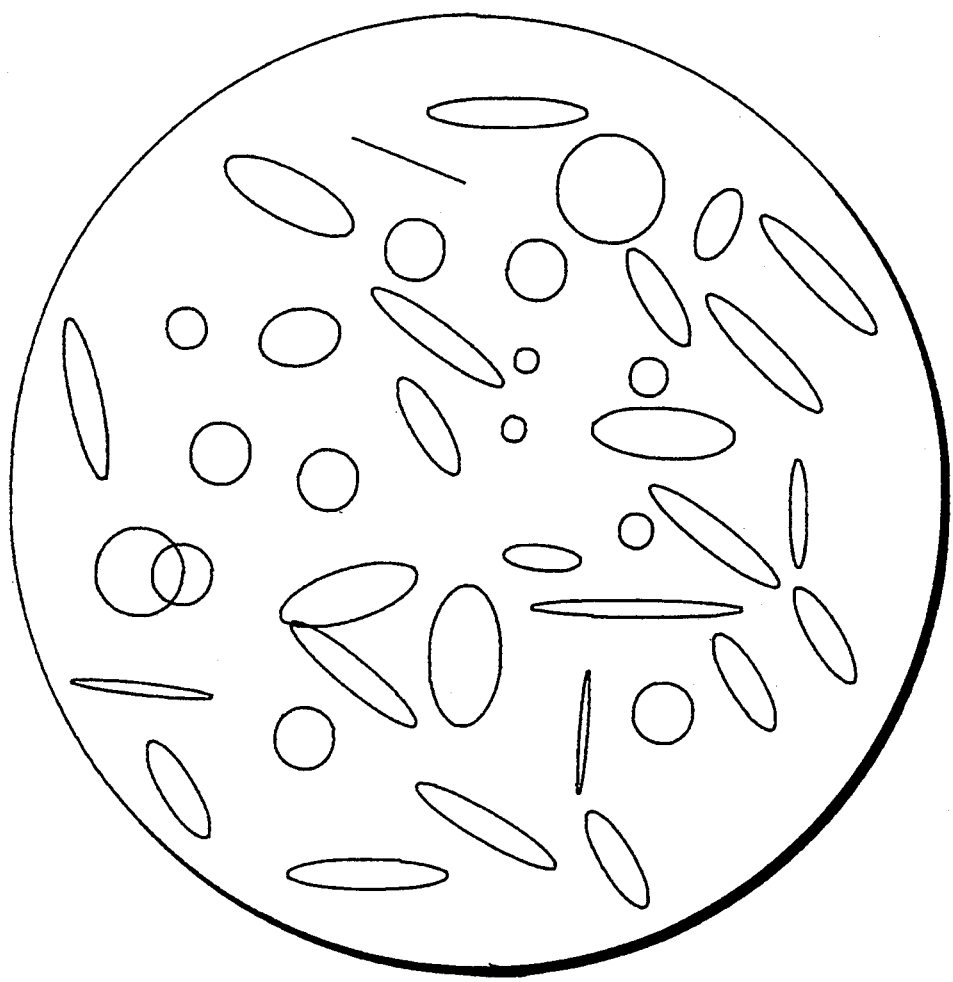
FIGS. 15-19 are schematic cross-section representations of a proteinaceous, fat globule mimicking particle of the present invention illustrating various stages of fat replicating architecture.

FIG. 15 depicts the proteinaceous particle after it has been comminuted for approximately ten minutes. The particle is made up of a proteinaceous sponge-like core that binds and imbibes the serum entrapped by curd precipitate. As the knives comminute the curd, the free serum is liberated. The continued application of sheer forces and high pressure by the blades rounds and finishes the particles producing a substantially spherical shape.

Figure 16:
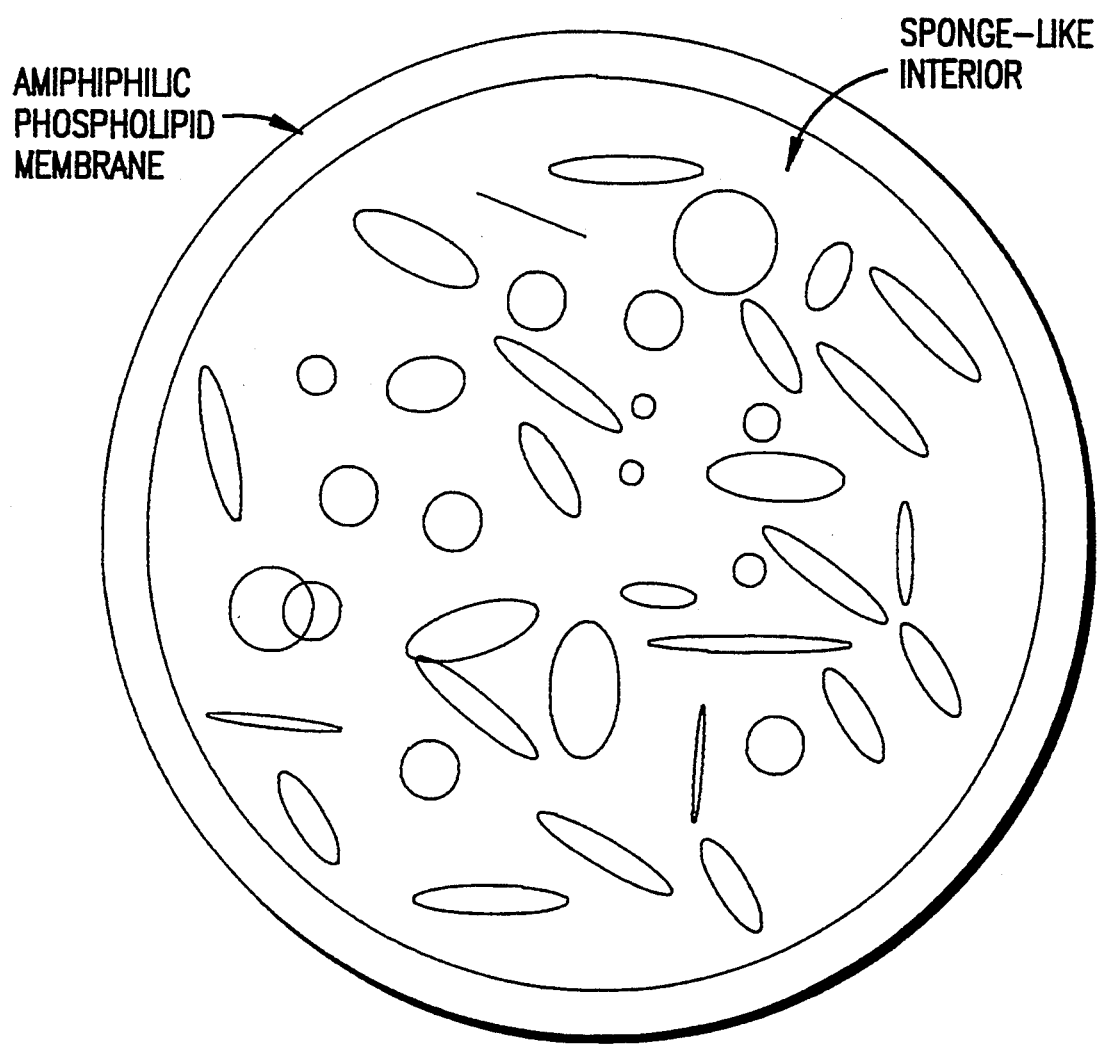

FIG. 16 depicts the proteinaceous particle after a liposome comprised of lecithin phospholipid fractions introduced in the chopper form a membrane which envelops the particle. Electrostatic forces of repulsion are created and amphophilic charges as explained herein, believed to be imparted to the surface of the particle. Particles, as depicted in FIG. 16, now repel each other whereby a first order of increase in the level of stability is achieved.

Figure 17:
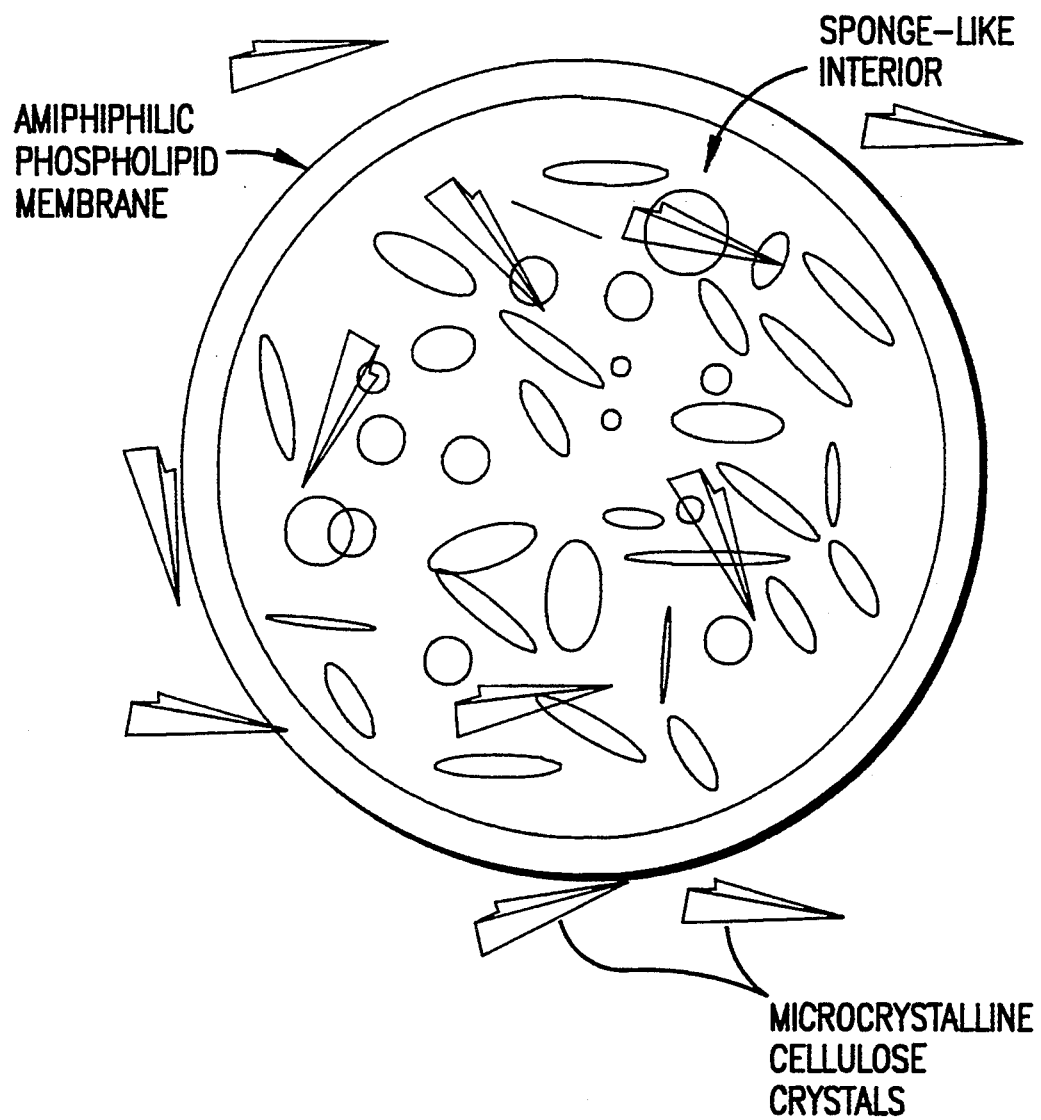

FIG. 17 illustrates the embodiment of the present invention relating to deposition of microcrystalline cellulose crystals on the particle and/or penetrating into the core of the particle and the presence of such crystals in the continuous aqueous phase in which the particle is suspended; that is, between particles. The gradients created by the particles and their resulting hydration further enhance the repulsion forces and it is believed, provide a level of stability that is virtually irreversible upon the withdrawal of sheer forces. The microcrystalline cellulose crystals in between the particles, it is believed, further enhance stability.

Figure 18:
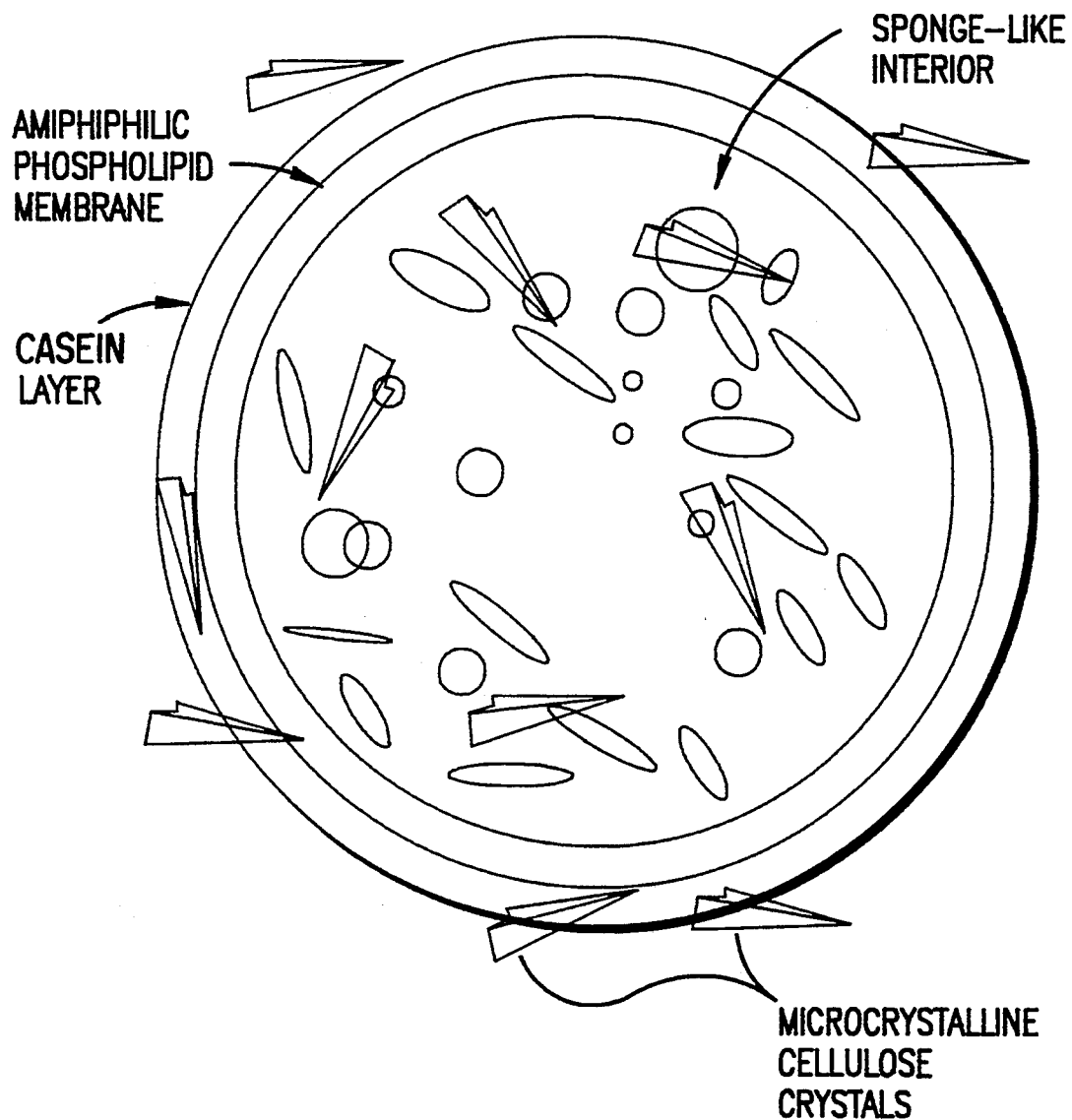

FIG. 18 shows the development of a polylayered membrane on the proteinaceous particle. The coating is comprised of casein from a casein-containing source suitably nonfat milk solids or sodium caseinate. Homogenization of the particle depicted in FIG. 18, suitable at high pressure, causes this layer to become thicker and more dense entrapping more microcrystalline cellulose in the process. The particles now repel each other with greater force and more closely replicate natural fat globule conformation and identity.

Figure 19:
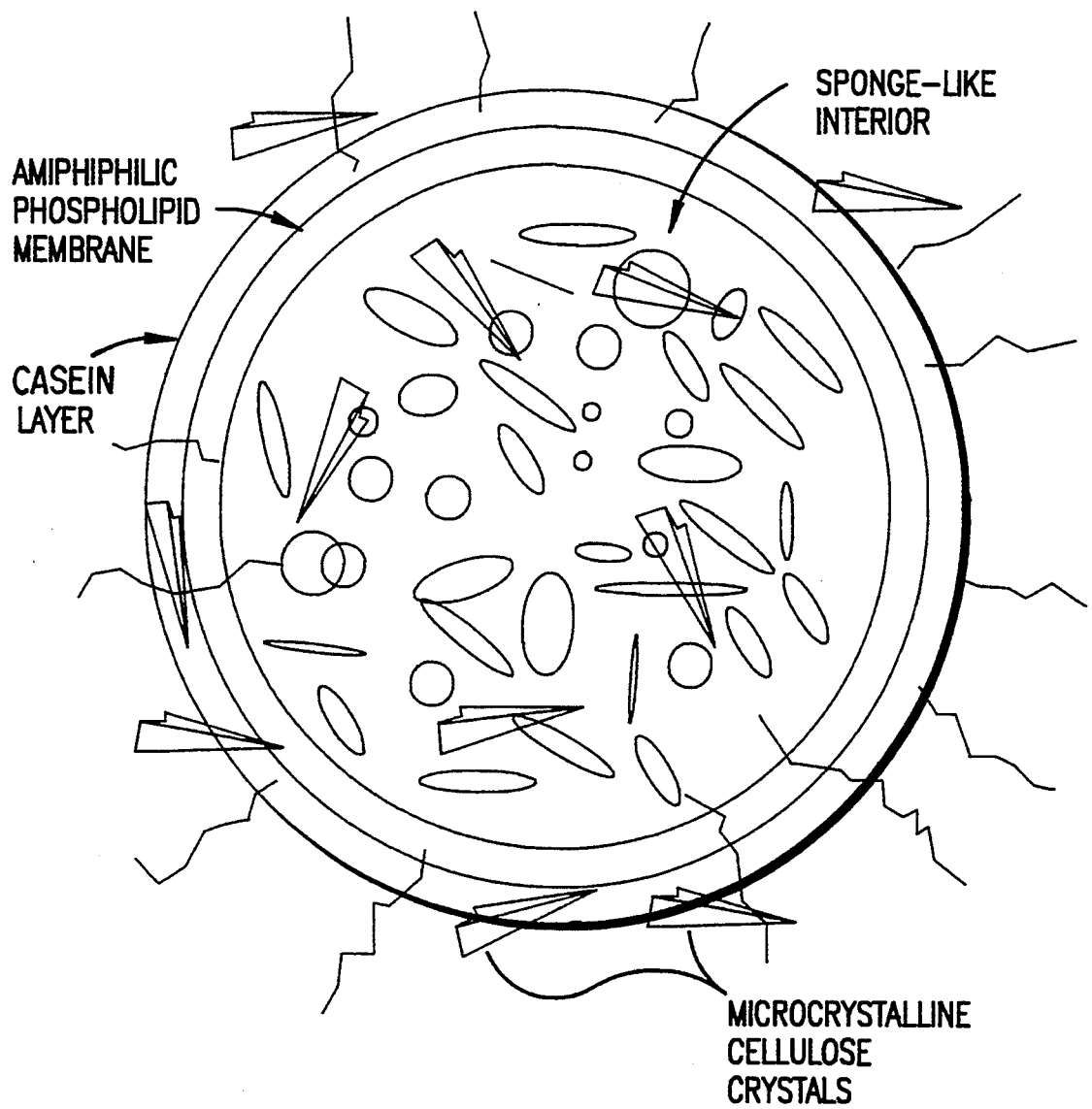

FIG. 19 depicts the hairiness of the casein layer after high pressure homogenization or application of additional sheer forces using other means. The hairiness shown, it is believed, causes further repulsion by spring coil reaction as the particles approach each other and then repel each other. The hairiness also causes an increase in viscosity as the particles increase in number due to the increased friction as the free serum has to pass by the "hairs." It is believed that this phenomenon creates a further tactile sensation in the mouth of richness.

When the membrane is discussed herein and when an attempt is made to describe the membrane architecture, it needs to be understood that the drawings presented are schematic and that, though the basic structure of the liposome membrane is set forth herein, the architecture attributed to membrane additives and the manipulation steps, such as homogenization, are incapable of precise characterization.

The recognition of the advantages of liposome enrobement comes as a result of observing the unexpected ability of enrobement to increase both the rate of and stability of particle dispersibility. Indeed, it appears that the integrity of the serum component of spongy proteinaceous particles is preserved by liposome encapsulation.

Deductions regarding variables in liposomes actually formed and used are based on the specifications of the commercially used materials found to produce liposomes, that is, the lecithin fractions available and used primarily in the pharmaceutical industry.

In the present invention, proprietary compounds described hereinafter, such as ALCOLEC SFG and NATHAN 140 have been used with success.

ALCOLEC SFG contains high levels of glycolipids which appear of equal importance along with the enumerated phosphatides described herein in that it is believed glycolipids combine with the glycoproteins (heated milk protein-sugar reactions, Mailliard) to form an outer membrane layer. The combination of glycolipids with glycoprotein is believed to cement the outer protein to the phospholipids of the inner membrane.

The phospholipid membrane is believed to be a bilayer layer membrane. There are normally two phospholipids involved in liposome formation. In the preferred embodiment of the present invention, the membrane is really a multi-layer membrane or polylayer membrane when it contains edible microcrystals such as microcrystalline cellulose and/or proteins.

ALCOLEC SFG contains high levels of glycolipids and phosphatidyl choline. These fractions are highly hydrophilic or water loving. The glycolipids also have a great affinity for proteins at the outside layer. This makes the outside layer more water loving and the inside part more water hating. ALCOLEC SFG also contains inositol which is anionic or hydrophobic.

NATHAN 140 is 40 percent choline and it, by itself, will form a bilayer membrane or liposome with water and sheer. Parts of it are lipophilic and hydrophilic, i.e., amphoteric. In water, it turns the hydrophilic part to the outside and hydrophobic part to the inside forming liposomes. Whey proteins being globular proteins, display the same conformity. By denaturing the whey protein with heat, the hydrophobic part is turned to the outside and it precipitates.

In accordance with the present invention, the liposome can be tailored to its intended use. The phosphatidyl make-up or composition can be changed by using different fractions that give different results. It is, in part, the ratio of aqueous phase to particles dispersed therein that determines the amount of choline to ethanolamine to inositol to glycolipids. Choline content in the mayonnaise examples is increased because the aqueous phase had less solids and, therefore, the objective was to duplicate the oil in water natural emulsion. Accordingly, the amount of NATHIN (choline) was increased, which resulted in less viscosity and more lubricity.

Where the liposome's intended use is in a system to duplicate butter, ethanolamine fractions content (the proportion of such fractions) would increase to achieve a ratio of ethanolamine to choline which imparts heavier viscosity and thick clustered type of particles. Increasing inositol, an anionic fraction, also would change the flowability of the butter globule replicating particles.

The blends of lipid fractions ultimately will vary for each application. The protein-containing membrane of the present invention is polylayered and the involved membrane technology is highly complex. What the embodiment of the present invention relating to membrane formation concerns in final analysis is modifying the behavior of the particles in the aqueous phase by influencing the characteristics of both phases. The more hairy a particle is in an acid pH aqueous phase, the greater resistance to flow the particle will have and thus, the higher and heavier texture the perception of fat-like character, i.e., sour cream texture. But in another instance, the low pH or acid taste would not be characteristic of the food, i.e., butter; thus, a different approach has to be used, i.e., changing the composition of the membrane so that the particle will behave like a water in oil emulsion by increasing the microcrystalline cellulose to duplicate the natural crystals that occur in butter and giving the dispersion stickiness and spreadiness. Sour cream is thick and viscous, but does not spread.

STRUCTURE BUILDERS AND ENHANCERS

Most natural systems are made up of building blocks or frameworks. This invention is no different in that it requires a structure in which the order remains stable and rigid. The requirement for this structure in this invention is evident because of the high moisture content and the sponge like physical character of the hydrated protein particle of the present invention. Water is an essential ingredient that imparts fluidity to the system and since it is the major component, it serves to reduce the caloric content of the final food. It is this high water content that makes it preferable to include a structure builder in this system. The aqueous phase has to remain stable and somewhat rigid so that the particles do not aggregate and lose the fat like character. The system must resist the free movement of water and one of the major characteristics of a structure builder in this invention is to bind or absorb water preferably at the rate of 8 to 10 times its own weight. It is believed that the motion of water in this system has deleterious effects upon the hydration of the protein particles during storage and further processing. The hydration of the protein particle must be preserved so that it exhibits the fat like character by rolling across the tactile sensors in the mouth. If the hydration level is changed, the particle shape and/or size is altered. Aggregation and the loss of the phospholipid can occur and the senses now perceive a grainy or chalky texture. Several well known structure builders have been successfully employed in the development of the present invention and microcrystalline cellulose has proved to be the best in most systems either alone or in combination with larger particle size celluloses or silica gels.

Microcrystalline cellulose, also known as colloidal grade cellulose, when dispersed in water, sets up a network of cellulose crystallites which are submicron in size. Microcrystalline cellulose is marketed under the brand AVICEL ©, a trademark of the FMC Corporation. The microcrystalline network locates in the aqueous dispersed phase. Under shear, the network breaks down; yet, when the shear force is removed, the network will reform with a minimal loss of viscosity.

In the present invention, microcrystalline cellulose is believed to form a fibrous network in the aqueous/continuous phase of the dispersion where it acts as a physical barrier, separates the protein particles, and retards coalescence of the particles. The presence of microcrystalline cellulose in the fat substitute product of the present invention is preferred. The fibers provide a short texture that adds body without creating a gummy or pasty texture and since the microcrystalline crystals/fibers are insoluble, they provide a clean mouthfeel and do not mask flavor.

STABILIZER

The stabilizer or combination of stabilizers employed may be selected from any number of commercially available dairy product stabilizers; typically, hydrocolloids (hydrocolloid gums) of the type enumerated in U.S. Pat. No. 4,379,175. The stabilizer of the present invention is preferably a thixotropic agent chosen from the well known list of thickeners known as viscosity increasing or gelling agents, the same being described in U.S. Pat. No. 4,515,825. The stabilizer(s) selected is/are preferably pseudoplastic stabilizer(s), that is, the viscosity of the dispersion stabilized with it recovers almost instantaneously once application of shear force is discontinued. If the functional properties of a hydrocolloid gum are desired in any finished product and that particular hydrocolloid is not pseudoplastic, then it should preferably be combined with a hydrocolloid gum that is pseudoplastic.

The pseudoplastic suspension stabilizer added to the coated protein particles of the present invention is a compound that functions to suspend and stabilize the coated protein particles in the dispersion of the present invention. Such stabilizers act by creating viscosity in the continuous phase (serum) to prevent coalescence and create separation of the dispersed phase (the membrane-coated protein particle phase).

Examples of suspension/dispersion stabilizers suitable for use of stabilized fat substitute compositions are the following compounds:

| Source | Compound |
| --- | --- |
| Marine plants | Agar, alginates, carrageenan and furcellaran, propylene glycol alginate. |
| Terrestrial plants | Guar gum, logust bean gum; gum tragacanth, karaya gum, and specialty pectins. |
| Microbial polysaccharides | Dextran; rhamsan gum; welan gum and xanthan gum, and milk ferments. |
| Polysaccharide derivitives | Carboxymethylcellulose, Methyl hydroxypropylcellulose, hydroxy propyl cellulose, hydroxyethyl cellulose; hydroxypropyl guar and modified starch. |

For use with milk whey protein, the stabilizers of choice are xanthan gum and pectin. Viscosity enhancement with xanthan gum is inversely proportional to the amount of shear force applied to the dispersion in which it is the additive. Xanthan gum has a very limited milk protein reactivity index and monovalent or divalent salts do not effect xanthan gum and are not required to produce the rheology thereof. Beside variations in pH, the characteristic of the fat substitute product of the present invention do not alter the rheology of xanthan gum.

It is readily appreciated that where the fat substitute product of the present invention is incorporated into products containing milk protein, despite the origin of the whey used to produce such fat substitute products, the stabilizer selected must be compatible with milk protein in the final product.

Moreover, in selecting the stabilizer, consideration needs to be given to the conditions of fat substitute production and use. Thus, where the fat substitute product of the present invention is used in the production of ice cream protein, active stabilizers such as carrageenan, locust bean gum and carboxymethyl cellulose may be suitable. On the other hand, the use of carrageenan and/or locust bean gum in bakers cheese would be unsatisfactory because the locust bean gum and carrageenan and milk protein used in the production of the baker's cheese would complex at the conditions of preparation (at pH 5.2 and below). This chemical bonding or complexing would form a precipitate at the pH of baker's cheese production and storage.

RELATIONSHIP OF PH TO DISPERSIBILITY OF THE CURD

The pH of the dairy whey that is used to produce the product of the present invention varies based on the origin of the whey.

In the case of whey originating from skim milk cottage cheese production, the whey typically has pH of about 4.6 and contains proteolytic enzymes in a very small amount compared to sweet whey. Whey, recovered from mozzarella production using the method set forth in Example 1 (following fine removal, clarification and ultrafiltration) provides a protein concentrate having a pH above 6.0 as seen by reference to protein concentrates produced in Example 1.

Of note is the option of inducing curd formation in accordance with the present invention by mixing low pH cottage cheese whey and the whey from rennet induced cheese production.

Optimally, the whey that is used in the process of the present invention should be intact, that is hydrolysis of protein in the whey due to acid/enzymes prior to whey protein curd formation should not reach a level and/or degree where yield and/or precipitate formation is adversely effected. This occurs where the pH of fresh whey drops substantially and substantial levels of protein hydrolysis occur.

Selecting the optimal pH for curd formation from whey and/or whey protein concentrate depends on the type of rennet and/or starter culture used. Typically the pH of whey originating from enzyme-induced cheese making (see the whey derived from mozzarella production of Example 1) should remain above about 6.0 so that the whey protein concentrate produced from it remains above about 6.1 pH. If the pH decreases below such level, the coagulating enzyme will begin hydrolyzing protein and either a reduced yield and/or curd of unsatisfactory texture (the protein is not hard enough) results during agglomeration. In fact, where pH of whey originating from mozzarella making has been allowed to reach substantially reduced pH levels, e.g., 5.6, it has been observed that after cooking and acidification, as called for by the present invention, no appreciable curd yield occurs and the curd present is soft and does not form the requisite agglomerate.

The optimum pH for coagulation of the coprecipitated curd is dependent on whether and to what extent other types of protein are present with whey protein. If casein or egg protein is present, then the pH approaches 6.0. The ionic strength is a factor as it will require a lower pH to coagulate a low ionic strength whey protein concentrate.

DEFINITIONS OF PARTICLE SIZE ANALYSIS

Since particle size is an element in the definition of colloidal and insoluble dispersions, a means of determining the particle size of the fat substitute of the present invention via a repeatable and reproducible standard method was undertaken. One purpose of a standard method would be to facilitate control of the production and make procedures for the products of the present invention.

The first method attempted was the simple preparation of slides for optical microscope analysis. Methods normally used for the counting of direct bacterial analysis or somatic cells outlined in "Standard Methods for the Examination of Dairy Products" were employed. It was found that the repeatable results of the preparation methods were extremely low. The first observation was that the time from one step to the other in the aforesaid method was critical. This is because the hydrated protein particle loses shape and size immediately upon dilution with water. The sample must be diluted with water as other organic solvents were found to dehydrate the particle and in some cases, caused clumping and even visible aggregation. It was found that, when a drop of diluted sample containing the protein particles of the present invention was placed on a slide and the particles watched, the particles began to immediately lose shape and size. The reason for this phenomenon is believed to be that the osmotic pressure changes very rapidly in the aqueous phase and the particle is compressed due to the architecture of the interior of the protein particle.

It is a known fact that denatured milk proteins will bind 3-10 times their weight in water. It has been found that the curd produced according to the present invention will not allow less than about 60 percent moisture to be expelled from the curd by application of physical force that is normally used in the art to remove excess serum or whey from cheese curd. The 60 percent moisture curd of the present invention appears dry, which indicates that the serum is tightly imbibed and bound. Thus, the water of dilution added for particle size testing will cause immediate osmotic pressure upon the particle and the creation of an artifact. What has been observed is that the particles of the present invention are very sensitive to their environment. The dilution step required in the above methods caused an immediate size reduction and thus, any observations and conclusions are based upon artifacts. The nature of the artifact was found to be dependent upon the timing and the skill of the technician, with results varying by as much as 80 percent.

The diluted samples were then observed with a common technique used for determining the quality of dispersions. This technique is known as the Hanging Drop Method in which a drop of the dispersed particles is placed upon a cover slide and the cover slide is inverted over a convex area in a hanging drop microscope slide. The motion of the particles can then be observed to determine "Brownian Movement." Such method is used to determine the quality of dispersions in several fields of art. The degree of the movement indicates the quality of the dispersion. A very active particle movement shows that the particles are charged and repulsion charges are great. When this technique was used, it was immediately noticed that the particles observed were of various sizes and began to shrink immediately as a result of the heat generation by the microscope illumination. Thus, this method only provided a qualitative evaluation of the repulsion charges placed upon the particle. Neither the size nor the distribution of the protein particles could be determined, as observation and counting require that particles be in an immobilized state.

Figure 2:
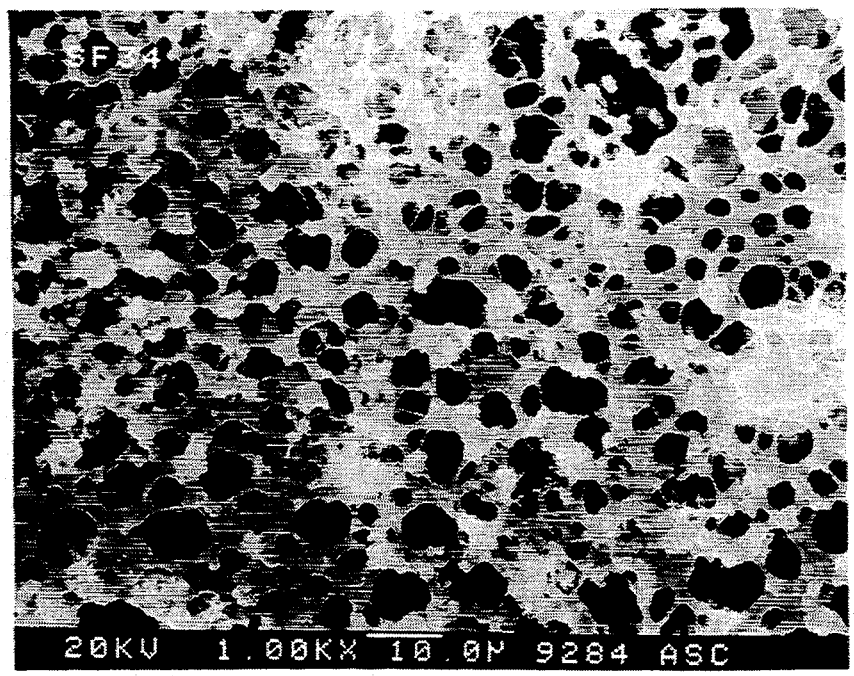
FIG. 2 is an electron micrograph photograph of a TV monitor representation of a particle artifact derived from a sample of the baker's cheese produced in Example 1, taken at 1,000 times (1,000×) magnification.
Figure 3:
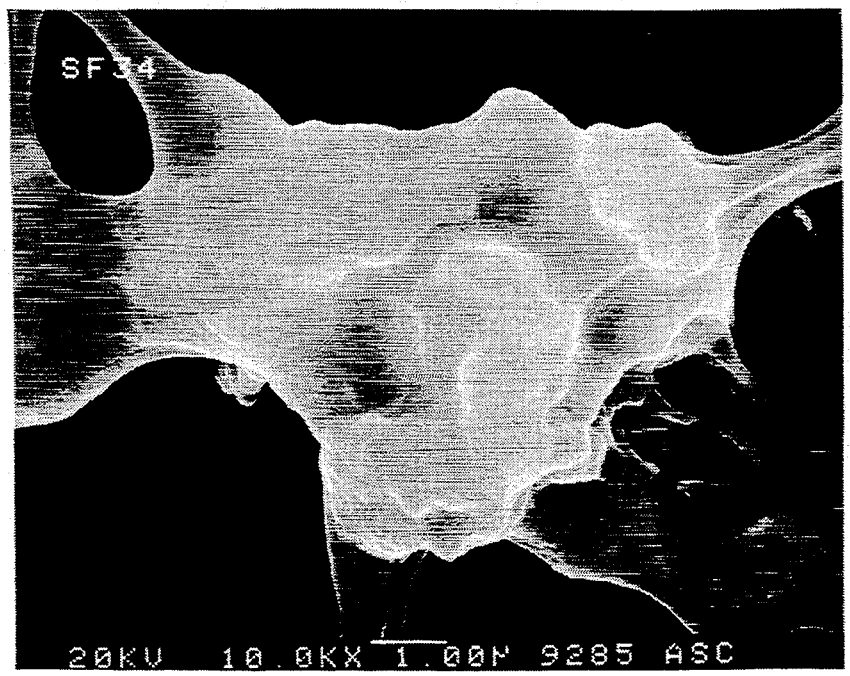
FIG. 3 is a photograph of a TV monitor representation of a particle artifact derived from a sample of the baker's cheese produced in Example 1, taken at 10,000 times (10,000×) magnification.
Figure 4C:
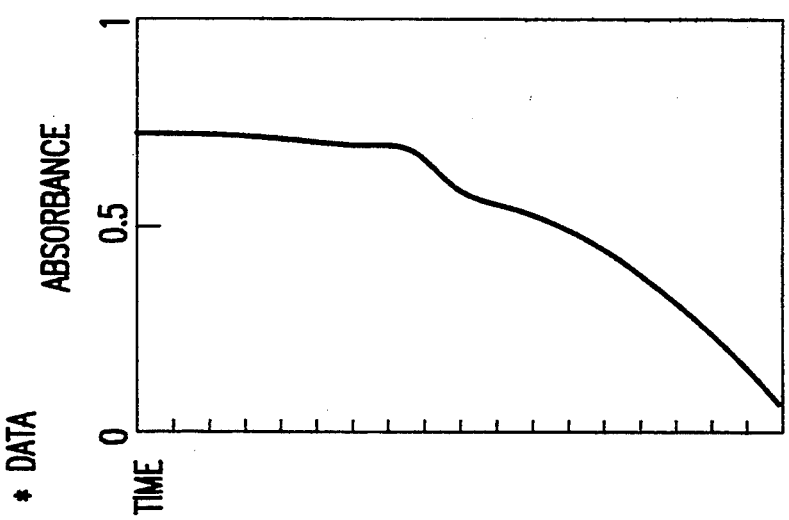
FIG. 4 represents five (5) multiple Data Absorbance versus Time Curves of samples of the present invention suggests a change in absorbance (particle size) over time generated using a CAPA-700 CENTRIFUGAL SIZE DISTRIBUTION ANALYZER.
Figure 4B:
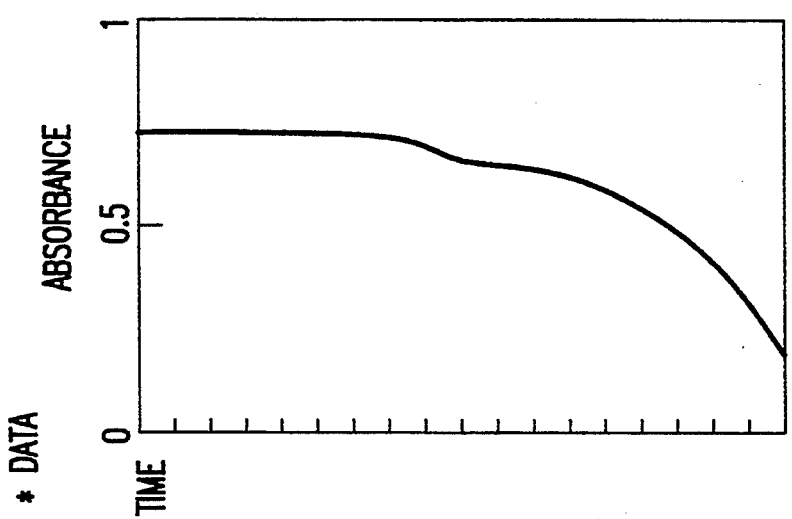
Figure 4A:
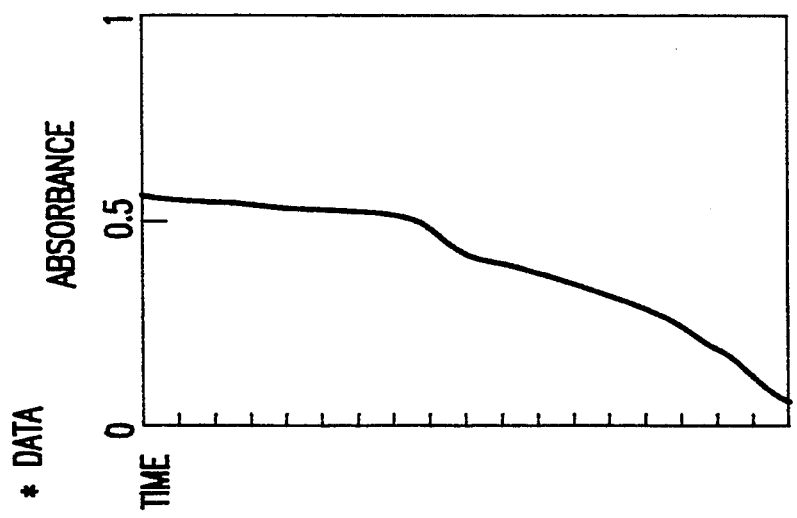
Figure 4E:
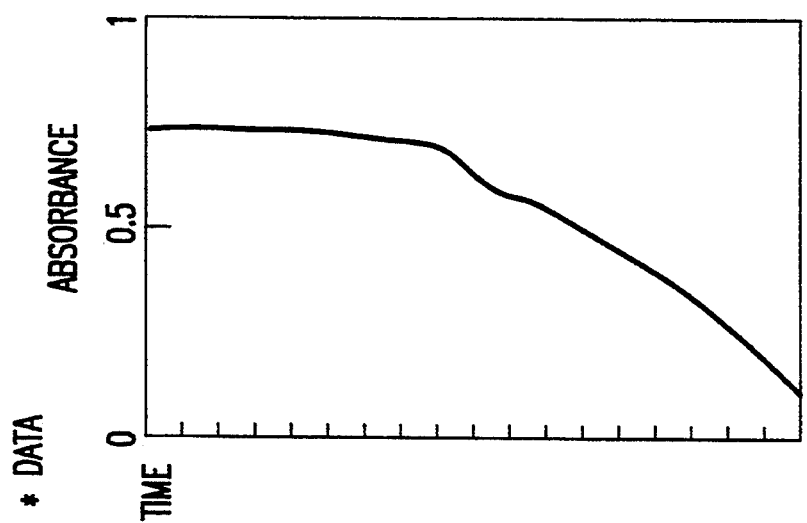
Figure 4D:
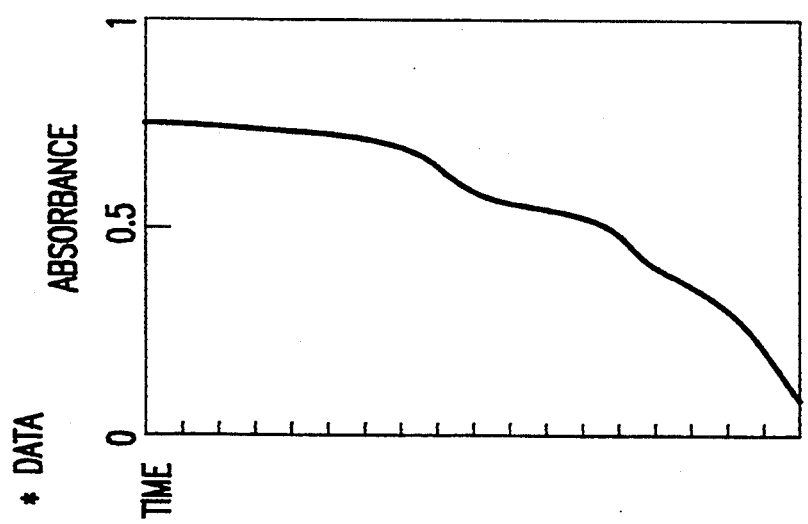

The low temperature Scanning Electron Microscope (SEM) method was used to determine the particle size of the protein particle as close to "in vitro" (the particle's state and size in the dispersion of the present invention) as possible. This technique has been used successfully in the art for the detailed observation of frozen liquids and very soft, hydrated specimens. The SEM used in this analysis was an EM Scope SP2000 made by EM Lab, Kent, England. The low temperature SEM technique involved freezing the undiluted in vitro sample quickly to $-175°$ C. on stainless steel to avoid contamination by other electrons. The preparation chamber was evacuated by vacuum and the sample was fractured and coated with gold as the conductive layer. The sample was then transferred to the microscope under vacuum where the $-175°$ C. temperature and vacuum were maintained while observation is conducted. The vacuum drying left large voids where the water of hydration existed, thus, a massive artifact was created. The structure was observed to be greatly disrupted and little information could be gathered about particle size. The electron micrograph in FIG. 2 represents a $1,000\times$ magnification of the structure left after the water of hydration was removed from a test sample obtained from the baker's cheese of Example 1 herein. The black voids suggest where the water of hydration once existed. The voids are surrounded by an ultrastructure of an interlaced latticework. The structure can be characterized as sponge-like and, it can be readily deduced why the particles bind water tightly at such a high level (usually at least about 60 percent by weight based on total weight of the curd) by reference to the indicated particle architecture. FIG. 3 is the same field at a higher degree (10,000×) of magnification. The fragile nature of the ultrastructure can be readily observed. Although the fibriles appear to be thin and a lattice work structure is shown, this is an artifact and the strand is highly dehydrated representing a small artifact of what actually existed when the contained water was 60 percent of the strand.

Of the major particle size analyzers investigated, the instruments selected and tried were those manufactured by Horiba, Ltd., Kyoto, Japan. The CAPA-700 CENTRIFUGAL SIZE DISTRIBUTION ANALYZER was the first instrument evaluated at the Horiba facility in Irvine, Calif., 92714. This instrument uses the Stokes. law sedimentation equation combined with the proportional relationship between light absorbency and the particle concentration. The density of the particle must be known along with the density and viscosity of the dispersant liquid. The instrument conducts both gravitational and centrifugal tests over a 15-minute period. When the two phases are linked by the computer, the results are compiled into the size distribution and printed out. This size distribution is based upon the change in optical absorbance of the suspension as a function of time. The instrument also conducts an absorbance coefficient correction for particles of different diameters caused by light attenuation efficiencies. The absorbance vs. time curve shows the changes in the optical absorbance of the suspended particles over the time period of the conducted tests. The horizontal axis represents the absorbance from 0 to 1.0 and the vertical axis represents time, but the divisions are the programmed size fractions on a non-linear time basis. A normal curve would be smooth over the time period whereas a change in absorbance of the particle indicates an unreliable and questionable result. FIG. 4 shows multiple Data Absorbance vs. Time curves of various computations of Examples set forth herein. The ragged appearance typical of unreliable results is evident by reference to the test results represented in FIG. 4. The change in particle size and density during the time required to run the test is believed to be the cause of the unsatisfactory and unreliable results obtained.

Figure 5:
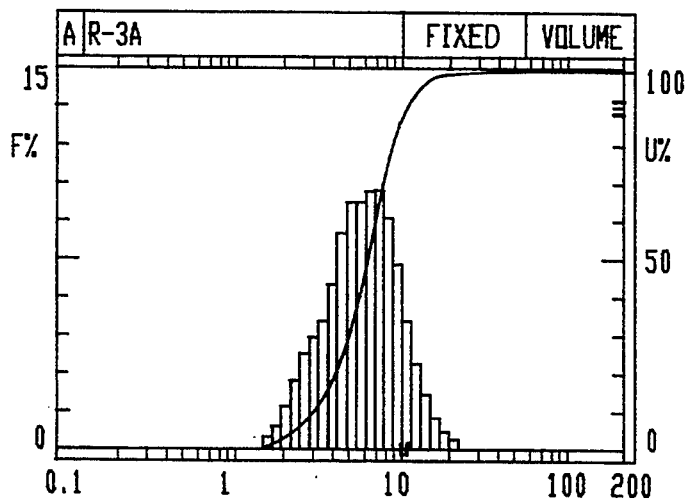
FIGS. 5-14, inclusive, represent print-outs generated using a L-500 LASER DIFFRACTION PARTICLE SIZE DISTRIBUTION ANALYZER, indicating particle size and distribution measurements of a series of food products made according to the method of the present invention.
Figure 6:
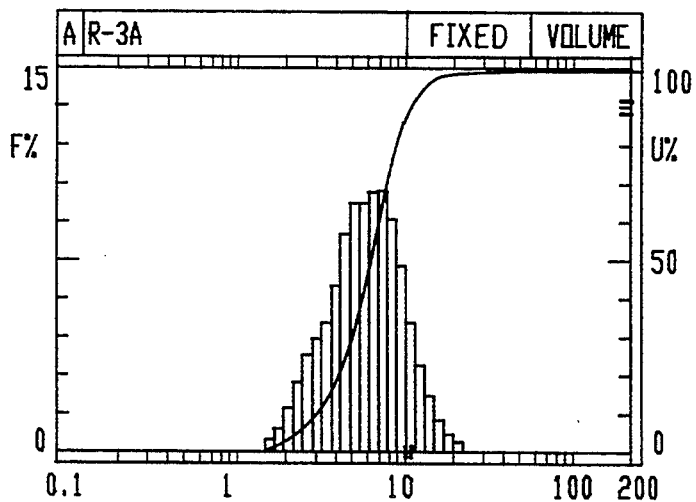
Figure 7:
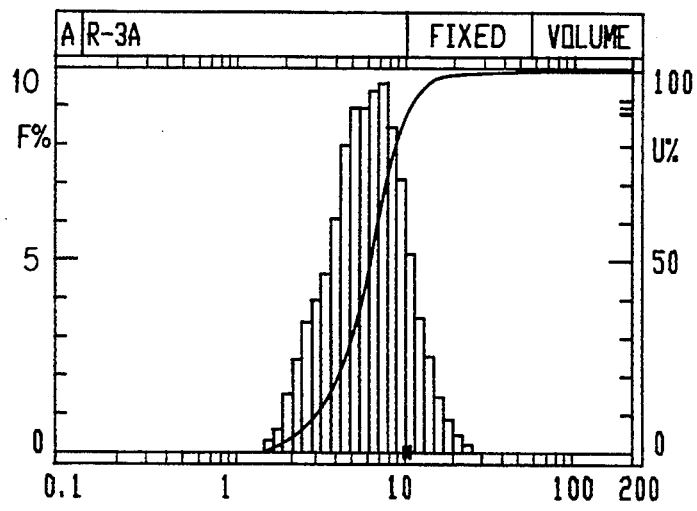
Figure 8:
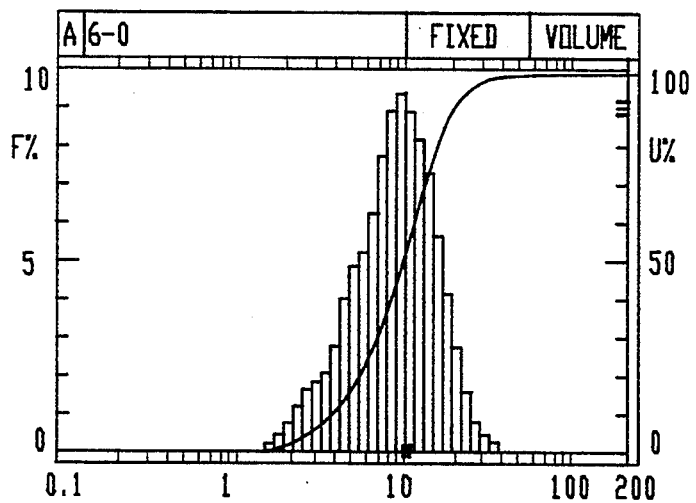
Figure 9:
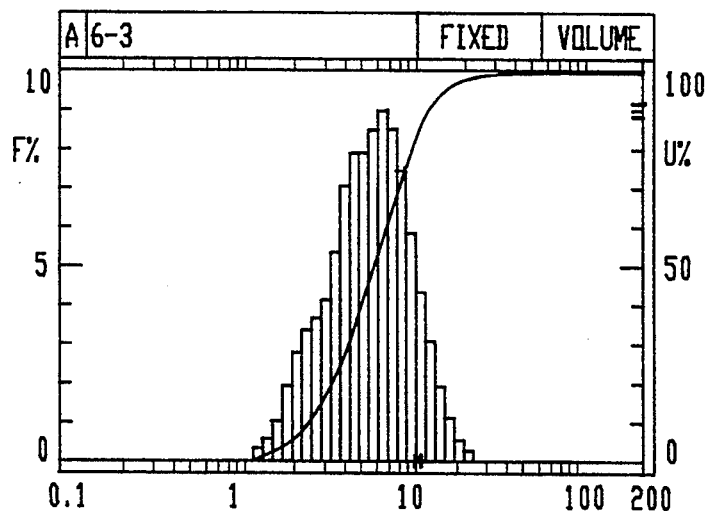
Figure 10:
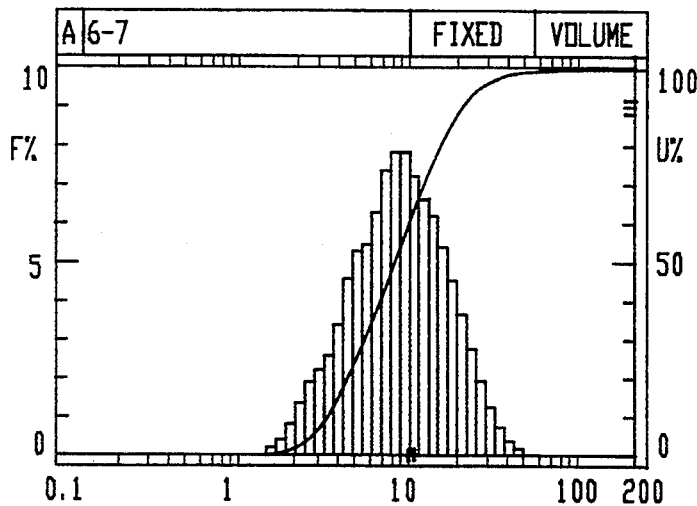
Figure 11:
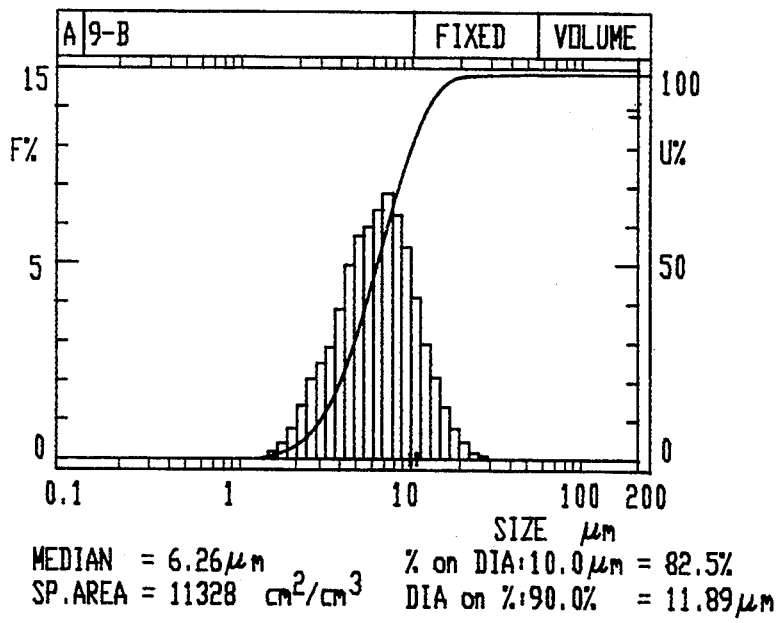
Figure 12:
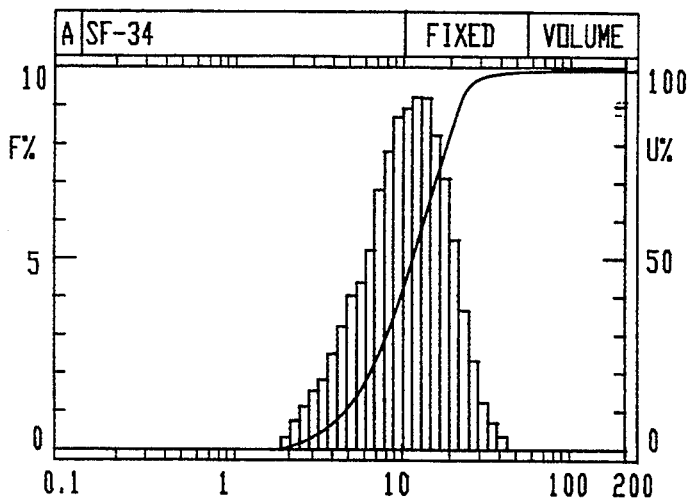
Figure 13:
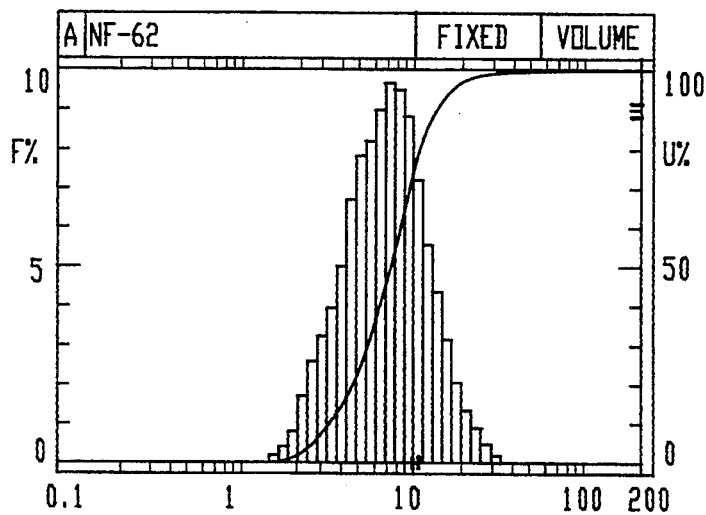
Figure 14:
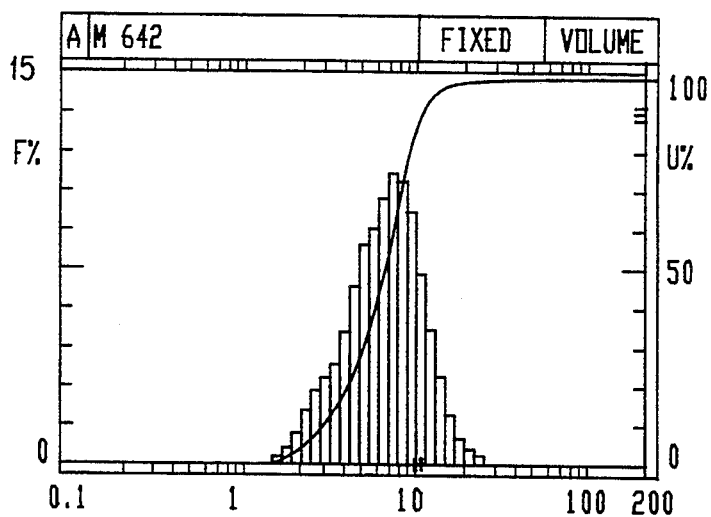

A Horiba LA-500 LASER DIFFRACTION PARTICLE SIZE DISTRIBUTION ANALYZER was then tried. This instrument applies the Fraunhofer diffraction and the Mie Scattering theories using a helium neon laser. The measurement time for a sample is 20–50 seconds depending upon resolution. This device was found to provide the closest "in vitro" measurement of particle size and distribution of the products of this invention. The only variable that influences this method is the change in optical refractive index whereas all previous methods were influenced by the changing nature of the density, the lack of homogeneity of the sample, and the changing size of the particle itself. The time from dilution to the completion of the analysis, moreover, is less than one minute. The test results using samples from Example 1 are represented in FIGS. 5, 6 and 7. These samples were all prepared at the same time. In FIGS. 5 and 6, the test results for samples run successively are reported. The test results correlate and demonstrate the repeatable results of the test protocol. FIG. 7 reports the test results of a sample that was reserved for 6 minutes and then tested. This example shows that some agglomeration of the particles occurred during the six minute interval between sample preparation and testing. FIG. 8 represents the test results of the first in the series of runs of Example 2, FIG. 9 represents the test results of the third in a series of runs of Example 2 and FIG. 10 represents the test results of the seventh in a series of runs of Example 2. The cheesecakes baked from the cheesecake formula evaluated in FIGS. 8 and 10 were almost identical whereas the cheesecake baked from the cheesecake formula evaluated in FIG. 9 displayed some gummy texture. The mean average particle sizes of the samples evaluated in FIGS. 9 and 10 were almost identical at 8.9 and 8.8 microns respectively. The mean particle size of samples evaluated in FIG. 9 was 6.09 microns. It is believed that the gummy texture could be a result of the smaller particle size or it could be a result of the fact that the third run was at the high end of the moisture range. FIG. 11 represents test results using the same cheesecake formula as in the previous cheesecake formula samples with the exception that microcrystalline cellulose was substituted for powdered cellulose. The smaller particle size of the microcrystalline cellulose is evidenced by the smaller mean size reported in the test results represented in FIG. 11. The cheesecake produced by the formula containing microcrystalline cellulose also displayed a gummy texture that is believed was a result of the smaller particle size binding more water in the baking process. FIG. 12 represents the test results obtained from the evaluation of the Soft Fresh Cheese of Example 3 which displayed a very smooth texture that was stable over a long period of time including the incorporation of herbs and spices. The mean particle size was 10.82 microns. The test results obtained from the evaluation of the Fat Free Ricotta produced in Example 11 are represented in FIG. 13. This Example contained Enzymatic Modified Cheese that was grainy in texture, but was smoothed out in the comminution step. The test Fat Free Ricotta developed a grainy mouthfeel within 10 days, yet the particle size after this grainy mouthfeel developed had a mean size of 6.87 microns. Analysis of the Particle Size Distribution Table does not reveal data that would indicate large particle sizes lead to chalky mouthfeel. FIG. 14 represents the test result obtained from the testing of the Mayonnaise of Example 4 that became grainy after 14 days and was perceived as grainy by most evaluators. The mean size of the particles was 6.55 microns.

As can be seen from the above-reported results, the size of the denatured protein particle as determined by the best state of the art instrumentation does not provide the complete description of the product of the present invention, nor does particle size alone prove to be a reliable predictor of dispersion properties. The denatured protein particles of the present invention produce fat mimicking properties at several different sizes. It is further apparent that the state of the art instrumentation does not have the ability to predict the chalky or grainy mouthfeel even after it occurs. It is believed that the fat mimicking properties of denatured protein particles of the present invention may have more to do with particle shape and the composition of the resulting products. The composition of membrane-forming agents, surface charge formers (surface-active agents), structure builders, and/or stabilizers play an important part in the property of the fat substitute and the food products prepared from it.

The data generated from the testing of each sample is shown by reference to FIGS. 5 through 14 inclusive which each represent the print-out generated for the samples tested. A DISTRIBUTION TABLE is presented in the two columns set forth in the lower half of each Figure. A histogram representation of the data in the DISTRIBUTION TABLE is presented in the HISTOGRAM set forth in the upper half of each Figure.

By reference to FIGS. 5 through 14, it will be noted that the mean particle size of the tested particles in the food products of the present invention fall between the range of approximately 5–11 microns. The metes and bounds of both particle size and distribution of the present invention have not yet been measured. Dispersions of mean particle size and distribution outside the very specific range of the dispersions tested are contemplated by the present invention and it is believed the advantages of the present invention can be achieved at mean particle sizes ranging from about 3 or less to about 15 microns or more provided that no substantial quantities of particles substantially outside the range are present that override the organoleptic properties expected where the mean particle range is between 3–15 microns. Further, experiments with particle size determination has shown that agglomerates of 30 to 50 particles as observed under the microscope in attempting to break down the individual particles so that the particles can be measured, will shown a high perception of fat-like characteristics. It is believed that the particles will still exhibit fat characteristics even if the particles are loosely agglomerated and will continue to slide and roll against each other. Thus, adding a high level of stabilizer may decrease the ability of the particles to roll over one another.

When reference to particle size of the product of the present invention is referred to herein, the method of measurement is by means of a HORIBA LA-500 LASER DIFFRACTION PARTICLE SIZE DISTRIBUTION ANALYZER.

In the final analysis, tactile, visual and mouthfeel analysis of the product as described herein provides the most direct and dependable basis for evaluating the fat substitute products of the present invention and delimiting the corollary particle size and distribution found in the fat substitute product and foods containing same.

The examples that follow demonstrate the method of making the fat substitute of the invention and further demonstrate the use of the fat substitute in the preparation of a series of nonfat and lowfat products.

EXAMPLE 1

A process for preparing a fat substitute is described, beginning with whey formation and recovery. The whey of this example is a rennet whey derived from a typical cheese-making process. The rennet whey is further processed to produce whey protein concentrate. Whey protein concentrate is the preferred whey starting material for the preparation of the fat substitute which is the present invention.

Whey Formation

Whey was formed during the production of mozzarella cheese from milk. A series of eight batches, each of fifty thousand pounds, was processed following the same procedure, and in substantially the same manner, as the process described below.

Fifty thousand pounds of milk averaging 3.4% protein with a fat content standardized to about 3.1% were pasteurized at 165 degrees F. for 20 seconds. The milk was pumped into 50,000 pound capacity DAMAROW DOUBLE "00" cheese vats manufactured by the DAMAROW COMPANY of Fondulac, Wis. When the DOUBLE "00" cheese vat contained approximately 8,000 pounds of milk, starter culture was added under slow agitation and the filling process continued. When each vat contained 50,000 pounds of milk, rennet was added, and the agitation was terminated. Curd was formed at a pH of 6.6 to 6.65.

The curds and whey were then cooked with ramped stirring to a temperature of about 110 degrees F. Approximately half the whey was pre-drawn from the vats and pumped into one of two whey holding tanks. The remaining curds and whey mixture was pumped into three enclosed finishing vats, each having a 10,000 lb. capacity manufactured by the DAMAROW COMPANY, Fondulac, Wis. The whey was recovered from the enclosed finishing vats and combined with the pre-drawn whey in the whey holding tanks.

Whey in this example came from the production of mozzarella cheese exclusively. On other occasions, the whey in the whey holding tank would be a combination of whey from the production of several other types of cheeses. Examples two through thirteen were made from whey from various types of cheese.

The whey from the eight batches of mozzarella described above varied in composition, within the following ranges:

| | | |
|---|---|---|
| FAT CONTENT | = | 0.4%–0.46% by wt. |
| PROTEIN | = | 0.84%–0.93% by wt. |
| TOTAL SOLIDS | = | 7.01%–7.19% by wt. |
| pH | = | 6.23–6.42 |

Whey Protein Concentrate Production

The next step is to concentrate the whey protein via sieve separation, centrifugal clarification, centrifugal separation, and ultrafiltration.

Cheese fines were removed from the whey via sieve separation using a thirty micron sieve in a fine saver manufactured by Sermia LTD, Quebec, Canada.

Thereafter the whey was clarified and slime removal was achieved in a centrifugal clarifier of 100,000 pounds per hour capacity manufactured by WESTPHALIA CENTRICO INC. Northvale, N.J. 07647.

The clarified whey was then treated in a centrifugal separator to produce:

3. A whey containing between approximately 0.06 to 0.08 percent fat content; and 4. A whey cream of approximately 30% butterfat content.

An ALTERN brand centrifugal separator of 61,000 pounds per hour capacity was used for this purpose. The substantially fat free whey was then pasteurized at 165° F. for about 20 seconds and then cooled to 110° F. in an APV CREPACO HIGH TEMPERATURE SHORT TIME pasteurizer ( APV CREPACO, Chicago, Ill. 60631).

The whey produced via the foregoing procedure was subjected to ultrafiltration to produce whey protein concentrate. The ultrafiltration unit used was manufactured by THOMAS FRACTIONATORS of Minn. A KOCH brand spiral membrane, model SO-HFK-131, manufactured by KOCH was used ( KOCH, Wilmington, Mass. 01887 ). Ultrafiltration was effected at a cooled whey temperature of 100 degrees F., at sufficient pressure to produce an average protein concentrate solids content of 14% by weight. The pressure required on the retention side of the membrane varied from about 80 psi at the beginning of ultrafiltration up to about 130 psi as ultrafiltration continued until membrane fouling occurred. When the 140 psi operating level was reached, the membrane was washed to remove fouling materials and ultrafiltration was resumed.

The whey protein concentrate was cooled in a plate heat exchanger to a temperature of about 40 degrees F.

The eight batches of cheese described above produced whey protein concentrates having compositions within the following ranges:

| FAT | 0.70%–1.00% | by wt. |
| --- | --- | --- |
| PROTEIN | 6.61%–7.14% | by wt. |
| SOLIDS | 13.78%–14.82% | by wt. |
| pH | 6.18–6.32 | |

Fat Substitute Formation From Whey Protein Concentrate

In the here exemplified fat substitute production process, sodium caseinate is added to the whey protein concentrate to form a coprecipitate curd. This is optional in the process of the present invention. The curd is then comminuted to form a dispersion of denatured whey protein particles and the comminuted particles in the curd are then coated with membrane and surface active agent(s) to form a more stable dispersion. The dispersion is then further stabilized with structuring and stabilizing agent(s) to form the present invention. Comminution of the curd, formation of the membrane, and addition of the surface-active agent(s) is achieved using a chopper. It has been found that choppers used in meat processing have particular utility in the comminution of the denatured protein in the curd produced according to the present invention.

Curd Formation (Denaturing And Agglomeration)

The starting material for production of the curd used to form the stable protein dispersion of the present invention was made up of the whey protein concentrate described above including sodium caseinate as a protein additive.

The sodium caseinate additive was incorporated into the whey protein concentrate by adding ten pounds of sodium caseinate to approximately 50 pounds of whey protein concentrate drawn from the whey protein concentrate described above to form a caseinate-protein premix. This premix of sodium caseinate and whey protein concentrate were mixed in a STEPHAN brand cooker which has the means for blending/mixing the ingredients. A STEPHAN brand steam injection, high shear, mixer-cooker, model #UM 40E-GNi Pilot of 40 liter capacity (hereinafter, the STEPHAN cooker), was used for this purpose. The STEPHAN cooker was operated at a blade mixing speed of 3,000 RPM, without heat, for approximately 2 minutes. Thereafter, mixing was interrupted and the contents of the STEPHAN cooker examined. Visual examination indicated an absence of lumps and an absence of observable undissolved particles. This confirmed that the caseinate was fully hydrated.

The mixture from the STEPHAN cooker was then added to whey protein concentrate in an F.P.E.C. ( F.P.E.C. CORP. Santa Fe Springs, Calif. 90670 ) brand cooker (hereinafter, the FPEC cooker) with a modified bottom in which drain lines were substituted for two of the six steam inlets in the FPEC cooker bottom. After the mixture from the STEPHAN cooker was added to the FPEC cooker, the total batch weight in the FPEC cooker was approximately 1,100 pounds.

The batch was heated to 185 degrees F. by introduction of steam through the FPEC cooker bottom at a temperature of about 240 degrees F. with constant agitation by two augers oriented lengthwise overlying the FPEC cooker bottom.

During steam introduction, the agitation was monitored and controlled to form a foam matrix, that is, a steam-entrained whey-casein matrix throughout which water vapor (steam) is dispersed. The formation of a foam matrix signifies that steam bubbles are entrained in the whey protein concentrate casein dispersion—a phenomenon that is observable by an increase in the liquid volume and the formation of foam on the surface of the solution. In the present case, a volume increase in the 15% to 20% range was achieved and foam was observed on the surface of the heated solution. During this heating and steam matrix forming step, a viscosity increase of the FPEC cooker contents occurred.

After the temperature of the solution reached a target temperature of 185 degrees F., 150 grain Vinegar (acetic acid) was added in sufficient quantity to reduce the pH to between 5.6 and 5.65—the optimum pH for denaturing of whey protein concentrate and casein mixtures of the composition used.

Had whey protein concentrate been used alone, the pH would have been lowered to 5.4 to 5.45—the optimum level where pure whey protein concentrate is used as the starting material. As additional caseinate is added to the whey protein concentrate, the optimal pH increases.

Upon addition of acetic acid, curd was formed which rose to the top of the whey solution. When this was observed, agitation was terminated and curd formation was allowed to continue. A mat of curd formed on the surface of the whey. The FPEC cooker's agitator was activated momentarily about once a minute to loosen and release any curd adhering to the agitators or the bottom of the FPEC cooker.

Five minutes after continuous agitation was discontinued, curd mat appeared to be fully formed. At that time, the whey was drained from the bottom of the FPEC cooker and the curd mat settled onto the bottom. The curd was recovered from the bottom using the auger/spiral agitators to break-up and move the curd in the mat toward the front of the cooker where doors are situated and are opened to allow the curd to be expelled from the FPEC cooker.

The curd was then loaded into a false bottom cart for transport to the next step of fat substitute manufacture—deagglomeration/comminution of the denatured coprecipitate curd. During transport, whey continued to drain from the curd. The curd at this point in the process is typically from approximately 65% to 80% water by weight. The moisture content is inversely proportional to the cooking temperature. The curd produced in this example had a moisture content in the 75% to 80% by weight range.

Deagglomeration of The Curd; Dispersion Formation

The drained curd of moisture content in the 75% to 80% by weight range was deagglomerated using a 200 liter capacity open atmosphere chopper manufactured by Maselinenfabrik Seydelmann. In the United States, such choppers are distributed by the Food Equipment Division of Robert Reiser & Co., Inc., located at 253 Summer Street, Boston, Mass. 02210. Experience has shown that optimal deagglomeration conditions occur where curd weights of about 200 pounds are processed in choppers of 200 liter capacity.

Choppers, long used in the food processing industry for sausage processing, have been found to have utility in (1) deagglomerating the curd formed in accordance with the present invention to form the curd into a dispersion of micron sized particles suspended in a continuous aqueous phase; (2) to coat the micron sized particles, to charge the particles with a surface active agent, and to build structure—thereby increasing the particles' stability; and, (3) to incorporate a stabilizer into the aqueous phase of the dispersion further enhancing the stability of the fat substitute product.

In the process described in the present example, a twelve knife array was selected for use in the chopper. The knives in this array were SECURITY-SYSTEM-4-CUT-KNIVES available from G. Walter Steffans, 563 Remscheid 14, Uterholterfelder Strasse 60, Germany. The knives were composed of high quality stainless knife steel. The cutting edge of the blade of these knives was formed on the camber side at an original grinding angle of 27 degrees. The knives were then mounted on a single shaft adapted for use in configurations involving up to twelve knives. The back/trailing edges of the knives' blades are flat and taper from 5 mm at the shaft to 3 mm proximate the point of the blade where the camber that forms the blade edge begins.

The twelve knives were oriented on the shaft in the following manner. The first and second knives at the upstream end of curd flow—flow is induced by rotating the bowl of the chopper—are positioned 180 degrees opposite one another. The distance between the knives, as measured along the shaft, is about 5 mm. The knife holder is 10 mm thick and the knife is 5 mm thick. The third knife is offset 30 degrees behind the first knife and a 5 mm spacer is used to increase the distance between the second and third knives by 5 mm to about 10 mm. The fourth knife is positioned 180 degrees opposite the third knife. Here again, the distance between opposing knife pairs 3 and 4, as measured along the knife-holder shaft is about 5mm. The fifth knife is offset 30 degrees behind the third knife. The sixth knife is positioned 180 degrees opposite the fifth knife. The remaining three knife pairs, namely, 7 and 8, 9 and 10, and 11 and 12, are positioned with knife 7, 30 degrees behind knife 5; knife 9, 30 degrees behind knife 7; and knife 11, 30 degrees behind knife 9. No spacers are used in positioning the last knife pairs, and knives of each pair are oriented 180 degrees opposite each other.

The increased spacing at the front of the knife array, between knives 2 and 3, has been observed to improve performance of the chopper by allowing a greater volume of curd to enter the knife array. Where the leading 180 degrees opposed pairs are spaced apart the same distances as the succeeding opposed pairs, build up of curd and/or dispersion occurs and a dam of curd is formed forward of the upstream leading knife.

To maximize efficiency, the cutting edges of the chopper knives were sharpened and tested to insure an order of sharpness that cuts paper. Also, the side surfaces of the knife were highly polished before comminution began.

Two hundred pounds of curd were transferred from the false bottomed kitchen cart to the chopper. The chopper was operated at a high bowl speed of 18 RPM's and a knife shaft speed of 2,500 RPM's for ten minutes to comminute the denatured whey protein casein coprecipitate curd. A dispersion was formed of the deagglomerated denatured whey protein casein coprecipitate in a continuous phase aqueous medium. The aqueous medium was formed by the aqueous component released during comminution/deagglomeration of the curd.

Stephan Cooker Step Number 1

While the chopper was operated to form the dispersion described in the preceding paragraph, a membrane-forming composition, including a surface-active agent and a structure-building agent, was being prepared in the STEPHAN cooker for addition to the curd during the above-described comminution procedure.

The membrane-forming, surface-active, and structure-building agents were prepared in the STEPHAN cooker using steam-injection and high agitation to form dispersions of same very quickly. The components listed in table one were used for this purpose.

TABLE 1

| Ingredient | Pounds |
| --- | --- |
| Water | 7.0 |
| Nathin 140 | 1.0 |
| Lecithol G | 1.0 |
| Water | 8.0 |
| Avicel RC591 | 5.0 |

Note:
1. NATHIN 140 is available from Nattermann Phospholipid, Inc., located at 33 Turner Road, Danbury, Connecticut 06813-1905. This product is approximately 40% phosphatidyl choline by weight.
2. Lecicon G. is available from Nattermann Phospholipid, Inc., located at 33 Turner Road, Danbury, Connecticut 06813-1905.

Step 1

Seven pounds of water were poured into the STEPHAN cooker to which the following ingredients were added: (i) One pound of NATHAN 140 which contains approximately 40% phosphatidyl choline by weight; (ii) one pound Lecicon G which is high in inositol and glycolipids content.

These contents were processed in the STEPHAN cooker for minutes at 120 degrees F. with the lower knife blade operating at 3,000 RPM and the side scraper blade on high speed in order to form liposomes. At the end of 8 minutes, the blade/scraper action was interrupted and the STEPHAN cooker opened to visually examine the contents for even dispersion. Once even dispersion was confirmed, pounds of hydration water were added to the liposomes together with 5 pounds of micro-crystalline cellulose. The microcrystalline cellulose used was from the Food and Pharmaceutical Products Division of FMC located at 200 Market Street, Philadelphia, Pa. 19103, sold under the designation AVICEL RC-591F. The STEPHAN cooker was used to mix these contents at the 3,000 RPM speed and steam injection was used to raise the temperature to 180 degrees F. The required time to do this was about two minutes. The lecithin-microcrystalline cellulose complex formed in the STEPHAN Cooker was added to the curd dispersion in the chopper.

The chopper was operated for an additional 15 minutes (hereinafter, the second comminution phase) to form a membrane around the denatured whey protein-casein coprecipitate particles, to place amphoteric charges on them with surface active agents, and to build structure. The membrane is believed to be formed by the liposome-lecithin mixture. This membrane produces electrostatic charges on the particle surface facilitating the steric repulsion of the particles. The structure building agents stabilize the aqueous phase such that the particles cannot reagglomerate. Thus, a very stable dispersion is created with extended shelf life and heat stability during baking.

As the second comminution phase proceeded, the contents of the chopper began to take on a glossy appearance that resembled products of high fat composition. This is believed to be the result of light refraction by the non-fat curd particles that now behave much like the fat globules occurring naturally in fat emulsions such as cream. The size and distribution of the particles at this point are believed to be the same that occurs in bovine butterfat emulsions such as unhomogenized milk.

At the end of twenty minutes of continual comminuting, the fat substitute hydrated protein product developed a still higher glossy appearance. The product at this point, when rubbed between the thumb and forefinger, displayed the greasy lubricity and slip that is characteristic of high fat compositions or emulsions. The organoleptic evaluation of the product proved to be the same as a heavy cream with a butterfat content of 50 to 60 percent.

Stabilization of The Fat Substitute

If one stopped the process at this point, a stabilized fat substitute having the mouthfeel of fat-water or water-fat emulsions would have been produced. To improve the stability of the product against the development of a chalky mouthfeel or bacterial growth, a hydrocolloid gum such as xanthan gum, and a microbial growth inhibitor such as potassium sorbate, can be added.

Stabilization of the fat substitute is desirable when it is to be stored and/or shipped for later use in production of nonfat foodstuffs. Stabilization is achieved by adding a thickener/pseudoplastic stabilizer, such as xanthan gum, which imparts thixotropic properties. An aqueous dispersion of xanthan gum is produced in the STEPHAN cooker and added to the chopper to achieve a xanthan gum content of about 0.25 to 0.5 weight percent of the fat substitute.

Hydrocolloid gum is added to the dispersion of coated particles in the chopper to incorporate the gum into the continuous phase of the dispersion. Besides hydrocolloid gum addition, it is preferable to add microbial growth inhibitors to the fat substitute and/or stabilized fat substitute. Suitable microbial growth inhibitors such as sodium benzoate, potassium sorbate, or natural microbial inhibitors such as dehydrated cheese culture can be used. The products used in this example were Alta 2331, Alta 1801, Alta 2001, and Alta 1705 which are natural microbial inhibitors available from Quest-Microlife Technics, Inc. of Sarasota, Fla., 34230. Each of these products shows inhibitory effects against different microorganisms and was chosen accordingly.

A microbial stabilizer was also added to the mixture in the STEPHAN cooker, which was subsequently added to the chopper to improve stability. This microbial stabilizer was Enrich 101 and is primarily a fermented milk product in dehydrated form containing xanthan-like hydrocolloids. This product is available from Quest-Microlife Technics, Inc. of Sarasota, Fla., 34230. G P Maltodextrin 040, available from Grain Processing Corporation of Muscatine, Iowa 52761, was added to further enhance the stability of the product, impart spreadability, and reduce the apparent viscosity.

To improve the flavor beyond that of culture distillate, a flavor dehydrated starter culture was added. This was Accel 4201 available from Quest-Microlife Technics, Inc. of Sarasota, Fla., 34230.

At this point, the Stabilized Fat Substitute "SFS" contained in the bowl of the chopper was further processed into fat free cholesterol free baker's cheese. This was accomplished by preparing further ingredients in the STEPHAN Cooker and adding them to the chopper.

Stephan Cooker Number 2

Four pounds of xanthan gum ("Keltrol T", Kelco, San Diego, Calif. 92123 ), and 30 pounds of water were mixed in the STEPHAN cooker at 3,000 rpm with steam injection at a steam pressure of about 40 pounds until a temperature of 120 F. was reached. This process required approximately 2 minutes. The STEPHAN cooker was then opened and the contents examined to insure that xanthan gum was fully dispersed and hydrated. This was determined by tactile examination—rubbing the sample between fingers—and visually checking for presence of undissolved particles.

Upon confirmation that the xanthan gum was in solution, the following ingredients were added to the xanthan-water mixture in the STEPHAN cooker:

| Ingredient | Pounds |
| --- | --- |
| Water | 30.0 |
| Keltrol T Xanthan Gum | 4.0 |
| Enrich 101 | 1.0 |
| Alta 2331 | 0.5 |
| Alta 1801 | 0.5 |
| Alta 2001 | 3.0 |
| Alta 1705 | 0.5 |
| Accel 4201 | 2.0 |
| GP Maltodexdrin 040 | 6.0 |
| Salt | 1.0 |

The above ingredients were dispersed at 3,000 RPM with steam injection at a steam pressure of about 40 pounds to a temperature of 120 degrees F. for 1 to 2 minutes. The STEPHAN cooker was then opened and the product examined to verify the absence of lumps and that the ingredients had been uniformly dispersed. The STEPAN cooker was then closed and the temperature raised to 180 degrees F. by steam injection with agitation at 3,000 RPM in order to pasteurize the contents. When the temperature reached 180 degrees F., the steam flow was terminated, the cooker was opened, and the contents were transferred to a clean sterilized bucket and slowly added to the chopper.

Final Process

The chopper continued to operate at a bowl speed of 18 RPM and a knife shaft speed of 2,500 RPM to achieve a uniform mixture of Stephan Cooker Step 2 ingredients and stabilized fat substitute. After the contents of the chopper were thoroughly mixed for 2 to 3 minutes, a sample was withdrawn and analyzed for pH. The pH was adjusted to 5.1 to 5.2 by adding approximately 14 ounces of lactic acid available from CCA BIOCHEM B. V. of The Netherlands to the chopper. After the pH was adjusted, 150 mls. of starter distillate, designated Hansen's 15X, available from Chs. Hansen's Laboratory, Inc. Milwaukee, Wis. 53214, was added to the continually operating chopper with mixing for about one minute.

The mixture was transferred from the chopper to a kitchen cart and then transferred to RISCO (Modello RS 3000) vacuum stuffer and packed into a 120mm by 20" plastic casing with a Niedecker DFC-08061 clipper. The encased mixture was cooled in a brine tank to a core temperature of 40 F. The resulting 12 pound casings were packed four to a case.

A sample of the product was analyzed for chemical and microbiological assay. Fourteen identical batches were made in the above manner with the following ranges:

| | |
|---|---|
| Moisture | 70.61–74.1 |
| pH | 5.13–5.21 |
| Fat | 0.2–0.4 |
| Salt | 1.4–1.7 |
| SPC | <100 |
| COLI | <10 |
| Yeast/Mold | 0/0 |

EXAMPLE 2 BASE FOR FAT FREE CHOLESTEROL FREE CHEESECAKE

A stabilized fat substitute "SFS" cheesecake base was produced by first forming a dispersion of deagglomerated denatured whey protein-casein coprecipitate in a continuous phase aqueous medium according to the procedure of Example 1. Ten pounds of sodium caseinate were added to 120 gallons of whey protein concentrate comprising approximately 14% solids and 9% protein. The mixture was then heated by steam injection to 185 degrees F. and acidified to a pH of 5.6 to 5.65 by the addition of acetic acid. This resulted in the formation of a curd precipitate.

Two hundred pounds of curd were transferred from FPEC cooker to chopper using a false bottom kitchen cart. Comminution/deagglomeration of the curd was achieved according to the procedure described in Example 1. The resulting fat substitute product was further processed into a fat free, cholesterol free base for cheesecake as described below.

The following components were incorporated with the fat substitute product produced as described above to prepare a cheesecake base.

TABLE 1

| COMPONENTS | QUANTITY/POUND |
|---|---|
| Water | 7.0 |
| Nathan 140 | 1.0 |
| Lecicon G | 1.0 |

STEP 1

Liposome formation was achieved in a manner similar to that set out in Example 1 in which the membrane-forming and surface active agents were prepared using the STEPHAN cooker. The lecithin fractions (Nattermann Phospholipids) were added to water in the STEPHAN cooker to form liposomes as described in Example 1. The STEPHAN cooker was operated for 8 minutes at 120 degrees F. Thereafter, the STEPHAN cooker was opened and the lecithin liposome mixture visually examined for the presence of undissolved particles to insure complete dispersion. Upon confirmation that the mixture had been uniformly dispersed, a cream-like appearance was observed. The STEPHAN cooker was then closed and the temperature raised to 180 degrees F. by steam injection with mixing. When the temperature reached 180 degrees F., the steam flow was terminated, the STEPHAN cooker was opened, and the mixture transferred to a clean sterilized bucket and slowly added to the chopper. The pasteurized lecithin mixture was processed in the chopper for 15 minutes to form a membrane around the curd particles and to place amphoteric charges on the curd particles as described in Example 1.

STEP 2

A stabilizer and structure building ingredient for the SFS described in step one was produced from the components in Table 2.

TABLE 2

| COMPONENTS | QUANTITY/POUND |
|---|---|
| Water | 10.0 |
| Solka Floc 200 | 3.0 |
| Xanthan gum Keltrol T | 1.0 |

The stabilizer and structure building ingredient from Table 2 was prepared in the STEPHAN cooker. The mixture was prepared by adding SOLKA FLOC 200 and xanthan gum to water in the STEPHAN cooker. SOLKA FLOC 200 is a refined, purified, edible cellulose powder, which is available from the James River Corp., Saddle Brook, N.J. The number "200" denotes the cellulose fiber length in microns. Xanthan gum Keltrol T is available from Kelco, a Division of Merck & Co. Inc., San Diego, Calif. 92123.

The ingredients were mixed in the STEPHAN cooker for 2 minutes at high speed (3,000 rpm) with steam injection at a steam pressure of about 40 pounds to a temperature of 120 degrees F. When 120 degrees F. was achieved, the steam flow was terminated, agitation was ceased, and the pressured was released. The STEPHAN cooker was then opened and the contents examined by tactile and visual inspection as described in Example 1—STEPHAN Cooker, Step 2. The STEPHAN cooker was then closed and the temperature raised to 180 degrees F. by steam injection with high speed agitation. When the temperature reached 180 F., agitation was ceased, steam flow was terminated, and the pressure was released. The STEPHAN cooker was then opened and the contents handled in the same manner as described in Step 1 above, i.e., added slowly to the continually operating chopper. The mixture was processed in the chopper for 5 minutes.

TABLE 3

| COMPONENTS | QUANTITY/POUND |
|---|---|
| Water | 26.0 |
| Enrich 101 | 16.0 |
| Alta 2331 | 0.5 |
| Alta 1801 | 0.5 |
| Alta 2001 | 0.5 |
| Alta 1705 | 0.5 |
| Avebe Parselli SA-2 | 6.0 |
| Sugar | 10.0 |
| Salt | 1.0 |

TABLE 3-continued

| COMPONENTS | QUANTITY/POUND |
|---|---|
| Non Fat Dry Milk | 10.0 |

STEP 3

Microbial growth inhibitors and stabilizers (Table 3) were prepared in the STEPHAN cooker and added to the "SFS" cheesecake base. The maltodextrin (AVEBE PARSELLI SA-2) in this case was a potato starch derivative available from Avebe America, Inc., Princeton, N.J. 08540. This particular maltodextrin imparts a tough structure with very little flavor masking properties. The addition of sugar to the base improves the long term storage properties and balances the moisture in the particle. The above ingredients were prepared and handled in the same manner as described in step 2 above.

FINAL PROCESS

The final process was handled according to the procedure outlined in Example 1 in which the mixture was acidified to a pH of 5.1 to 5.2 by adding lactic acid (CCA Biochem b. v. Holland) and 8 ounces of starter distillate (Hansen's 15X) to the continually operating chopper and comminuting this mixture for approximately three additional minutes.

The cheesecake base was then cooled and packaged as described in Example 1.

Eight batches were made in the above manner over a period of about 4 weeks.

The chemical and microbiological analysis of the cheesecake base fell within the following ranges:

TABLE 4

| MOISTURE | 66.50–67.98 |
|---|---|
| pH | 5.13–5.56 |
| FAT | 0.1%–0.3% |
| SALT | 1.4%–1.7% |
| STANDARD PLATE COUNT | <100 |
| COLI | <10 |
| YEAST/MOLD | 0/0 |

The finished cheesecake base was then baked into a finished cheesecake according to the following formula:

TABLE 5

| INGREDIENT | WEIGHT PERCENT (%) |
|---|---|
| Cheesecake base | 62.49 |
| Granulated sugar | 25.39 |
| Lemon extract | 0.02 |
| Lemon emulsion | 0.13 |
| Fresh egg whites | 11.95 |
| | 100.00 |

The above ingredients, except the egg whites, were beaten for 3 minutes in a 5 1/2 qt. Kitchen Aid bowl with a whisk to form a creamed cheese mixture. The egg whites were placed in a separate, clean, grease-free Kitchen Aid bowl and beaten at the highest speed capable by the device (speed 10) for 10 minutes. The foamed egg whites were then evenly folded into the creamed cheese mixture with a rubber spatula. This resulted in a finished cheesecake filling which was poured into an 8 $\frac{1}{2}\times 3$ inch springform pan lined with grease-resisting bakery dollies. The cheesecake was baked in a home oven at 425 degrees F. for 5 minutes and for an additional 50 minutes at 325 degrees F. or until the center was set. The oven was then turned off and the cheesecake allowed to remain therein for an additional 30 minutes. After the cheesecake was removed from the oven and cooled completely at room temperature, it was chilled overnight at 45 degrees F.

Using this formula, eight batches of cheesecake base from various production dates were simultaneously baked into finished cheesecakes in a large commercial bakery laboratory. The resulting cheesecakes were then evaluated for (i) differences among the eight cheesecakes, and (ii) their organoleptic and physical characteristics. The purpose of this trial was to test reproducibility over time and to determine whether the same product could be produced from different cheese wheys made on different production days under differing conditions.

The eight cheesecakes exhibited some variation which was traced to differences in comminution time. The trials proved that satisfactory duplication of results occurs when all procedures are followed. Expert baking judges evaluated the finished cheesecakes and found them clearly acceptable. It was their opinion that consumers would not be able to detect any differences from one purchase to another. The cheesecakes displayed unique baking temperature stability as the product resembled the typical "New York Style" cheesecake. The cheesecakes had a rich, cream-like mouthfeel resembling cheesecake made with real butterfat cream cheese.

EXAMPLE 2a BASE FOR FAT FREE CHOLESTEROL FREE CHEESECAKE

A stabilized fat substitute "SFS" Cheesecake base was produced by first forming a dispersion of deagglomerated denatured whey protein-casein coprecipitate in a continuous phase aqueous medium according to the procedure of Example 1. Ten pounds of sodium caseinate were added to 120 gallons of whey protein concentrate comprising approximately 14% solids and 9% protein. The mixture was then heated by steam injection to 185 degrees F. and acidified to a pH of 5.6 to 5.65 by the addition of acetic acid. This resulted in the formation of a curd precipitate.

Two hundred pounds of curd were transferred from FPEC cooker to chopper using a false bottom kitchen cart. Comminution/deagglomeration of the curd was achieved according to the procedure described in Example 1. The resulting fat substitute product was further processed into Fat Free Cholesterol Free Base for Cheesecake as described below.

The following components were incorporated with the fat substitute product produced as described above to prepare a Cheesecake base.

TABLE 1

| COMPONENTS | QUANTITY/POUND |
|---|---|
| Water | 7.0 |
| Nathan 140 | 1.0 |
| Lecicon G | 1.0 |
| Water | 7.0 |
| Avicel RC591 | 2.0 |

STEP 1

Liposome and structure building formation was achieved in a similar manner to that set out in Example 1 in which the membrane-forming, surface active, and structure building agents were prepared using the STEPHAN cooker. The lecithin fractions (Nattermann Phospholipids) were added to water in the STEPHAN cooker to form liposomes as described in Example 1. The STEPHAN cooker was operated for 8 minutes at 120 degrees F. with a steam pressure of approximately 40 pounds. Thereafter, STEPHAN cooker was opened and the lecithin liposome mixture was visually examined for the presence of undissolved particles to insure complete dispersion. Upon confirmation that the mixture had been uniformly dispersed, a cream-like appearance was observed. An Additional 7 pounds of hydration water were added to the liposomes in the STEPHAN cooker along with 2 pounds of microcrystalline cellulose and mixed for approximately 5 minutes. The cooker was opened and visually examined for proper dispersion. Upon confirming that proper dispersion had been achieved, the STEPHAN cooker was closed and the temperature raised to 180 degrees F. by steam injection with mixing. Upon reaching 180 degrees F., the steam flow was terminated, the STEPHAN cooker was opened, and the mixture was transferred to a clean sterilized bucket and slowly added to the chopper. The pasteurized lecithin-microcrystalline cellulose complex was processed in the chopper for 15 minutes to form a membrane around the curd particles, to place amphoteric charges upon the curd particles, and to create structure in the aqueous phase as described in Example 1.

TABLE 2

| COMPONENTS | QUANTITY/POUND |
|---|---|
| Water | 26.0 |
| Xanthan Gum | 1.0 |
| Enrich 101 | 16.0 |
| Alta 2331 | 0.5 |
| Alta 1801 | 0.5 |
| Alta 2001 | 0.5 |
| Alta 1705 | 0.5 |
| Avebe Parselli SA-2 | 6.0 |
| Sugar | 14.0 |
| Salt | 1.0 |
| Non Fat Dry Milk | 10.0 |
| TOTAL | 76.5 |

STEP 2

Microbial inhibitors and stabilizers listed in Table 2 were prepared by using the STEPHAN cooker. Xanthan gum was added to water and mixed in the STEPHAN cooker for 2 minutes at high speed (3,000 rpm) with steam injection at a steam pressure of about 40 pounds to a temperature of 120 degrees F. When the temperature of 120 degrees F. was achieved, the steam flow was terminated, the agitation ceased, and the pressure released. The STEPHAN cooker was then opened and the contents subjected to tactile and visual examination as described in Example 1-Stephan Cooker Step 2. When satisfactory results were achieved, i.e., even dispersion, the remaining ingredients were then added to the STEPHAN cooker and mixed for approximately 2 minutes at 120 degrees F. before increasing the temperature to 180 degrees F. by steam injection with high speed agitation. When the temperature reached 180 F. steam flow was terminated, and the pressure released. The STEPHAN cooker was then opened and the contents were handled in the same manner as described in Step 1 above, i.e., added slowly to the continually operating chopper. The mixture was mixed in the chopper for 5 minutes.

FINAL PROCESS

The final process was carried out according to the procedure outlined in Example 1 in which the mixture was acidified to a pH of 5.1–5.2 by adding lactic acid (CCA Biochem b. v. Holland) and 6 ounces of starter distillate (Hansen's 15X) to the continually operating bowl chopper and comminuting this mixing for approximately one minute.

The Cheesecake base was cooled and packaged as described in Example 1.

The chemical and microbiological analysis of the cheesecake base is as follows:

TABLE 4

| MOISTURE | 66.40 |
|---|---|
| pH | 5.46 |
| FAT | 0.20% |
| SALT | 1.40% |
| STANDARD PLATE COUNT | <100 |
| COLI | <10 |
| YEAST/MOLD | 0/0 |

The finished Cheesecake base was then baked into a finished cheesecake according to the following formula:

TABLE 5

| INGREDIENT | WEIGHT PERCENT (%) |
|---|---|
| Cheesecake base | 62.49 |
| Granulated sugar | 25.39 |
| Lemon extract | .02 |
| Lemon emulsion | .13 |
| Fresh egg whites | 11.95 |
| | 100.00 |

The above ingredients except the egg whites were beaten for 3 minutes in a 5 ½ qt. Kitchen Aid bowl with a whisk to form a creamed cheese mixture. The egg whites were placed in a separate, clean, grease-free Kitchen Aid bowl and beat at the highest speed capable by the device (speed 10) for 10 minutes. The foamed egg whites were then evenly folded into the creamed cheese mixture with a rubber spatula. This resulted in a finished cheesecake filling which was poured into an 8 ½×3 inch springform pan lined with grease-resisting bakery dollies. The cheesecake was baked in a home oven at 425 degrees F. for 5 minutes and for an additional 50 minutes at 325 degrees F. or until the center was set. The oven was turned off and the cheesecake allowed to remain therein for an additional 30 minutes. After the cheesecake was removed from the oven and cooled completely at room temperature, it was chilled overnight at 45 degrees F.

The resulting cheesecake was then evaluated for organoleptic and physical characteristics. The cheesecake displayed unique baking temperature stability and had a firm texture. It had a rich cream-like mouthfeel resembling cheesecake made with real butterfat cream cheese. It was observed that the cheesecake was slightly chewy upon 10 days in storage.

EXAMPLE 3 FAT FREE CHOLESTEROL FREE SOFT FRESH CHEESE

A stabilized fat substitute "SFS" soft fresh cheese was produced by first forming a dispersion of deagglomerated denatured whey protein-casein coprecipitate in a continuous phase aqueous medium according to the procedure of Example 1. Ten pounds of sodium caseinate were added to 120 gallons of whey protein concentrate comprising approximately 14% solids and 9% protein. The mixture was heated by steam injection to 185 degrees F. and acidified to a pH of 5.6 to 5.65 by the addition of acetic acid. This resulted in the formation of a curd precipitate.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, soft fresh cheese as described below.

The following components were incorporated with the fat substitute product produced as described above to prepare a soft fresh cheese.

TABLE 1

| COMPONENTS | QUANTITY/POUND |
| --- | --- |
| Water | 8.0 |
| Nathan 140 | 1.0 |
| Lecicon G | 1.0 |
| Water | 18.0 |
| Avicel RC591 | 8.0 |

STEP 1

Liposome and structure building formation was achieved in a similar manner to that set out in Example 1 in which the membrane-forming, surface active, and structure building agents were prepared in the STEPHAN cooker. The lecithin fractions (Nattermann Phospholipids) were added to water in the STEPHAN cooker to form liposomes as described in Example 1. The STEPHAN cooker was operated for 8 minutes at 120 degrees F. Thereafter, the STEPHAN cooker was opened and the lecithin liposome mixture was visually examined for the presence of undissolved particles to insure complete dispersion. Upon confirmation that the mixture had been uniformly dispersed, a cream-like appearance was observed. An additional 18 pounds of hydration water were added to the liposomes in the STEPHAN cooker together with 8 pounds of microcrystalline cellulose and mixed for approximately 5 minutes. The STEPHAN cooker was then opened and visually examined for proper dispersion. Upon confirming that proper dispersion had been achieved, the STEPHAN cooker was closed and the temperature raised to 180 degrees F. by steam injection with mixing. Upon reaching 180 degrees F., the steam flow was terminated, the STEPHAN cooker opened, and the mixture was transferred to a clean sterilized bucket and slowly added to the chopper. The pasteurized lecithin-microcrystalline cellulose complex was processed in the chopper for 15 minutes to form a membrane around the curd particles, to place amphoteric charges on the curd particles, and to create structure in the aqueous phase as described in Example 1.

STEP 2

A stabilizer was produced from the components in Table 2.

TABLE 2

| COMPONENTS | QUANTITY/POUND |
| --- | --- |
| Water | 15.00 |
| Nutricol KC 56 | 0.75 |

The stabilizer from Table 2 was prepared by adding NUTRICOL KC 56 to water in a steam-injected STEPHAN cooker. NUTRICOL KC 56 contains Konjac flour and carrageenan and is available from FMC Corp., Marine Colloids Division, Philadelphia, Pa. The ingredients were mixed in the STEPHAN cooker for 2 minutes at high speed (3,000 rpm) with steam injection at a steam pressure of approximately 40 pounds to a temperature of 120 degrees F. When the temperature of 120 degrees F. was achieved, the steam flow was terminated, the agitation ceased, and the pressure released. The STEPHAN cooker was then opened and the contents subjected to tactile and visual examination as described in Example 1—Stephan Cooker Step 2. The STEPHAN cooker was then closed and the temperature raised to 205 degrees F. by steam injection with high speed agitation. When 180 F. was achieved, the steam flow was terminated, the agitation ceased, and the pressure released. The STEPHAN cooker was then opened and the contents handled in the same manner as described in Step 1 above, i.e., added slowly to the continually operating chopper. The mixture was processed in the chopper for 5 minutes.

STEP 3

Stabilizers and microbial inhibitors were prepared in the STEPHAN cooker using the components from Table 3.

TABLE 3

| COMPONENTS | QUANTITY/POUND |
| --- | --- |
| Water | 26.0 |
| Xanthan Gum | 1.0 |
| Enrich 101 | 8.0 |
| Alta 2331 | 0.5 |
| Alta 1801 | 0.5 |
| Alta 2001 | 1.5 |
| Alta 1705 | 2.0 |
| Enrich 221 | 8.0 |
| Avebe Parselli SA-2 | 8.0 |
| Enzyme modified cheese No. 6 | 2.0 |
| Salt | 2.0 |
| Non Fat Dry Milk | 12.0 |

Note: ENZYME MODIFIED CHEESE NO 6 is a product manufactured by Cacique Cheese. This product is used as a flavor enhancer.

The ingredients were mixed in the STEPHAN cooker for 2 minutes at high speed (3,000 rpm) with steam injection at a steam pressure of approximately 40 pounds to a temperature of 120 degrees F. When the temperature of 120 degrees F. was achieved, the steam flow was terminated, the agitation ceased, and the pressure released. The STEPHAN cooker was then opened and the contents subjected to tactile and visual examination as described in Example 1—STEPHAN Cooker Step 2. When satisfactory results were achieved, i.e., even dispersion, the STEPHAN cooker was closed and the temperature raised to 180 degrees F. by steam injection with high speed agitation. When the temperature reached 180 degrees F., agitation was ceased, steam flow was terminated, and the pressure released. The STEPHAN cooker was then opened and the contents handled in the same manner as described in Step 1 above, i.e., added slowly to the continually operating chopper.

FINAL PROCESS

The final process was carried out according to the procedure outlined in Example 1 in which the mixture was acidified to a pH of 5.1 to 5.2 by adding lactic acid (CCA Biochem b. v. Holland) and 6 ounces of starter distillate (Hansen×s 15X) to the continually operating chopper and mixing for about one minute. The resulted in the production of soft fresh cheese.

The soft fresh cheese was cooled and packaged as described in Example 1.

The chemical and microbiological analysis of this product is as follows:

| | |
|---|---|
| pH | 5.44 |
| FAT | 0.20% |
| SALT | 1.80% |
| STANDARD PLATE COUNT | <100 |
| COLI | <10 |
| YEAST/MOLD | 0/0 |

The components listed in Table 4, below, were added to the soft fresh cheese produced via the procedures described above. This resulted in garlic and herb flavored soft spreadable cheese.

TABLE 4

| INGREDIENT | WEIGHT PERCENT (%) |
|---|---|
| Soft Fresh Cheese | 98.16 |
| Garlic Powder | 0.20 |
| Exotic Basil | 0.14 |
| San Francisco Seasoning | 0.38 |
| Coarse Parsley | 0.12 |
| Salt | 1.00 |
| | 100.00 |

The above ingredients were blended for 1 minute in a 5 ½ qt. Kitchen Aid bowl with a paddle. The resulting spread was evaluated against two commercial low cholesterol spreadable cheeses for spreadability, texture and smoothness. In comparisons of spreadability, no significant differences were detected. In comparisons of texture, syneresis was detected in one of the commercial products. However, the product produced via the above described procedures continued to exhibit its creamy texture. The overall smoothness and organoleptic qualities of the product were comparable to that of high fat, spreadable cheese with butterfat ranges of 12% to 30%.

EXAMPLE 4 FAT FREE CHOLESTEROL FREE MAYONNAISE

A stabilized fat substitute "SFS" mayonnaise was produced by first forming a dispersion of deagglomerated denatured whey protein in a continuous phase aqueous medium according to the procedure of Example 1 with the exception that ten pounds of sodium caseinate were not added to 120 gallons of whey protein concentrate comprising approximately 14% solids and 9% protein. The mixture was heated by steam injection to 185 degrees F. and acidified to a pH of 5.4 to 5.45 by the addition of acetic acid. This resulted in the formation of a curd precipitate.

Two hundred pounds of curd were transferred from cooker to chopper using a false bottom kitchen cart. Comminution/deagglomeration of the curd was achieved according to the procedure described in Example 1. The resulting fat substitute product was further processed into fat free cholesterol free mayonnaise as described below.

The following components were incorporated with the fat substitute product produced as described above to prepare mayonnaise.

TABLE 1

| COMPONENTS | QUANTITY/POUND |
|---|---|
| Water | 8.0 |
| Nathan 140 | 1.0 |
| Lecicon G | 1.0 |
| Water | 15.0 |
| Avicel RC591 | 6.0 |

STEP 1

Liposome and structure building formation was achieved in a manner similar to that set out in Example 1 in which the membrane-forming, surface active, and structure building agents were prepared using a steam-injected STEPHAN cooker. The lecithin fractions (Nattermann Phospholipids) were added to water in the STEPHAN cooker to form liposomes as described in Example 1. The STEPHAN cooker was operated for 8 minutes at 120 degrees F. Thereafter, the STEPHAN cooker was opened and the lecithin liposome mixture was visually examined for the presence of undissolved particles to insure complete dispersion. Upon confirmation that the mixture had been uniformly dispersed, a cream-like appearance was observed. An additional 15 pounds of hydration water were added to the liposomes in the STEPHAN cooker together with 6 pounds of microcrystalline cellulose and mixed for approximately 5 minutes. The STEPHAN cooker was then opened and visually examined for proper dispersion. Upon proper determination that dispersion had been achieved, the STEPHAN cooker was closed and the temperature raised to 180 degrees F. by steam injection with mixing. When the temperature reached 180 degrees F., the steam flow was terminated, the STEPHAN cooker opened, and the mixture transferred to a clean sterilized bucket and slowly added to the chopper. The pasteurized lecithin—microcrystalline cellulose complex was processed in the chopper for 15 minutes to form a membrane around the curd particles, to place amphoteric charges on the curd particles, and to create structure in the aqueous phase as described in Example 1.

STEP 2

Microbial growth inhibitors and stabilizers were produced from the components listed in Table 2.

TABLE 2

| COMPONENTS | QUANTITY/POUND |
|---|---|
| Water | 25.0 |
| Enrich 221 | 8.0 |
| Alta 2331 | 0.5 |
| Alta 1801 | 0.5 |
| Alta 2001 | 2.0 |
| Alta 1705 | 1.0 |
| Mustard Flour | 2.0 |
| Avebe Parselli SA-2 | 6.0 |
| Salt | 3.5 |
| GP Maltodextrin 040 | 3.0 |
| Sugar | 4.0 |

Note: The MUSTARD FLOUR, Coleman's No. 80006, is available from Durkee-French Foods, Spring Field, MO 65804.

The above ingredients were mixed in the STEPHAN cooker for 2 minutes at high speed (3,000 rpm) with steam injection at a steam pressure of approximately 40 pounds to a temperature of 120 degrees F. The STEPHAN cooker was then opened and the contents examined by tactile and visual determination as described in Example 1—STEPHAN Cooker, Step 2. The STE- PHAN cooker was then closed and the temperature raised to 180 degrees F. by steam injection with high speed agitation. When the temperature reached 180° F. steam flow was terminated. The STEPHAN cooker was opened and the contents were handled in the same manner described in Step 1 above, i.e., added slowly to the continually operating chopper. The mixture was processed in the chopper for 5 minutes.

FINAL PROCESS

The final process was handled according to the procedure outlined in Example 1 in which the mixture was acidified to a pH of 4.9 by adding 300 grains of acetic acid to the continually operating bowl chopper and thereafter mixing for approximately one minute.

The mayonnaise was cooled and packaged in a manner set out in Example 1.

The chemical and microbiological analysis of the product is as follows:

| | |
|---|---|
| pH | 5.07 |
| FAT | 0.20% |
| SALT | 2.10% |
| STANDARD PLATE COUNT | <100 |
| COLI | <10 |
| YEAST/MOLD | 0/0 |

This product possessed the typical body and texture associated with mayonnaise. A slight graininess developed after 14 days of storage.

EXAMPLE 5 FAT FREE CHOLESTEROL FREE SOUR CREAM SUBSTITUTE

A stabilized fat substitute "SFS" sour cream substitute was produced by first forming a dispersion of deagglomerated denatured whey protein-casein coprecipitate in a continuous phase aqueous medium according to the procedure of Example 1. Ten pounds of sodium caseinate was added to 120 gallons of whey protein concentrate comprising approximately 14% solids and 9% protein. The mixture was then heated by steam injection to 185 degrees F. and acidified to a pH of 5.6 to 5.65 by the addition of acetic acid. This resulted in the formation of a curd precipitate.

Two hundred pounds of curd were transferred from FPEC cooker to chopper using a false bottom kitchen cart. Comminution/deagglomeration of the curd was achieved according to the procedure described in Example 1. The resulting fat substitute product was further processed into fat free, cholesterol free, sour cream substitute as described below.

The following components were incorporated with the fat substitute product produced as described above to prepare the sour cream substitute.

TABLE 1

| COMPONENTS | QUANTITY/POUND |
|---|---|
| Water | 7.0 |
| Nathan 140 | 1.0 |
| Lecicon G | 1.0 |
| Water | 15.0 |
| Avicel RC591 | 6.0 |

STEP 1

Liposome and structure building formation was achieved in a similar manner to that set out in Example 1 in which the membrane-forming, surface active, and structure building agents were prepared using the STEPHAN cooker. The lecithin fractions (Nattermann Phospholipids) were added to water in the STEPHAN cooker to form liposomes as described in Example 1. The STEPHAN cooker was operated for 8 minutes at 120 degrees F. with steam injection at a steam pressure of approximately 40 pounds. Thereafter, the STEPHAN cooker was opened and the lecithin liposome mixture was visually examined for the presence of undissolved particles to insure complete dispersion. Upon confirmation that the mixture had been uniformly dispersed, a cream-like appearance was observed. An additional 15 pounds of hydration water was added to the liposomes in the STEPHAN cooker together with 6 pounds of microcrystalline cellulose and mixed for approximately 5 minutes. The STEPHAN cooker was then opened and visually examined for proper dispersion. Upon confirming that proper dispersion had been achieved, the STEPHAN cooker was then closed and the temperature raised to 180 degrees F. by steam injection with mixing. When the temperature reached 180 degrees F., the steam flow was terminated, the STEPHAN cooker was then opened and the mixture was transferred to a clean sterilized bucket and slowly added to the chopper. The pasteurized lecithin-microcrystalline cellulose complex was added to the comminuted curd in the chopper. There, it was processed for 15 minutes to form a membrane around the curd particles, charge the curd particles, and coat the curd particles as described in Example 1.

STEP 2

TABLE 2

| COMPONENTS | QUANTITY/POUND |
|---|---|
| Water | 26.0 |
| Enrich 101 | 14.0 |
| Accel 4201 | 2.0 |
| Alta 2331 | 0.5 |
| Alta 1801 | 1.0 |
| Alta 2001 | 0.5 |
| Alta 1705 | 2.0 |
| Avebe Parselli SA-2 | 8.0 |
| Salt | 2.0 |
| Non Fat Dry Milk | 10.0 |

The microbial growth inhibitors and stabilizers listed in Table 2 were prepared and were mixed in the STEPHAN cooker for 2 minutes at 3,000 RPM with steam injection at a steam pressure of about 40 pounds to a temperature of 120 degrees F. The STEPHAN cooker was then opened and the contents examined by tactile and visual determination as described in Example 1—Stephan Cooker Step 2. The STEPHAN cooker was then closed and the temperature raised to 180 degrees F. by steam injection with high speed agitation. When the temperature reached 180 degrees F. steam flow was terminated, and the pressured released. The STEPHAN cooker was then opened and the contents handled in the same manner described in Step 1 above, i.e., added slowly to the continually operating chopper. The mixture was processed in the chopper for 5 minutes.

FINAL PROCESS

The final process was handled according to the procedure outlined in Example 1 in which the mixture was acidified to a pH of 4.9 to 5.0 by adding lactic acid (CCA Biochem b. v. Holland) and 8 ounces of starter distillate (Hansen's 15X) to the continually operating chopper and comminuting this mixture for approximately one additional minute.

The sour cream substitute was cooled and packaged in a manner that set out in example 1.

The chemical and microbiological analysis of this product fell within the following ranges:

| | |
|---|---|
| pH | 5.24 |
| FAT | 0.02 |
| SALT | 1.80 |
| STANDARD PLATE COUNT | <100 |
| COLI | <10 |
| YEAST/MOLD | 0/01 |

The sour cream substitute was mixed with two commercial dip bases and found to be a satisfactory replacement for real butterfat sour cream. The sour cream substitute was also used for an icing on the cheesecake of example 1 and found to work satisfactorily.

EXAMPLE 6 BASE FOR FAT FREE CHOLESTEROL FREE BAKERY ICING

A stabilized fat substitute "SFS" bakery icing base was produced by first forming a dispersion of deagglomerated denatured whey protein-casein coprecipitate in a continuous phase aqueous medium according to the procedure of Example 1. Ten pounds of sodium caseinate were added to 120 gallons of whey protein concentrate comprising approximately 14% solids and 9% protein. The mixture was then heated by steam injection to 185 degrees F. and acidified to a pH of 5.6 to 5.65 by the addition of acetic acid. This resulted in the formation of a curd precipitate.

Two hundred pounds of curd were transferred from FPEC cooker to chopper using a false bottom kitchen cart. Comminution/deagglomeration of the curd was achieved according to the procedure described in Example 1. The resulting fat substitute product was further processed into fat free, cholesterol free bakery icing base as described below.

The following components were incorporated with the above produced fat substitute product to prepare the base for bakery icing.

TABLE 1

| COMPONENTS | QUANTITY/POUND |
|---|---|
| Water | 10.0 |
| Nathan 140 | 1.0 |
| Lecicon G | 1.0 |
| Water | 10.0 |
| Avicel RC581 | 2.0 |

STEP 1

Liposome and structure building formation was achieved in a similar manner to that set out in Example 1 in which the membrane-forming, surface active, and structure building agents were prepared using the STEPHAN cooker. The lecithin fractions (Nattermann Phospholipids) were added to water in the STEPHAN cooker to form liposomes as described in Example 1. The Stephan cooker was operated for 8 minutes at 120 degrees F. with agitation and steam injection at a steam pressure of approximately 40 pounds. Thereafter, the agitation was ceased, the steam pressured terminated, the STEPHAN cooker opened, and the lecithin liposome mixture visually examined for the presence of undissolved particles to insure complete dispersion. Upon confirmation that the mixture had been uniformly dispersed, a cream-like appearance was observed. An additional 10 pounds of hydration water was then added to the liposomes in the STEPHAN cooker together with 2 pounds of microcrystalline cellulose and mixed for approximately 5 minutes. The STEPHAN cooker was then opened and visually examined for proper dispersion. Upon proper dispersion being confirmed, the STEPHAN cooker was then closed and the temperature raised to 180 degrees F. by steam injection with mixing. When the temperature reached 180 degrees F., the steam flow was terminated, the STEPHAN cooker was opened and the mixture was transferred to a clean sterilized bucket. The mixture was then homogenized in an APV Gaulin Model 15A at 2500 psi first stage and 1500 psi second stage before adding it to the chopper where it was processed for 15 minutes to form a membrane around the curd particles, to place amphoteric charges on the curd particles, and to create structure in the aqueous phase as described in Example 1.

STEP 2

The microbial inhibitors and stabilizers listed in Table 2 were prepared in the STEPHAN cooker.

TABLE 2

| COMPONENTS | QUANTITY/POUND |
|---|---|
| Water | 30.0 |
| Xanthan Gum | 2.0 |
| Kelco Gel IF | 2.0 |
| Gelatin 225 Bloom GMI | 1.0 |
| Sugar | 25.0 |
| Alta 2331 | 0.5 |
| Alta 1801 | 0.5 |
| Alta 2001 | 0.5 |
| Alta 1705 | 0.5 |
| Avebe Parselli SA-2 | 6.0 |
| Non Fat Dry Milk | 8.0 |

Note:
1. Kelco Gel IF, a gellum gum, is available from Kelco, San Diego, CA.
2. Gelatin 225 Bloom GMI is available from GMI, Inc., Maimi Beach, Fl. The bloom number 225 corresponds to the gel strength.

Xanthan gum, kelco gel IF, and gelatin 225 bloom were added to water and mixed in the STEPHAN cooker for 2 minutes at 3,000 RPM with steam injection at a steam pressure of about 40 pounds to a temperature of 120 degrees F. The STEPHAN cooker was then opened and the contents examined by tactile and visual determination as described in Example 1—STEPHAN Cooker Step 2. Thereafter the remaining ingredients were added to the STEPHAN cooker and mixed for approximately 2 minutes at 120 degrees F. before increasing the temperature to 180 degrees F. by steam injection with high speed agitation. When the temperature reached 180 F. steam flow was terminated, agitation was ceased, and the pressured was released. The cooker was then opened and the contents handled in the same manner described in Step 1 above, i.e., added slowly to the continually operating chopper. The mixture was processed in the chopper for 5 minutes.

The base for bakery icing was cooled and packaged in a manner set out in example 1.

The chemical and microbiological analysis of the product is as follows:

| | |
|---|---|
| pH | 5.78 |
| FAT | 0.20 |
| SALT | 0.70 |
| STANDARD PLATE COUNT | <100 |
| COLI | <10 |

-continued

| | |
|---|---|
| YEAST/MOLD | 0/0 |

The icing base was used by a large bakery supply house to formulate cooked icings for the retail baking trade.

EXAMPLE 7 FAT FREE CHOLESTEROL FREE FROZEN DESSERT

A stabilized fat substitute "SFS" for fat free cholesterol free frozen dessert was produced by first forming a dispersion of deagglomerated denatured whey protein-casein coprecipitate in a continuous phase aqueous medium according to the procedure of Example 1. Twenty-five (25) pounds of non fat milk powder were added to 110 gallons of whey protein concentrate containing approximately 14% solids and 9% protein. The mixture was then heated by steam injection to 185 degrees F. and acidified to a pH of 5.6 to 5.65 by the addition of acetic acid. This resulted in the formation of a curd precipitate.

One hundred pounds of curd were then transferred from the FPEC cooker to the chopper using a false bottom kitchen cart. The process of comminution/-deagglomeration of the curd was achieved by using a KRAMER GRABE RESEARCH MODEL, 60 liter capacity vacuum chopper (hereinafter, the KRAMER chopper). The KRAMER chopper was equipped with (i) a hood allowing chopping under vacuum, thereby improving comminution efficiency, (ii) heating and cooling control components capable of maintaining constant temperature in the substance being comminuted, and (iii) a knife shaft capable of maintaining constant speeds from 500 RPM's to 5,000 RPM's, allowing comminution rate control.

The curd was comminuted for 25 bowl revolutions under 0.6 bar vacuum at 180 degrees F. The vacuum hood was then opened and the following components were incorporated with the comminuted curd to prepare a base for fat free, cholesterol free, frozen dessert:

TABLE 1

| COMPONENTS | QUANTITY/POUND |
|---|---|
| Nathin 140 | 0.25 |
| Lexicon G | 0.25 |

STEP 1

Lecithin fractions were added directly to the KRAMER chopper so that preparation of the liposome mixture in the STEPHAN cooker was eliminated. The product temperature was maintained at 180 degrees F. via steam heating the KRAMER chopper bowl. The steam was injected through nozzles located beneath the chopper bowl preventing steam or moisture from being entrapped directly into the product.

The product was comminuted for 100 bowl revolutions with the product temperature maintained at 180 degrees F., vacuum of 0.6 bars, and knife shaft speed of 5,000 RPM's. The knife array was the same as in Example 1 except for the absence of the last two knifes since the KRAMER chopper blade shaft could accommodate only a 10 knife array. The knives were of the same design as in Example 1, but smaller in diameter to fit the smaller bowl of the KRAMER chopper.

STEP 2

The bowl hood was opened after 100 revolutions and the components listed in Table 2 were added:

TABLE 2

| COMPONENTS | QUANTITY/POUND |
|---|---|
| Solka Floc SW 200 | 3.0 |
| Spray Dried Gum Arabic | 0.1 |

Note:
1. Spray Dried Gum Arabic is available from TIC GUMS, Belcamp, MD 21107.
2. SOLKA FLOC is available from James River Corp., Saddle Brook, NJ 07601.

The vacuum hood was then closed and the temperature raised to 180 degrees F. by steam injection on the bottom of the bowl. The blade shaft speed started at 1500 RPM and then ramped up to 5,000 RPM'S while the vacuum was maintained at 0.6 bars. The comminution in the chopper continued for 25 bowl revolutions.

STEP 3

The ingredients in Table 3 were weighed and added very slowly in the dry form directly to the KRAMER chopper with the vacuum hood in the open, upright position while the bowl rotated and the shaft speed at 1,000 RPM.

TABLE 3

| COMPONENTS | QUANTITY/POUND |
|---|---|
| GRANULATED SUGAR | 16.0 |
| CORN SYRUP 42 D.E. | 6.0 |
| CMC 7HOP | 50.0 GRAMS |
| AVICEL 581 | 1.5 |
| MYROTEX 18-06 | 50.0 GRAMS |
| GP MALTODEXTRIN 040 | 3.0 |

Note:
1. MYROTEX 18-06 is available from Eastman Kodak Company, Kingsport, TN 37662.
2. CMC 7HOP is a carboxymethylcellulose gum available from Hercules, Inc., Wilmington, DE 19894.

When all the ingredients were uniformly dispersed, the vacuum hood was closed and product temperature maintained at 180 degrees F. Vacuum was increased to 0.7 bar and shaft speed was begun at 1,500 RPM and increased to 5,000 RPM when viscosity decreased. The chopper bowl continued to turn for 50 revolutions.

The base for fat free cholesterol free frozen dessert was packed in casings and cooled in the cold brine as described in Example 1.

STEP FOUR

TABLE 4

| COMPONENTS | QUANTITY/POUND |
|---|---|
| Water | 8.0 |
| Non Fat Dry Milk | 12.0 |
| Lactase Maxilact L2000 | 10.0 grams |

Maxilact L 2000 is a product of Gist Brocades, King of Prussia, PA 19406,

The ingredients in Table 4 were prepared and the lactase enzyme was allowed to hydrolyze at 90 degrees F. until the substance tasted very sweet. No attempt was made to analyze the degree of hydrolysis.

TABLE 5

| COMPONENTS | QUANTITY |
|---|---|
| CARBOXYMETHYCELLULOSE GUM | 25.0 GRAMS |
| AVICEL 581 | 85.0 GRAMS |
| MYROTEX 18-06 | 11.0 GRAMS |
| GP MALTODEXTRIN 040 | 0.4 POUNDS |
| CORN SYRUP 42 DE | 1.3 POUNDS |
| GRANULATED SUGAR | 3.4 POUNDS |

TABLE 5-continued

| COMPONENTS | QUANTITY |
|---|---|
| FAT FREE FROZEN DESSERT BASE | 25.0 POUNDS |

STEP FIVE

The ingredients from Tables 4 and 5 were combined in the STEPHAN cooker and heated to 175 degrees F. via the STEPHAN cooker's steam jacket while the STEPHAN cooker's small scaper/agitator was engaged at a slow speed until the temperature reached 175 degrees F. The heat and agitation were then terminated, the STEPHAN cooker opened, and the base for fat free cholesterol free frozen dessert produced by Step 3 was weighed (25 pounds) and introduced into the STEPHAN cooker. The STEPHAN cooker was then closed and the temperature again was raised to 175 degrees F. with slow agitation until the temperature reached 175 degrees F. The resulting mix for fat free cholesterol free frozen dessert was homogenized in a 15A APV Gaulin homogenizer at 3,000 pounds per square inch on the first stage and 1,500 pounds on the second stage. The mix was immediately cooled to 34 degrees F.

TABLE 6

| COMPONENTS | QUANTITY |
|---|---|
| FAT FREE FROZEN DESSERT MIX | 3.5 GALLONS |
| VANILLA 2 FOLD FLAVOR BECK | 21.0 MILLICITERS |
| ANNATTO COLOR HANSEN'S | 3.0 MILLICITERS |

STEP 6

The ingredients in Table 6 were added to an EMERY THOMPSON 5 gallon capacity ice cream freezer. The freezer was operated at the maximum freeze setting since no fat was present. The draw temperature was 19 degrees F. The frozen fat free dessert displayed the correct consistency for this draw temperature. The overrun at the first draw was 60 percent with succeeding draws and continual mutation with continued air incorporation. The maximum overrun that this freezer could incorporate was 85 percent.

The fat free frozen dessert was quick hardened with dry ice and then stored at 20 degrees below zero. The frozen dessert was evaluated by experts in the art of ice cream manufacturing. All believed that this fat free frozen dessert would be a viable substitute for ice cream. The fat free frozen dessert was stored and checked periodically. A rough, grainy texture began to appear after 3 months.

EXAMPLE 8 CHOCOLATE FAT FREE CHOLESTEROL FREE FROZEN DESSERT

A stabilized fat substitute "SFS" for chocolate fat free, cholesterol free frozen dessert was produced by first forming a dispersion of deagglomerated denatured whey protein-casein coprecipitate in a continuous phase aqueous medium according to the procedure of Example 1. Twenty five pounds of non fat milk powder were added to 110 gallons of whey protein concentrate containing approximately 14% solids and 9% protein. The mixture was heated by steam injection to 185 degrees F. and acidified to a pH of 5.6 to 5.65 by the addition of acetic acid. This resulted in the formation of a curd precipitate.

One hundred pounds of curd were transferred from the FPEC cooker to the chopper using a false bottom kitchen cart. The process of comminution/deagglomeration of the curd was achieved by using the KRAMER GRABE RESEARCH MODEL, 60 liter capacity vacuum chopper referred to in Example 7.

The curd was comminuted for 25 bowl revolutions under 0.6 bar vacuum at 180 degree F. The vacuum hood was then opened and the components in Table 1 were incorporated with the comminuted curd to prepare a base for chocolate fat free cholesterol free frozen dessert:

TABLE 1

| COMPONENTS | QUANTITY/POUND |
|---|---|
| Nathin 140 | 0.25 |
| Lexicon G | 0.25 |

STEP 1

Lecithin fractions were added directly to the KRAMER chopper so that preparation of the liposome mixture in the STEPHAN cooker was eliminated. The product temperature was maintained at 180 degrees F. via steam heating the bowl. The steam was injected through nozzles located beneath the chopper bowl preventing steam or moisture from becoming entrapped directly into the product.

The product was comminuted for 100 bowl revolutions with the product temperature maintained at 180 degrees F., vacuum at 0.6 bars, and the knife shaft speed at 5,000 RPM's. The knife array was the same as in Example 7.

STEP 2

The bowl hood was opened after 100 revolutions and the components listed in Table 2 were added as shown below:

TABLE 2

| COMPONENTS | QUANTITY/POUND |
|---|---|
| Solka Floc SW 200 | 3.0 |
| Spray Dried Gum Arabic | 0.1 |

Note:
1. Spray Dried Gum Arabic is available from TIC GUMS, Belcamp, MD 21107.
2. SOLKA FLOC is available from James River Corp., Saddle Brook, NJ 07601.

The vacuum hood was then closed and the temperature raised to 180 degrees F. by steam injection on the bottom of the bowl. The blade shaft speed was started at 1,500 RPM and then ramped up to 5,000 RPM'S while the vacuum was maintained at 0.6 bars. The commutation in the KRAMER chopper continued for 25 bowl revolutions.

TABLE 3

| COMPONENTS | QUANTITY |
|---|---|
| GRANULATED SUGAR | 20.0 POUNDS |
| CORN SYRUP 42 D.E. | 3.0 POUNDS |
| CMC 7HOP | 40.0 GRAMS |
| AVICEL 581 | 1.0 POUNDS |
| MYROTEX 18-06 | 50.0 GRAMS |
| GP MALTODEXTRIN 040 | 3.0 POUNDS |
| COCOA POWDER BENSDORP RED | 2.0 POUNDS |
| COCOA POWDER BENSDORP DIEMER | 2.0 POUNDS |

STEP 3

The ingredients in Table 3 were added very slowly in dry form directly to the KRAMER chopper with the vacuum hood in the open, upright position while the bowl rotated and the knife shaft speed was maintained at 1,000 RPM. When all of the ingredients were well dispersed, the vacuum hood was closed and the product temperature was maintained at 180 degrees F. Vacuum was increased to 0.7 bar and the shaft speed was started at 1,500 RPM and increased to 5,000 RPM when the viscosity decreased. The KRAMER chopper bowl continued to rotate for 50 revolutions.

The base for chocolate fat free cholesterol free frozen dessert was packed in casings and cooled in the cold brine as described in Example 1.

TABLE 4

| COMPONENTS | QUANTITY |
| --- | --- |
| WATER | 7.0 POUNDS |
| NON FAT MILK POWDER | 12.0 POUNDS |
| CARBOXYMETHYCELLULOSE GUM | 20.0 GRAMS |
| AVICEL 581 | 185.0 GRAMS |
| MYROTEX 18-06 | 11.0 GRAMS |
| GP MALTODEXTRIN 040 | 0.4 POUNDS |
| GRANULATED SUGAR | 4.5 POUNDS |
| COCOA POWDER BENSDORP RED | 2.0 POUNDS |
| COCOA POWDER BENSDORP DIEMER | 2.0 POUNDS |

STEP FIVE

The ingredients from Tables 4 were combined in the STEPHAN cooker and slowly agitated until 175 degrees F. was achieved via the STEPHAN cooker's steam jacket. The heat and agitation were then terminated, the STEPHAN cooker was opened, and 25 pounds of the base for fat free cholesterol free frozen dessert produced by Step 3 were introduced into the STEPHAN Cooker. The STEPHAN cooker was then closed and the contents slowly agitated until the temperature again reached 175 degrees F. The resulting mix for chocolate fat free cholesterol free frozen dessert was homogenized in a 15A APV GAULIN homogenizer at 3,000 pounds per square inch on the first stage and 1,500 pounds per square inch on the second stage. The mix was immediately cooled to 34 degrees F.

TABLE 6

| COMPONENTS | QUANTITY |
| --- | --- |
| CHOCOLATE FAT FREE FROZEN DESSERT MIX | 3.5 GALLONS |
| VANILLA 2 FOLD FLAVOR BECK | 10.0 MILLILITERS |

STEP 6

The ingredients in Table 6 were added to an EMERY THOMPSON 5 gallon capacity ice cream freezer. The freezer was operated at the maximum freeze setting since no fat was present. The draw temperature was 19 degrees F. The fat free frozen dessert displayed the correct consistency for this draw temperature. The overrun at the first draw was 60 percent with succeeding draws and continual mutation with continued air incorporation. The maximum overrun that this freezer could incorporate was 75 percent.

The chocolate fat free frozen dessert was quick hardened with dry ice and then stored at 20 degrees below zero. The frozen dessert was evaluated by experts in the art of ice cream manufacturing. All believed that the chocolate fat free frozen dessert would be a viable substitute for ice cream. The chocolate fat free frozen dessert was stored and checked periodically. The rough, grainy texture did not appear until after 4 months. The additional sugar and total solids may have helped to prevent the grainy or sandy defect.

The samples of lower overrun, ie, less than 50% did not display the grainy defect, thus, the defect is also a result of the air matrix upon the denatured protein particle.

EXAMPLE 9 FAT FREE CHOLESTEROL FREE PROCESSED CHEESE

A stabilized fat substitute "SFS" base for fat free, cholesterol free processed cheese was produced by first forming a dispersion of deagglomerated denatured whey protein-casein coprecipitate in a continuous phase aqueous medium according to the procedure of Example 1. Ten pounds of sodium caseinate was added to 120 gallons of whey protein concentrate containing approximately 14% solids and 9% protein. The mixture was heated by steam injection to 185 degrees F. and acidified to a pH of 5.6 to 5.65 by the addition of acetic acid. This resulted in the formation of a curd precipitate.

Two hundred pounds of curd were transferred from the FPEC cooker to the chopper using a false bottom kitchen cart. Comminution/deagglomeration of the curd was achieved according to the procedure described in Example 1. The resulting fat substitute product was further processed into a base for fat free, cholesterol free, processed cheese.

The following components were incorporated with the fat substitute product produced as described above to prepare the dressing for fat free cholesterol free processed cheese.

TABLE 1

| COMPONENTS | QUANTITY/POUND |
| --- | --- |
| Water | 7.0 |
| Nathan 140 | 1.0 |
| Lecicon G | 1.0 |

STEP 1

Liposome formation was produced in a manner similar to that set out in Example 1 in which the membrane-forming and surface active agents were prepared using a STEPHAN cooker, The lecithin fractions (Nattermann Phospholipids) were added to water in the cooker to form liposomes as described in Example 1, The STEPHAN cooker was operated for 8 minutes at 120 degrees F., with steam injection at a pressure of approximately 40 pounds, Thereafter the STEPHAN cooker was opened and the lecithin liposome mixture was visually examined for the presence of undissolved particles to insure complete dispersion.

TABLE 2

| COMPONENTS | QUANTITY/POUND |
| --- | --- |
| Water | 10.0 |
| AVICEL RC591 | 8.0 |

Upon confirmation that the mixture had been uniformly dispersed, a cream-like appearance was observed. The structure building component and water in Table 2 was added to the STEPHAN cooker. The STEPHAN cooker was then closed and the temperature raised to 180 degrees F. by steam injection with mixing. When the temperature reached 180 degrees F., the steam flow was terminated, the STEPHAN cooker was then opened and the mixture was transferred to a clean sterilized bucket and slowly added to the chopper.

The pasteurized lecithin-microcrystalline mixture was comminuted in the chopper for an additional for 15 minutes to form a membrane around the curd particles, to place amphoteric charges on the curd particles, and to create structure in the aqueous phase as described in Example 1.

TABLE 3

| COMPONENTS | QUANTITY/POUND |
|---|---|
| Water | 30.0 |
| Enrich 221 | 2.0 |
| Enrich 101 | 2.0 |
| Alta 2001 | 1.0 |
| Salt | 4.0 |
| Non Fat Dry Milk | 12.0 |
| Accel 4331 | 2.0 |
| Sodium Caseinate | 3.0 |

STEP 3

Microbial inhibitors and stabilizers listed in Table 3 were prepared in the same manner as described in step 2 above. The Enrich 221, Enrich 101, Alta 2001, and Accel 4331 are products of Microlife Technics, as previously discussed in Example 1, which are fermented dairy cheese starters in dehydrated form. The lipolized butter is a product of whey butter manufactured by Cacique, Inc., 14940 Proctor Avenue, Industry, Calif. 91715.

The base for fat free cholesterol free processed cheese was packaged in the manner outlined in Example 1.

TABLE 4

| COMPONENT | QUANTITY/POUNDS |
|---|---|
| WATER | 10.0 |
| NATHIN 140 | 3.0 |
| LECICON G | 3.0 |

STEP 4

The liposome formation was performed as described in Step 1 above.

TABLE 5

| COMPONENT | QUANTITY/POUNDS |
|---|---|
| WATER | 20.0 |
| AVICEL RC 591F | 9.0 |

The structure building and liposome mixture was processed as described in Step 2 above.

TABLE 6

| COMPONENT | QUANTITY/POUNDS |
|---|---|
| BESNIER RENNET CASEINATE | 15.0 POUNDS |
| JOHA 230 | 0.75 POUNDS |
| WATER | 15.0 POUNDS |
| EMC NO 6 | 3.0 POUNDS |
| LACTIC ACID | 6.0 OUNCES |
| LECITHIN-MICROCRYSTALLINE MIXTURE | 10.0 POUNDS |

Note:
1. Rennet caseinate is product of Besnier Proteines, Paris, France.
2. JOHA salts is available from B K LANDENBURG, Benckiser-knapsack GmBH, Germany.
3. The EMC is a product of Cacique, Inc.

STEP 6

The rennet caseinate, JOHA 230, and water were mixed in the STEPHAN cooker with agitation at 3,000 RPM and steam injection at approximately 40 pounds until the temperature was raised to 120 degrees F. The STEPHAN cooker was then opened and visually checked for undissolved particles. The EMC and lactic acid were added to the STEPHAN cooker and agitated at 3,000 RPM and heated with steam injection until the temperature reached 180 degrees F.

TABLE 7

| COMPONENT | QUANTITY/POUNDS |
|---|---|
| TRISODIUM CITRATE | 1.0 |
| SODIUM ALUMINUM PHOSPHATE (KSAL) | 0.5 |
| SALT | 0.5 |
| POLISH SKIM CHEESE | 15.0 |
| BASE FOR PROCESSED CHEESE | 20.0 |

Note:
1. Trisodium citrate is a product of Miles Laboratories, Elkhart, ID.
2. Sodium Aluminum Phosphate is a product of Chemische Fabrik Budenheim GmBH, Budenheim, Germany.
3. The Polish Skim Cheese is exported from Poland by B. V. Trading Company de Vaart, Holland.

STEP NO 7

The components in Table 7, except the base for processed cheese, were added to the product created in the STEPHAN cooker in Step 6 and the temperature increased to 175 degrees F. The resultant product was immediately packaged and cooled as outlined in Example 1.

The following is the chemical and bacteriological analysis of the fat free, cholesterol free processed cheese:

| MOISTURE | 58.1 PERCENT |
|---|---|
| FAT | <0.5 PERCENT |
| SALT | 3.0 PERCENT |
| pH | 5.4 |
| STANDARD PLATE COUNT | <100 |
| COLI | <10 |

The fat free, cholesterol free processed cheese melted and stretched with good properties. The cheese was used as an ingredient in a fat free, cholesterol free lasagna with the fat free, cholesterol free curd style ricotta of Example 10. The resulting lasagna was found to be a replication of lasagna made with whole milk ricotta containing 50 percent butterfat on a dry matter basis, and whole milk mozzarella containing 50 percent butterfat on a dry matter basis.

EXAMPLE 10 FAT FREE CHOLESTEROL FREE RICOTTA CHEESE

The stabilized fat substitute "SFS" was made into a dressing for fat free cholesterol free ricotta cheese generally according to the procedure outlined in Example 1, in which 10 pounds of sodium caseinate mixture were added to 120 gallons of whey protein concentrate containing approximately 14% solids and 9% protein. This mixture was heated by steam injection to 185 degrees F. and acidified to a pH of 5.6 to 5.65 by the addition of acetic acid. This resulted in the formation a curd precipitate.

Two hundred pounds of curd were transferred from the FPEC cooker to the chopper by using a false bottom kitchen cart. Comminution/deagglomeration of the curd was achieved according to the procedure described in Example 1. The resulting fat substitute product was further processed into dressing for fat free, cholesterol free, curd style ricotta cheese.

The following components were employed in the preparation of the dressing for fat free, cholesterol free curd style ricotta cheese.

TABLE 1

| COMPONENTS Step 1 | QUANTITY/POUND |
|---|---|
| Water | 7.0 |
| Nathan 140 | 1.0 |
| Lecicon G | 1.0 |

STEP 1

Liposome formation was produced in a similar manner to that set out in Example 1 in which the membrane-forming and surface active agents were prepared in the STEPHAN cooker. The lecithin fractions (Nattermann Phospholipids) were added to water in the STEPHAN cooker to form liposomes as described in Example 1. The STEPHAN cooker was operated for 8 minutes at 120 degrees F. Thereafter, the STEPHAN cooker was opened and the lecithin liposome mixture was visually examined for the presence of undissolved particles to insure complete dispersion. Upon confirmation that the mixture had been uniformly dispersed, a cream-like appearance was observed. The STEPHAN cooker was then closed and the temperature raised to 180 degrees F. by steam injection with mixing. When the temperature reached 180 degrees F., the steam flow was terminated, the STEPHAN cooker opened, and the mixture was transferred to a clean sterilized bucket and slowly added to the chopper. The pasteurized lecithin mixture was processed in the chopper for 15 minutes to form a membrane around the curd particles and to place amphoteric charges on the curd particles as described in Example 1.

TABLE 2

| COMPONENTS | QUANTITY/POUND |
|---|---|
| Water | 10.0 |
| Solka Floc | 3.0 |
| Xanthan Gum | 1.0 |

STEP/2

The stabilizer and structure building ingredient in Table 2 was prepared and incorporated into the dressing for fat free cholesterol free curd style ricotta cheese in the STEPHAN cooker. The ingredients were mixed in the STEPHAN cooker for 2 minutes at 3,000 RPM with steam injection at a steam pressure of approximately 40 pounds to a temperature of 120 F. The STEPHAN cooker was opened and the contents examined by tactile and visual determination as described in Example 1 STEPHAN cooker step 2. The STEPHAN cooker was then closed and the temperature raised to 180 degrees F. by steam injection with high speed agitation. When the temperature reached 180 degrees F. steam flow was terminated, the STEPHAN cooker was opened, and the contents were handled in the same manner described in step 1 above, i.e., slowly added to the continually operating chopper. The mixture was processed in the chopper for an additional 5 minutes.

TABLE 3

| COMPONENTS | QUANTITY/POUND |
|---|---|
| Water | 30.0 |
| Gelatin GMI 225 | 2.0 |
| Xanthan Gum | 1.0 |
| Enrich 221 | 3.0 |
| Enrich 101 | 3.0 |
| Alta 2331 | 0.75 |
| Alta 2001 | 1.0 |
| Alta 1705 | 0.5 |
| Salt | 4.0 |
| Non Fat Dry Milk | 12.0 |
| Sodium Caseinate | 3.0 |
| Lipolized Butter | 0.5 |
| Sea Kem GP 418 | 0.25 |

STEP 3

The ingredients in Table 3 were prepared in the STEPHAN cooker and added to the "SFS" to produce dressing for fat free cholesterol free curd style ricotta cheese. The gelatin is a product of GMI, Inc. Maimi Beach, Fla. with a bloom of 225. The Enrich 221 is a product of Microlife previously mentioned and is a fermented dairy cheese starter in dehydrated form that has the hydrocolloid gum carboxymethylcellulose as the primary product of fermentation. Sea Kem GP 418 is a carrageenan product of Marine Colloids. The lipolized butter is a product of whey butter manufactured by Cacique, Inc. The above ingredients were prepared and handled in the same manner as described in step 2 above.

TABLE 4

| COMPONENTS | QUANTITY/POUND |
|---|---|
| Water | 30.0 |
| Gelatin GMI 225 | 2.0 |
| Xanthan Gum | 1.0 |
| Enrich 221 | 3.0 |
| Enrich 101 | 3.0 |
| Alta 2331 | 0.75 |
| Alta 2001 | 1.0 |
| Alta 1705 | 0.5 |
| Salt | 4.0 |
| Non Fat Dry Milk | 12.0 |
| Sodium Caseinate | 3.0 |
| Lipolized Butter | 0.5 |
| Sea Kem GP 418 | 0.25 |

STEP FOUR

The ingredients in Table 4 were prepared and added to the chopper as in the procedure for Table 3.

STEP FIVE

The FPEC cooker in was washed with water to remove the loose curd particles. The STEPHAN cooker was used to dissolve 150 pounds of non fat dry milk powder into water. The water was filled to the 120 gallon mark in the FPEC cooker. The solids content of the reconstituted non fat milk was approximately 14 percent. The non fat milk was acidulated to pH 5.75 with lactic acid used in Example 1. The non fat milk was heated to 178 degrees F. with very slight agitation. A curd formed and was allowed to rise to the top of the whey for 10 minutes. The whey was then drained off through the bottom ports of the FPEC cooker.

FINAL PROCESS

The final process was the addition of the dressing for fat free cholesterol free curd style ricotta cheese dressing from the chopper back into the FPEC cooker. The agitators were moved very slowly to thoroughly mix the dressing and the non fat curd. The fat free cholesterol free curd style ricotta cheese was cooled and packaged in the manner outlined in Example 1.

The chemical and microbiological analysis of the fat free cholesterol free curd style ricotta cheese fell within the following ranges:

TABLE 5

| MOISTURE | 68.50 |
| --- | --- |
| pH | 5.85 |
| FAT | 0.1%–0.3% |
| SALT | 1.4%–1.7% |
| SPC | <100 |
| COLI | <10 |
| YEAST/MOLD | 0/0 |

The finished fat free cholesterol free curd style ricotta cheese was then stuffed into pasta shells, tortellini, ravioli, etc. and baked. The ricotta displayed unique stability to heat and retained its creamy texture without grainy or chalky aftertaste. The pasta was frozen and the ricotta did not degrade as a result of the freeze thaw cycles.

EXAMPLE 11 FAT FREE CHOLESTEROL FREE RICOTTA CHEESE DRESSING

The stabilized fat substitute "SFS" was made into a dressing for fat free cholesterol free ricotta cheese generally according to the procedure outlined about in Example 1, in which 10 pounds of sodium caseinate mixture were added to 120 gallons of whey protein concentrate containing approximately 14% solids and 9% protein. The mixture was heated by steam injection to 185 degrees F. and acidified to a pH of 5.6 to 5.65 by the addition of acetic acid. Upon the addition of acid, curd was formed.

Two hundred pounds of curd were transferred from the FPEC cooker to the chopper by using a false bottom kitchen cart. Comminution/deagglomeration of the curd was achieved according to the procedures described in Example 1. The resulting fat substitute product was further processed into dressing for fat free cholesterol free curd style ricotta cheese.

The following components were employed in the preparation of the dressing for fat free cholesterol free curd style ricotta cheese.

TABLE 1

| COMPONENTS | QUANTITY/POUND |
| --- | --- |
| Water | 10.0 |
| Nathan 140 | 1.0 |
| Lecicon G | 1.0 |

STEP 1

Liposome formation was produced in a manner similar to that set out in Example 1 in which the membrane-forming and surface active agents were prepared using the STEPHEN cooker. Lecithin fractions (Nattermann Phospholipids) were added to water in the STEPHAN cooker to form liposomes as described in Example 1. The STEPHAN cooker was operated for 8 minutes at 120 degrees F. with steam pressure of approximately 40 pounds. Thereafter the STEPHAN cooker was opened and the lecithin liposome mixture visually examined for the presence of undissolved particles and to insure full dispersion. Upon confirmation that the mixture had been uniformly dispersed, a cream-like appearance was observed. The STEPHAN cooker was then closed and the temperature raised to 180 degrees F. by steam injection with mixing. When the temperature reached 180 degrees F. steam flow was terminated, the STEPHAN cooker opened, and the mixture was transferred to a clean sterilized bucket and slowly added the chopper. The pasteurized lecithin mixture was processed in the chopper for 15 minutes to form a membrane around the curd particles and to place amphoteric charges on the curd particles as described in Example 1.

TABLE 2

| COMPONENTS | QUANTITY/POUND |
| --- | --- |
| Water | 10.0 |
| Solka Floc 300 | 1.0 |
| Xanthan Gum | 1.0 |

STEP 2

The stabilizer and structure building ingredient in Table 2 was prepared and incorporated into the dressing for fat free cholesterol free curd style ricotta cheese by using the STEPHAN cooker. The ingredients were mixed in the STEPHAN cooker for 2 minutes at 3,000 RPM with steam injection at a steam pressure of about 40 pounds to a temperature of 120 degrees F. The STEPHAN cooker was then opened and the contents examined by tactile and visual inspection as described in Example 1—STEPHAN cooker step 2. The STEPHAN cooker was then closed and the contents agitated at high speed while the temperature was raised to 180 degrees F. by steam injection. When the temperature reached 180 degrees F., the steam was terminated, the cooker was opened, and the contents were handled in the manner described in Step 1 above, i.e., slowly added to the continually operating chopper. This mixture was processed in the chopper for an additional 5 minutes.

TABLE 3

| COMPONENTS | QUANTITY/POUND |
| --- | --- |
| Water | 30.0 |
| Gelatin GMI 225 | 2.0 |
| Xanthan Gum | 1.0 |
| Enrich 221 | 3.0 |
| Enrich 101 | 3.0 |
| Alta 2331 | 0.75 |
| Alta 2001 | 1.0 |
| Alta 1705 | 0.5 |
| Salt | 4.0 |
| Non Fat Dry Milk | 12.0 |
| Sodium Caseinate | 2.0 |
| Lipolized Butter | 0.5 |
| TOTAL | 59.75 |

STEP 3

The ingredients in Table 3 were prepared in the STEPHAN cooker and added to the "SFS" to manufacture the dressing for fat free cholesterol free curd style ricotta cheese. Microlife previously mentioned is a fermented dairy cheese starter in dehydrated form that has the hydrocolloid gum carboxymethylcellulose as the primary product of fermentation. The lipolized butter is a product of whey butter manufactured by Cacique, Inc. The above ingredients were prepared and handled in the same manner as described in step 2 above.

TABLE 4

| COMPONENTS | QUANTITY/POUND |
| --- | --- |
| Water | 30.0 |

TABLE 4-continued

| COMPONENTS | QUANTITY/POUND |
|---|---|
| Gelatin GMI 225 | 2.0 |
| Xanthan Gum | 1.0 |
| Enrich 221 | 3.0 |
| Enrich 101 | 3.0 |
| Alta 2331 | 0.75 |
| Alta 2001 | 1.0 |
| Alta 1705 | 0.5 |
| Salt | 4.0 |
| Non Fat Dry Milk | 12.0 |
| Sodium Caseinate | 2.0 |
| Lipolized Butter | 0.5 |
| TOTAL | 59.75 |

STEP FOUR

The ingredients in Table 4 were prepared and added to the chopper as in the procedure for Table 3.

FINAL PROCESS

The fat free cholesterol free dressing for ricotta cheese was cooled and packaged in the manner outlined in Example 1.

The chemical and microbiological analysis of the fat free cholesterol free curd style ricotta cheese fell within the following ranges:

TABLE 5

| MOISTURE | 71.55 |
|---|---|
| pH | 5.65 |
| FAT | 0.1%–0.3% |
| SALT | 1.4%–1.7% |
| SPC | <100 |
| COLI | <10 |
| YEAST/MOLD | 0/0 |

The fat free, cholesterol free dressing for curd style Ricotta cheese was shipped to a manufacturer of Ricotta cheese in the Eastern United States.

EXAMPLE 12 LOW FAT RICOTTA CHEESE

The procedures for manufacturing low fat ricotta cheese generally resemble the procedure outlined in Example 1, in which 25 pounds of non fat dry milk powder was added to 110 gallons of whey protein concentrate containing approximately 14% solids and 9% protein. In addition, 50 pounds of whey cream with a fat content of 31.2 percent was added to the FPEC cooker. The mixture was heated to 185 degrees F. and acidified to a pH of 5.4 to 5.5 by the addition of acetic acid. Upon the addition of the acid, a curd containing fat was formed.

Two hundred pounds of curd were transferred from the FPEC cooker to the chopper using a false bottom kitchen cart. Comminution/deagglomeration of the curd was achieved according to the procedure described in Example 1. The resulting low fat ricotta curd product was further processed into low fat ricotta cheese.

The following components were employed in the preparation of the low fat ricotta cheese.

TABLE 1

| COMPONENTS | QUANTITY/POUND |
|---|---|
| Cream | 40.0 POUNDS |
| Gum Arabic SD | 50.0 GRAMS |
| Centrolex X Lecithin Granules | 50.0 GRAMS |
| Gelatin GMI 225 | 1.0 POUNDS |

STEP 1

The mixture in Table 1 was prepared according to the steps in Example 1. The mixture was heated to 120 degrees F. with high agitation and the STEPHAN cooker was then opened for visual examination for undissolved particles and to insure that the components were fully dispersed. Upon confirmation that the mixture had been uniformly dispersed, a cream-like appearance was observed. At this point, the components in Table 2 were added to the STEPHAN cooker.

TABLE 2

| COMPONENTS | QUANTITY/POUND |
|---|---|
| Enrich 221 | 4.0 |
| Alta 2331 | 1.0 |
| Alta 2001 | 2.0 |
| Alta 1801 | 1.0 |
| Salt | 1.25 |
| Non Fat Dry Milk | 4.0 |
| Enzyme Modified Cheese No 6 | 0.5 |

Note: Enzyme Modified Cheese No. 6 is a product of Cacique, Inc.

STEP 2

The ingredients in Table 2 were prepared in the STEPHAN cooker by mixing at a high speed and then checked to observe whether the components were fully dispersed and hydrated. After full dispersion and hydration were confirmed, agitation was initiated at a high speed with steam injection at approximately 40 pounds until the temperature reached 180 degrees F. When this temperature was achieved, the steam flow was terminated and the agitation was discontinued. The mixture was then added to the deagglomerated curd containing butterfat in the chopper.

FINAL PROCESS

The low fat cheese was cooled and packaged in the manner outlined in Example 1.

ANALYSIS

The chemical and microbiological analysis of the low fat ricotta cheese fell within the following ranges:

TABLE 5

| MOISTURE | 70.50 |
|---|---|
| pH | 5.75 |
| FAT | 7.0%–8.5% |
| SALT | 1.2%–1.5% |
| SPC | <100 |
| COLI | <10 |
| YEAST/MOLD | 0/0 |

The product was then stuffed into pasta shells, tortellini, ravioli, etc. and baked. The ricotta displayed a unique stability to heat and retained its creamy texture without grainy or chalky aftertaste. The pasta was frozen and the ricotta did not degrade as a result of freeze-thaw cycles.

EXAMPLE 13 HIGH FAT IMPASTATA CHEESE

The procedures for manufacturing high fat impastata cheese generally resemble the procedure outlined in Example 12, and pounds of spray dried sodium caseinate were added to 90 gallons of whey protein concentrate containing approximately 14% solids and 9% protein. In addition, 250 pounds of whey cream with a fat content of 30.8 percent were added to the FPEC cooker. The mixture was heated to 182 degrees F. and acidified to a pH of 5.5 to 5.6 by the addition of acetic acid. Upon the addition of the acid, curd containing a high content of butterfat was formed.

Two hundred pounds of curd were transferred from the FPEC cooker to the chopper by using a false bottom kitchen cart. Comminution/deagglomeration of the curd was achieved according to the procedure described in Example 1. The resulting high fat ricotta curd product was further processed into high fat impastata cheese.

The following components were employed in the preparation of the high fat impastata cheese.

TABLE 1

| COMPONENTS | QUANTITY/POUND |
|---|---|
| Water | 8.0 POUNDS |
| Solka Floc 200 | 1.0 POUNDS |
| Centrolex M Lecithin Granules | 100.0 GRAMS |

STEP 1

The mixture in Table 1 was prepared according to the steps in Example 11. The mixture was heated to 120 degrees F. in the STEPHAN cooker with high agitation. The STEPHAN cooker was then opened and checked for undissolved particles and to insure that the components were fully dispersed. Upon confirmation that the mixture had been uniformly dispersed, a cream-like appearance was observed. The components in Table 2 were then added to the STEPHAN cooker.

TABLE 2

| COMPONENTS | QUANTITY/POUND |
|---|---|
| Whey Cream | 35.0 |
| Gelatin GMI 225 | 0.75 |
| Enrich 101 | 8.0 |
| Alta 2331 | 0.5 |
| Alta 2001 | 0.5 |
| Alta 1801 | 0.5 |
| Salt | 0.5 |
| Non Fat Dry Milk | 10.0 |
| Enzyme Modified Cheese No 6 | 3.0 |

STEP 2

The ingredients from Tables 1 and 2 were mixed at high speed in the STEPHAN cooker and then checked to observe whether the components were fully dispersed and hydrated. After full dispersion and hydration were confirmed, the temperature was increased to 180 degrees F. and the mixture was added to the deagglomerated high butterfat containing curd in the chopper.

FINAL PROCESS

The high fat impastata cheese was cooled and packaged in the manner outlined in Example 1.

ANALYSIS

The chemical and microbiological analysis of the high fat impastata cheese fell within the following ranges:

TABLE 5

| MOISTURE | 64.50 |
|---|---|
| pH | 5.85 |
| FAT | 17.0%–18.5% |
| SALT | 1.0%–1.5% |
| SPC | <100 |
| COLI | <10 |
| YEAST/MOLD | 0/0 |

The finished high fat impastata cheese was then stuffed into pasta shells, tortellini, ravioli, etc. and baked. The ricotta displayed a unique stability to heat and retained its creamy texture without grainy or chalky aftertaste. The pasta was frozen and the impastata did not degrade as a result of the freeze-thaw cycles.

EXAMPLE 14

A process for preparing a fat substitute is described, beginning with whey formation and recovery. The whey of this example is a rennet whey derived from a typical cheese-making process. The rennet whey is further processed to produce whey protein concentrate. Whey protein concentrate is the preferred whey starting material for the preparation of the fat substitute which is the present invention.

Whey Formation

Whey is formed during the production of Fresh Hispanic Part Skim Cheese from milk. A series of twelve batches, each containing fifty thousand pounds of milk and culture, is processed following the same procedure, and in substantially the same manner, as the process described below.

Fifty thousand pounds of milk averaging 3.34% protein with a fat content are standardized to about 2.9% and pasteurized at 165 degrees F. for 20 seconds. The milk is pumped into a 50,000 pound capacity DAMAROW DOUBLE "00" cheese vat manufactured by the DAMAROW COMPANY of Fondulac, Wis. When the DOUBLE "00" cheese vat contains approximately 8,000 pounds of milk, starter culture is added under slow agitation and the filling process proceeds. When each vat contains 50,000 pounds of milk, rennet is added, and the agitation is terminated. Curd is formed at a pH of 6.6 to 6.65.

The curds and whey are then cooked with ramped stirring to a temperature of about 106 degrees F. Approximately half the whey is pre-drawn from the vats and pumped to one of two whey holding tanks. The remaining curds and whey mixture are pumped to a continuous de-whey belt manufactured by the DAMAROW COMPANY, Fondulac, Wis. The whey is recovered from the de-whey belt and combined with the predrawn whey in the whey holding tanks.

Whey in this example comes from the production of Hispanic cheese exclusively. On other occasions, the whey in the whey holding tank would be a combination of whey from the production of several types of cheese.

Examples two through thirteen were made from whey from various types of cheeses.

The whey from the twelve batches of Hispanic cheese described above varies in composition, within the following ranges:

| FAT CONTENT | = | 0.35%–0.40% by wt. |
|---|---|---|
| PROTEIN | = | 0.85%–0.95% by wt. |
| TOTAL SOLIDS | = | 7.05%–7.25% by wt. |
| pH | = | 6.35–6.53 |

Whey Protein Concentrate Production

The next step is to concentrate the above-described whey protein via sieve separation, centrifugal clarification, centrifugal separation, and ultrafiltration.

Cheese fines are removed from the whey via sieve separation using a thirty micron sieve in a fine saver manufactured by Sermia LTD, Quebec, Canada.

Thereafter the whey is clarified and slime removal achieved in a centrifugal clarifier of 100,000 pounds per hour capacity manufactured by WESTPHALIA CENTRICO INC. Northvale, N.J. 7647.

The clarified whey is then treated in a centrifugal separator to produce:

1. A whey containing between approximately 0.06 to 0.08 percent fat content; and
2. A whey cream of approximately 30% butterfat content.

An ALTERN brand centrifugal separator of 61,000 pounds per hour capacity is used for this purpose. The substantially fat free whey is then pasteurized at 165° F. for about 20 seconds and then cooled to 110° F. in an APV CREPACO HIGH TEMPERATURE SHORT TIME pasteurizer (APV CREPACO, Chicago, Ill. 60631).

The whey produced via the foregoing procedure is subjected to ultrafiltration to produce whey protein concentrate. The ultrafiltration unit is manufactured by THOMAS FRACTIONATORS of Minn. A KOCH brand spiral membrane, model SO-HFK-131, is manufactured by KOCH is used (KOCH, Wilmington, Mass. 01887). Ultrafiltration is effected at a cooled whey temperature of 100 degrees F., at sufficient pressure to produce an average protein concentrate with a solids content of 14% by weight. The pressure required on the retention side of the membrane varies from about 80 psi at the beginning of ultrafiltration period to about 130 psi as ultrafiltration continues until membrane fouling occurs. When the 140 psi operating level is reached, the membrane is washed to remove fouling materials and ultrafiltration is thereafter resumed.

The whey protein concentrate is cooled in a plate heat exchanger to a temperature of about 40 degrees F.

The twelve batches of cheese described above produce whey protein concentrates having compositions within the following ranges:

| | |
|---|---|
| FAT | 0.55%–0.85% by wt. |
| PROTEIN | 6.23%–7.56% by wt. |
| SOLIDS | 13.92%–14.91% by wt. |
| pH | 6.25–6.45 |

Fat Substitute Formation From Whey Protein Concentrate

In the here exemplified fat substitute production process, sodium caseinate is added to the whey protein concentrate to form a coprecipitate curd. This is an optional step in the process of the present invention. The curd is then comminuted to form a dispersion of denatured whey protein particles and the comminuted particles in the curd are then coated with membrane and surface active agent(s) to form a more stable dispersion. The dispersion is then further stabilized with structuring and stabilizing agent(s) to form the present invention. Comminution of the curd, formation of the membrane, and addition of the surface-active agent(s) are achieved using a chopper. It has been found that choppers used in meat processing have particular utility in the comminution of the denatured protein in the curd produced according to the present invention. The final product formulation is then homogenized under high pressure to further add to its stability. The homogenizing step is optional.

Curd Formation (Denaturing And Agglomeration)

The starting material for production of the curd used to form the stable protein dispersion of the present invention is made up of the whey protein concentrate described above including sodium caseinate as a protein additive.

The sodium caseinate additive is incorporated into the whey protein concentrate by adding 80 pounds of sodium caseinate to approximately 500 pounds of whey protein concentrate drawn from the whey protein concentrate described above. This pre-mix of sodium caseinate and whey protein concentrate is mixed in a BREDDO LIKWIKIER brand solubilizer which has high agitation as the means for blending/mixing the ingredients. The BREDDO LIKWIKIER brand Solubilizer is a high shear solubilizer and is a mixer of 100 gallon capacity (hereinafter, known as the LIKWIKIER) used for mixing dry ingredients into liquids. The LIKWIKEIR is operated at a pump shaft mixing speed of 3,800 RPM, without heat, for approximately 5 minutes. Thereafter, mixing is interrupted and the contents of the LIKWIKIER MIXER examined. Visual examination indicates an absence of lumps and an absence of observable undissolved particles. This confirms that the caseinate is fully hydrated.

The mixture from the LIKWIKIER mixer is then added to whey protein concentrate in an MUELLER 1000 gallon domed top multiwall processor. (Paul Mueller Company, Springfield, Mo. 65801) (hereinafter, the Mueller Processor). After the mixture from the LIKWIKIER is pumped to the MUELLER PROCESSOR, the total batch weight in the MUELLER PROCESSOR is approximately 8600 pounds.

The mixture is then standardized from pH 6.40 to pH 6.87 with SODA ASH (Calcium Carbonate) from Arm and Hammer. (Church and DeWright, New York, N.Y.) The pH is raised to prevent premature coagulation and curd settling. If the curd settles to the bottom of the processor, the curd and whey mixture cannot be pumped from the processor as the settled curd will clog the outlet.

The batch is heated to 195 degrees F. by the indirect heated water jacket of the processor. The heating step will take 45 minutes to reach 193 degrees and then the heat exchanger is shut off. The temperature will continue to climb to 195 degrees.

After the temperature of the solution reaches a target temperature 195 degrees F., 150 grain Vinegar (acetic acid) is added to water and the water-vinegar mixture is added to the processor in sufficient quantity to reduce the pH of the whey protein concentrate-caseinate mixture to between 5.6 and 5.65—the optimum pH for denaturing of whey protein concentrate and casein mixtures of the composition used.

If whey protein concentrate had been used alone, the pH would be lowered to 5.4 to 5.45—the optimum level when pure whey protein concentrate is used as the starting material. As additional caseinate is added to the whey protein concentrate, the optimal pH for coagulation increases.

Upon the addition of acetic acid during high speed agitation, curd is formed. It is kept in suspension in the whey solution by continued high speed agitation. The vinegar-water solution is added continually to the processor until a clear green whey is observed, then pH readings are taken. When the optimum pH is reached, the addition of the vinegar-water mixture is discontinued.

After five minutes of continuous agitation, the curd-whey slurry is pumped via a rotary positive pump (Ladish NO. 4) through a pipeline and to a fine saver. This fine saver uses sieve separation utilizing a thirty micron sieve in a fine saver manufactured by Sermia LTD, Quebec, Canada. The hot whey that is extracted from the slurry is pumped into a storage tank.

The curd is then loaded into a false bottom cart for transport to the next step of fat substitute manufacture—the deagglomeration/comminution of the denatured coprecipitate curd. During transport, whey continues to drain from the curd. The curd at this point is typically from approximately 65% to 80% water by weight. The moisture content is inversely proportional to the final cooking temperature. The curd produced in this example has a moisture content in the 75% to 80% by weight range.

Deagglomeration of The Curd; Dispersion Formation

The drained curd with a moisture content in the 75% to 80% by weight range is deagglomerated using a 200 liter capacity vacuum chopper manufactured by MEISSNER AG. The model number is RSM 200VAC. In the United States, such choppers are distributed by RMF-CHALLENGE located at 4417 East 119th Street, Grandview, Mo. 64030. Experience has shown that optimal deagglomeration conditions occur when the curd batch processed in choppers of 200 liter capacity weighs about 200 pounds. The described chopper is equipped with a vacuum hood whereby a vacuum of 28 inches of mercury can be pulled. The hood is also equipped with a carbon dioxide injection hood and exhaust exit. The bowl of the chopper can also be heated or cooled with water or steam via sprays underneath the enclosed bowl.

Choppers, long used in the food processing industry for sausage processing, have been found to have utility in (1) deagglomerating the curd formed in accordance with the present invention to form the curd into a dispersion of micron sized particles suspended in a continuous aqueous phase; (2) coating the micron sized particles, to charge the particles with a surface active agent, and build structure—thereby increasing the particles' stability; and, (3) incorporating a stabilizer into the aqueous phase of the dispersion further enhancing the stability of the fat substitute product.

In the process described in the present example, a ten knife array is selected for use in the chopper. The knives in this array were SECURITY-SYSTEM-4-CUT-KNIVES available from G. Walter Steffans, 563 Remscheid 14, Uterholterfelder Strasse 60, Germany. The knives are composed of high quality stainless knife steel. The cutting edge of the blade of these knives was formed on the camber side at an original grinding angle of 27 degrees. The knives were then mounted on a single shaft adapted for use in configurations involving up to twelve knives. The back/trailing edges of the knives' blades are flat and taper from 5 mm at the shaft to 3 mm proximate the point of the blade where the camber that forms the blade edge begins.

The ten knives are oriented on the shaft in the following manner: The first and second knives at the upstream end of curd flow—flow is induced by rotating the bowl of the chopper—are positioned 180 degrees opposite one another. The distance between the knives, as measured along the shaft, is about 5 mm. The knife holder is 10 mm thick and the knife is 5 mm thick. The third knife is offset 30 degrees behind the first knife and a 5 mm spacer is used to increase the distance between the second and third knives by 5 mm to about 10 mm. The fourth knife is positioned 180 degrees opposite the third knife. Here again, the distance between opposing knife pairs 3 and 4, as measured along the knife-holder shaft, is about 5mm. The fifth knife is offset 30 degrees behind the third knife. The sixth knife is positioned 180 degrees opposite the fifth knife. The remaining three knife pairs, namely, 7 and 8, 9 and 10, are positioned with knife 7, 30 degrees behind knife 5; knife 9, 30 degrees behind knife 7. No spacers are used in positioning the last knife pairs, and knives of each pair are oriented 180 degrees opposite each other.

The increased spacing at the front of the knife array, between knives 2 and 3, has been observed to improve performance of the chopper by allowing a greater volume of curd to enter the knife array. Where the leading 180 degrees opposed pairs are spaced apart the same distances as the succeeding opposed pairs, build up of curd and/or dispersion occurs and a dam of curd is formed forward of the upstream leading knife.

To maximize efficiency, the cutting edges of the chopper knives were sharpened and tested to insure an order of sharpness that cuts paper. Also, the side surfaces of the knife were highly polished before comminution began.

Two hundred pounds of curd are transferred from the false bottomed kitchen cart to the chopper. The chopper is operated at a high bowl speed of 16 RPM's and a knife shaft speed of 3,000 RPM's for ten minutes to comminute the denatured whey protein casein coprecipitate curd. Steam is turned on the automatic control to maintain a temperature of 175 degrees F. A vacuum of 25 inches is maintained. A dispersion is formed of the deagglomerated denatured whey protein casein coprecipitate in a continuous phase aqueous medium. The aqueous medium is formed by the aqueous component released during comminution/deagglomeration of the curd.

Stephan Cooker Step Number 1:

While the chopper is operated to form the dispersion described in the preceding paragraph, a membrane-forming composition, including a surface-active agent and a structure-building agent, is being prepared in the STEPHAN cooker for addition to the curd during the above-described comminution procedure.

The membrane-forming agents, surface-active agents, and structure-building agents were prepared in the STEPHAN cooker using steam-injection and high agitation to form dispersions of the same very quickly. The components listed in table one were used for this purpose.

TABLE 1

| Ingredient | Pounds |
| --- | --- |
| Water | 8.0 |
| Alcolec 140 | 2.0 |
| Alcolec SFG | 1.0 |
| Water | 13.0 |

TABLE 1-continued

| Ingredient | Pounds |
| --- | --- |
| Avicel RC591 | 5.0 |

1. ALCOLEC 140 is available from American Lecithin Company, located at 33 Turner Road, Danbury, Connecticut 06813-1905. This product is approximately 40% phosphatidyl choline by weight.
2. ALCOLEC SFG is available from American Lecithin Company, located at 33 Turner Road, Danbury, Connecticut 06813-1905.

Step 1:

Eight pounds of water are poured into the STEPHAN cooker into which the following ingredients are added: (i) two pounds of ALCOLEC 140 which contains approximately 40% phosphatidyl choline by weight; (ii) one pound ALCOLEC SFG which is high in inositol and glycolipids content.

These contents are processed in the STEPHAN cooker for 8 minutes at 120 degrees F. with the lower knife blade operating at 3,000 RPM and the side scraper blade on high speed in order to form liposomes. At the end of 8 minutes, the blade/scraper action is interrupted and the STEPHAN cooker opened to visually examine the contents for even dispersion. Once even dispersion is confirmed, 13 pounds of hydration water are added to the liposomes and high speed agitation is again applied for four minutes. The 5 pounds of micro-crystalline cellulose is then added to the liposome mixture and high speed agitation is again applied. The microcrystalline cellulose is available from the Food and Pharmaceutical Products Division of FMC located at 200 Market Street, Philadelphia, Pa. 19103, sold under the designation AVICEL RC-591F. The STEPHAN cooker is used to mix these contents at the 3,000 RPM speed and steam injection is used to raise the temperature to 180 degrees F. The required time to do this is about five minutes. The lecithin-microcrystalline complex is checked under a polarized light microscope to insure that the microcrystalline cellulose is properly dispersed. If the microcrystalline cellulose is properly dispersed, the cellulose crystals are evenly dispersed in the liposomes with no clumping or affinity. The lecithin-microcrystalline cellulose complex is formed in the STEPHAN Cooker and added to the curd dispersion in the chopper.

The chopper continues operation for an additional 15 minutes (hereinafter, the second comminution phase) to form a membrane around the denatured whey protein-casein precipitate particles, and to place amphoteric charges on them with surface active agents, and to build structure. The membrane is believed to be formed by the liposomes-lecithin mixture. This membrane produces electrostatic charges on the particle surface facilitating the steric repulsion of the particles. The structure building agents stabilize by creating viscosity in the aqueous phase such that the particles cannot reagglomerate readily. Thus, a very stable dispersion is created with extended shelf life and heat stability during baking.

As the second comminution phase proceeds, the contents of the chopper begin to take on a glossy appearance that resembles products of high fat composition. This is believed to be the result of light refraction by the non-fat curd particles that now behave much like the fat globules occurring naturally in fat emulsions such as cream. The size and distribution of the particles at this point are believed to be the same that occurs in bovine butterfat emulsions such as unhomogenized milk.

At the end of twenty minutes of continual comminuting, the fat substitute hydrated protein product further develops a high glossy appearance. The product at this point, when rubbed between the thumb and forefinger, displays the greasy lubricity and slip that is characteristic of high fat compositions or emulsions. The organoleptic evaluation of the product proved to be the same as a heavy cream with a butterfat content of 50 to 60 percent.

Stabilization of The Fat Substitute

If one stopped the process at this point, a stabilized fat substitute having the mouthfeel of fat-water or water-fat emulsions is produced. To improve the stability of the product against the development of a chalky mouthfeel or bacterial growth, a hydrocolloid gum such as xanthan gum, and microbial growth inhibitors such as potassium sorbate, can be added.

Stabilization of the fat substitute is desirable where it is to be stored and/or shipped for later use in production of nonfat foodstuffs. Stabilization is achieved by adding a thickener/pseudoplastic stabilizer, such as xanthan gum, which imparts thixotropic properties. An aqueous dispersion of xanthan gum is produced in the STEPHAN cooker and added to the chopper to achieve a xanthan gum content of about 0.25 to 0.5 weight percent of the fat substitute.

Hydrocolloid gum is added to the dispersion of coated particles in the chopper to incorporate the gum into the continuous phase of the dispersion. Besides hydrocolloid gum addition, it is preferable to add microbial growth inhibitors to the fat substitute and/or stabilized fat substitute. Suitable microbial growth inhibitors such as sodium benzoate, potassium sorbate, or natural microbial inhibitors such as dehydrated cheese culture can be used. The products used in this example were Alta 2331, Alta 1801, Alta 2001, Alta 1705, and Microguard 300. The Alta products are natural microbial inhibitors available from Quest-Microlife Technics, Inc. of Sarasota, Fla., 34230. Microguard 300 is a natural fermentation product from Wesman Foods of Beaverton, Oreg. 97006. Each of these products shows inhibitory effects against different microorganisms and are chosen accordingly.

A microbial stabilizer is also added to the mixture in the STEPHAN cooker, which is subsequently added to the chopper, to improve stability. This microbial stabilizer is Enrich 101 and is primarily a fermented milk product in dehydrated form containing xanthan-like hydrocolloids. This product is available from Quest-Microlife Technics, Inc. of Sarasota, Fla., 34230. G P Maltodextrin 040, available from Grain Processing Corporation of Muscatine, Iowa 52761, is added to further enhance the stability of the product, impart spreadability, and reduce the apparent viscosity. Paselli SA-2 is added for the same purpose as Maltodextrin 040, but further enhances viscosity. A combination of the two maltodextrins will provide the desired body and texture. AVEBE PARSELLI SA-2 is a product of Avebe America, Inc., Princeton, N.J. 08540.

To improve the flavor beyond that of culture distillate, a flavor dehydrated starter culture is added. This is Accel 4201 available from Quest-Microlife Technics, Inc. of Sarasota, Fla., 34230.

At this point, the Stabilized Fat Substitute "SFS" contained in the bowl of the chopper is further processed into fat free cholesterol free base for cheesecake. This is accomplished by preparing further ingredients in the STEPHAN Cooker and adding them to the chopper.

Stephan Cooker Number 2:

| INGREDIENT | POUNDS |
|---|---|
| Water | 26.00 |
| Xanthan gum | 0.25 |
| Pectin | 0.75 |
| Carrageen | 0.25 |
| Gelatin | 4.00 |

Three quarters of a pound of SLENDID specialty pectin is dispersed in 26 pounds of water in the Stephan cooker under high agitation for 6 minutes [No liposome? ]. SLENDID pectin is a product of Hercules Incorporated, Fragrance and Food Ingredients Group, Hercules Plaza, Wilmington, Del. 19894. One quarter pound of Keltrol T xanthan gum from Kelco, San Diego, Calif. 92123, 4 pounds of 225 Bloom Gelatin from GMI, Inc., North Miami Beach, Fla. 33179, and 0.25 pound of Gelerin GP 911 Carrageen from the Food and Pharmaceutical Products Division of FMC located at 200 Market Street, Philadelphia, Pa. 19103, are mixed in the STEPHAN cooker at 3,000 rpm. This process requires approximately 5 minutes. The STEPHAN cooker is opened and the contents are examined to insure that hydrocolloid gums are fully dispersed and hydrated. This is determined by tactile examination—rubbing the sample between fingers—and visually checking for presence of undissolved particles.

Upon confirmation that the hydrocolloid gums are in solution, the following ingredients are added to the hydrocolloid gum-water mixture in the STEPHAN cooker:

Stephan Cooker Number 3:

| INGREDIENT | POUNDS |
|---|---|
| Sugar | 12.00 |
| Salt | 2.00 |

Upon confirmation that the sugar and salt are in solution, the following ingredients are added to the mixture in the STEPHAN cooker:

Stephan Cooker Number 4:

| INGREDIENT | POUNDS |
|---|---|
| Alta 1705 | 0.25 |
| Alta 2001 | 0.50 |
| Alta 1801 | 0.50 |
| Alta 2331 | 0.25 |
| Microguard 300 | 1.75 |
| Accel 4301 | 4.00 |

Upon confirmation that the microorganism inhibitors are in solution, the following ingredient is added to the mixture in the STEPHAN cooker:

Stephan Cooker Number 5:

| INGREDIENT | POUNDS |
|---|---|
| Enrich 101 | 5.00 |

Upon confirmation that the Enrich is in solution, the following ingredient is added to the mixture in the STEPHAN cooker:

Stephan Cooker Number 6:

| INGREDIENT | POUNDS |
|---|---|
| Non Fat Milk Solids | 22.00 |

The above ingredients are dispersed at 3,000 RPM with steam injection at a steam pressure of about 40 pounds to a temperature of 120 degrees F. for 1 to 2 minutes. The STEPHAN cooker was then opened and the product examined to verify the absence of lumps and that the ingredients had been uniformly dispersed. The STEPHEN cooker was then closed and the temperature raised to 180 degrees F. by steam injection with agitation at 3,000 RPM in order to pasteurize the contents. When the temperature reached 180 degrees F., the steam flow was terminated, the cooker was opened, the contents transferred to a clean sterilized bucket and slowly added to the chopper.

Direct Addition to Chopper

The chopper continues to operate at a bowl speed of 18 RPM and a knife shaft speed of 2,500 RPM and achieves a uniform mixture of Stephan Cooker ingredients and stabilized fat substitute. The 8 pounds of G P Maltodextrin and 6 pounds of Parselli SA-2 are added slowly to the chopper. After the contents of the chopper are thoroughly mixed for 2 to 3 minutes, a sample is withdrawn and analyzed for pH. The pH is adjusted to 5.1 to 5.2 by adding approximately 14 ounces of lactic acid available from CCA BIOCHEM B. V. of The Netherlands to the chopper. After the pH was adjusted, 70 mls. of starter distillate designated Hansen's 15X available from Chs. Hansen's Laboratory, Inc. Milwaukee, Wis. 53214, 300 mls. of Beck's Vanilla No. C-7281 and 600 mls. of Flavorcraft Lemon Emulsion No. 1302 are added to the continually operating chopper with mixing for about three minutes.

DIRECT ADDITION TO CHOPPER

| INGREDIENT | POUNDS |
|---|---|
| Parselli SA-2 | 6.00 |
| GP Maltodextrin 040 | 8.00 |
| Beck's Vanilla | 300 mls |
| Lemon Emulsion | 600 mls |
| Starter Distillate | 70 mls |
| Lactic Acid | a/r |

The resulting mixture is transferred to a kitchen cart and then into the funnel inlet of the Moyno pump. A special high pressure APV RANNIE Hyper homogenizer built by APV RANNIE, Copenhagen, DN. and sold by APV RANNIE, 445 Enta Street, St. Paul, Minn. 55106, and a Niro Soave high pressure homogenizer sold by Niro Atomizer, 1600 County Road F, Hudson, Wis. 54016 are used to homogenize the final product. Hyper Homogenization is considered to be over 10,000 pounds per square inch. The Hyper homogenization utilizes two stages wherein typically 10 to 15 percent of the pressure is applied to the second stage to create back pressure in the camber between the two stages, thereby increasing the cavitation forces and reducing particle size. The first stage pressure is 10,000 pounds per square inch and the second stage pressure is 1,500 PSI. This high pressure Hyper Homogenization creates a temperature increase in the product and will cause implosion in the cylinder or the camber. As a rule of thumb, this increase approximates five (5) degrees for every one thousand (1,000) pounds of pressure. Thus, the temperature of the cheesecake base was lowered to 140 degrees F. by the addition of carbon dioxide in solid form in the Meissner chopper before the base was discharged.

The cheesecake base is packed into a 120mm by 20" plastic casing directly at the outlet of the homogenizer. The encased mixture is cooled in a brine tank to a core temperature of 400 F.

A sample of the product is analyzed for chemical and microbiological assay. The results are as follows:

| | |
|---|---|
| Moisture | 55.6–56.4 |
| pH | 5.13–5.21 |
| Fat | 0.2–0.4 |
| Salt | 2.1–2.3 |
| SPC | <100 |
| COLI | <10 |
| Yeast/Mold | 0/0 |

EXAMPLE 15 FAT FREE CHOLESTEROL FREE SOFT FRESH CHEESE

A stabilized fat substitute "SFS" soft fresh cheese was produced by first forming a dispersion of deagglomerated denatured whey protein-casein coprecipitate in a continuous phase aqueous medium according to the procedure of Example 1. Ten pounds of sodium caseinate were added to 120 gallons of whey protein concentrate comprising approximately 14% solids and 9% protein. The mixture was heated by steam injection to 185 degrees F. and acidified to a pH of 5.6 to 5.65 by the addition of acetic acid. This resulted in the formation of a curd precipitate.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, soft fresh cheese as described below.

The following components were incorporated with the fat substitute product produced as described above to prepare a soft fresh cheese.

TABLE 1

| COMPONENTS | QUANTITY/POUND |
|---|---|
| Water | 8.0 |
| Alcolec 140 | 1.0 |
| Alcolec SFG | 1.0 |
| Water | 13.0 |
| Avicel RC591 | 5.0 |

STEP 1

Liposome and structure building formation was achieved in a similar manner to that set out in Example 1 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 1. The STEPHAN cooker was operated for 8 minutes at 120 degrees F. Thereafter, the STEPHAN cooker was opened and the lecithin liposome mixture was visually examined for the presence of undissolved particles to insure complete dispersion. Upon confirmation that the mixture had been uniformly dispersed, a cream-like appearance was observed. An additional 13 pounds of hydration water was added to the liposomes in the STEPHAN cooker together with 5 pounds of microcrystalline cellulose and mixed for approximately 10 minutes. The STEPHAN cooker was then opened and visually examined under a polarized light microscope for proper dispersion. Upon confirming that proper dispersion had been achieved, the STEPHAN cooker was closed and the temperature raised to 180 degrees F. by steam injection with mixing. Upon reaching 180 degrees F., the steam flow was terminated, the STEPHAN cooker opened, and the mixture was transferred to a clean sterilized bucket and slowly added to the chopper. The pasteurized lecithin-microcrystalline cellulose complex was processed in the chopper for 10 minutes to form a membrane around the curd particles, to place amphoteric charges on the curd particles, and to create structure in the aqueous phase as described in Example 1.

STEP 2

A stabilizer was produced from the components in Table 2.

TABLE 2

| COMPONENTS | QUANTITY/POUND |
|---|---|
| Water | 26.00 |
| Slendid Pectin | 2.0 |
| Gelatin 250 Bloom | 1.0 |

The stabilizer from Table 2 was prepared by adding SLENDID pectin and the Gelatin 250 Bloom to water in a steam-injected STEPHAN cooker. SLENDID pectin contains a specialty processed pectin distributed by Hercules, Inc., Wilmington, Del. 19894-000 and manufactured by Copenhagen Pectin, DK 4623, Skensved, Denmark. The ingredients were mixed in the STEPHAN cooker for 5 minutes at high speed (3,000 rpm) with no steam injection. The STEPHAN cooker was then opened and the contents subjected to tactile and visual examination as described in Example 1—Stephan Cooker Step 2.

STEP 3

Additional microbial inhibitors and salt were prepared in the STEPHAN cooker using the components from Table 3. These ingredients were added to those in Step 2.

TABLE 3

| COMPONENTS | QUANTITY/POUND |
|---|---|
| Salt | 3.0 |
| Alta 2331 | 0.5 |
| Alta 1801 | 0.5 |
| Alta 2001 | 1.5 |
| Alta 1705 | 2.0 |

The ingredients were mixed in the STEPHAN cooker for 5 minutes at high speed (3,000 rpm) The STEPHAN cooker was then opened and the contents subjected to tactile and visual examination as described in Example 1—STEPHAN Cooker Step 2.

STEP 4

The component in Table 4 was added to those in Step 3.

TABLE 4

| COMPONENTS | QUANTITY/POUND |
| --- | --- |
| Enrich 101 | 5.0 |

The ingredients were mixed in the STEPHAN cooker for 5 minutes at high speed (3,000 rpm) The STEPHAN cooker was then opened and the contents subjected to tactile and visual examination as described in Example 1—STEPHAN Cooker Step 2.

STEP 5

The components in Table 5 were added to those in Step 4.

TABLE 5

| COMPONENTS | QUANTITY/POUND |
| --- | --- |
| Non Fat Dry Milk Powder | 17.0 |
| Cultured Non Fat Buttermilk | 5.0 |

The ingredients were mixed in the STEPHAN cooker for 5 minutes at high speed (3,000 rpm) The STEPHAN cooker was then opened and the contents subjected to tactile and visual examination as described in Example 1—STEPHAN Cooker Step 2.

The Non Fat Dry Milk powder utilized was a product of Foster Farms Dairy, Modesto, Calif. 95351 and the Cultured Non Fat Buttermilk utilized was a product of Land 'O Lakes, Arden Hills, Minn. 55126.

STEP 6

The components in Table 6 were added to those in Step 5.

TABLE 6

| COMPONENTS | QUANTITY/POUND |
| --- | --- |
| Parselli SA-2 | 4.0 |
| Cream Cheese Powder | 4.0 |

The ingredients were mixed in the STEPHAN cooker for 5 minutes at high speed (3,000 rpm) The STEPHAN cooker was then opened and the contents subjected to tactile and visual examination as described in Example 1—STEPHAN Cooker Step 2.

When satisfactory results were achieved, i.e., even dispersion, the STEPHAN cooker was closed and the temperature raised to 180 degrees F. by steam injection with high speed agitation. When the temperature reached 180° F., agitation was ceased, steam flow was terminated, and the pressure released. The STEPHAN cooker was then opened and the contents were added slowly to the continually operating chopper.

ACIDIFICATION PROCESS

The acidification process was carried out according to the procedure outlined in Example 1 in which the mixture was acidified to a pH of 4.9 to 5.0 by adding lactic acid (CCA Biochem b. v. Holland) and 20 ml of starter distillate (Hansen's 15X) to the continually operating chopper and mixing for about one minute.

HOMOGENIZATION PROCESS

The homogenization process was carried out by using a Moyno pump to force the heavy, vicious Fat Free Soft Cheese through the inlet valves of a high pressure homogenizer. The stuffing pressure had to exceed 150 pounds to prevent implosion. A APV RANNIE high pressure homogenizer was used at a first stage pressure of 10,000 pounds per square inch and a second stage pressure of 1,500 pounds per square inch.

The homogenized soft fresh cheese was cooled and packaged as described in Example 1.

The chemical and microbiological analysis of this product was as follows:

| | |
| --- | --- |
| pH | 5.01 |
| FAT | 0.20% |
| SALT | 2.40% |
| STANDARD PLATE COUNT | <100 |
| COLI | <10 |
| YEAST/MOLD | 0/0 |

The components listed in Table 7, below, were added to the soft fresh cheese produced via the procedures described above. This resulted in garlic and herb flavored soft spreadable cheese.

TABLE 7

| INGREDIENT | WEIGHT PERCENT (%) |
| --- | --- |
| Soft Fresh Cheese | 99.00 |
| Herb and Garlic C208-B | 1.0 |
| | 100.00 |

The Garlic and Herb Base is a product of Saratoga Specialties, Elmhurst, IL 60126.

The above ingredients were blended for 1 minute in a 5 ½ qt. KITCHEN AID bowl with a paddle. The resulting spread was evaluated against two commercial low cholesterol spreadable cheeses for spreadability, texture and smoothness. In comparisons of spreadability, no significant differences was detected. In comparisons of texture, syneresis was detected in one of the commercial products. However, the product produced via the above described procedures continued to exhibit its creamy texture. The overall smoothness and organoleptic qualities of the product were comparable to that of high fat, spreadable cheese with butterfat ranges of 12% to 30%.

EXAMPLE 16 FAT FREE CHOLESTEROL FREE MAYONNAISE DRESSING-INDIRECT HEAT METHOD

A stabilized fat substitute "SFS" mayonnaise dressing is produced by using two hundred pounds of curd from Example 14. The curd is made by indirect heating of the whey protein-caseinate mixture to produce a coprecipitate.

The two hundred pounds of curd are transferred from the BLANCO Blender cooker to the bowl chopper using a false bottom kitchen cart. Comminution/-deagglomeration of the curd is achieved according to the procedure described in Example 14. The resulting fat substitute product is further processed into fat free, cholesterol free, mayonnaise dressing as described below.

The following components are incorporated with the fat substitute product produced as described above to prepare a mayonnaise dressing.

TABLE 1

| COMPONENTS | QUANTITY/POUND |
| --- | --- |
| Water | 8.0 |
| Alcolec 140 | 4.0 |

TABLE 1-continued

| COMPONENTS | QUANTITY/POUND |
| --- | --- |
| Alcolec SFG | 1.0 |
| Water | 13.0 |
| Avicel RC591 | 5.0 |

STEP 1

The liposome and structure building formation is achieved in a similar manner to that set out in Example 14 in which the membrane-forming, surface active, and structure building agents are prepared in the STEPHAN cooker. The lecithin fractions (American Lecithin Company, Danbury, Conn. 06813-1908) are added to water in the STEPHAN cooker to form liposomes as described in Example 14. The STEPHAN cooker is operated for 8 minutes at 120 degrees F. Thereafter, the STEPHAN cooker is opened and the liposomes made from the lecithin-water mixture are visually examined for the presence of undissolved particles and to insure complete dispersion. Upon confirmation that the mixture is uniformly dispersed and that liposomes are formed, a caramel cream-like appearance is observed. An additional 13 pounds of hydration water is added to the liposomes in the STEPHAN cooker together with 5 pounds of microcrystalline cellulose and mixed for approximately 10 minutes. The STEPHAN cooker is then opened and the liposome mixture is visually examined under a polarized light microscope for proper dispersion. Upon confirming that proper dispersion is achieved, the STEPHAN cooker is closed and the temperature raised to 180 degrees F. by steam injection with high speed agitation. Upon reaching 180 degrees F., the steam flow is terminated, the STEPHAN cooker is opened, and the mixture is transferred to a clean sterilized bucket and slowly added to the chopper. The pasteurized lecithin-microcrystalline cellulose complex is processed in the chopper for 10 minutes to form a membrane around the Curd particles, to place amphoteric charges on the curd particles, and to create structure in the aqueous phase as described in Example 14.

STEP 2

A stabilizer is produced from the components in Table 2.

TABLE 2

| COMPONENTS | QUANTITY/POUND |
| --- | --- |
| Water | 26.00 |
| Slendid Pectin | 2.0 |
| Gelatin 250 Bloom | 0.5 |
| Calcium Chloride Solution | 20 mls. |

The stabilizer from Table 2 is prepared by adding Slendid Pectin to the 26 pounds of water in the STEPHAN cooker. The bottom agitator is set at high speed and the side agitator is turned on for 5 minutes. The STEPHAN cooker is then opened and the the pectin dispersion is then inspected for complete dispersion. The 250 Bloom Gelatin is then added to the water-pectin dispersion. The ingredients are mixed in the STEPHAN cooker for 5 minutes at high speed (3,000 rpm) with no steam injection. The STEPHAN cooker is then opened and the calcuim chloride solution is added and mixed for 2 minuts. The STEPHAN cooker is then opened and the contents subjected to tactile and visual examination as described in Example 14—STEPHAN Cooker Step 2. SLENDID pectin is a specialty processed pectin distributed by Hercules, Inc., Wilmington, Del. 19894-000 and manufactured by Copenhagen Pectin, DK 4623, Skensved, Denmark.

STEP 3

Additional microbial inhibitors, sugar, and salt are prepared in the STEPHAN cooker using the components from Table 3. These ingredients are added to those made in Step 2 above.

TABLE 3

| COMPONENTS | QUANTITY/POUND |
| --- | --- |
| Salt | 3.5 |
| Sugar | 2.0 |
| Alta 2331 | 0.5 |
| Alta 1801 | 0.5 |
| Alta 2001 | 0.5 |
| Alta 1705 | 0.5 |

The ingredients are mixed in the STEPHAN cooker for 2 minutes at high speed (3,000 rpm) The STEPHAN cooker is then opened and the contents subjected to tactile and visual examination as described in Example 14—STEPHAN Cooker Step 2.

STEP 4

The component in Table 4 is added to those in Step 3.

TABLE 4

| COMPONENTS | QUANTITY/POUND |
| --- | --- |
| Enrich 221 | 6.0 |

The ingredients are mixed in the STEPHAN cooker for 2 minutes at high speed (3,000 rpm) The STEPHAN cooker is then opened and the contents subjected to tactile and visual examination as described in Example 14—STEPHAN Cooker Step 2. The ENRICH 221 is a natural microbial stabilizer available from Quest-Microlife Technics, Inc. of Sarasota, Fla., 34230.

STEP 5

The component in Table 5 is added to those in Step 4.

TABLE 5

| COMPONENT | QUANTITY/POUND |
| --- | --- |
| Non Fat Dry Milk Powder* | 4.0 |

Non fat dry milk powder is a product of Foster Farms Dairy, Modesto, CA 95351.

The ingredient is mixed in the STEPHAN cooker for 2 minutes at high speed (3,000 rpm). The STEPHAN cooker is then opened and the contents subjected to tactile and visual examination as described in Example 14—STEPHAN Cooker Step 2.

STEP 6

The components in Table 6 is added to those in Step 5.

TABLE 6

| COMPONENTS | QUANTITY/POUND |
| --- | --- |
| Parselli SA-2 | 6.0 |
| GP Maltodextrin 040 | 3.0 |
| Coleman's Mustard Flour | 3.0 |
| Corn Syrup 42 D.E. | 4.0 |

The ingredients are mixed in the STEPHAN cooker for 2 to 3 minutes at high speed (3,000 rpm). The STEPHAN cooker is then opened and the contents subjected to tactile and visual examination as described in Example 14—STEPHAN Cooker Step 2. When satisfactory results are achieved, i.e., even dispersion, the STEPHAN cooker is then closed and the temperature raised to 180 degrees F. by steam injection with high speed agitation. When the temperature reached 180 F., agitation is ceased, steam flow is terminated, and the pressure released. The STEPHAN cooker is then opened and the contents are added slowly to the continually operating chopper. COLEMAN'S Mustard Flour is a product of the R. T. French Company of Rochester, N.Y. 14692.

ACIDIFICATION PROCESS

The acidification process is carried out according to the procedure outlined in Example 14 in which the mixture is acidified to a pH of 4.9 to 5.0 by adding acetic acid in the form of 300 grain vinegar. The 300 grain vinegar is a product of Integrated Ingredients, Montebello, Calif.

HOMOGENIZATION PROCESS

The homogenization process is carried out by using a Moyno pump to force the heavy, vicious mayonnaise dressing through the inlet valves of the high pressure homogenizer. The stuffing pressure produced by the Moyno pump has to exceed 150 to 200 pounds per square inch to prevent implosion. Since the mayonnaise dressing at this point has a viscosity between 40,000 and 50,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer is used at a first stage pressure of 10,000 pounds per square inch and 1,500 pounds on the second stage.

The mayonnaise dressing is cooled and packaged as described in Example 14.

The chemical and microbiological analysis of this product is as follows:

| | |
|---|---|
| pH | 4.89 |
| FAT | 0.80% |
| SALT | 3.5% |
| STANDARD PLATE COUNT | <100 |
| COLI | <10 |
| YEAST/MOLD | 0/0 |

EXAMPLE 17 FAT FREE CHOLESTEROL FREE MAYONNAISE DRESSING

A stabilized fat substitute "SFS" mayonnaise dressing was produced by first forming a dispersion of deagglomerated denatured whey protein-casein coprecipitate in a continuous phase aqueous medium according to the procedure of Example 1. Ten pounds of sodium caseinate were added to 120 gallons of whey protein concentrate comprising approximately 14.15% solids and 6.59% protein. The mixture was heated by steam injection to 185 degrees F. and acidified to a pH of 5.6 to 5.65 by the addition of acetic acid in the form of vinegar. This resulted in the formation of a curd coprecipitate of whey protein and casein.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, mayonnaise dressing as described below.

The following components were incorporated with the fat substitute product produced as described above to prepare a mayonnaise dressing.

TABLE 1

| COMPONENTS | QUANTITY/POUND |
|---|---|
| Water | 8.0 |
| Alcolec 140 | 4.0 |
| Alcolec SFG | 1.0 |
| Water | 13.0 |
| Avicel RC591 | 5.0 |

STEP 1

The liposome and structure building formation was achieved in a similar manner to that set out in Example 1 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 1. The STEPHAN cooker was operated for 8 minutes at 120 degrees F. Thereafter, the STEPHAN cooker was opened and the liposomes made from the lecithin-water mixture were visually examined for the presence of undissolved particles and to insure complete dispersion. Upon confirmation that the mixture was uniformly dispersed and that liposomes were formed, a caramel cream-like appearance was observed. An additional 13 pounds of hydration water was added to the liposomes in the STEPHAN cooker together with 5 pounds of microcrystalline cellulose and mixed for approximately 10 minutes. The STEPHAN cooker was then opened and the liposome mixture was visually examined under a polarized light microscope for proper dispersion. Upon confirming that proper dispersion was achieved, the STEPHAN cooker was closed and the temperature raised to 180 degrees F. by steam injection with high speed agitation. Upon reaching 180 degrees F., the steam flow was terminated, the STEPHAN cooker was opened, and the mixture was transferred to a clean sterilized bucket and slowly added to the chopper. The pasteurized lecithin-microcrystalline cellulose complex was processed in the chopper for 10 minutes to form a membrane around the curd particles, to place amphoteric charges on the curd particles, and to create structure in the aqueous phase as described in Example 1.

STEP 2

A stabilizer was produced from the components in Table 2.

TABLE 2

| COMPONENTS | QUANTITY/POUND |
|---|---|
| Water | 26.00 |
| Slendid Pectin | 2.0 |
| Gelatin 250 Bloom | 0.5 |
| Calcium Chloride Solution | 20 mls. |

The stabilizer from Table 2 was prepared by adding SLENDID pectin to the 26 pounds of water in the STEPHAN cooker. The bottom agitator was set at high speed and the side agitator was turned on for 5 minutes. The STEPHAN cooker was then opened and the pectin dispersion was then inspected for complete dispersion. The 250 Bloom Gelatin was then added to the water-pectin dispersion. The ingredients were mixed in the STEPHAN cooker for 5 minutes at high speed (3,000 rpm) with no steam injection. The STEPHAN cooker was then opened and the calcium chloride solution was added and mixed for 2 minutes. The STEPHAN cooker was then opened and the contents subjected to tactile and visual examination as described in Example 1—STEPHAN Cooker Step 2. SLENDID pectin is a specialty processed pectin distributed by Hercules, Inc., Wilmington, Del. 19894-000 and manufactured by Copenhagen Pectin, DK 4623, Skensved, Denmark.

STEP 3

Additional microbial inhibitors, sugar, and salt were prepared in the STEPHAN cooker using the components from Table 3. These ingredients were added to those made in Step 2 above.

TABLE 3

| COMPONENTS | QUANTITY/POUND |
| --- | --- |
| Salt | 3.5 |
| Sugar | 2.0 |
| Alta 2331 | 0.5 |
| Alta 1801 | 0.5 |
| Alta 2001 | 0.5 |
| Alta 1705 | 0.5 |

The ingredients were mixed in the STEPHAN cooker for 2 minutes at high speed (3,000 rpm) The STEPHAN cooker was then opened and the contents subjected to tactile and visual examination as described in Example 1—STEPHAN Cooker Step 2.

STEP 4

The component in Table 4 was added to those in Step 3.

TABLE 4

| COMPONENTS | QUANTITY/POUND |
| --- | --- |
| ENRICH 221 | 6.0 |

The ingredients were mixed in the STEPHAN cooker for 2 minutes at high speed (3,000 rpm) The STEPHAN cooker was then opened and the contents subjected to tactile and visual examination as described in Example 1—STEPHAN Cooker Step 2. The ENRICH 221 is a natural microbial stabilizer available from Quest-Microlife Technics, Inc. of Sarasota, Fla., 34230.

STEP 5

The component in Table 5 was added to those in Step 4.

TABLE 5

| COMPONENT | QUANTITY/POUND |
| --- | --- |
| Non Fat Dry Milk Powder* | 4.0 |

*Non Fat Dry Milk powder is a product of Foster Farms Dairy, Modesto, CA 95351.

The ingredient was mixed in the STEPHAN cooker for 2 minutes at high speed (3,000 rpm). The STEPHAN cooker was then opened and the contents subjected to tactile and visual examination as described in Example 1—STEPHAN Cooker Step 2.

STEP 6

The components in Table 6 was added to those in Step 5.

TABLE 6

| COMPONENTS | QUANTITY/POUND |
| --- | --- |
| Parselli SA-2 | 6.0 |
| GP Maltodextrin 040 | 3.0 |
| Coleman's Mustard Flour | 3.0 |
| Corn Syrup 42 D.E. | 4.0 |

The ingredients were mixed in the STEPHAN cooker for 2 to 3 minutes at high speed (3,000 rpm). The STEPHAN cooker was then opened and the contents subjected to tactile and visual examination as described in Example 1—STEPHAN Cooker Step 2. When satisfactory results were achieved, i.e., even dispersion, the STEPHAN cooker was then closed and the temperature raised to 180 degrees F. by steam injection with high speed agitation. When the temperature reached 180 degrees F., agitation was ceased, steam flow was terminated, and the pressure released. The STEPHAN cooker was then opened and the contents were added slowly to the continually operating chopper. COLEMAN'S Mustard Flour is a product of the R. T. French Company of Rochester, N.Y. 14692.

ACIDIFICATION PROCESS

The acidification process was carried out according to the procedure outlined in Example 1 in which the mixture was acidified to a pH of 4.7 to 4.8 by adding acetic acid in the form of 300 grain vinegar. The 300 grain vinegar is a product of Integrated Ingredients, Montebello, Calif.

HOMOGENIZATION PROCESS

The homogenization process was carried out by using a Moyno pump to force the heavy, viscous mayonnaise dressing through the inlet valves of the high pressure homogenizer. The stuffing pressure produced by the Moyno pump has to exceed 150 to 200 pounds per square inch to prevent implosion. Since the mayonnaise dressing at this point has a viscosity between 40,000 and 50,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer was used at a first stage pressure of 10,000 pounds per square inch and 1,500 pounds on the second stage.

The mayonnaise dressing was cooled and packaged as described in Example 1.

The chemical and microbiological analysis of this product was as follows:

| | |
| --- | --- |
| pH | 4.92 |
| FAT | 0.72% |
| SALT | 3.5% |
| STANDARD PLATE COUNT | <100 |
| COLI | <10 |
| YEAST/MOLD | 0/0 |

EXAMPLE 18 FAT FREE CHOLESTEROL FREE MAYONNAISE DRESSING WHEY PROTEIN PRECIPITATE

A stabilized fat substitute "SFS" mayonnaise dressing was produced by first forming a dispersion of deagglomerated denatured whey protein precipitate in a continuous phase aqueous medium according to the procedure of Example 1. The whey protein concentrate was heated to 190 degrees F. The whey protein concentrate contained approximately 14.1% solids and 6.12% protein. The mixture was heated by steam injection to 185 degrees F. and acidified to a pH of 5.4 to 5.45 by the addition of acetic acid in the form of vinegar. This resulted in the formation of a curd precipitate of whey protein.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, mayonnaise dressing as described below.

The following components were incorporated with the fat substitute product produced as described above to prepare a mayonnaise dressing.

TABLE 1

| COMPONENTS | QUANTITY/POUND |
|---|---|
| Water | 8.0 |
| Alcolec 140 | 4.0 |
| Alcolec SFG | 1.0 |
| Water | 13.0 |
| Avicel RC591 | 5.0 |

STEP 1

The liposome and structure building formation was achieved in a similar manner to that set out in Example 1 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 1. The STEPHAN cooker was operated for 8 minutes at 120 degrees F. Thereafter, the STEPHAN cooker was opened and the liposomes made from the lecithin-water mixture were visually examined for the presence of undissolved particles and to insure complete dispersion. Upon confirmation that the mixture was uniformly dispersed and that liposomes were formed, a caramel cream-like appearance was observed. An additional 13 pounds of hydration water was added to the liposomes in the STEPHAN cooker together with 5 pounds of microcrystalline cellulose and mixed for approximately 10 minutes. The STEPHAN cooker was then opened and the liposome mixture was visually examined under a polarized light microscope for proper dispersion. Upon confirming that proper dispersion was achieved, the STEPHAN cooker was closed and the temperature raised to 180 degrees F. by steam injection with high speed agitation. Upon reaching 180 degrees F., the steam flow was terminated, the STEPHAN cooker was opened, and the mixture was transferred to a clean sterilized bucket and slowly added to the chopper. The pasteurized lecithin-microcrystalline cellulose complex was processed in the chopper for 10 minutes to form a membrane around the curd particles, to place amphoteric charges on the curd particles, and to create structure in the aqueous phase as described in Example 1.

STEP 2

A stabilizer was produced from the components in Table 2.

TABLE 2

| COMPONENTS | QUANTITY/POUND |
|---|---|
| Water | 26.00 |
| Slendid Pectin | 2.0 |
| Gelatin 250 Bloom | 0.5 |
| Calcium Chloride Solution | 20 mls. |

The stabilizer from Table 2 was prepared by adding SLENDID pectin to the 26 pounds of water in the STEPHAN cooker. The bottom agitator was set at high speed and the side agitator was turned on for 5 minutes. The STEPHAN cooker was then opened and the pectin dispersion was then inspected for complete dispersion. The 250 Bloom Gelatin was then added to the water-pectin dispersion. The ingredients were mixed in the STEPHAN cooker for 5 minutes at high speed (3,000 rpm) with no steam injection. The STEPHAN cooker was then opened and the calcium chloride solution was added and mixed for 2 minutes. The STEPHAN cooker was then opened and the contents subjected to tactile and visual examination as described in Example 1—STEPHAN Cooker Step 2. SLENDID pectin is a specialty processed pectin distributed by Hercules, Inc., Wilmington, Del. 19894-000 and manufactured by Copenhagen Pectin, DK 4623, Skensved, Denmark.

STEP 3

Additional microbial inhibitors, sugar, and salt were prepared in the STEPHAN cooker using the components from Table 3. These ingredients were added to those made in Step 2 above.

TABLE 3

| COMPONENTS | QUANTITY/POUND |
|---|---|
| Salt | 3.5 |
| Sugar | 2.0 |
| Alta 2331 | 0.5 |
| Alta 1801 | 0.5 |
| Alta 2001 | 0.5 |
| Alta 1705 | 0.5 |

The ingredients were mixed in the STEPHAN cooker for 2 minutes at high speed (3,000 rpm) The STEPHAN cooker was then opened and the contents subjected to tactile and visual examination as described in Example 1—STEPHAN Cooker Step 2.

STEP 4

The component in Table 4 was added to those in Step 3.

TABLE 4

| COMPONENTS | QUANTITY/POUND |
|---|---|
| Enrich 221 | 6.0 |

The ingredients were mixed in the STEPHAN cooker for 2 minutes at high speed (3,000 rpm) The STEPHAN cooker was then opened and the contents subjected to tactile and visual examination as described in Example 1—STEPHAN Cooker Step 2. The ENRICH 221 is a natural microbial stabilizer available from Quest-Microlife Technics, Inc. of Sarasota, Fla., 34230.

STEP 5

The component in Table 5 was added to those in Step 4.

TABLE 5

| COMPONENT | QUANTITY/POUND |
|---|---|
| Non Fat Dry Milk Powder* | 4.0 |

*Non Fat Dry Milk powder is a product of Foster Farms Dairy, Modesto, CA 95351.

The ingredient was mixed in the STEPHAN cooker for 2 minutes at high speed (3,000 rpm). The STEPHAN cooker was then opened and the contents subjected to tactile and visual examination as described in Example 1—STEPHAN Cooker Step 2.

STEP 6

The components in Table 6 was added to those in Step 5.

TABLE 6

| COMPONENTS | QUANTITY/POUND |
|---|---|
| Parselli SA-2 | 6.0 |
| GP Maltodextrin 040 | 3.0 |
| Coleman's Mustard Flour | 3.0 |
| Corn Syrup 42 D.E. | 4.0 |

The ingredients were mixed in the STEPHAN cooker for 2 to 3 minutes at high speed (3,000 rpm). The STEPHAN Cooker was then opened and the contents subjected to tactile and visual examination as described in Example 1—STEPHAN Cooker Step 2. When satisfactory results were achieved, i.e., even dispersion, the STEPHAN cooker was then closed and the temperature raised to 180 degrees F. by steam injection with high speed agitation. When the temperature reached 180 F., agitation was ceased, steam flow was terminated, and the pressure released. The STEPHAN cooker was then opened and the contents were added slowly to the continually operating chopper. COLEMAN'S Mustard Flour is a product of the R. T. French Company of Rochester, N.Y. 14692.

ACIDIFICATION PROCESS

The acidification process was carried out according to the procedure outlined in Example 1 in which the mixture was acidified to a pH of 4.7 to 4.80 by adding acetic acid in the form of 300 grain vinegar. The 300 grain vinegar is a product of Integrated Ingredients, Montebello, Calif.

HOMOGENIZATION PROCESS

The homogenization process was carried out by using a Moyno pump to force the heavy, vicious mayonnaise dressing through the inlet valves of the high pressure homogenizer. The stuffing pressure produced by the Moyno pump has to exceed 150 to 200 pounds per square inch to prevent implosion. Since the mayonnaise dressing at this point has a viscosity between 40,000 and 50,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer was used at a first stage pressure of 10,000 pounds per square inch and 1,500 pounds on the second stage.

The mayonnaise dressing was cooled and packaged as described in Example 1.

The chemical and microbiological analysis of this product was as follows:

| pH | 4.72 |
|---|---|
| FAT | 0.92% |
| SALT | 3.5% |
| STANDARD PLATE COUNT | <100 |
| COLI | <10 |
| YEAST/MOLD | 0/0 |

The mayonnaise dressing was then used as an ingredient in several household recipes that called for mayonnaise. The major brand of mayonnaise was used as the control in each of these recipes. The recipes were then evaluated by a consumer panel of housewife made up of employees of Cacique. The recipes were tuna salad, chicken salad, ham and cheese sandwiches, potato salad, and macaroni salad. The two mayonnaise dressings were considered compatible substitutes for the major brands with over half of the respondents finding no difference in the recipes containing the major brand and the recipes containing both of the mayonnaise dressings produced in Examples 17 and 18.

EXAMPLE 19 FAT FREE CHOLESTEROL FREE FAT SUBSTITUTE

A stabilized fat substitute "SFS" was produced by first forming a dispersion of deagglomerated denatured whey protein-casein coprecipitate in a continuous phase aqueous medium according to the procedure of Example 1. Ten pounds of sodium caseinate were added to 120 gallons of whey protein concentrate comprising approximately 14.45% solids and 6.64% protein. The mixture was heated by steam injection to 185 degrees F. and acidified to a pH of 5.6 to 5.65 by the addition of acetic acid in the form of vinegar. This resulted in the formation of a curd coprecipitate of whey protein and casein.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, fat substitute as described below.

The following components were incorporated with the fat substitute product produced as described above to prepare a fat substitute.

TABLE 1

| COMPONENTS | QUANTITY/POUND |
|---|---|
| Water | 8.0 |
| Alcolec 140 | 2.0 |
| Alcolec SFG | 1.0 |
| Water | 13.0 |
| Avicel RC591 | 5.0 |

STEP 1

The liposome and structure building formation was achieved in a similar manner to that set out in Example 1 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 1. The STEPHAN cooker was operated for 8 minutes at 120 degrees F. Thereafter, the STEPHAN cooker Was opened and the liposomes made from the lecithin-water mixture were visually examined for the presence of undissolved particles and to insure complete dispersion. Upon confirmation that the mixture was uniformly dispersed and that liposomes were formed, a caramel cream-like appearance was observed. An additional 13 pounds of hydration water was added to the liposomes in the STEPHAN cooker together with 5 pounds of microcrystalline cellulose and mixed for approximately 10 minutes. The STEPHAN cooker was then opened and the liposome mixture was visually examined under a polarized light microscope for proper dispersion. Upon confirming that proper dispersion was achieved, the STEPHAN cooker was closed and the temperature raised to 180 degrees F. by steam injection with high speed agitation. Upon reaching 180 degrees F., the steam flow was terminated, the STEPHAN cooker was opened, and the mixture was transferred to a clean sterilized bucket and slowly added to the chopper. The pasteurized lecithin-microcrystalline cellulose complex was processed in the chopper for 10 minutes to form a membrane around the curd particles, to place amphoteric charges on the curd particles, and to create structure in the aqueous phase as described in Example 1.

STEP 2

A stabilizer was produced from the components in Table 2.

TABLE 2

| COMPONENTS | QUANTITY/POUND |
|---|---|
| Water | 20.00 |
| Slendid Pectin | 2.0 |
| Genu Pectin | 0.5 |
| Calcium Chloride Solution | 20 mls. |

The stabilizer from Table 2 was prepared by adding SLENDID Pectin and the Genu pectin to the 20 pounds of water in the STEPHAN cooker. The bottom agitator was set at high speed and the side agitator was turned on for 5 minutes. The STEPHAN cooker was then opened and the pectin dispersion was then inspected for complete dispersion. The ingredients were mixed in the STEPHAN cooker for 5 minutes at high speed (3,000 rpm) with no steam injection. The STEPHAN cooker was then opened and the calcium chloride solution was added and mixed for 2 minutes. The STEPHAN cooker was then opened and the contents subjected to tactile and visual examination as described in Example 1—STEPHAN Cooker Step 2. SLENDID and GENU pectins are specialty processed pectins distributed by Hercules, Inc., Wilmington, Del. 19894-000.

STEP 3

Additional microbial inhibitors were prepared in the STEPHAN cooker using the components from Table 3. These ingredients were added to those made in Step 2 above.

TABLE 3

| COMPONENTS | QUANTITY/POUND |
|---|---|
| Alta 2331 | 0.5 |
| Alta 1801 | 0.5 |

TABLE 3-continued

| COMPONENTS | QUANTITY/POUND |
|---|---|
| Alta 2001 | 0.5 |
| Alta 1705 | 0.5 |

The ingredients were mixed in the STEPHAN cooker for 2 minutes at high speed (3,000 rpm). The STEPHAN cooker was then opened and the contents subjected to tactile and visual examination as described in Example 1—STEPHAN Cooker Step 2.

STEP 4

The component in Table 4 was added to those in Step 3.

TABLE 4

| COMPONENT | QUANTITY/POUND |
|---|---|
| Enrich 221 | 2.0 |

The ingredients were mixed in the STEPHAN cooker for 2 minutes at high speed (3,000 rpm). The STEPHAN cooker was then opened and the contents subjected to tactile and visual examination as described in Example 1—STEPHAN Cooker Step 2. The ENRICH 221 is a natural microbial stabilizer available from Quest-Microlife Technics, Inc. of Sarasota, Fla., 34230.

STEP 5

The component in Table 5 was added to those in Step 4.

TABLE 5

| COMPONENT | QUANTITY/POUND |
|---|---|
| Non Fat Dry Milk Powder | 3.0 |

The ingredient was mixed in the STEPHAN cooker for 2 minutes at high speed (3,000 rpm). The STEPHAN cooker was then opened and the contents subjected to tactile and visual examination as described in Example 1—STEPHAN Cooker Step 2. Non Fat Dry Milk powder is a product of Foster Farms Dairy, Modesto, Calif. 95351.

STEP 6

The components in Table 6 was added to those in Step 5.

TABLE 6

| COMPONENTS | QUANTITY/POUND |
|---|---|
| Parselli SA-2 | 2.0 |
| GP Maltodextrin 040 | 2.0 |

The ingredients were mixed in the STEPHAN cooker for 2 to 3 minutes at high speed (3,000 rpm). The STEPHAN cooker was then opened and the contents subjected to tactile and visual examination as described in Example 1—STEPHAN Cooker Step 2. When satisfactory results were achieved, i.e., even dispersion, the STEPHAN cooker was then closed and the temperature raised to 180 degrees F. by steam injection with high speed agitation. When the temperature reached 180 F., agitation was ceased, steam flow was terminated, and the pressure released. The STEPHAN cooker was then opened and the contents were added slowly to the continually operating chopper.

HOMOGENIZATION PROCESS

The homogenization process was carried out by using a Moyno pump to force the heavy, viscous fat substitute through the inlet valves of the high pressure homogenizer. The stuffing pressure produced by the Moyno pump has to exceed 150 to 200 pounds per square inch to prevent implosion. Since the fat substitute at this point has a viscosity between 35,000 and 45,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer was used at a first stage pressure of 10,000 pounds per square inch and 1,500 pounds on the second stage.

The fat substitute was cooled and packaged as described in Example 1.

The chemical and microbiological analysis of this product was as follows:

| | |
|---|---|
| pH | 5.85 |
| FAT | 0.98% |
| SALT | 1.5% |
| STANDARD PLATE COUNT | <100 |
| COLI | <10 |
| YEAST/MOLD | 0/0 |

The fat substitute was held for 90 days at refrigerated temperatures and analysis was preformed for Standard Plate Count and for the appearance of grainey or rough mouthfeel or chalkiness. The SPC had increased to less than 1,000 CFU and the fat substitute did not have any indication of degradation of the fat-like mouthfeel.

EXAMPLE 20 FAT FREE CHOLESTEROL FREE FAT SUBSTITUTE

A stabilized fat substitute "SFS" was produced by first forming a dispersion of deagglomerated denatured whey protein-casein coprecipitate in a continuous phase aqueous medium according to the procedure of Example 1. Ten pounds of sodium caseinate were added to 120 gallons of whey protein concentrate comprising approximately 14.32% solids and 6.41% protein. The mixture was heated by steam injection to 185 degrees F. and acidified to a pH of 5.6 to 5.65 by the addition of acetic acid in the form of vinegar. This resulted in the formation of a curd coprecipitate of whey protein and casein.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, fat substitute as described below.

The following components were incorporated with the fat substitute product produced as described above to prepare a fat substitute.

TABLE 1

| COMPONENTS | QUANTITY/POUND |
|---|---|
| Water | 8.0 |
| Alcolec 140 | 2.0 |
| Alcolec SFG | 1.0 |
| Water | 13.0 |
| Avicel RC591 | 5.0 |

STEP 1

The liposome and structure building formation was achieved in a similar manner to that set out in Example 1 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 1. The STEPHAN cooker was operated for 8 minutes at 120 degrees F. Thereafter, the STEPHAN cooker was opened and the liposomes made from the lecithin-water mixture were visually examined for the presence of undissolved particles and to insure complete dispersion. Upon confirmation that the mixture was uniformly dispersed and that liposomes were formed, a caramel cream-like appearance was observed. An additional 13 pounds of hydration water was added to the liposomes in the STEPHAN cooker together with 5 pounds of microcrystalline cellulose and mixed for approximately 10 minutes. The STEPHAN cooker was then opened and the liposome mixture was visually examined under a polarized light microscope for proper dispersion. Upon confirming that proper dispersion was achieved, the STEPHAN cooker was closed and the temperature raised to 180 degrees F. by steam injection with high speed agitation. Upon reaching 180 degrees F., the steam flow was terminated, the STEPHAN cooker was opened, and the mixture was transferred to a clean sterilized bucket and slowly added to the chopper. The pasteurized lecithin-microcrystalline cellulose complex was processed in the chopper for 10 minutes to form a membrane around the curd particles, to place amphoteric charges on the curd particles, and to create structure in the aqueous phase as described in Example 1.

STEP 2

A stabilizer was produced from the components in Table 2.

TABLE 2

| COMPONENTS | QUANTITY/POUND |
|---|---|
| Water | 20.00 |
| Slendid Pectin | 2.0 |
| Genu Pectin | 0.5 |
| Calcium Chloride Solution | 20 mls. |

The stabilizer from Table 2 was prepared by adding SLENDID Pectin and the GENU pectin to the 20 pounds of water in the STEPHAN cooker. The bottom agitator was set at high speed and the side agitator was turned on for 5 minutes. The STEPHAN cooker was then opened and the pectin dispersion was then inspected for complete dispersion. The ingredients were mixed in the STEPHAN cooker for 5 minutes at high speed (3,000 rpm) with no steam injection. The STEPHAN cooker was then opened and the calcium chloride solution was added and mixed for 2 minutes. The STEPHAN cooker was then opened and the contents subjected to tactile and visual examination as described in Example 1—Stephan Cooker Step 2. SLENDID and GENU pectins are specialty processed pectins distributed by Hercules, Inc., Wilmington, Del. 19894-000.

STEP 5

Additional microbial inhibitors were prepared in the STEPHAN cooker using the components from Table 3. These ingredients were added to those made in Step 2 above.

TABLE 3

| COMPONENTS | QUANTITY/POUND |
|---|---|
| Alta 2331 | 0.5 |
| Alta 1801 | 0.5 |
| Alta 2001 | 0.5 |
| Alta 1705 | 0.5 |

The ingredients were mixed in the STEPHAN cooker for 2 minutes at high speed (3,000 rpm) The STEPHAN cooker was then opened and the contents subjected to tactile and visual examination as described in Example 1—STEPHAN Cooker Step 2.

STEP 4

The component in Table 4 was added to those in Step 3.

TABLE 4

| COMPONENT | QUANTITY/POUND |
|---|---|
| Non Fat Dry Milk Powder* | 3.0 |

*Non Fat Dry Milk powder is a product of Foster Farms Dairy, Modesto, CA 95351.

The non fat milk powder was mixed in the STEPHAN cooker for 2 minutes at high speed (3,000 rpm). The STEPHAN cooker was then opened and the contents subjected to tactile and visual examination as described in Example 1—STEPHAN Cooker Step 2.

The ingredients were mixed in the STEPHAN cooker for 2 to 3 minutes at high speed (3,000 rpm). The STEPHAN cooker was then opened and the contents subjected to tactile and visual examination as described in Example 1—STEPHAN Cooker Step 2. When satisfactory results were achieved, i.e., even dispersion, the STEPHAN cooker was then closed and the temperature raised to 180 degrees F. by steam injection with high speed agitation. When the temperature reached 180° F., agitation was ceased, steam flow was terminated, and the pressure released. The STEPHAN cooker was then opened and the contents were added slowly to the continually operating chopper.

HOMOGENIZATION PROCESS

The homogenization process was carried out by using a Moyno pump to force the heavy, viscous fat substitute through the inlet valves of the high pressure homogenizer. The stuffing pressure produced by the Moyno pump has to exceed 150 to 200 pounds per square inch to prevent implosion. Since the fat substitute at this point has a viscosity between 35,000 and 45,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer was used at a first stage pressure of 10,000 pounds per square inch and 1,500 pounds on the second stage.

The fat substitute was cooled and packaged as described in Example 1.

The chemical and microbiological analysis of this product was as follows:

| pH | 5.85 |
|---|---|
| FAT | 0.85% |
| SALT | 1.65% |
| STANDARD PLATE COUNT | <100 |
| COLI | <10 |
| YEAST/MOLD | 0/0 |

The fat substitute was held for 90 days at refrigerated temperatures and analysis was preformed for Standard Plate Count and for the appearance of grainey or rough mouthfeel or chalkiness. The SPC had increased to less than 1,000 CFU and the fat substitute did not have any indication of degradation of the fat-like mouthfeel.

EXAMPLE 21 FAT FREE CHOLESTEROL FREE FAT SUBSTITUTE

A stabilized fat substitute "SFS" was produced by first forming a dispersion of deagglomerated denatured whey protein-casein coprecipitate in a continuous phase aqueous medium according to the procedure of Example 1. Ten pounds of sodium caseinate were added to 120 gallons of whey protein concentrate comprising approximately 14.46% solids and 6.26% protein. The mixture was heated by steam injection to 185 degrees F. and acidified to a pH of 5.6 to 5.65 by the addition of acetic acid in the form of vinegar. This resulted in the formation of a curd coprecipitate of whey protein and casein.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, fat substitute as described below.

The following components were incorporated with the fat substitute product produced as described above to prepare a fat substitute.

TABLE 1

| COMPONENTS | QUANTITY/POUND |
|---|---|
| Water | 8.0 |
| Alcolec 140 | 2.0 |
| Alcolec SFG | 1.0 |
| Water | 13.0 |
| Avicel RC591 | 5.0 |

STEP 1

The liposome and structure building formation was achieved in a similar manner to that set out in Example 1 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 1. The STEPHAN cooker was operated for 8 minutes at 120 degrees F. Thereafter, the STEPHAN cooker was opened and the liposomes made from the lecithin-water mixture were visually examined for the presence of undissolved particles and to insure complete dispersion. Upon confirmation that the mixture was uniformly dispersed and that liposomes were formed, a caramel cream-like appearance was observed. An additional 13 pounds of hydration water was added to the liposomes in the STEPHAN cooker together with 5 pounds of microcrystalline cellulose and mixed for approximately 10 minutes. The STEPHAN cooker was then opened and the liposome mixture was visually examined under a polarized light microscope for proper dispersion. Upon confirming that proper dispersion was achieved, the STEPHAN cooker was closed and the temperature raised to 180 degrees F. by steam injection with high speed agitation. Upon reaching 180 degrees F., the steam flow was terminated, the STEPHAN cooker was opened, and the mixture was transferred to a clean sterilized bucket and slowly added to the chopper. The pasteurized lecithin-microcrystalline cellulose complex was processed in the chopper for 10 minutes to form a membrane around the curd particles, to place amphoteric charges on the curd particles, and to create structure in the aqueous phase as described in Example 1.

STEP 2

A stabilizer was produced from the components in Table 2.

TABLE 2

| COMPONENTS | QUANTITY/POUND |
|---|---|
| Water | 15.00 |
| Slendid Pectin | 2.0 |
| Genu Pectin | 0.5 |
| Calcium Chloride Solution | 20 mls. |

The stabilizer from Table 2 was prepared by adding SLENDID pectin and the GENU pectin to the 15 pounds of water in the STEPHAN cooker. The bottom agitator was set at high speed and the side agitator was turned on for 5 minutes. The STEPHAN cooker was then opened and the pectin dispersion was then inspected for complete dispersion. The ingredients were mixed in the STEPHAN cooker for 5 minutes at high speed (3,000 rpm) with no steam injection. The STEPHAN cooker was then opened and the calcium chloride solution was added and mixed for 2 minutes. The STEPHAN cooker was then opened and the contents subjected to tactile and visual examination as described in Example 1—STEPHAN Cooker Step 2. SLENDID and GENU pectins are specialty processed pectins distributed by Hercules, Inc., Wilmington, Del. 19894-000.

STEP 3

Additional microbial inhibitors were prepared in the STEPHAN cooker using the components from Table 3. These ingredients were added to those made in Step 2 above.

TABLE 3

| COMPONENTS | QUANTITY/POUND |
|---|---|
| Alta 2331 | 0.5 |
| Alta 1801 | 0.5 |
| Alta 2001 | 0.5 |
| Alta 1705 | 0.5 |

The ingredients were mixed in the STEPHAN cooker for 2 minutes at high speed (3,000 rpm) The STEPHAN cooker was then opened and the contents subjected to tactile and visual examination as described in Example 1—STEPHAN Cooker Step 2.

The ingredients were mixed in the STEPHAN cooker for 2 to 3 minutes at high speed (3,000 rpm). The STEPHAN cooker was then opened and the contents subjected to tactile and visual examination as described in Example 1—STEPHAN Cooker Step 2. When satisfactory results were achieved, i.e., even dispersion, the STEPHAN cooker was then closed and the temperature raised to 180° F. by steam injection with high speed agitation. When the temperature reached 180° F., agitation was ceased, steam flow was terminated, and the pressure released. The STEPHAN cooker was then opened and the contents were added slowly to the continually operating chopper.

HOMOGENIZATION PROCESS

The homogenization process was carried out by using a Moyno pump to force the heavy, viscous fat substitute through the inlet valves of the high pressure homogenizer. The stuffing pressure produced by the Moyno pump has to exceed 150 to 200 pounds per square inch to prevent implosion. Since the fat substitute at this point has a viscosity between 35,000 and 45,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer was used at a first stage pressure of 10,000 pounds per square inch and 1,500 pounds on the second stage.

The fat substitute was cooled and packaged as described in Example 1.

The chemical and microbiological analysis of this product was as follows:

| | |
|---|---|
| pH | 5.72 |
| FAT | 0.85% |
| SALT | 1.65% |
| STANDARD PLATE COUNT | <100 |
| COLI | <10 |
| YEAST/MOLD | 0/0 |

The fat substitute was held for 90 days at refrigerated temperatures and analysis was performed for Standard Plate Count and for the appearance of grainey or rough mouthfeel or chalkiness. The SPC had increased to less than 1,000 CFU. The fat substitute did not have any indication of degradation of the fat-like mouthfeel until 60 days had passed. It was concluded that the non fat milk solids contributed to the stability of the fat substitute. This is more than likely due to the fact that the non fat milk solids contribute casein to the surface of the membrane and make it thicker, thereby giving the fat substitute greater stability. The charges upon the particles are increased due to the hydration of the casein attached to the membrane. This not only increases the size of the membrane by swelling the casein by hydration due the heat of pasteurization in the STEPHAN cooker, but gives the particle more hydrophilic properties.

EXAMPLE 22 FAT FREE CHOLESTEROL FREE FAT SUBSTITUTE

A stabilized fat substitute "SFS" was produced by first forming a dispersion of deagglomerated denatured whey protein-casein coprecipitate in a continuous phase aqueous medium according to the procedure of Example 1. Ten pounds of sodium caseinate were added to 120 gallons of whey protein concentrate comprising approximately 14.24% solids and 6.38% protein. The mixture was heated by steam injection to 185 degrees F. and acidified to a pH of 5.6 to 5.65 by the addition of acetic acid in the form of vinegar. This resulted in the formation of a curd coprecipitate of whey protein and casein.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, fat substitute as described below.

The following components were incorporated with the fat substitute product produced as described above to prepare a fat substitute.

TABLE 1

| COMPONENTS | QUANTITY/POUND |
| --- | --- |
| Water | 8.0 |
| Alcolec 140 | 2.0 |
| Alcolec SFG | 1.0 |
| Water | 13.0 |
| Avicel RC591 | 5.0 |

STEP 1

The liposome and structure building formation was achieved in a similar manner to that set out in Example 1 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 1. The STEPHAN cooker was operated for 8 minutes at 120 degrees F. Thereafter, the STEPHAN cooker was opened and the liposomes made from the lecithin-water mixture were visually examined for the presence of undissolved particles and to insure complete dispersion. Upon confirmation that the mixture was uniformly dispersed and that liposomes were formed, a caramel cream-like appearance was observed. An additional 13 pounds of hydration water was added to the liposomes in the STEPHAN cooker together with 5 pounds of microcrystalline cellulose and mixed for approximately 10 minutes. The STEPHAN cooker was then opened and the liposome mixture was visually examined under a polarized light microscope for proper dispersion. Upon confirming that proper dispersion was achieved, the STEPHAN cooker was closed and the temperature raised to 180 degrees F. by steam injection with high speed agitation. Upon reaching 180 degrees F., the steam flow was terminated, the STEPHAN cooker was opened, and the mixture was transferred to a clean sterilized bucket and slowly added to the chopper. The pasteurized lecithin-microcrystalline cellulose complex was processed in the chopper for 10 minutes to form a membrane around the curd particles, to place amphoteric charges on the curd particles, and to create structure in the aqueous phase as described in Example 1.

STEP 2

A stabilizer was produced from the components in Table 2.

TABLE 2

| COMPONENTS | QUANTITY/POUND |
| --- | --- |
| Water | 15.00 |
| Slendid Pectin | 2.0 |
| Genu Pectin | 0.5 |
| Calcium Chloride Solution | 20 mls. |

The stabilizer from Table 2 was prepared by adding SLENDID pectin and the GENU pectin to the 15 pounds of water in the STEPHAN cooker. The bottom agitator was set at high speed and the side agitator was turned on for 5 minutes. The STEPHAN cooker was then opened and the pectin dispersion was then inspected for complete dispersion. The ingredients were mixed in the STEPHAN cooker for 5 minutes at high speed (3,000 rpm) with no steam injection. The STEPHAN cooker was then opened and the calcium chloride solution was added and mixed for 2 minutes. The STEPHAN cooker was then opened and the contents subjected to tactile and visual examination as described in Example 1—STEPHAN Cooker Step 2. SLENDID and GENU pectins are specialty processed pectins distributed by Hercules, Inc., Wilmington, Del. 19894-000.

STEP 3

Additional microbial inhibitors were prepared in the STEPHAN cooker using the components from Table 3. These ingredients were added to those made in Step 2 above.

TABLE 3

| COMPONENTS | QUANTITY/POUND |
| --- | --- |
| Alta 2331 | 0.5 |
| Alta 1801 | 0.5 |
| Alta 2001 | 0.5 |
| Alta 1705 | 0.5 |

The ingredients were mixed in the STEPHAN cooker for 2 to 3 minutes at high speed (3,000 rpm). The STEPHAN cooker was then opened and the contents subjected to tactile and visual examination as described in Example 1—STEPHAN Cooker Step 2. When satisfactory results were achieved, i.e., even dispersion, the STEPHAN cooker was then closed and the temperature raised to 180 degrees F. by steam injection with high speed agitation. When the temperature reached 180° F., agitation was ceased, steam flow was terminated, and the pressure released. The STEPHAN cooker was then opened and the contents were added slowly to the continually operating chopper.

HOMOGENIZATION PROCESS

The homogenization process was carried out by using a Moyno pump to force the heavy, viscous fat substitute through the inlet valves of the high pressure homogenizer. The stuffing pressure produced by the Moyno pump has to exceed 150 to 200 pounds per square inch to prevent implosion. Since the fat substitute at this point has a viscosity between 35,000 and 45,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer was used at a first stage pressure of 10,000 pounds per square inch and 1,500 pounds on the second stage.

The fat substitute was cooled and packaged as described in Example 1.

The chemical and microbiological analysis of this product was as follows:

| | |
|---|---|
| pH | 5.72 |
| FAT | 0.85% |
| SALT | 1.65% |
| STANDARD PLATE COUNT | <100 |
| COLI | <10 |
| YEAST/MOLD | 0/0 |

The fat substitute was held for 90 days at refrigerated temperatures and analysis was preformed for Standard Plate Count and for the appearance of grainy or rough mouthfeel or chalkiness. The SPC had increased to less than 1,000 CFU. The fat substitute did not have any indication of degradation of the fat-like mouthfeel until 60 days had passed. It was concluded that the non fat milk solids contributed to the stability of the fat substitute. This is more than likely due to the fact that the non fat milk solids contribute casein to the surface of the membrane and make it thicker, thereby giving the fat substitute greater stability. The charges upon the particles are increased due to the hydration of the casein attached to the membrane. This not only increases the size of the membrane by swelling the casein by hydration due the heat of pasteurization in the STEPHAN cooker, but gives the particle more hydrophilic properties.

EXAMPLE 23 FAT FREE CHOLESTEROL FREE FAT SUBSTITUTE

A stabilized fat substitute "SFS" was produced by first forming a dispersion of deagglomerated denatured whey protein-casein coprecipitate in a continuous phase aqueous medium according to the procedure of Example 1. Ten pounds of sodium caseinate were added to 120 gallons of whey protein concentrate comprising approximately 14.67% solids and 6.54 protein. The mixture was heated by steam injection to 185 degrees F. and acidified to a pH of 5.6 to 5.65 by the addition of acetic acid in the form of vinegar. This resulted in the formation of a curd coprecipitate of whey protein and casein.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, fat substitute as described below.

The following components were incorporated with the fat substitute product produced as described above to prepare a fat substitute.

STEP 1

TABLE 1

| COMPONENTS | QUANTITY/POUND |
|---|---|
| Water | 8.0 |
| Alcolec 140 | 2.0 |
| Alcolec SFG | 1.0 |
| Water | 5.0 |

The liposome and structure building formation was achieved in a similar manner to that set out in Example 1 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 1. The STEPHAN cooker was operated for 8 minutes at 120 degrees F. Thereafter, the STEPHAN cooker was opened and the liposomes made from the lecithin-water mixture were visually examined for the presence of undissolved particles and to insure complete dispersion. Upon confirmation that the mixture was uniformly dispersed and that liposomes were formed, a caramel cream-like appearance was observed. An additional 5 pounds of hydration water was added to the liposomes in the STEPHAN cooker and mixed for approximately 10 minutes. The STEPHAN cooker was then opened and the liposome mixture was visually examined under a polarized light microscope for proper dispersion. Upon confirming that proper dispersion was achieved, the STEPHAN cooker was closed and the temperature raised to 180 degrees F. by steam injection with high speed agitation. Upon reaching 180 degrees F., the steam flow was terminated, the STEPHAN cooker was opened, and the mixture was transferred to a clean sterilized bucket and slowly added to the chopper. The pasteurized lecithin-water liposome complex was processed in the chopper for 10 minutes to form a membrane around the curd particles, to place amphoteric charges on the curd particles, and to create structure in the aqueous phase as described in Example 1.

STEP 2

A stabilizer was produced from the components in Table 2.

TABLE 2

| COMPONENTS | QUANTITY/POUND |
|---|---|
| Water | 15.00 |
| Slendid Pectin | 2.0 |
| Genu Pectin | 0.5 |
| Calcium Chloride Solution | 20 mls. |

The stabilizer from Table 2 was prepared by adding Slendid Pectin and the Genu pectin to the 15 pounds of water in the STEPHAN cooker. The bottom agitator was set at high speed and the side agitator was turned on for 5 minutes. The STEPHAN cooker was then opened and the pectin dispersion was then inspected for complete dispersion. The ingredients were mixed in the STEPHAN cooker for 5 minutes at high speed (3,000 rpm) with no steam injection. The STEPHAN cooker was then opened and the calcium chloride solution was added and mixed for 2 minutes. The STEPHAN cooker was then opened and the contents subjected to tactile and visual examination as described in Example 1—Stephan Cooker Step 2. SLENDID and GENU pectins are specialty processed pectins distributed by Hercules, Inc., Wilmington, Del. 19894-000.

STEP 3

Additional microbial inhibitorst were prepared in the STEPHAN cooker using the components from Table 3. These ingredients were added to those made in Step 2 above.

TABLE 3

| COMPONENTS | QUANTITY/POUND |
|---|---|
| Alta 2331 | 0.5 |
| Alta 1801 | 0.5 |

TABLE 3-continued

| COMPONENTS | QUANTITY/POUND |
| --- | --- |
| Alta 2001 | 0.5 |
| Alta 1705 | 0.5 |

The ingredients were mixed in the STEPHAN cooker for 2 to 3 minutes at high speed (3,000 rpm). The STEPHAN cooker was then opened and the contents subjected to tactile and visual examination as described in Example 1—STEPHAN Cooker Step 2. When satisfactory results were achieved, i.e., even dispersion, the STEPHAN cooker was then closed and the temperature raised to 180 degrees F. by steam injection with high speed agitation. When the temperature reached 180° F., agitation was ceased, steam flow was terminated, and the pressure released. The STEPHAN cooker was then opened and the contents were added slowly to the continually operating chopper.

HOMOGENIZATION PROCESS

The homogenization process was carried out by using a Moyno pump to force the heavy, viscous fat substitute through the inlet valves of the high pressure homogenizer. The stuffing pressure produced by the Moyno pump has to exceed 150 to 200 pounds per square inch to prevent implosion. Since the fat substitute at this point has a viscosity between 35,000 and 45,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer was used at a first stage pressure of 10,000 pounds per square inch and 1,500 pounds on the second stage.

The fat substitute was cooled and packaged as described in Example 1.

The chemical and microbiological analysis of this product was as follows:

| | |
| --- | --- |
| pH | 5.76 |
| FAT | 0.98% |
| SALT | 1.46% |
| STANDARD PLATE COUNT | <100 |
| COLI | <10 |
| YEAST/MOLD | 0/0 |

The fat substitute was held for 90 days at refrigerated temperatures and analysis was preformed for Standard Plate Count and for the appearance of grainey or rough mouthfeel or chalkiness. The SPC had increased to less than 1,000 CFU. The fat substitute did not have any indication of degradation of the fat-like mouthfeel until 30 days had passed. It was concluded that the non fat milk solids and the microcrystaline cellulose contributed to the significantly to the stability of the fat substitute. This is more than likely due to the fact that the non fat milk solids contribute casein to the surface of the membrane and make it thicker, thereby giving the fat substitute greater stability. The charges on the particles are believed to be increased due to the hydration of the casein attached to the membrane. This, it is believed, not only increases the size of the membrane by swelling the casein by hydration due the heat of pasteurization in the STEPHAN cooker, but gives the particle more hydrophilic properties.

EXAMPLE 24 FAT FREE CHOLESTEROL FREE FAT SUBSTITUTE

A stabilized fat substitute "SFS" was produced by first forming a dispersion of deagglomerated denatured whey protein-casein coprecipitate in a continuous phase aqueous medium according to the procedure of Example 1. Ten pounds of sodium caseinate were added to 120 gallons of whey protein concentrate comprising approximately 14.72% solids and 6.43 protein. The mixture was heated by steam injection to 185 degrees F. and acidified to a pH of 5.6 to 5.65 by the addition of acetic acid in the form of vinegar. This resulted in the formation of a curd coprecipitate of whey protein and casein.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, fat substitute as described below.

The following components were incorporated with the fat substitute product produced as described above to prepare a fat substitute.

STEP 1
TABLE 1

| COMPONENTS | QUANTITY/POUND |
| --- | --- |
| Water | 8.0 |
| Alcolec 140 | 2.0 |
| Alcolec SFG | 1.0 |
| Water | 5.0 |

The liposome and structure building formation was achieved in a similar manner to that set out in Example 1 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 1. The STEPHAN cooker was operated for 8 minutes at 120 degrees F. Thereafter, the STEPHAN cooker was opened and the liposomes made from the lecithin-water mixture were visually examined for the presence of undissolved particles and to insure complete dispersion. Upon confirmation that the mixture was uniformly dispersed and that liposomes were formed, a caramel cream-like appearance was observed. An additional 5 pounds of hydration water was added to the liposomes in the STEPHAN cooker and mixed for approximately 10 minutes. The STEPHAN cooker was then opened and the liposome mixture was visually examined under a polarized light microscope for proper dispersion. Upon confirming that proper dispersion was achieved, the STEPHAN cooker was closed and the temperature raised to 180 degrees F. by steam injection with high speed agitation. Upon reaching 180 degrees F., the steam flow was terminated, the STEPHAN cooker was opened, and the mixture was transferred to a clean sterilized bucket and slowly added to the chopper. The pasteurized lecithin-water liposome complex was processed in the chopper for 10 minutes to form a membrane around the curd particles, to place amphoteric charges on the curd particles, and to create structure in the aqueous phase as described in Example 1.

STEP 2

A stabilizer was produced from the components in Table 2.

TABLE 2

| COMPONENTS | QUANTITY/POUND |
| --- | --- |
| Water | 15.00 |
| Slendid Pectin | 2.0 |
| Genu Pectin | 0.5 |
| Calcium Chloride Solution | 20 mls. |

The stabilizer from Table 2 was prepared by adding SLENDID pectin and the GENU pectin to the 15 pounds of water in the STEPHAN cooker. The bottom agitator was set at high speed and the side agitator was turned on for 5 minutes. The STEPHAN cooker was then opened and the pectin dispersion was then inspected for complete dispersion. The ingredients were mixed in the STEPHAN cooker for 5 minutes at high speed (3,000 rpm) with no steam injection. The STEPHAN cooker was then opened and the calcium chloride solution was added and mixed for 2 minutes. The STEPHAN cooker was then opened and the contents subjected to tactile and visual examination as described in Example 1—STEPHAN Cooker Step 2. When satisfactory results were achieved, i.e., even dispersion, the STEPHAN cooker was then closed and the temperature raised to 180 degrees F. by steam injection with high speed agitation. When the temperature reached 180 degree F., agitation was ceased, steam flow was terminated, and the pressure released. The STEPHAN cooker was then opened and the contents were added slowly to the continually operating chopper.

HOMOGENIZATION PROCESS

The homogenization process was carried out by using a Moyno pump to force the heavy, viscous fat substitute through the inlet valves of the high pressure homogenizer. The stuffing pressure produced by the Moyno pump has to exceed 150 to 200 pounds per square inch to prevent implosion. Since the fat substitute at this point has a viscosity between 35,000 and 45,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer was used at a first stage pressure of 10,000 pounds per square inch and 1,500 pounds on the second stage.

The fat substitute was cooled and packaged as described in Example 1.

The chemical and microbiological analysis of this product was as follows:

| pH | 5.76 |
| --- | --- |
| FAT | 0.98% |
| SALT | 1.46% |
| STANDARD PLATE COUNT | <100 |
| COLI | <10 |
| YEAST/MOLD | 0/0 |

The fat substitute was held for 30 days at refrigerated temperatures and analysis was preformed for Standard Plate Count and for the appearance of grainey or rough mouthfeel or chalkiness. The SPC had increased to less than 50,000 CFU. The fat substitute did not have any indication of degradation of the fat-like mouthfeel until 30 days had passed. It was concluded that the non fat milk solids and the microcrystaline cellulose contributed to the significantly to the stability of the fat substitute. This is more than likely due to the fact that the non fat milk solids contribute casein to the surface of the membrane and make it thicker, thereby giving the fat substitute greater stability. The charges on the particles are believed increased due to the hydration of the casein attached to the membrane. This, it is believed, not only increases the size of the membrane by swelling the casein by hydration due the heat of pasteurization in the STEPHAN cooker, but gives the particle more hydrophilic properties.

EXAMPLE 25 FAT FREE CHOLESTEROL FREE FAT SUBSTITUTE

A stabilized fat substitute "SFS" was produced by first forming a dispersion of deagglomerated denatured whey protein-casein coprecipitate in a continuous phase aqueous medium according to the procedure of Example 1. Ten pounds of sodium caseinate were added to 120 gallons of whey protein concentrate comprising approximately 14.61% solids and 6.58 protein. The mixture was heated by steam injection to 185 degrees F. and acidified to a pH of 5.6 to 5.65 by the addition of acetic acid in the form of vinegar. This resulted in the formation of a curd coprecipitate of whey protein and casein.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, fat substitute as described below.

The following components were incorporated with the fat substitute product produced as described above to prepare a fat substitute.

STEP 1
TABLE 1

| COMPONENTS | QUANTITY/POUND |
| --- | --- |
| Water | 8.0 |
| Alcolec 140 | 2.0 |
| Alcolec SFG | 1.0 |
| Water | 5.0 |

The liposome and structure building formation was achieved in a similar manner to that set out in Example 1 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 1. The STEPHAN cooker was operated for 8 minutes at 120 degrees F. Thereafter, the STEPHAN cooker was opened and the liposomes made from the lecithin-water mixture were visually examined for the presence of undissolved particles and to insure complete dispersion. Upon confirmation that the mixture was uniformly dispersed and that liposomes were formed, a caramel cream-like appearance was observed. An additional 5 pounds of hydration water was added to the liposomes in the STEPHAN cooker and mixed for approximately 10 minutes. The STEPHAN cooker was then opened and the liposome mixture was visually examined under a polarized light microscope for proper dispersion. Upon confirming that proper dispersion was achieved, the STEPHAN cooker was closed and the temperature raised to 180 degrees F. by steam injection with high speed agitation. Upon reaching 180 degrees F., the steam flow was terminated, the STEPHAN cooker was opened, and the mixture was transferred to a clean sterilized bucket and slowly added to the chopper. The pasteurized lecithin-water liposome complex was processed in the chopper for 10 minutes to form a membrane around the curd particles, to place amphoteric charges on the curd particles, and to create structure in the aqueous phase as described in Example 1.

HOMOGENIZATION PROCESS

The homogenization process was carried out by using a Moyno pump to force the heavy, viscous fat substitute through the inlet valves of the high pressure homogenizer. The stuffing pressure produced by the Moyno pump has to exceed 150 to 200 pounds per square inch to prevent implosion. Since the fat substitute at this point has a viscosity between 35,000 and 45,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer was used at a first stage pressure of 10,000 pounds per square inch and 1,500 pounds on the second stage.

The fat substitute was cooled and packaged as described in Example 1.

The chemical and microbiological analysis of this product was as follows:

| | |
|---|---|
| pH | 5.76 |
| FAT | 0.98% |
| SALT | 1.46% |
| STANDARD PLATE COUNT | <100 |
| COLI | <10 |
| YEAST/MOLD | 0/0 |

The fat substitute was held for 30 days at refrigerated temperatures and analysis was preformed for Standard Plate Count and for the appearance of grainey or rough mouthfeel or chalkiness. The SPC had increased to less than 50,000 CFU. The fat substitute did not have any indication of degradation of the fat-like mouthfeel until 30 days had passed. It was concluded that the non fat milk solids and the microcrystaline cellulose contributed to the significantly to the stability of the fat substitute. This is more than likely due to the fact that the non fat milk solids contribute casein to the surface of the membrane and make it thicker, thereby giving the fat substitute greater stability. The charges on the particles are believed increased due to the hydration of the casein attached to the membrane. This, it is believed, not only increases the size of the membrane by swelling the casein by hydration due the heat of pasteurization in the STEPHAN cooker, but gives the particle more hydrophilic properties.

EXAMPLE 26 LECITHIN BASE FOR FAT FREE CHOLESTEROL FREE FAT SUBSTITUTE PRODUCTS

A lecithin base for stabilized fat substitute "SFS" was produced by first dispersing the lecithin fractions in a water-lecithin complex.

The following components were mixed and heated in the STEPHAN cooker.

STEP 1

TABLE 1

| COMPONENTS | QUANTITY/POUND |
|---|---|
| Water | 56.0 |
| Alcolec 140 | 14.0 |
| Alcolec SFG | 7.0 |

The liposome premix was heated to 180 degrees F. in the STEPHAN cooker. The premix was transferred a 200 liter capacity vacuum chopper manufactured by MEISSNER AG. The model number is RSM 200VAC. Experience has shown that optimal liposome formation conditions occur when total weights of about 230 to 260 pounds are processed in choppers of 200 liter capacity. This chopper is equipped with a vacuum hood whereby a vacuum of 28 inches of mercury can be produced. The hood is also equipped with a carbon dioxide injection hood and exhaust exit. The bowl of the chopper can also be heated or cooled with water or steam via sprays underneath the enclosed bowl.

Choppers, long used in the food processing industry for sausage processing, have been found to have utility in producing liposomes formed in accordance with the present invention. In this ease, vacuum was employed to reduce the entrapment of air. Air entrapment during the creation of liposomes reduces the efficiency if it is done in an open air environment. As air entrapment increases, more air is entrapped at an increasing rate. The small air bubbles act like liposomes and thus, the of the production phase decreases at an increasing rate. Thus, the employment of vacuum reduces the time required for liposome production and the suspension of microcrystalline cellulose.

The following component were mixed and heated in the STEPHAN cooker.

STEP 2

TABLE 2

| COMPONENTS | QUANTITY/POUND |
|---|---|
| Water | 91.0 |

The water was heated to 180 degrees F. by steam injection with high speed agitation. Upon reaching 180 degrees F., the steam flow was terminated, the STEPHAN cooker was opened, and the water was transferred to a clean sterilized bucket and slowly added to the chopper. The pasteurized lecithin-water liposome complex was processed in the chopper for 20 minutes to form liposomes. The same knife pattern was used as in Example 14. steam was applied to the bottom of the bowl to maintain a temperature of 180 degrees F. Vacuum was applied at 25 inches.

The following component was incorporated with the liposomes to produce the final lecithin-microcrystalline complex.

TABLE 3

| COMPONENTS | QUANTITY/POUND |
|---|---|
| Avicel RC-591 | 36.0 |

The microcrystalline cellulose was added to the chopper and mixed for approximately 30 minutes maintaining the vacuum at 25 inches and the temperature at 180 degrees F. The chopper was then opened and the liposome mixture was visually examined under a polarized light microscope for proper dispersion. Upon confirming that proper dispersion was achieved, the contents of the chopper was unloaded into 5 gallon pails for use in further processing. This process eliminated the preparation of liposomes in the STEPHAN cooker.

EXAMPLE 27 FAT FREE CHOLESTEROL FREE DRESSING FOR COTTAGE CHEESE-INDIRECT HEAT METHOD

A stabilized fat substitute "SFS" non fat cottage cheese dressing is produced by using two hundred pounds of curd from the Example 14. The curd is made by indirect heating of the whey protein-caseinate mixture to produce a coprecipitate.

The two hundred pounds of curd are transferred from the BLANCO Blender cooker to the bowl chopper using a false bottom kitchen cart. Comminution/deagglomeration of the curd is achieved according to the procedure described in Example 14. The resulting fat substitute product is further processed into fat free, cholesterol free, non fat cottage cheese dressing as described below.

The following components are incorporated with the fat substitute product produced as described above to prepare a non fat cottage cheese dressing.

TABLE 1

| COMPONENTS | QUANTITY/POUND |
|---|---|
| Water | 8.0 |
| Alcolec 140 | 2.0 |
| Alcolec SFG | 1.0 |
| Water | 13.0 |
| Avicel RC591 | 5.0 |

STEP 1

The liposome and structure building formation is achieved in a similar manner to that set out in Example 14 in which the membrane-forming, surface active, and structure building agents are prepared in the STEPHAN cooker. The lecithin fractions (American Lecithin Company, Danbury, Conn. 06813-1908) are added to water in the STEPHAN cooker to form liposomes as described in Example 14. The STEPHAN cooker is operated for 8 minutes at 120 degrees F. Thereafter, the STEPHAN cooker is opened and the liposomes made from the lecithin-water mixture are visually examined for the presence of undissolved particles and to insure complete dispersion. Upon confirmation that the mixture is uniformly dispersed and that liposomes are formed, a caramel cream-like appearance is observed. An additional 13 pounds of hydration water is added to the liposomes in the STEPHAN cooker together with 5 pounds of microcrystalline cellulose and mixed for approximately 10 minutes. The STEPHAN cooker is then opened and the liposome mixture is visually examined under a polarized light microscope for proper dispersion. Upon confirming that proper dispersion is achieved, the STEPHAN cooker is closed and the temperature raised to 180 degrees F. by steam injection with high speed agitation. Upon reaching 180 degrees F., the steam flow is terminated, the STEPHAN cooker is opened, and the mixture is transferred to a clean sterilized bucket and slowly added to the chopper. The pasteurized lecithin-microcrystalline cellulose complex is processed in the chopper for 10 minutes to form a membrane around the curd particles, to place amphoteric charges on the curd particles, and to create structure in the aqueous phase as described in Example 14.

STEP 2

A stabilizer is produced from the components in Table 2.

TABLE 2

| COMPONENTS | QUANTITY/POUND |
|---|---|
| Water | 26.00 |
| Slendid Pectin | 4.0 |
| Gelatin 250 Bloom | 1.0 |
| Genu Fast Set Pectin | 1.0 |
| Calcium Chloride Solution | 20 mls. |

The stabilizer from Table 2 is prepared by adding SLENDID Pectin to the 26 pounds of water in the STEPHAN cooker. The bottom agitator is set at high speed and the side agitator is turned on for 5 minutes. The STEPHAN cooker is then opened and the the pectin dispersion is then inspected for complete dispersion. The 250 Bloom Gelatin is then added to the water-pectin dispersion. The ingredients are mixed in the STEPHAN cooker for 5 minutes at high speed (3,000 rpm) with no steam injection. The STEPHAN cooker is then opened and the contents subjected to tactile and visual examination as described in Example 14—Stephan Cooker Step 2.

STEP 3

Additional microbial inhibitors and salt are prepared in the STEPHAN cooker using the components from Table 3. These ingredients are added to those made in Step 2 above.

TABLE 3

| COMPONENTS | QUANTITY/POUND |
|---|---|
| Salt | 4.0 |
| Alta 2331 | 1.5 |
| Alta 1801 | 2.5 |
| Alta 2001 | 1.5 |
| Alta 1705 | 2.0 |

The ingredients are mixed in the STEPHAN cooker for 2 minutes at high speed (3,000 rpm) The STEPHAN cooker is then opened and the contents subjected to tactile and visual examination as described in Example 14—STEPHAN Cooker Step 2.

STEP 4

The component in Table 4 is added to those in Step 3.

TABLE 4

| COMPONENTS | QUANTITY/POUND |
|---|---|
| Enrich 101 | 5.0 |

The ingredients are mixed in the STEPHAN cooker for 2 minutes at high speed (3,000 rpm) The STEPHAN cooker is then opened and the contents subjected to tactile and visual examination as described in Example 14—STEPHAN Cooker Step 2.

STEP 5

The components in Table 5 is added to those in Step 4.

TABLE 5

| COMPONENTS | QUANTITY/POUND |
|---|---|
| Non Fat Dry Milk Powder | 10.0 |
| Cultured Non Fat Buttermilk | 10.0 |

The ingredients are mixed in the STEPHAN cooker for 2 minutes at high speed (3,000 rpm). The STEPHAN cooker is then opened and the contents subjected to tactile and visual examination as described in Example 14—STEPHAN Cooker Step 2.

STEP 6

The components in Table 6 is added to those in Step 5.

TABLE 6

| COMPONENTS | QUANTITY/POUND |
|---|---|
| Parselli SA-2 | 4.0 |

The ingredients are mixed in the STEPHAN cooker for 2 to 3 minutes at high speed (3,000 rpm) The STEPHAN cooker is then opened and the contents subjected to tactile and visual examination as described in Example 14—STEPHAN Cooker Step 2.

When satisfactory results are achieved, i.e., even dispersion, the STEPHAN cooker is then closed and the temperature raised to 180 degrees F. by steam injection with high speed agitation. When the temperature reached 180° F., agitation is ceased, steam flow is terminated, and the pressure released. The STEPHAN cooker is then opened and the contents are added slowly to the continually operating chopper.

STEP 7

The components in Table 7 are made and added to the chopper in a separate step.

TABLE 7

| COMPONENTS | QUANTITY/POUND |
|---|---|
| Salt | 10.0 |
| Water | 70.0 |

The ingredients are mixed in the STEPHAN cooker for 2 to 3 minutes at high speed (3,000 rpm) The STEPHAN cooker is then opened and the contents subjected to tactile and visual examination as described in Example 14—STEPHAN Cooker Step 2.

When satisfactory results are achieved, i.e., even dispersion, the STEPHAN cooker is then closed and the temperature raised to 180 degrees F. by steam injection with high speed agitation. When the temperature reached 180 degrees F., agitation is ceased, steam flow is terminated, and the pressure released. The STEPHAN cooker is then opened and the contents are added slowly to the continually operating chopper.

ACIDIFICATION PROCESS

The acidification process is carried out according to the procedure outlined in Example 14 in which the mixture is acidified to a pH of 5.9 to 6.0. by adding lactic acid (CCA Biochem b. v. Holland) and 20 ml of starter distillate (HANSEN'S 15X) to the continually operating chopper and mixing for about one minute.

HOMOGENIZATION PROCESS

The homogenization process is carried out by using a Moyno pump to force the heavy, viscous Fat Free Soft Cheese through the inlet valves of the high pressure homogenizer. The stuffing pressure produced by the Moyno pump has to exceed 150 to 200 pounds per square inch to prevent implosion. Since the cottage cheese dressing cheese at this point has a viscosity between 25,000 and 40,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer is used at a first stage pressure of 10,000 pounds per square inch and 1,500 pounds on the second stage.

The non fat cottage cheese dressing is cooled and packaged as described in Example 14.

The chemical and microbiological analysis of this product is as follows:

| | |
|---|---|
| pH | 6.01 |
| FAT | 0.20% |
| SALT | 4.0% |
| STANDARD PLATE COUNT | <100 |
| COLI | <10 |
| YEAST/MOLD | 0/0 |

EXAMPLE 28 NON FAT COTTAGE CHEESE AND CHEESECAKE MADE FROM ACID WHEY

A process for preparing a fat substitute is described, beginning with whey formation and recovery. The whey of this example is a acid whey derived from a typical cottage cheese-making process. This acid whey could also be recovered for the production of acid caseinate production resulting in sodium or calcium caseinate. The acid whey is further processed to produce a whey protein concentrate. Whey protein concentrate is the preferred whey starting material for the preparation of the fat substitute which is the present invention.

Whey in this example comes from the production of cottage cheese exclusively. On other occasions, the whey in the whey holding tank would be a combination of whey from the production of several other types of cheese.

Whey Formation

Whey is formed during the production of Fresh Cottage Skim Cheese Curd from skim milk. A series of two batches, each containing eighty eight hundred pounds of skim milk and culture, is processed following the same procedure, and in substantially the same manner, as the process described below.

Eighty eight hundred pounds of skim milk averaging 3.65 protein with a fat content of 0.9% is pasteurized at 1650 degrees F. for 20 seconds. The Non Fat Solids content of the milk is 10.2 percent and the set temperature of the milk is 800 degrees F. The separated skim is fortified with non fat dry milk powder. The milk is pumped into a 10,000 pound capacity KUSEL cheese vat manufactured by the KUSEL EQUIPMENT COMPANY of Watertown, Wis. 53094. When the straight sided open cheese vat contains approximately 1,000 pounds of milk, freeze dried starter culture is added under slow agitation and the filling process proceeds. When each vat contains 8,800 pounds of milk, 0.64 mls. of single strength rennet is added, and the agitation is terminated. The proper set curd is formed at a pH of 4.65 with a whey titrate acidity of 0.51. This occurs 5 hours and 35 minutes after the rennet is added.

The solid curd mass is cut into curds with ⅜ inch cheese harps or knifes. The curds are allowed to rest for 20 minutes so that they heal. The cooking process begins with very slow hand agitation and then cooked with ramped stirring to a temperature of about 128 degrees F. The cooking process takes 196 minutes from the 80 degree set temperature to 128 degrees. Preferred temperature increase should approximate 5 degrees F. for every 20 minutes cook time. When the desired cook temperature is reached, the curd is checked for firmness by pulling the curds apart and checking for free moisture in pockets. The curd should have a firm, meaty texture with no free water. The curd can also be placed in cold water at 38 to 42 degrees for 3 to 4 minutes and then placed in the mouth. A firm, slightly flexible curd structure should prevail. A soft, spongy texture indicates that the curd needs further cooking or holding time. The whey is drained from the vat via the exit gate with a full strainer in place. The whey is pumped to a isolated whey holding tank. The whey should be drained so that the curds are just exposed. Fill the vat to the former milk level with water at approximately 65 degrees F. so that the temperature of the curds, whey and water are approximately 80 degrees. The water should be adjusted to pH 6.4 to 6.8 with phosphoric or lactic acid. The water-whey mixture and pump to the reverse osmosis holding tank. The second washing of the curd is commenced with treated water and chilled water adjusted to pH 6.52 so that the curd and water mixture is 62 degrees F. The water-whey mixture is again drained and pumped to the reverse osmosis tank. Chilled water which that is adjusted to pH 6.54 and chlorinated to 10 PPM (parts per million) is added to the drained curds. The chilled water is allowed to remain on the curds for a period of 25 minutes. At this time, the curds are at a temperature of 38 degrees F. and the chilled water is drained form the vat.

The curds are trenched and allowed to drain for twenty minutes. When the curds have drained completely, the FAT FREE dressing mixture of Example 27 is evenly distributed upon the curd and mixed in with the agitators. It is estimated that the vat contained 890 pounds of non fat cottage cheese curd. The FAT FREE dressing weight is 480 pounds.

The curd is removed form the vat and placed in kitchen carts. The FAT FREE finished cottage cheese is placed into casings via a RISCO stuffer as previously described in other examples.

The chemical and microbiological assay for the fat free cottage cheese is:

|  |  |
|---|---|
| Moisture | 78.4–81.2 |
| pH | 5.13–5.21 |
| Fat | 0.2–0.4 |
| Salt | 1.5–1.65 |
| SPC | <100 |
| COLI | <10 |
| Yeast/Mold | 0/0 |

The whey from the two batches of cottage cheese described above varies in composition, within the following ranges:

|  |  |
|---|---|
| FAT CONTENT = | 0.00%–0.10% by wt. |
| PROTEIN = | 0.85%–0.95% by wt. |

-continued

|  |  |
|---|---|
| TOTAL SOLIDS = | 7.05%–7.25% by wt. |
| pH = | 4.45–4.65 |

Whey Protein Concentrate Production

The next step is to concentrate the whey protein via sieve separation, centrifugal clarification, and ultrafiltration.

Cheese fines are removed from the whey via sieve separation using a thirty micron sieve in a fine saver manufactured by Sermia LTD, Quebec, Canada.

The cottage cheese whey is then standardized from pH an average pH of 4.55 to pH 6.45 with SODA ASH (Calcium Carbonate) from Arm and Hammer (Church and Dwight Co., Inc. Princeton, N.J. 08543-5297) The pH is raised to prevent premature coagulation of the whey protein during pasteurization and ultrafiltration.

Thereafter the whey is clarified, and slime removal achieved, in a centrifugal clarifier of 100,000 pounds per hour capacity manufactured by WESTPHALIA CENTRICO INC. Northvale, N.J. 07647.

The neutralized cottage cheese whey is then pasteurized at 165° F. for about 20 seconds and then cooled to 110° F. in an APV CREPACO HIGH TEMPERATURE SHORT TIME pasteurizer (APV CREPACO, Chicago, Ill. 60631).

The whey produced via the foregoing procedure is subjected to ultrafiltration and difiltration to produce whey protein concentrate. The ultrafiltration unit is manufactured by Thomas Fractionators of Minn. A KOCH brand spiral membrane, model SO-HFK-131, is manufactured by KOCH is used (KOCH, Wilmington, Mass. 01887). Ultrafiltration is effected at a cooled whey temperature of 100 degrees F., at sufficient pressure to produce an average protein concentrate with a solids content of 14% by weight. The pressure required on the retention side of the membrane varies from about 80 psi at the beginning of ultrafiltration period to about 130 psi as ultrafiltration continues until membrane fouling occurs. When the 140 psi operating level is reached, the membrane is washed to remove fouling materials and ultrafiltration is thereafter resumed. In this process, difiltration is also effected by the addition of softened water to the whey from cottage cheese to prevent fouling and to increase the protein content of the whey protein concentrate.

The whey protein concentrate is cooled in a plate heat exchanger to a temperature of about 40 degrees F.

The two batches of cottage cheese whey described above produces whey protein concentrates having compositions within the following ranges:

|  |  |
|---|---|
| FAT | 0.35%–0.55% by wt. |
| PROTEIN | 6.23%–7.43% by wt. |
| SOLIDS | 13.92%–14.51% by wt. |
| pH | 6.35–6.45 |

Fat Substitute Formation From Whey Protein Concentrate

In the here exemplified fat substitute production process, sodium caseinate is added to the whey protein concentrate from cottage cheese production to form a coprecipitate curd. This is an optional step in the process of the present invention. The curd is then comminuted to form a dispersion of denatured whey protein particles and the comminuted particles in the curd are then coated with membrane and surface active agent(s) to form a more stable dispersion. The dispersion is then further stabilized with structuring and stabilizing agent(s) to form the present invention. Comminution of the curd, formation of the membrane, and addition of the surface-active agent(s) is achieved using a chopper. It has been found that choppers used in meat processing have particular utility in the comminution of the denatured protein in the curd produced according to the present invention. The final product formulation is then homogenized under high pressure to further add to its stability. The homogenizing step is optional.

Curd Formation (Denaturing And Agglomeration)

The starting material for production of the curd used to form the stable protein dispersion of the present invention is made up of the whey protein concentrate from cottage production described above including sodium caseinate as a protein additive.

The sodium caseinate additive is incorporated into the whey protein concentrate by adding ten pounds of sodium caseinate to approximately 50 pounds of whey protein concentrate drawn from the whey protein concentrate described above to form a caseinate-protein premix. This pre-mix of sodium caseinate and whey protein concentrate are mixed in a STEPHAN brand cooker which has the means for blending/mixing the ingredients. A STEPHAN brand steam injection, high shear, mixer-cooker, model #UM40E-GNi Pilot of 40 liter capacity (hereinafter, the STEPHAN cooker), is used for this purpose. The STEPHAN cooker is operated at a blade mixing speed of 3,000 RPM, without heat, for approximately 2 minutes. Thereafter, mixing is interrupted and the contents of the STEPHAN cooker examined. Visual examination indicated an absence of lumps and an absence of observable undissolved particles. This confirmed that the caseinate is fully hydrated.

The mixture from the STEPHAN cooker is then added to whey protein concentrate in an F.P.E.C. (F.P.E.C. CORP. Santa Fe Springs, Calif. 90670) brand cooker (hereinafter, the FEPC cooker) with a modified bottom in which drain lines are substituted for two of the six steam inlets in the FPEC cooker bottom. After the mixture from the STEPHAN cooker is added to the FPEC cooker, the total batch weight in the FPEC cooker is approximately 1100 pounds.

The batch is heated to 185 degrees F. by introduction of steam through the FPEC cooker bottom at a temperature of about 240 degrees F. with constant agitation by two augers oriented lengthwise overlying the FPEC cooker bottom.

During steam introduction, the agitation is monitored and controlled to form a foam matrix, that is, a steam-entrained whey-casein matrix throughout which water vapor (steam) is dispersed. The formation of a foam matrix signifies that steam bubbles are entrained in the whey protein concentrate casein dispersion—a phenomenon that is observable by an increase in the liquid volume and the formation of foam on the surface of the solution. In the present case, a volume increase in the 15% to 20% range is achieved and foam is observed on the surface of the heated solution. During this heating and steam matrix forming step, a viscosity increase of the FPEC cooker contents occurred.

After the temperature of the solution reached a target temperature 185 degrees F., 150 grain Vinegar (acetic acid) is added in sufficient quantity to reduce the pH to between 5.6 and 5.65—the optimum pH for denaturing of whey protein concentrate and casein mixtures of the composition used.

Had whey protein concentrate been used alone, the optimum pH would have been lowered to 5.4 to 5.45—the optimum level where pure whey protein concentrate is used as the starting material. As additional caseinate is added to the whey protein concentrate, the optimal pH increases.

Upon addition of acetic acid, curd is formed which rose to the top of the whey solution. When this is observed, agitation is terminated and curd formation is allowed to continue. A mat of curd formed on the surface of the whey. The FPEC cooker's agitator is activated momentarily about once a minute to loosen and release any curd adhering to the agitators or the bottom of the FPEC cooker.

Five minutes after continuous agitation is discontinued, the curd mat is fully formed. At this time, the whey is drained from the bottom of the FPEC cooker and the floating curd mat settles to the bottom of the cooker. The curd is recovered from the bottom using the auger/spiral agitators to break-up and move the curd in the mat to the front of the cooker where doors are situated that are opened to allow the curd to be expelled from the FPEC cooker.

The curd is then loaded into a false bottom carts for transport to the next step of fat substitute manufacture—deagglomeration/comminution of the denatured coprecipitate curd. During transport, whey continues to drain from the curd. The curd at this point in the process is typically from approximately 65% to 80% water by weight. The moisture content is inversely proportional to the cooking temperature. The curd in this example had a moisture content in the 75% to 80% by weight range.

Deagglomeration/Comminution Of The Curd; Dispersion Formation

The drained curd with a moisture content in the 75% to 80% by weight range is deagglomerated using a 200 liter capacity vacuum chopper manufactured by Meissner AG. The model number is RSM 200VAC. In the United States, such choppers are distributed by RMF-CHALLENGE located at 4417 East 119th Street, Grandview, Mo. 64030. Experience has shown that optimal deagglomeration/comminution conditions occur when curd weights of about 200 pounds are processed in choppers of 200 liter capacity. This chopper is equipped with a vacuum hood whereby a vacuum of 28 inches of mercury can be pulled. The hood is also equipped with a carbon dioxide injection hood and exhaust exit. The bowl of the chopper also can be heated or cooled with water or steam via sprays underneath the enclosed bowl.

Choppers, long used in the food processing industry for sausage processing, have been found to have utility in (1) comminuting/deagglomerating the curd formed by the present invention to form the curd into a dispersion of micron sized particles suspended in a continuous aqueous phase; (2) to coat the micron sized particles, to charge the particles with a surface active agent, and to build structure—thereby increasing the particles' stability; and, (3) to incorporate a stabilizer into the aqueous phase of the dispersion further enhancing the stability of the fat substitute product. In this case, vacuum is employed to reduce the entrapment of air. Air entrapment during the deagglomerating/comminution phase creates increased viscosity that becomes an efficiency problem in an open air environment. As the viscosity increases, more air is entrapped at an increasing rate. The small air bubbles act like protein particles and thus, the efficiency of the comminution/deagglomeration phase decreases at an increasing rate. Thus, the employment of vacuum reduces the time required for deagglomeration and comminution. The reduction in the incorporation of air also prevents the lecithin phospholipid liposome mixture from coating the air cells instead of the protein precipitate particles. Thus, vacuum allied during the communication step spares the liposome mixture so that it is more e efficient. Additionally, The air when coated with liposomes creates difficulty in using the fat substitute in food formulations. In example, cheesecake would have more leavening made in a chopper without vacuum and of a different kind as the air cells incorporated with the liposome membrane would act differently than those without the membrane.

In the process described in the present example, a ten knife array is selected for use in the chopper. The knives in this array are SECURITY-SYSTEM-4-CUT-KNIVES available from G. Walter Steffans, 563 Remscheid 14, Uterholterfelder Strasse 60, Germany. The knives are composed of high quality stainless knife steel. The cutting edge of the blade of these knives is formed on the camber side at an original grinding angle of 27 degrees. The knives are then mounted on a single shaft adapted for use in configurations involving up to twelve knives. The back/trailing edges of the knives' blades are flat and taper from 5 mm at the shaft to 3 mm proximate the point of the blade where the camber that forms the blade edge begins.

The ten knives are oriented on the shaft in the following manner. The first and second knives at the upstream end of curd flow—flow is induced by rotating the bowl of the chopper—are positioned 180 degrees opposite one another. The distance between the knives, as measured along the shaft, is about 5 mm. The knife holder is 10 mm thick and the knife is 5 mm thick. The third knife is offset 30 degrees behind the first knife and a 5 mm spacer is used to increase the distance between the second and third knives by 5 mm to about 10 mm. The fourth knife is positioned 180 degrees opposite the third knife. Here again, the distance between opposing knife pairs 3 and 4, as measured along the knife-holder shaft is about m. The fifth knife is offset 30 degrees behind the third knife. The sixth knife is positioned 180 degrees opposite the fifth knife. The remaining three knife pairs, namely, 7 and 8, 9 and 10, are positioned with knife 7, 30 degrees behind knife 5; knife 9, 30 degrees behind knife 7. No spacers are used in positioning the last knife pairs, and knives of each pair are oriented 180 degrees opposite each other.

The increased spacing at the front of the knife array, between knives 2 and 3, has been observed to improve performance of the chopper by allowing a greater volume of curd to enter the knife array. Where the leading 180 degrees opposed pairs are spaced apart the same distances as the succeeding opposed pairs, build up of curd and/or dispersion occurs and a dam of curd is formed forward of the upstream leading knife.

To maximize efficiency, the cutting edges of the chopper knives are sharpened and tested to insure an order of sharpness that cuts paper. Also, the side surfaces of the knife are highly polished before comminution begins.

The efficiency of the comminution/deagglomeration is also increased by installing baffles at the exit of the knifes. The baffle creates pressure within the rotating knifes to reduce the size of eddies behind the knife as it passes though the comminuted/deagglomerated curd. The smaller eddies reduces the size of the particle and increases the flow rate of the eddies. The resulting pressure maintains more volume around the knifes and maintains more of the curd in the top of the hood or knife cover. The result is smaller particles in less time.

Two hundred pounds of curd are transferred from the false bottomed kitchen cart to the chopper. The chopper is operated at a high bowl speed of 16 RPM's and a knife shaft speed of 3,000 RPM's for ten minutes to comminute the denatured whey protein casein coprecipitate curd. Steam is turned on the automatic control to maintain a temperature of 175 degrees F. A vacuum of 25 inches is maintained. A dispersion is formed of the deagglomerated denatured whey protein casein coprecipitate in a continuous phase aqueous medium. The aqueous medium is formed by the aqueous component released during comminution/deagglomeration of the curd.

Stephan Cooker Step Number 1

While the chopper is operated to form the dispersion described in the preceding paragraph, a membrane-forming composition, including a surface-active agent and a structure-building agent, is being prepared in the STEPHAN cooker for addition to the curd during the above-described comminution procedure.

The membrane-forming, surface-active, and the structure-building agents are prepared in the STEPHAN cooker using steam-injection and high agitation to form dispersions of same very quickly. The components listed in table one are used for this purpose.

TABLE 1

| Ingredient | Pounds |
| --- | --- |
| Water | 8.0 |
| Alcolec 140 | 2.0 |
| Alcolec SFG | 1.0 |
| Water | 13.0 |
| Avicel RC591 | 5.0 |

Note:
1. ALCOLEC 140 is available from American Lecithin Company, located at 33 Turner Road, Danbury, Connecticut 06813-1905. This product is approximately 40% phosphatidyl choline by weight.
2. ALCOLEC SFG is available from American Lecithin Company, located at 33 Turner Road, Danbury, Connecticut 06813-1905.

Step 1

Eight pounds of water are poured into the STEPHAN cooker to which the following ingredients are added:

(i) Two pounds of ALCOLEC 140 that contains approximately 40% phosphatidyl choline by weight;

(ii) one pound ALCOLEC SFG which is high in inositol and glycolipids content.

These contents are processed in the STEPHAN cooker for 8 minutes at 120 degrees F. with the lower knife blade operating at 3,000 RPM and the side scraper blade on high speed in order to form liposomes. At the end of 8 minutes, the blade/scraper action is interrupted and the STEPHAN cooker opened to visually examine the contents for even dispersion. Once even dispersion is confirmed, 13 pounds of hydration water are added to the liposomes and high speed agitation is again applied for four minutes. The 5 pounds of microcrystalline cellulose are then added to the liposome mixture and high speed agitation is again applied. The microcrystalline cellulose is available from the Food and Pharmaceutical Products Division of FMC located at 200 Market Street, Philadelphia, Pa. 19103, sold under the designation AVICEL RC-591F. The STEPHAN cooker is used to mix these contents at the 3,000 RPM speed and steam injection is used to raise the temperature to 180 degrees F. The required time to do this is about five minutes. The lecithin-microcrystalline complex is checked under a polarized light microscope to insure that the microcrystalline cellulose is properly dispersed. If the microcrystalline cellulose is properly dispersed, the cellulose crystals are evenly dispersed inside the vesicular structures (liposomes) with no clumping or agglomeration. The lecithin-microcrystalline cellulose liposome complex is formed in the STEPHAN Cooker and added to the curd dispersion in the chopper.

The chopper continues operation for an additional 15 minutes (hereinafter, the second comminution phase) to form a membrane around the denatured whey protein-casein precipitated particles, and to place amphoteric charges on them with surface active agents, and to build structure. The membrane is believed to be formed by the liposomes created by the lecithin fractions and water mixture. The vesicles created in the STEPHAN cooker envelop the whey protein-caseinate particles with a multi-layer membrane that approaches the characteristics of membranes found in natural occurring biological systems. This membrane produces electrostatic charges on the particle surface facilitating the stearic repulsion of the particles. The structure building agent (microcrystalline cellulose) stabilizes the system by placing needle-like or toothpick-like structures between the individual whey protein-caseinate coprecipitate particles in the aqueous phase such that the particles cannot reagglomerate readily. Thus, a very stable dispersion is created with extended shelf life and heat stability during baking.

As the second comminution phase proceeds, the contents of the chopper begin to take on a glossy appearance that will resemble products of high fat composition. This is believed to be the result of light refraction by the non-fat curd particles that now behave much like the fat globules occurring naturally in fat emulsions such as cream. The size and distribution of the particles at this point are believed to be the same that occurs in bovine butterfat emulsions such as unhomogenized milk.

At the end of twenty minutes of continual comminuting, the fat substitute hydrated protein product further develops a high glossy appearance. The product at this point, when rubbed between the thumb and forefinger, displays the greasy lubricity and slip that is characteristic of high fat compositions or emulsions. The organoleptic evaluation of the product proved to be the same as a heavy cream with a butterfat content of 50 to 60 percent.

Stabilization Of The Fat Substitute

If one stopped the process at this point, a stabilized fat substitute having the mouthful of fat-water or water-fat emulsions is produced. To improve the stability of the product against the development of a chalky mouth feel or bacterial growth, a hydrocolloid gum such as xanthan gum, and a microbial growth inhibitors such as potassium sorbate, can be added.

Stabilization of the fat substitute is desirable where it is to be stored and/or shipped for later use in production of nonfat foodstuffs. Stabilization is achieved by adding a thickener/pseudoplastic stabilizer, such as xanthan gum, which imparts thixotropic properties. An aqueous dispersion of xanthan gum is produced in the STEPHAN cooker and added to the chopper to achieve a xanthan gum content of about 0.25 to 0.5 weight percent of the fat substitute.

Hydrocolloid gum is added to the dispersion of coated particles in the chopper to incorporate the gum into the continuous phase of the dispersion. Besides hydrocolloid gum addition, it is preferable to add microbial growth inhibitors to the fat substitute and/or stabilized fat substitute. Suitable microbial growth inhibitors such as sodium benzoate, potassium sorbate, or natural microbial inhibitors such as dehydrated cheese culture can be used. The products used in this example are Alta 2331, Alta 1801, Alta 2001, Alta 1705, and Microguard 300. The Alta products are natural microbial inhibitors available from Quest-Microlife Technics, Inc. of Sarasota, Fla., 34230. Microguard 300 is a natural fermentation product from Wesman Foods of Beaverton, Oreg. 97006. Each of these products shows inhibitory effects against different microorganisms and are chosen accordingly.

A microbial stabilizer is also added to the mixture in the STEPHAN cooker, which is subsequently added to the chopper, to improve stability. This microbial stabilizer is ENRICH 101 and is primarily a fermented milk product in dehydrated form containing xanthan-like hydrocolloids. This product is available from Quest-Microlife Technics, Inc. of Sarasota, Fla., 34230. G P Maltodextrin 040, available from Grain Processing Corporation of Muscatine, Iowa 52761, is added to further enhance the stability of the product, impart spreadable characteristics, and reduce the apparent viscosity. AVEBE PARSELLI SA-2 is added for the same purpose as Maltodextrin 040, but further enhances viscosity. A combination of the two maltodextrins will provide the desired body and texture. AVEBE PARSELLI SA-2 is a product of Avebe America, Inc., Princeton, N.J. 08540.

To improve the flavor beyond that of culture distillate, a flavor dehydrated starter culture is added. This is Accel 4201 available from Quest-Microlife Technics, Inc. of Sarasota, Fla., 34230.

At this point, the Stabilized Fat Substitute "SFS" contained in the bowl of the chopper is further processed into fat free cholesterol free base for cheesecake. This is accomplished by preparing further ingredients in the STEPHAN Cooker and adding them to the chopper.

Stephan Cooker Number 2

| INGREDIENT | POUNDS |
| --- | --- |
| Water | 26.00 |
| Xanthan gum | 0.25 |
| Pectin | 0.75 |
| Carrageen | 0.25 |
| Gelatin | 4.00 |

Three quarters of a pound of SLENDID specialty pectin is dispersed in 26 pounds of water in the STEPHAN cooker under high agitation for 6 minutes. Slendid pectin is a product of Hercules Incorporated, Fragrance and Food Ingredients Group, Hercules Plaza, Wilmington, Del. 19894. One quarter pound of KELTROL T xanthan gum from Kelco, San Diego, Calif. 92123, 4 pounds of 225 Bloom Gelatin from GMI, Inc., North Miami Beach, Fla. 33179, and 0.25 pound of GELERIN GP 911 Carrageen from the Food and Pharmaceutical Products Division of FMC located at 200 Market Street, Philadelphia, Pa. 19103, are mixed in the STEPHAN cooker at 3,000 rpm. This process requires approximately 5 minutes. The STEPHAN cooker is opened and the contents are examined to insure that hydrocolloid gums are fully dispersed and hydrated. This is determined by tactile examination—rubbing the sample between fingers—and visually checking for presence of undissolved particles.

Upon confirmation that the hydrocolloid gums are in solution, the following ingredients are added to the hydrocolloid gum-water mixture in the STEPHAN cooker:

| INGREDIENT | POUNDS |
| --- | --- |
| Sugar | 12.00 |
| Salt | 2.00 |

Upon confirmation that the sugar and salt are in solution, the following ingredients are added to the mixture in the STEPHAN cooker:

Stephan Cooker Number 4

| INGREDIENT | POUNDS |
| --- | --- |
| Alta 1705 | 0.25 |
| Alta 2001 | 0.50 |
| Alta 1801 | 0.50 |
| Alta 2331 | 0.25 |
| Microguard 300 | 1.75 |
| Accel 4301 | 4.00 |

Upon confirmation that the microorganism inhibitors are full dispersed, the following ingredient is added to the mixture in the STEPHAN cooker:

Stephan Cooker Number 5

| INGREDIENT | POUNDS |
| --- | --- |
| Enrich 101 | 5.00 |

Upon confirmation that the Enrich is in solution, the following ingredient is added to the mixture in the STEPHAN cooker:

Stephan Cooker Number 6

| INGREDIENT | POUNDS |
| --- | --- |
| Non Fat Milk solids | 22.00 |

The above ingredients are dispersed at 3,000 RPM with steam injection at a steam pressure of about 40 pounds to a temperature of 120 degrees F. for 1 to 2 minutes. The STEPHAN cooker is opened and the product examined to verify the absence of lumps and that the ingredients have been uniformly dispersed. The STEPHEN cooker is then closed and the temperature is raised to 180 degrees F. by steam injection with agitation at 3,000 RPM to pasteurize the contents. When the temperature reaches 180 degrees F., the steam flow is terminated, the cooker is opened, and the contents are transferred to a clean sterilized bucket and slowly added to the chopper.

Direct Addition to Chopper

The chopper continues to operate at a bowl speed of 18 RPM and a knife shaft speed of 2,500 RPM until a uniform mixture of the Stephan Cooker ingredients and stabilized fat substitute is achieved. The 8 pounds of G P Maltodextrin and 6 pounds of Parselli SA-2 are added slowly to the chopper. After the contents of the chopper are thoroughly mixed for 2 to 3 minutes, a sample is withdrawn and analyzed for pH. The pH is adjusted to 5.1 to 5.2 by adding approximately 14 ounces of lactic acid available from CCA BIOCHEM B. V. of The Netherlands to the chopper. After the pH is adjusted, 70 ml. of starter distillate designated Hansen's 15X available from Chs. Hansen's Laboratory, Inc. Milwaukee, Wis. 53214, 300 ml. of Beck's Vanilla No. C-7281 available from Beck Flavors, P O Box 22509, St. Louis, Mo. 63147, and 600 mls. of Flavorcraft Lemon Emulsion No. 1302 available from. Flavorcraft, City of Industry, Calif. 91744, are added to the continually operating chopper with mixing for about five minutes.

DIRECT ADDITION TO CHOPPER

| INGREDIENT | QUANTITY/POUNDS |
| --- | --- |
| Parselli SA-2 | 6.00 |
| GP Maltodextrin 040 | 8.00 |
| Beck's Vanilla | 300 mls |
| Lemon Emulsion | 600 mls |
| Starter Distillate | 70 mls |
| Lactic Acid | a/r |

The resulting mixture is transferred to a kitchen cart and then into the funnel inlet of the Moyno pump. A special high pressure APV RANNIE Hyper homogenizer built by APV Rannie, Copenhagen, DN. and sold by APV Rannie, 445 Enta Street, St. Paul, Minn. 55106, and a Niro Soave high pressure homogenizer sold by Niro Atomizer, 1600 County Road F, Hudson, Wis. 54016 are used to homogenize the final product. Hyper homogenization is considered over 10,000 pounds per square inch. The hyper homogenization uses two stages in which typically 10 to 15 percent of the pressure is applied to the second stage to create back pressure in the camber between the two stages, thereby increasing the cavitation forces and reducing particle size. The first stage pressure is 10,000 pounds per square inch and the second stage pressure is 1,500 psi. This high pressure hyper homogenization creates a temperature increase in the product and will cause implosion in the cylinder or the camber. As a rule of thump, this increase approximates five degrees (5) for every one thousand pounds (1,000) of pressure. Thus, the temperature of the cheesecake base is lowered to 140 degrees F. by the addition of carbon dioxide in solid form in the Meissner chopper before the base is discharged.

The cheesecake base is packed into a 120 mm. by 20" plastic casing directly at the outlet of the homogenizer. The encased mixture is cooled in a brine tank to a core temperature of 40° F.

The chemical and microbiological assay for the cheesecake base:

| Moisture | 57.2–59.1 |
| --- | --- |
| pH | 5.09–5.15 |

-continued

| | |
|---|---|
| Fat | 0.2-0.4 |
| Salt | 2.1-2.3 |
| SPC | <100 |
| COLI | <10 |
| Yeast/Mold | 0/0 |

The Cheesecake base is the baked into finished cheesecakes using the following procedures and formulas.

TABLE 5

| INGREDIENT | WEIGHT PERCENT (%) | WEIGHT (GRAMS) |
|---|---|---|
| Cheesecake base | 50.00 | 350.00 |
| Granulated sugar | 20.00 | 140.00 |
| Egg whites | 30.00 | 210.00 |
| TOTAL | 100.00 | 700.00 |

The above ingredients, except the egg whites, are beaten at low speed for 1 minute and then at medium speed for 4 minutes in a 5 ½ qt. KITCHEN AID bowl with a whisk to form a creamed cheese-sugar mixture. Egg whites are then added to the above creamed cheese-sugar mixture and beaten at low speed for 30 seconds and at medium speed for 30 seconds. This resulted in a finished fat free cheesecake batter and 1.5 pounds of the fat free cheesecake batter is poured into a 7×3 inch Springform pan lined with 7 ounces of graham crust. The graham crumbs are a product of HBR Quality Bakers, Inc., Los Alamitos, Calif. 90720. The graham crust is formed by gradually adding 13.50 % of water to 86.50 % of the graham crumbs and are mixed at high speed for about 30 seconds in a 5 ½ qt. KITCHEN AID bowl with a dough hook. The crust is lightly patted into the Springform pan and allowed to remain at room temperature for 10-15 minutes. The cheesecake is baked in a home oven at 325 degrees F. for 40-50 minutes or to an internal temperature of 155-160 degrees F. It is then removed from the oven and cooled at room temperature for approximately 20-30 minutes and then is chilled overnight at 45 degrees F.

EXAMPLE 29 FAT FREE CHOLESTEROL FREE SOUR CREAM SUBSTITUTE

A stabilized fat substitute "SFS" sour cream sustitute is produced by first forming a dispersion of deagglomerated denatured whey protein-casein copre-cipitate in a continuous phase aqueous medium according to the procedure of Example 1. Ten pounds of sodium caseinate are added to 120 gallons of whey protein concentrate comprising approximately 14.74% solids and 6.71% protein. The mixture is heated by steam injection to 185 degrees F. and acidified to a pH of 5.6 to 5.65 by the addition of acetic acid in the form of vinegar. This resulted in the formation of a curd coprecipitate of whey protein and casein.

Two hundred pounds of curd are transferred from the FPEC cooker to the bowl chopper using a false bottom kitchen cart. Comminution/deagglomeration of the curd is achieved according to the procedure described in Example 1. The resulting fat free sour cream substitute product is further processed into fat free, cholesterol free, fat free sour cream substitute as described below.

The following components are incorporated with the fat free sour cream substitute product produced as described above to prepare a fat free sour cream substitute.

TABLE 1

| COMPONENTS | QUANTITY/POUND |
|---|---|
| Water | 8.0 |
| Alcolec 140 | 2.0 |
| Alcolec SFG | 1.0 |
| Water | 13.0 |
| Avicel RC591 | 5.0 |

The liposome and structure building formation is achieved in a similar manner to that set out in Example 1 in which the membrane-forming, surface active, and structure building agents are prepared in the STEPHAN cooker. The lecithin fractions (American Lecithin Company, Danbury, Conn. 06813-1908) are added to water in the STEPHAN cooker to form liposomes as described in Example 1. The STEPHAN cooker is operated for 8 minutes at 120 degrees F. Thereafter, the STEPHAN cooker is opened and the liposomes made from the lecithin-water mixture are visually examined for the presence of undissolved particles and to insure complete dispersion. Upon confirmation that the mixture is uniformly dispersed and that liposomes are formed, a caramel cream-like appearance is observed. An additional 13 pounds of hydration water is added to the liposomes in the STEPHAN cooker together with 5 pounds of microcrystalline cellulose and mixed for approximately 10 minutes. The STEPHAN cooker is then opened and the liposome mixture is visually examined under a polarized light microscope for proper dispersion. Upon confirming that proper dispersion is achieved, the STEPHAN cooker is closed and the temperature raised to 180 degrees F. by steam injection with high speed agitation. Upon reaching 180 degrees F., the steam flow is terminated, the STEPHAN cooker is opened, and the mixture is transferred to a clean sterilized bucket and slowly added to the chopper. The pasteurized lecithin-microcrystalline cellulose complex is processed in the chopper for 10 minutes to form a membrane around the curd particles, to place amphoteric charges on the curd particles, and to create structure in the aqueous phase as described in Example 1.

STEP 2

A stabilizer is produced from the components in Table 2.

TABLE 2

| COMPONENTS | QUANTITY/POUND |
|---|---|
| Water | 26.00 |
| Slendid Pectin | 4.0 |
| Genu Pectin | 0.5 |
| Calcium Chloride Solution | 20 mls. |

The stabilizer from Table 2 is prepared by adding SLENDID pectin and the GENU pectin to the 26 pounds of water in the STEPHAN cooker. The bottom agitator is set at high speed and the side agitator is turned on for 5 minutes. The STEPHAN cooker is then opened and the pectin dispersion is then inspected for complete dispersion. The ingredients are mixed in the STEPHAN cooker for 5 minutes at high speed (3,000 rpm) with no steam injection. The STEPHAN cooker is then opened and the calcium chloride solution is added and mixed for 2 minutes. The STEPHAN cooker is then opened and the contents subjected to tactile and visual examination as described in Example 1—STEPHAN Cooker Step 2.

STEP 3

Additional microbial inhibitors are prepared in the STEPHAN cooker using the components from Table 3. The ingredients are added to Step 2 above.

TABLE 3

| COMPONENTS | QUANTITY/POUND |
|---|---|
| Alta 2020 | 1.5 |
| Alta 2001 | 0.5 |
| Alta 1705 | 0.5 |

The ingredients are mixed in the STEPHAN cooker for 2 minutes at high speed (3,000 rpm). The STEPHAN cooker is then opened and the contents subjected to tactile and visual examination as described in Example 1—STEPHAN Cooker Step 2.

STEP 4

The component in Table 4 is added to those in Step 3.

TABLE 4

| COMPONENT | QUANTITY/POUND |
|---|---|
| Enrich 221 | 4.0 |

The ingredients are mixed in the STEPHAN cooker for 2 minutes at high speed (3,000 rpm). The STEPHAN cooker is then opened and the contents subjected to tactile and visual examination as described in Example 1—STEPHAN Cooker Step 2.

STEP 5

The component in Table 5 is added to those in Step 4.

TABLE 5

| COMPONENT | QUANTITY/POUND |
|---|---|
| Non Fat Dry Milk Powder | 8.0 |

The ingredient is mixed in the STEPHAN cooker for 2 minutes at high speed (3,000 rpm). The STEPHAN cooker is then opened and the contents subjected to tactile and visual examination as described in Example 1—STEPHAN Cooker Step 2.

STEP 6

The components in Table 6 is added to those in Step 5.

TABLE 6

| COMPONENTS | QUANTITY/POUND |
|---|---|
| Parselli SA-2 | 2.0 |
| GP Maltodextrin 040 | 2.0 |

The ingredients are mixed in the STEPHAN cooker for 2 to 3 minutes at high speed (3,000 rpm). The STEPHAN cooker is then opened and the contents subjected to tactile and visual examination as described in Example 1—STEPHAN Cooker Step 2. When satisfactory results are achieved, i.e., even dispersion, the STEPHAN cooker is then closed and the temperature raised to 180 degrees F. by steam injection with high speed agitation. When the temperature reached 180 F., agitation is ceased, steam flow is terminated, and the pressure released. The STEPHAN cooker is then opened and the contents are added slowly to the continually operating chopper.

HOMOGENIZATION PROCESS

The homogenization process is carried out by using a Moyno pump to force the heavy, viscous fat free sour cream substitute through the inlet valves of the high pressure homogenizer. The stuffing pressure produced by the Moyno pump has to exceed 150 to 200 pounds per square inch to prevent implosion. Since the fat free sour cream substitute at this point has a viscosity between 35,000 and 45,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer is used at a first stage pressure of 10,000 pounds per square inch and 1,500 pounds on the second stage.

The fat free sour cream substitute premix is cooled and packaged as described in Example 1.

The chemical and microbiological analysis of this premix product is as follows:

| MOISTURE | 71.64% |
|---|---|
| pH | 5.85 |
| FAT | 0.98% |
| SALT | 1.5% |
| STANDARD PLATE COUNT | <100 |
| COLI | <10 |
| YEAST/MOLD | 0/0 |

The sour cream premix formulated previously was mixed with the following ingredients in Table 7.

TABLE 7

| INGREDIENT | WEIGHT PERCENT (%) | WEIGHT (POUNDS) |
|---|---|---|
| Sour cream premix | 65.00 | 52.00 |
| Non fat milk solids | 12.00 | 9.6 |
| Water | 23.00 | 18.4 |
| TOTAL | 100.00 | 80.00 |

The ingredients in Table 7 are mixed in the STEPHAN cooker for 2 to 3 minutes at high speed (3,000 rpm). The STEPHAN cooker is then opened and the contents subjected to tactile and visual examination as described in Example 14—STEPHAN Cooker Step 2. When satisfactory results are achieved, i.e., even dispersion, the STEPHAN cooker is then closed and the temperature raised to 185 degrees F. by steam injection with high speed agitation. When the temperature reached 180° F., agitation is ceased, steam flow is terminated, and the pressure released. The cold water is then turned on the jacket of the STEPHAN cooker and the fat free sour cream substitute base is cooled to 160 degrees F.

HOMOGENIZATION PROCESS

The homogenization process is carried out by using a funnel to pour the fat free sour cream substitute into the inlet of the high pressure homogenizer. The stuffing pressure produced by the height of the funnel is sufficent to feed the homogenizer. A APV RANNIE high pressure homogenizer is used with a first stage pressure of 2,500 pounds per square inch and 1,000 pounds on the second stage.

The fat free sour cream substitute premix is cooled to 720 degrees F. and innoculated with Sieries 300 and 700 Sour Cream cultures available from Quest-Microlife Technics, Inc. of Sarasota, Fla., 34230. The Sieres 300 provide body while the 700 provides flavor. Several batches of the same formula are made and packaged into 5 gallon pails. The fat free sour cream substitute is allowed the ferment for 14 to 16 hours until the pH reaches 4.65. The pails are then moved to the chilled brine and the fat free sour cream is allowed to cool to 400 degrees F. and then stored under refrigeration.

The chemical and microbiological analysis of this fat free sour cream substitute product is as follows:

| | |
|---|---|
| MOISTURE | 72.27% |
| pH | 4.58 |
| FAT | 0.98% |
| SALT | 0.65% |
| STANDARD PLATE COUNT | TNTC |
| COLI | <10 |
| YEAST/MOLD | 0/0 |

EXAMPLE 30 FAT FREE CHOLESTEROL FREE SOFT FRESH CHEESE FROM INJECTION AND JACKET HEATING

A stabilized fat substitute "SFS" fat free soft fresh cheese is produced by first forming a dispersion of deagglomerated denatured whey protein-casein co-precipitate in a continuous phase aqueous medium. In this example, 250 pounds of whey protein concentrate form the cottage cheese production of Example 28 is mixed with 250 pounds of whey protein concentrate produced as in Example 1. Five pounds of sodium caseinate are added to the 500 pound mixture which now comprises a composite with a composition of approximately 15.45% solids and 7.61% protein. The mixture is acidified to a pH of 5.6 to 5.65 by the addition of lactic acid mixed with water and heated by steam injection and a steam jacket to 190 degrees F. This resulted in the formation of a curd coprecipitate of whey protein and casein. The heating process is preformed in the 40 liter STEPHAN cooker with 50 pounds of the above mixture placed into the cooker for each batch. The curd yield from each batch is approxiately 16 to 18 pounds and the process is repeated until two hundred pounds are accumulated.

Two hundred pounds of accumulated curd are transferred to the bowl chopper using a false bottom kitchen cart. Comminution/deagglomeration of the curd is achieved according to the procedure described in Example 14. The resulting fat free soft fresh cheese product is further processed into fat free, cholesterol free, soft fresh cheese as described below.

The following components are incorporated with the fat free soft fresh cheese product produced as described above to prepare a fat free soft fresh cheese.

TABLE 1

| COMPONENTS | QUANTITY/POUND |
|---|---|
| Water | 8.0 |
| Alcolec 140 | 2.0 |
| Alcolec SFG | 1.0 |
| Water | 13.0 |
| Avicel RC591 | 5.0 |

STEP 1

The liposome and structure building formation is achieved in a similar manner to that set out in Example 1 in which the membrane-forming, surface active, and structure building agents are prepared in the STEPHAN cooker. The lecithin fractions (American Lecithin Company, Danbury, Conn. 06813-1908) are added to water in the STEPHAN cooker to form liposomes as described in Example 1. The STEPHAN cooker is operated for 8 minutes at 120 degrees F. Thereafter, the STEPHAN cooker is opened and the liposomes made from the lecithin-water mixture are visually examined for the presence of undissolved particles and to insure complete dispersion. Upon confirmation that the mixture is uniformly dispersed and that liposomes are formed, a caramel cream-like appearance is observed. An additional 13 pounds of hydration water is added to the liposomes in the STEPHAN cooker together with 5 pounds of microcrystalline cellulose and mixed for approximately 10 minutes. The STEPHAN cooker is then opened and the liposome mixture is visually examined under a polarized light microscope for proper dispersion. Upon confirming that proper dispersion is achieved, the STEPHAN cooker is closed and the temperature raised to 180 degrees F. by steam injection with high speed agitation. Upon reaching 180 degrees F., the steam flow is terminated, the STEPHAN cooker is opened, and the mixture is transferred to a clean sterilized bucket and slowly added to the chopper. The pasteurized lecithin-microcrystalline cellulose complex is processed in the chopper for 10 minutes to form a membrane around the curd particles, to place amphoteric charges on the curd particles, and to create structure in the aqueous phase as described in Example 1.

STEP 2

A stabilizer is produced from the components in Table 2.

TABLE 2

| COMPONENTS | QUANTITY/POUND |
|---|---|
| Water | 26.00 |
| Slendid Pectin | 4.0 |
| Genu Pectin | 1.5 |
| Calcium Chloride Solution | 20 mls. |

The stabilizer from Table 2 is prepared by adding SLENDID pectin and the GENU pectin to the 26 pounds of water in the STEPHAN cooker. The bottom agitator is set at high speed and the side agitator is turned on for 5 minutes. The STEPHAN cooker is then opened and the pectin dispersion is then inspected for complete dispersion. The ingredients are mixed in the STEPHAN cooker for 5 minutes at high speed (3,000 rpm) with no steam injection. The STEPHAN cooker is then opened and the calcium chloride solution is added and mixed for 2 minutes. The STEPHAN cooker is then opened and the contents subjected to tactile and visual examination as described in Example 1—STEPHAN Cooker Step 2.

STEP 3

Additional microbial inhibitors are prepared in the STEPHAN cooker using the components from Table 3. The ingredients are added to Step 2 above.

TABLE 3

| COMPONENTS | QUANTITY/POUND |
| --- | --- |
| Alta 2301 | 0.5 |
| Alta 1803 | 0.5 |
| Alta 2020 | 1.5 |
| Alta 2001 | 0.5 |
| Alta 1705 | 0.5 |
| Accel 4301 | 4.0 |

The ingredients are mixed in the STEPHAN cooker for 2 minutes at high speed (3,000 rpm). The STEPHAN cooker is then opened and the contents subjected to tactile and visual examination as described in Example 1—STEPHAN Cooker Step 2.

STEP 4

The component in Table 4 is added to those in Step 3.

TABLE 4

| COMPONENT | QUANTITY/POUND |
| --- | --- |
| Enrich 101 | 5.0 |

The ingredients are mixed in the STEPHAN cooker for 2 minutes at high speed (3,000 rpm). The STEPHAN cooker is then opened and the contents subjected to tactile and visual examination as described in Example 1—STEPHAN Cooker Step 2.

STEP 5

The component in Table 5 is added to those in Step 4.

TABLE 5

| COMPONENT | QUANTITY/POUND |
| --- | --- |
| Non Fat Dry Milk Powder | 8.0 |
| Cultured Non Fat Buttermilk | 10.0 |

The ingredient is mixed in the STEPHAN cooker for 2 minutes at high speed (3,000 rpm). The STEPHAN cooker is then opened and the contents subjected to tactile and visual examination as described in Example 1—STEPHAN Cooker Step 2.

STEP 6

The components in Table 6 is added to those in Step 5.

TABLE 6

| COMPONENTS | QUANTITY/POUND |
| --- | --- |
| Parselli SA-2 | 4.0 |
| GP Maltodextrin 040 | 4.0 |

The ingredients are mixed in the STEPHAN cooker for 2 to 3 minutes at high speed (3,000 rpm). The STEPHAN cooker is then opened and the contents subjected to tactile and visual examination as described in Example 1—STEPHAN Cooker Step 2. When satisfactory results are achieved, i.e., even dispersion, the STEPHAN cooker is then closed and the temperature raised to 180 degrees F. by steam injection with high speed agitation. When the temperature reached 180 F., agitation is ceased, steam flow is terminated, and the pressure released. The STEPHAN cooker is then opened and the contents are added slowly to the continually operating chopper.

ACIDIFICATION PROCESS

The acidification process is carried out according to the procedure outlined in Example 14 in which the mixture is acidified to a pH of 4.9 to 5.0 by adding lactic acid (CCA Biochem b. v. Holland) and 20 ml of starter distillate (HANSEN'S 15X) to the continually operating chopper and mixing for about one minute.

HOMOGENIZATION PROCESS

The homogenization process is carried out by using a Moyno pump to force the heavy, viscous fat free soft fresh cheese through the inlet valves of the high pressure homogenizer. The stuffing pressure produced by the Moyno pump has to exceed 150 to 200 pounds per square inch to prevent implosion. Since the fat free soft fresh cheese at this point has a viscosity between 35,000 and 45,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer is used at a first stage pressure of 10,000 pounds per square inch and 1,500 pounds on the second stage.

The fat free soft fresh cheese premix is cooled and packaged as described in Example 1.

The chemical and microbiological analysis of this premix product is as follows:

The chemical and microbiological analysis of this product is as follows:

| pH | 5.01 |
| --- | --- |
| FAT | 0.20% |
| SALT | 2.40% |
| STANDARD PLATE COUNT | <100 |
| COLI | <10 |
| YEAST/MOLD | 0/0 |

FINAL FLAVORING PROCESS

The components listed in Table 7, below, are added to the soft fresh cheese produced via the procedures described above. This resulted in garlic and herb flavored soft spreadable cheese.

TABLE 7

| INGREDIENT | WEIGHT PERCENT (%) |
| --- | --- |
| Soft Fresh Cheese | 99.00 |
| Herb and Garlic C208-B | 1.0 |
| | 100.00 |

The Garlic and Herb Base is a product of Saratoga Specialties, Elmhurst, IL 60126.

The above ingredients are blended for 1 minute in a 5½ qt. Kitchen Aid bowl with a paddle. The resulting spread is evaluated against two commercial low cholesterol spreadable cheeses for spread characteristics, texture and smoothness. In comparisons of spread characteristics, no significant differences are detected. In comparisons of texture, synersis was detected in one of the commercial products. However, the product produced via the above described procedures continued to exhibit its creamy texture. The overall smoothness and organoleptic qualities of the product are comparable to that of high fat, spreadable cheese with butterfat ranges of 12% to 30%.

EXAMPLE 31 SOUR CREAM CHEESECAKE

A sour cream cheesecake filling is produced by incorporating the following components:

TABLE 1

| COMPONENTS | WEIGHT PERCENT (%) |
|---|---|
| Cheesecake base (Example 14) | 45.00 |
| Granulated sugar | 20.00 |
| Sour cream substitute (Example 29) | 15.00 |
| Egg whites | 15.00 |
| TOTAL | 100.00 |

The cheesecake base as described in example 14 is combined with granulated sugar and mix at low speed (speed 2) for 1 minute and at medium speed (speed 6) for 3 minutes in a 5 ½ qt. Kitchen Aid bowl with a whisk to form a creamed cheese mixture. Sour cream subsititute as described in example 29 is added to the above creamed cheese mixture and is mixed for an additional minute at medium speed (speed 6) or until an homogeneous composition is formed. Egg whites is then added to the above contents and mix at low speed (speed 2) for 30 seconds and at medium speed (speed 6) for 30 seconds or until it reaches the specific gravity between 0.75–0.80. The resulting finished sour cream cheesecake filling is baked into a chessecake in accordance with the method described in example 14.

EXAMPLE 32 FAT FREE CHOLESTEROL FREE FAT SUBSTITUTE

A stabilized fat substitute "SFS" was produced by first forming a dispersion of deagglomerated denatured whey protein-casein coprecipitate in a continuous phase aqueous medium according to the procedure of Example 1. Ten pounds of sodium caseinate were added to 120 gallons of whey protein concentrate comprising approximately 14.45% solids and 6.64% protein. The mixture was heated by steam injection to 185 degrees F. and acidified to a pH of 5.6 to 5.65 by the addition of acetic acid in the form of vinegar. This resulted in the formation of a curd coprecipitate of whey protein and casein.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, fat substitute as described below.

The following components were incorporated with the fat substitute product produced as described above to prepare a fat substitute.

TABLE 1

| COMPONENTS | QUANTITY/POUND |
|---|---|
| Water | 8.0 |
| Alcolec 140 | 2.0 |
| Alcolec SFG | 1.0 |
| Water | 13.0 |
| Avicel RC591 | 5.0 |

STEP 1

The liposome and structure building formation was achieved in a similar manner to that set out in Example 1 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 1. The STEPHAN cooker was operated for 8 minutes at 120 degrees F. Thereafter, the STEPHAN cooker was opened and the liposomes made from the lecithin-water mixture were visually examined for the presence of undissolved particles and to insure complete dispersion. Upon confirmation that the mixture was uniformly dispersed and that liposomes were formed, a caramel cream-like appearance was observed. An additional 13 pounds of hydration water was added to the liposomes in the STEPHAN cooker together with 5 pounds of microcrystalline cellulose and mixed for approximately 10 minutes. The STEPHAN cooker was then opened and the liposome mixture was visually examined under a polarized light microscope for proper dispersion. Upon confirming that proper dispersion was achieved, the STEPHAN cooker was closed and the temperature raised to 180 degrees F. by steam injection with high speed agitation. Upon reaching 180 degrees F., the steam flow was terminated, the STEPHAN cooker was opened, and the mixture was transferred to a clean sterilized bucket and slowly added to the chopper. The pasteurized lecithin-microcrystalline cellulose complex was processed in the chopper for 10 minutes to form a membrane around the curd particles, to place amphoteric charges on the curd particles, and to create structure in the aqueous phase as described in Example 1.

STEP 2

A stabilizer was produced from the components in Table 2.

TABLE 2

| COMPONENTS | QUANTITY/POUND |
|---|---|
| Water | 20.00 |
| Slendid Pectin | 2.0 |
| Genu Pectin | 0.5 |
| Calcium Chloride Solution | 20 mls. |

The stabilizer from Table 2 was prepared by adding SLENDID pectin and the GENU pectin to the 20 pounds of water in the STEPHAN cooker. The bottom agitator was set at high speed and the side agitator was turned on for 5 minutes. The STEPHAN cooker was then opened and the pectin dispersion was then inspected for complete dispersion. The ingredients were mixed in the STEPHAN cooker for 5 minutes at high speed (3,000 rpm) with no steam injection. The STEPHAN cooker was then opened and the calcium chloride solution was added and mixed for 2 minutes. The STEPHAN cooker was then opened and the contents subjected to tactile and visual examination as described in Example 1—Stephan Cooker Step 2. SLENDID and GENU pectins are specialty processed pectins distributed by Hercules, Inc., Wilmington, Del. 19894-000.

STEP 3

Additional microbial inhibitors were prepared in the STEPHAN cooker using the components from Table 3. These ingredients were added to those made in Step 2 above.

TABLE 3

| COMPONENTS | QUANTITY/POUND |
|---|---|
| Alta 2331 | 0.5 |
| Alta 1801 | 0.5 |

TABLE 3-continued

| COMPONENTS | QUANTITY/POUND |
| --- | --- |
| Alta 2001 | 0.5 |
| Alta 1705 | 0.5 |

The ingredients were mixed in the STEPHAN cooker for 2 minutes at high speed (3,000 rpm). The STEPHAN cooker was then opened and the contents subjected to tactile and visual examination as described in Example 1—STEPHAN Cooker Step 2.

STEP 4

The component in Table 4 was added to those in Step 3.

TABLE 4

| COMPONENT | QUANTITY/POUND |
| --- | --- |
| Enrich 221 | 2.0 |

The ingredients were mixed in the STEPHAN Cooker for 2 minutes at high speed (3,000 rpm). The STEPHAN cooker was then opened and the contents subjected to tactile and visual examination as described in Example 1—STEPHAN Cooker Step 2. The Enrich 521 is a natural microbial stabilizer available from Quest-Microlife Technics, Inc. of Sarasota, Fla., 34230.

STEP 5

The component in Table 5 was added to those in Step 4.

TABLE 5

| COMPONENT | QUANTITY/POUND |
| --- | --- |
| Cal Pro 50 Whey Protein | 2.0 |

The ingredient was mixed in the STEPHAN cooker for 2 minutes at high speed (3,000 rpm). The STEPHAN cooker was then opened and the contents subjected to tactile and visual examination as described in Example 1—STEPHAN Cooker Step 2. Non Fat Dry Milk powder is a product of Cal Pro Proteins, corona, Calif. 91720.

STEP 6

The components in Table 6 was added to those in Step 5.

TABLE 6

| COMPONENTS | QUANTITY/POUND |
| --- | --- |
| Parselli SA-2 | 2.0 |
| GP Maltodextrin 040 | 2.0 |

The ingredients were mixed in the STEPHAN cooker for 2 to 3 minutes at high speed (3,000 rpm). The STEPHAN cooker was then opened and the contents subjected to tactile and visual examination as described in Example 1—STEPHAN Cooker Step 2. When satisfactory results were achieved, i.e., even dispersion, the STEPHAN cooker was then closed and the temperature raised to 180 degrees F. by steam injection with high speed agitation. When the temperature reached 180 F., agitation was ceased, steam flow was terminated, and the pressure released. The STEPHAN cooker was then opened and the contents were added slowly to the continually operating chopper.

HOMOGENIZATION PROCESS

The homogenization process was carried out by using a Moyno pump to force the heavy, viscous fat substitute through the inlet valves of the high pressure homogenizer. The stuffing pressure produced by the Moyno pump has to exceed 150 to 200 pounds per square inch to prevent implosion. Since the fat substitute at this point has a viscosity between 35,000 and 45,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer was used at a first stage pressure of 10,000 pounds per square inch and 1,500 pounds on the second stage.

The fat substitute was cooled and packaged as described in Example 1.

The chemical and microbiological analysis of this product was as follows:

| pH | 5.82 |
| --- | --- |
| FAT | 0.81% |
| SALT | 1.55% |
| STANDARD PLATE COUNT | <100 |
| COLI | <10 |
| YEAST/MOLD | 0/0 |

The fat substitute was held for 90 days at refrigerated temperatures and analysis was preformed for Standard Plate Count and for the appearance of grainey or rough mouthfeel or chalkiness. The SPC had increased to less than 1,000 CFU and the fat substitute did not have any indication of degradation of the fat-like mouthfeel. This fat sustitute would be applicable where pH is a factor in stability. Since casein is a factor in the formulation of Example 19 as a component of the non fat milk solids in Step No. 5, whey protein was substituted in place of the non fat solids. Casein will precipitate at pH 4.6, whereas whey protein will not until the pH of 3.3 is reached. Thus, the fat substitute in this example will remain acid pH stable.

EXAMPLE 33 FAT FREE CHOLESTEROL FREE MAYONNAISE DRESSING WHEY PROTEIN PRECIPITATE/CASEIN PRECIPITATE pH ADJUSTED

A stabilized fat substitute "SFS" mayonnaise dressing was produced by first forming a dispersion of deagglomerated denatured whey protein/casein precipitate in a continuous phase aqueous medium according to the procedure of Example 1. The whey protein concentrate/casein premix was pH adjusted to 7.3 and then heated to 183 degrees F. The premix was held at this temperature for 10 minutes. The pH adjustment was accomplished by the addition of Calcuim Carbonate as in Example 14. The heating of the whey-caseinate premix to high temperature at a pH of greater than 6.8, but less than 8 creates molecular cross linkages —S—S— that occur when egg whites are heated. The curd resulting from this process had a thicker body, yet softer texture than that made form from either whey protein or whey protein-caseinate coprecipitate. It is important not to heat for too long, or at a too high temperature, and not to raise the pH above about 8.0. Any of these circumstances will cause the premix to gel instead of creating a curd. The gel structure makes it difficult, if not immmpossible to separate the whey from the precipitate.

The whey protein concentrate/casein premix contained approximately 15.8% solids and 7.43% protein. The mixture was heated by steam injection to 183 degrees F., held at this temperature for tem minutes, and then acidified to a pH of 5.75 to 5.85 by the addition of acetic acid in the form of vinegar. This resulted in the formation of a curd coprecipitate of whey protein and casein.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, mayonnaise dressing as described below.

The following components were incorporated with the fat substitute product produced as described above to prepare a mayonnaise dressing.

TABLE 1

| COMPONENTS | QUANTITY/POUND |
|---|---|
| Water | 8.0 |
| Alcolec 140 | 4.0 |
| Alcolec SFG | 1.0 |
| Water | 13.0 |
| Avicel RC591 | 5.0 |

STEP 1

The liposome and structure building formation was achieved in a similar manner to that set out in Example 1 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 1. The STEPHAN cooker was operated for 8 minutes at 120 degrees F. Thereafter, the STEPHAN cooker was opened and the liposomes made from the lecithin-water mixture were visually examined for the presence of undissolved particles and to insure complete dispersion. Upon confirmation that the mixture was uniformly dispersed and that liposomes were formed, a caramel cream-like appearance was observed. An additional 13 pounds of hydration water was added to the liposomes in the STEPHAN cooker together with 5 pounds of microcrystalline cellulose and mixed for approximately 10 minutes. The STEPHAN cooker was then opened and the liposome mixture was visually examined under a polarized light microscope for proper dispersion- Upon confirming that proper dispersion was achieved, the STEPHAN cooker was closed and the temperature raised to 180 degrees F. by steam injection with high speed agitation. Upon reaching 180 degrees F., the steam flow was terminated, the STEPHAN cooker was opened, and the mixture was transferred to a clean sterilized bucket and slowly added to the chopper. The pasteurized lecithin-microcrystalline cellulose complex was processed in the chopper for 10 minutes to form a membrane around the curd particles, to place amphoteric charges on the curd particles, and to create structure in the aqueous phase as described in Example 1.

STEP 2

A stabilizer was produced from the components in Table 2.

TABLE 2

| COMPONENTS | QUANTITY/POUND |
|---|---|
| Water | 26.00 |
| Slendid Pectin | 2.0 |
| Gelatin 250 Bloom | 0.5 |
| Calcium Chloride Solution | 20 mls. |

The stabilizer from Table 2 was prepared by adding SLENDID pectin to the 26 pounds of water in the STEPHAN cooker. The bottom agitator was set at high speed and the side agitator was turned on for 5 minutes. The STEPHAN cooker was then opened and the pectin dispersion was then inspected for complete dispersion. The 250 Bloom Gelatin was then added to the water-pectin dispersion. The ingredients were mixed in the STEPHAN cooker for 5 minutes at high speed (3,000 rpm) with no steam injection. The STEPHAN cooker was then opened and the calcium chloride solution was added and mixed for 2 minutes. The STEPHAN cooker was then opened and the contents subjected to tactile and visual examination as described in Example 1—STEPHAN Cooker Step 2. SLENDID pectin is a specialty processed pectin distributed by Hercules, Inc., Wilmington, Del. 19894-000 and manufactured by Copenhagen Pectin, DK 4623, Skensved, Denmark.

STEP 3

Additional microbial inhibitors, sugar, and salt were prepared in the STEPHAN cooker using the components from Table 3. These ingredients were added to those made in Step 2 above.

TABLE 3

| COMPONENTS | QUANTITY/POUND |
|---|---|
| Salt | 3.5 |
| Sugar | 2.0 |
| Alta 2331 | 0.5 |
| Alta 1801 | 0.5 |
| Alta 2001 | 0.5 |
| Alta 1705 | 0.5 |

The ingredients were mixed in the STEPHAN cooker for 2 minutes at high speed (3,000 rpm) The STEPHAN cooker was then opened and the contents subjected to tactile and visual examination as described in Example 1—STEPHAN Cooker Step 2.

STEP 4

The component in Table 4 was added to those in Step 3.

TABLE 4

| COMPONENTS | QUANTITY/POUND |
|---|---|
| Enrich 221 | 6.0 |

The ingredients were mixed in the STEPHAN cooker for 2 minutes at high speed (3,000 rpm) The STEPHAN cooker was then opened and the contents subjected to tactile and visual examination as described in Example 1—STEPHAN cooker Step 2. The Enrich 221 is a natural microbial stabilizer available from Quest-Microlife Technics, Inc. of Sarasota, Fla., 34230.

STEP 5

The component in Table 5 was added to those in Step 4.

TABLE 5

| COMPONENT | QUANTITY/POUND |
|---|---|
| Cal Pro 50 Whey Protein Powder | 3.0 |

The ingredient was mixed in the STEPHAN cooker for 2 minutes at high speed (3,000 rpm). The STEPHAN cooker was then opened and the contents subjected to tactile and visual examination as described in Example 1—STEPHAN Cooker Step 2. CAL PRO 50 whey protein powder contains 50 percent protein and is a product of Cal Pro proteins, corona, Calif. 91720.

STEP 6

The components in Table 6 was added to those in Step 5.

TABLE 6

| COMPONENTS | QUANTITY/POUND |
|---|---|
| Parselli SA-2 | 6.0 |
| GP Maltodextrin 040 | 3.0 |
| Coleman's Mustard Flour | 3.0 |
| Corn Syrup 42 D.E. | 4.0 |

The ingredients were mixed in the STEPHAN cooker for 2 to 3 minutes at high speed (3,000 rpm). The STEPHAN cooker was then opened and the contents subjected to tactile and visual examination as described in Example 1—STEPHAN Cooker Step 2. When satisfactory results were achieved, i.e., even dispersion, the STEPHAN cooker was then closed and the temperature raised to 180 degrees F. by steam injection with high speed agitation. When the temperature reached 180° F., agitation was ceased, steam flow was terminated, and the pressure released. The STEPHAN cooker was then opened and the contents were added slowly to the continually operating chopper. COLEMAN'S Mustard Flour is a product of the R. T. French Company of Rochester, N.Y. 14692.

ACIDIFICATION PROCESS

The acidification process was carried out according to the procedure outlined in Example 1 in which the mixture was acidified to a pH of 4.2 to 4.3 by adding acetic acid in the form of 300 grain vinegar. The 300 grain vinegar is a product of Integrated Ingredients, Montebello, Calif.

HOMOGENIZATION PROCESS

The homogenization process was carried out by using a Moyno pump to force the heavy, viscous mayonnaise dressing through the inlet valves of the high pressure homogenizer. The stuffing pressure produced by the Moyno pump has to exceed 150 to 200 pounds per square inch to prevent implosion. Since the mayonnaise dressing at this point has a viscosity between 40,000 and 50,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer was used at a first stage pressure of 10,000 pounds per square inch and 1,500 pounds on the second stage.

The mayonnaise dressing was cooled and packaged as described in Example 1.

The chemical and microbiological analysis of this product was as follows:

| pH | 4.72 |
|---|---|
| FAT | 0.92% |
| SALT | 3.5% |
| STANDARD PLATE COUNT | <100 |
| COLI | <10 |
| YEAST/MOLD | 0/0 |

The mayonnaise dressing produced in this Example had the heavy body of the typical high egg yolk formula than both of the mayonnaise dressings produced in Examples 17 and 18. The resulting pH was lower thereby facilitating additional shelf life.

EXAMPLE 34 FAT FREE CHOLESTEROL FREE MAYONNAISE DRESSING EGG WHITE/WHEY PROTEIN PRECIPITATE/CASEIN/PRECIPITATE pH ADJUSTED

A stabilized fat substitute "SFS" mayonnaise dressing was produced by first forming a dispersion of deagglomerated denatured egg white/whey protein/casein precipitate in a continuous phase aqueous medium according to the general procedure of Example 1. The composition of the protein concentrate premix is according to Table 1.

STEP NO. 1
TABLE NO. 1

| COMPONENTS | QUANTITY/POUND |
|---|---|
| Fresh Egg Whites | 600 |
| Whey Protein Concentrate | 500 |
| Sodium Caseinate | 10 |
| Cal Pro 50 Whey Protein | 15 |
| Dehydrated Egg Whites | 15 |
| TOTAL | 1140 |

The dehydrated egg whites are a specialty product of Henningsen Foods, Inc. 2 Corporate Park Drive, White Plains, N.Y., 10604. The product designation is P-110 High Gel Strength Type and has a neutral pH with excellent binding abilities.

The egg white/whey protein concentrate/casein premix was pH adjusted to 6.93 and then heated to 178 degrees F. The premix was held at this temperature for 5 minutes. The pH adjustment was accomplished by the addition of Calcium Carbonate as in Example 14. The heating of the egg white-whey protein—caseinate premix to high temperature at a pH of greater than 6.8, but less than 7.5 creates molecular cross linkages —S—S— that occur when egg whites are heated alone. The curd resulting from this process had a thicker, tougher body than Example 33. It is important not to heat for too long nor too high nor raise the pH above 7.5. Any of these circumstances will cause the premix to gel much like cooked egg white instead of creating a curd. The gel structure makes it difficult, if not impossible to separate the whey from the precipitate. Furthermore, the gel structure has a high moisture content that will adversely affect the finished products. The high moisture content of the gel would not allow for the manipulation or deagglomeration in the chopper to create the coprecipitate particles that are the subject of this invention.

The egg white/whey protein concentrate/casein premix contained approximately 17.26% solids and 7.95% protein. The mixture was heated by steam injection to 178 degrees F., held at this temperature for ten minutes, and then acidified to a pH of 5.75 to 5.85 by the addition of acetic acid in the form of vinegar. This resulted in the formation of a curd coprecipitate of whey protein and casein.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, mayonnaise dressing as described below.

The following components were incorporated with the fat substitute product produced as described above to prepare a mayonnaise dressing.

TABLE 1

| COMPONENTS | QUANTITY/POUND |
| --- | --- |
| Water | 8.0 |
| Alcolec 140 | 4.0 |
| Alcolec SFG | 1.0 |
| Water | 13.0 |
| Avicel RC591 | 5.0 |

STEP 1

The liposome and structure building formation was achieved in a similar manner to that set out in Example 1 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 1. The STEPHAN cooker was operated for 8 minutes at 120 degrees F. Thereafter, the STEPHAN cooker was opened and the liposomes made from the lecithin-water mixture were visually examined for the presence of undissolved particles and to insure complete dispersion. Upon confirmation that the mixture was uniformly dispersed and that liposomes were formed, a caramel cream-like appearance was observed. An additional 13 pounds of hydration water was added to the liposomes in the STEPHAN cooker together with 5 pounds of microcrystalline cellulose and mixed for approximately 10 minutes. The STEPHAN cooker was then opened and the liposome mixture was visually examined under a polarized light microscope for proper dispersion. Upon confirming that proper dispersion was achieved, the STEPHAN cooker was closed and the temperature raised to 180 degrees F. by steam injection with high speed agitation. Upon reaching 180 degrees F., the steam flow was terminated, the STEPHAN cooker was opened, and the mixture was transferred to a clean sterilized bucket and slowly added to the chopper. The pasteurized lecithin-microcrystalline cellulose complex was processed in the chopper for 10 minutes to form a membrane around the curd particles, to place amphoteric charges on the curd particles, and to create structure in the aqueous phase as described in Example 1.

STEP 2

A stabilizer was produced from the components in Table 2.

TABLE 2

| COMPONENTS | QUANTITY/POUND |
| --- | --- |
| Water | 26.00 |
| Slendid Pectin | 2.0 |
| Gelatin 250 Bloom | 0.5 |
| Calcium Chloride Solution | 20 mls. |

The stabilizer from Table 2 was prepared by adding SLENDID pectin to the 26 pounds of water in the STEPHAN cooker. The bottom agitator was set at high speed and the side agitator was turned on for 5 minutes. The STEPHAN cooker was then opened and the pectin dispersion was then inspected for complete dispersion. The 250 Bloom Gelatin was then added to the water-pectin dispersion. The ingredients were mixed in the STEPHAN cooker for 5 minutes at high speed (3,000 rpm) with no steam injection. The STEPHAN cooker was then opened and the calcium chloride solution was added and mixed for 2 minutes. The STEPHAN cooker was then opened and the contents subjected to tactile and visual examination as described in Example 1—Stephan Cooker Step 2. SLENDID pectin is a specialty processed pectin distributed by Hercules, Inc., Wilmington, Del. 19894-000 and manufactured by Copenhagen Pectin, DK 4623, Skensved, Denmark.

STEP 3

Additional microbial inhibitors, sugar, and salt were prepared in the STEPHAN cooker using the components from Table 3. These ingredients were added to those made in Step 2 above.

TABLE 3

| COMPONENTS | QUANTITY/POUND |
| --- | --- |
| Salt | 3.5 |
| Sugar | 2.0 |
| Alta 2331 | 0.5 |
| Alta 1801 | 0.5 |
| Alta 2001 | 0.5 |
| Alta 1705 | 0.5 |

The ingredients were mixed in the STEPHAN cooker for 2 minutes at high speed (3,000 rpm) The STEPHAN cooker was then opened and the contents subjected to tactile and visual examination as described in Example 1—STEPHAN Cooker Step 2.

STEP 4

The component in Table 4 was added to those in Step 3.

TABLE 4

| COMPONENTS | QUANTITY/POUND |
| --- | --- |
| Enrich 221 | 6.0 |

The ingredients were mixed in the STEPHAN cooker for 2 minutes at high speed (3,000 rpm) The STEPHAN cooker was then opened and the contents subjected to tactile and visual examination as described in Example 1—STEPHAN Cooker Step 2. The Enrich 221 is a natural microbial stabilizer available from Quest-Microlife Technics, Inc. of Sarasota, Fla., 34230.

STEP 5

The component in Table 5 was added to those in Step 4.

TABLE 5

| COMPONENTS | QUANTITY/POUND |
| --- | --- |
| Cal Pro 50 Whey Protein Powder | 3.0 |

The ingredient was mixed in the STEPHAN cooker for 2 minutes at high speed (3,000 rpm). The STEPHAN cooker was then opened and the contents subjected to tactile and visual examination as described in Example 1—STEPHAN Cooker Step 2. Cal Pro 50 Whey Protein powder contains 50 percent protein and is a product of Cal 12 Pro Proteins, Corona, Calif. 91720.

STEP 6

The components in Table 6 was added to those in Step 5.

TABLE 6

| COMPONENTS | QUANTITY/POUND |
| --- | --- |
| Parselli SA-2 | 6.0 |
| GP Maltodextrin 040 | 3.0 |
| Coleman's Mustard Flour | 3.0 |
| Corn Syrup 42 D.E. | 4.0 |

The ingredients were mixed in the STEPHAN cooker for 2 to 3 minutes at high speed (3,000 rpm). The STEPHAN cooker was then opened and the contents subjected to tactile and visual examination as described in Example 1—STEPHAN Cooker Step 2. When satisfactory results were achieved, i.e., even dispersion, the STEPHAN cooker was then closed and the temperature raised to 180 degrees F. by steam injection with high speed agitation. When the temperature reached 180 F., agitation was ceased, steam flow was terminated, and the pressure released. The STEPHAN cooker was then opened and the contents were added slowly to the continually operating chopper. COLEMAN'S Mustard Flour is a product of the R. T. French Company of Rochester, N.Y. 14692.

ACIDIFICATION PROCESS

The acidification process was carried out according to the procedure outlined in Example 1 in which the mixture was acidified to a pH of 4.2 to 4.3 by adding acetic acid in the form of 300 grain vinegar. The 300 grain vinegar is a product of Integrated Ingredients, Montebello, Calif.

HOMOGENIZATION PROCESS

The homogenization process was carried out by using a Moyno pump to force the heavy, viscous mayonnaise dressing through the inlet valves of the high pressure homogenizer. The stuffing pressure produced by the Moyno pump has to exceed 150 to 200 pounds per square inch to prevent implosion. Since the mayonnaise dressing at this point has a viscosity between 40,000 and 50,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer was used at a first stage pressure of 10,000 pounds per square inch and 1,500 pounds on the second stage.

The mayonnaise dressing was cooled and packaged as described in Example 1.

The chemical and microbiological analysis of this product was as follows:

| | |
| --- | --- |
| pH | 4.21 |
| FAT | 0.67% |
| SALT | 3.5% |
| STANDARD PLATE COUNT | <100 |
| COLI | <10 |
| YEAST/MOLD | 0/0 |

The mayonnaise dressing produced in this Example had the heavy body of the typical high egg yolk formula than both of the mayonnaise dressings produced in Examples 17 and 18. The resulting pH was lower thereby facilitating additional shelf life.

EXAMPLE 35 LOW FAT MEAN PRODUCTS WITH BEEF FAT ANALOG

A meat fat substitute "MFS" for low fat meat products is produced by first forming a dispersion of deagglomerated denatured whey protein-casein coprecipitate in a continuous phase aqueous medium according to the procedure of Example 1. Ten pounds (10) pounds of sodium caseinate are added to 110 gallons of whey protein concentrate containing approximately 14% solids and 6.52% protein. The mixture is then heated by steam injection to 190 degrees F. and acidified to a pH of 5.6 to 5.65 by the addition of acetic acid. This resulted in the formation of a curd precipitate.

One hundred pounds of curd are then transferred from the FPEC cooker to the chopper using a false bottom kitchen cart. The process of comminution/-deagglomeration of the curd is achieved by using a KRAMER GRABE RESEARCH MODEL, 60 liter capacity vacuum chopper (hereinafter, the KRAMER chopper). The KRAMER chopper is equipped with (i) a hood allowing chopping under vacuum, thereby improving comminution efficiency, (ii) heating and cooling control components capable of maintaining constant temperature in the substance being comminuted, and (iii) a knife shaft capable of maintaining constant speeds from 500RPM's to 5,000 RPM's, allowing comminution rate control.

The curd is comminuted for 50 bowl revolutions under 0.6 bar vacuum at 180 degrees F., and a knife speed of 5000 RPM's. The vacuum hood is then opened twenty pounds (20) of the lecithin-microcrystalline premix of Example 26 is added. The hood is closed and the curd is comminuted for another 50 revolutions under 0.6 bar vacuum, a knife speed of 5,000 RPM, and heat maintained at 180 degrees F. The vacuum hood is then opened and the following components are incorporated with the comminuted curd to prepare a "SFS" for low fat meat products.

TABLE 1

| COMPONENTS | QUANTITY/POUND |
| --- | --- |
| Nutricol XP 3151 | 1.50 |
| Parselli SA 2 | 5.00 |
| Sodium Citrate | 0.25 |

STEP 1

The above ingredients are premixed together and then added to chopper while the knife speed is lowered to 500 RPM. The product temperature is raised to 205 degrees F. via steam heating the bottom of the KRAMER chopper bowl and the knife speed is increased to 5,000 RPM. The steam is injected through nozzles located beneath the chopper bowl preventing steam or moisture from being entrapped directly into the product. NUTRICOL XP 3151 is a product of FMC Corporation, Marine Colloids Division, Philadelphia, Pa. 19103.

The product is comminuted for 50 bowl revolutions with the product temperature maintained at 205 degrees F., vacuum of 0.6 bars, and knife shaft speed of 5,000 RPM's. The knife array is the same as in Example 1 except for the absence of the last two knifes since the KRAMER chopper blade shaft could accommodate only a 10 knife array. The knives are of the same design as in Example 1, but smaller in diameter to fit the smaller bowl of the KRAMER chopper.

STEP 2

After 100 revolutions, the steam heating is terminated and cooling water is applied to the bottom of the bowl. The knife shaft speed is reduced to 2500 RPM. When the temperature reaches 160 degrees F., the knife speed is reduced to 500 RPM. The "SFS" begins to take on the appearance of hard beef fat at this point. When the temperature reaches 140 degrees F., the carbon dioxide was turned on and the knife speed is lowered to 100 RPM. The temperature is lowered to 110 degrees F. and the carbon dioxide cooling is terminated.

STEP 3

The vacuum hood is opened and approximately one and one-half pounds (1.5) of the lecithin-silica mixture is added to the Meat Fat Substitute (MFS). The bowl speed is reduced to slow and the knifes blades are turned in a reverse direction to mix and coat the "MFS". The approximate ½ inch MFS cubes are packed into 5 gallon buckets and placed into the cooler for further use.

The chemical and microbiological analysis of this product is as follows:

| | |
|---|---|
| pH | 5.72 |
| FAT | 0.92% |
| SALT | 0.5% |
| STANDARD PLATE COUNT | <100 |
| COLI | <10 |
| YEAST/MOLD | 0/0 |
| MOISTURE | 75.0% |

STEP 4

The next process of comminution, mixing, and emulsification is achieved of the summer sausage is achieved by using the same KRAMER GRABE RESEARCH MODEL, 60 liter capacity vacuum chopper. A three (3) blade knife array is used in the typical "Y" configuration used for chopping.

The following ingredients are added to the chopper and the blade speed is set at 1000 RPM. The temperature is maintained at 40 degrees F. utilizing the carbon dioxide injection system.

TABLE 4

| COMPONENTS | QUANTITY/POUND |
|---|---|
| Lean Beef (95-5) | 75.00 |
| Salt | 2.40 |

The comminution and chopping is maintained until the meat and salt mixture obtain a typical coarse texture of about ⅛ inch. The chopping process is terminated and the hood is opened.

STEP 5

The ingredients in Table 5 are weighed, premixed, and added very slowly in the dry form directly to the KRAMER chopper with the vacuum hood in the open, upright position while the bowl rotated and the shaft speed at 1,000 RPM.

TABLE 5

| COMPONENTS | QUANTITY/POUND |
|---|---|
| G-P Maltodextrin 040 | 0.77 |
| Ground White Pepper | 0.36 |
| PMS Cure | 0.23 |
| Ground Coriander | 0.11 |
| Ground Nutmeg | 0.05 |
| Sodium Erythorbate | 0.05 |
| Ground Allspice | 0.02 |

When all the ingredients are uniformly dispersed, the vacuum hood is closed and product temperature maintained at 40 degrees F. Vacuum is increased to 0.7 bar and shaft speed is set at 100 RPM in reverse mix mode until the ingredients are properly distributed.

STEP 6

TABLE 6

| COMPONENTS | QUANTITY/POUND |
|---|---|
| MEAT FAT SUBSTITUTE | 16.0 |

The meat fat substitute is added slowly to the chopper and the knife with the knife speed at 500 RPM. The speed is increased to 1,000 RPM and a Meat Lactic starter is added from Microlife Technics. The chopping process continues until a homogenous mass develops.

Fifty pounds (50) of the low fat summer sausage is packed in casing and hung in the smoke house until a pH of 4.9 develops. The temperature in the smokehouse is increased until the summer sausage reaches and internal temperature of 145 degrees F.

The chemical and microbiological analysis of the summer sausage is:

| | |
|---|---|
| pH | 4.85 |
| FAT | 4.59% |
| SALT | 2.5% |
| STANDARD PLATE COUNT | TNTC |
| COLI | <10 |
| YEAST/MOLD | 0/0 |

To the fifty pounds (50) of low fat summer sausage in the chopper, one (1) of lecithin—microcrystalline cellulose mixture from Example 26 is added along with 5 pounds of water. The knife speed is increased to 2,500 RPM and a typical meat emulsion is created. The emulsion is packed casings and hung in the smoke house until an internal temperature of 160 degrees is reached.

The emulsified low fat meat product was sliced after cooling. The product is comparable to commercial luncheon meats with 80% more fat. The meat fat substitute has the typical mouthfeel, lubricity, gelling characteristics, and will slice like typical beef fat.

EXAMPLE 36 LOW FAT MEAT PRODUCTS WITH BEEF FAT ANALOG-STABILIZER ADDED

A meat fat substitute "MFS" for low fat meat products is produced by first forming a dispersion of deagglomerated denatured whey protein-casein coprecipitate with stabilizers added to the premix in a continuous phase aqueous medium according to the procedure of Example 1. Ten pounds (10) pounds of sodium caseinate are added to 110 gallons of whey protein concentrate containing approximately 14% solids and 6.82% protein. In addition, kappa carrageenan, konjac flour, xanthan gum, and the mixture of liposomes containing fumed silica as in Table 1. The mixture is then heated by steam injection to 193° degrees F. and acidified to a pH of 5.6 to 5.65 by the addition of acetic acid. This resulted in the formation of a curd precipitate.

TABLE 1

| COMPONENTS | QUANTITY/POUND |
|---|---|
| Whey Protein Concentrate | 1100.0 |
| Sodium Caseinate | 10.0 |
| Nutricol XP 1005 | 5.5 |
| Viscarin SA 359 | 0.55 |
| Keltrol T Xanthan Gum | 1.1 |
| Liposome Mixture Example 43 | 1.0 |

The ingredients in Table 1 are mixed in the STEPHAN cooker with the whey protein concentrate as the liquid medium. The agitation is high speed for 5 minutes. The contents were then placed in the FPEC cooker and agitated for 10 minutes to insure homogeneity. VISCARIN and NUTRICOL are products of FMC Corporation, Marine Colloids Division, Philadelphia, Pa. 19103.

One hundred pounds of curd are then transferred from the FPEC cooker to the chopper using a false bottom kitchen cart. The process of comminution/deagglomeration of the curd is achieved by using a KRAMER GRABE RESEARCH MODEL, 60 liter capacity vacuum chopper (hereinafter, the KRAMER chopper). The KRAMER chopper is equipped with (i) a hood allowing chopping under vacuum, thereby improving comminution efficiency, (ii) heating and cooling control components capable of maintaining constant temperature in the substance being comminuted, and (iii) a knife shaft capable of maintaining constant speeds from 500 RPM's to 5,000 RPM's, allowing comminution rate control.

The curd is comminuted for 50 bowl revolutions under 0.6 bar vacuum at 180 degrees F., and a knife speed of 5000 RPM's. The vacuum hood is then opened fifteen pounds (15) of the lecithin-fumed silica premix of Example 43 is added, The hood is closed and the curd is comminuted for another 50 revolutions under 0.6 bar vacuum, a knife speed of 5,000 RPM, and heat maintained at 180 degrees F. The vacuum hood is then opened and the following components are incorporated with the comminuted curd to prepare a "SFS" for low fat meat products.

TABLE 2

| COMPONENTS | QUANTITY/POUND |
|---|---|
| Nutricol XP 3151 | 1.50 |
| Parselli SA 2 | 5.00 |
| Sodium Citrate | 0.25 |

STEP 2

The above ingredients are premixed together and then added to chopper while the knife speed is lowered to 500 RPM. The product temperature is raised to 205 degrees F. via steam heating the bottom of the KRAMER chopper bowl and the knife speed is again raised to 5,000 RPM. The steam is injected through nozzles located beneath the chopper bowl preventing steam or moisture from being entrapped directly into the product. NUTRICOL XP 3151 is a product of FMC Corporation, Marine Colloids Division, Philadelphia, Pa. 19103.

The product is comminuted for 50 bowl revolutions with the product temperature maintained at 205 degrees F., vacuum of 0.6 bars, and knife shaft speed of 5,000 RPM's. The knife array is the same as in Example 1 except for the absence of the last two knifes since the KRAMER chopper blade shaft could accommodate only a 10 knife array. The knives are of the same design as in Example 1, but smaller in diameter to fit the smaller bowl of the KRAMER chopper.

STEP 2

After 100 revolutions, the steam heating is terminated and cooling water is applied to the bottom of the bowl. The knife shaft speed is reduced to 2500 RPM. When the temperature reaches 160 degrees F., the knife speed is reduced to 500 RPM. The "SFS" begins to take on the appearance of hard beef fat at this point. When the temperature reaches 140 degrees F., the carbon dioxide was turned on and the knife speed is lowered to 100 RPM. The temperature is lowered to 110 degrees F. and the carbon dioxide cooling is terminated.

STEP 3

The vacuum hood is opened and approximately one and one-half pounds (1.5) of the lecithin-silica mixture is added to the Meat Fat Substitute (MFS). The bowl speed is reduced to slow and the knifes blades are turned in a reverse direction to mix and coat the "MFS". The approximate ½ inch MFS cubes are packed into 5 gallon buckets and placed into the cooler for further use.

The chemical and microbiological analysis of this product is as follows:

| | |
|---|---|
| pH | 5.76 |
| Fat | 0.86% |
| Salt | 0.7% |
| Standard Plate Count | <100 |
| Coli | <10 |
| Yeast/Mold | 0/0 |
| Moisture | 73.5% |

STEP 4

The next process of comminution, mixing, and emulsification is achieved of a ground meat is achieved by using the same KRAMER GRABE RESEARCH MODEL, 60 liter capacity vacuum chopper. A three (3) blade knife array is used in the typical "Y" configuration used for chopping.

The following ingredients are added to the chopper and the blade speed is set at 1000 RPM. The temperature is maintained 19 at 40 degrees F. utilizing the carbon dioxide injection system.

TABLE 4

| COMPONENTS | QUANTITY/POUND |
|---|---|
| Lean Beef (95-5) | 75.00 |
| Salt | 2.5 |

The comminution and chopping is maintained until the meat and salt mixture obtain a typical coarse texture of about ⅛ inch. The chopping process is terminated and the hood is opened.

STEP 5

The ingredients in Table 5 are weighed, premixed, and added very slowly in the dry form directly to the KRAMER chopper with the vacuum hood in the open, upright position while the bowl rotated and the shaft speed at 1,000 RPM.

TABLE 5

| COMPONENTS | QUANTITY/POUND |
|---|---|
| G-P Maltodextrin 040 | 0.77 |
| Ground White Pepper | 0.36 |
| PMS Cure | 0.23 |
| Ground Coriander | 0.11 |
| Ground Nutmeg | 0.05 |
| Sodium Erythorbate | 0.05 |
| Ground Allspic | 0.02 |

When all the ingredients are uniformly dispersed, the vacuum hood is closed and product temperature maintained at 40 degrees F. Vacuum is increased to 0.7 bar and shaft speed is set at 100 RPM in reverse mix mode until the ingredients are properly distributed. All of the ingredients in Table 5 except G-P Maltodextrin are products of Baltimore Spice, Garrison, Md. 21055.

STEP 6

TABLE 6

| COMPONENTS | QUANTITY/POUND |
|---|---|
| Meat Fat Substitute | 16.0 |

The meat fat substitute is of the process of steps 1 to 3 are added slowly to the chopper and the knife with the knife speed at 500 RPM. The speed is increased to 1,000 RPM and a Meat Lactic starter is added from Microlife Technics. The chopping process continues until a homogenous mass develops.

Fifty pounds (50) of the low fat summer sausage is packed in casing and hung in the smoke house until a pH of 4.9 develops. The temperature in the smokehouse is increased until the summer sausage reaches and internal temperature of 145 degrees F.

The chemical and microbiological analysis of the summer sausage is:

| pH | 4.85 |
|---|---|
| Fat | 4.59% |
| Salt | 2.5% |
| Standard Plate Count | TNTC |
| Coli | <10 |
| Yeast/Mold | 0/0 |

LOW FAT GROUND BEEF

A low fat ground beef product was made from the addition of 95-5 lean beef and meat fat substitute of Steps 1 –3.

STEP 7

TABLE 7

| COMPONENTS | QUANTITY/POUND |
|---|---|
| Meat FAt Substitute | 25.0 |
| Lean Beef (95-5) | 75.00 |

The comminution and chopping is maintained until the meat and salt mixture obtain a typical coarse texture of about ⅛ inch. The chopping process is terminated and the hood is opened.

The ground beef is packed in casings and was analyzed for cooking and eating properties. The ground beef is cooked against regular store purchased ground beef and is found to be a satisfactory replacement for 25% fat ground beef. The low fat ground beef did not dry out in the same manner as ground beef made with only hydrocolloid gums.

EXAMPLE 37 IMPROVED PASTEURIZED PROCESSED CHEESE SPREAD

A pasteurized process cheese spread was made from a blend of natural cheeses with liposomes made from lecithin fractions and microcrystalline cellulose. The processed cheese spread was produced by first comminuting the cheese in a 200 liter capacity open atmosphere chopper manufactured by Maselinenfabrik Seydelmann. The knives used to comminute the cheese and mix in the dry ingredients were SECURITY-SYSTEM-4-CUT-KNIVES. The comminuted cheese and dry ingredients were transferred via a inclined screw conveyor to the FEPC cooker used in previous examples for the cooking of curd. The drains were replaced by two steam injection nozzles.

The ingredients in Table 1 were placed in the chopper while in was running on slow speed. The cheeses were added slowly to insure homogeneity. The powder ingredients are added last and mixed in with the chopper in reverse mix mode. The individual chopper batches were made to make up the final cooker batch.

TABLE 1

| INGREDIENT | POUNDS |
|---|---|
| Fresh Hispanic Cheese | 50.0 |
| Manchego Cheese | 75.0 |
| Monterey Jack Cheese | 75.0 |
| Mozzarella | 50.0 |
| Danish Cheese Powder | 15.0 |
| Non Fat Milk Powder | 15.0 |
| ALTA 2020 | 3.0 |
| TOTAL | 280.0 |

The ingredients in Table I were produced in triplicate and conveyed to the cooker. This made a total cooker batch weight was 840 pounds. The Danish cheese powder is a product of Cremo Cheese Company, Tofte Gaadsvej 3, Glamsbjerg, Demark, DK 5620.

The cheese mixture in the cooker was heated via direct steam injection. As the cheese was melting, the ingredients in Table 2 were added in the order of sequence in Table 2.

TABLE 2

| INGREDIENT | POUNDS |
|---|---|
| Butter | 50.0 |
| Enzyme Modified Cheese | 25.0 |
| Liposome Mixture Example No. 26 | 2.5 |
| Lactic Acid | A/R |
| Sodium Citrate | 12.0 |
| Sodium Aluminum Phosphate | 6.0 |
| TOTAL | 95.5 |

When the cheese begins to melt, the butter is added to the cheese mass. The enzyme modified cheese is then added. The liposome mixture from Example 26 containing microcrystalline cellulose enveloped in lecithin fractions was added slowly to the cheese mass. The pH of the cheese is lowered to 5.3 to 5.4 with the addition of lactic acid until the processed cheese attains the typical stretch and string that is desired. Further heating raised the temperature to 165 degrees F. The sodium citrate and sodium aluminum phosphate were mixed with water and added slowly to the cheese mass. The finished weight of the batch was approximately 975 pounds with the weight of the steam condensation.

The finished cheese is unloaded into kitchen carts and stuffed into casings and cooled as in Example 1. The process cheese cylinders were hung on carts to avoid deformation. The processed cheese is sliced and packed into twelve ounce packages.

The chemical and microbiological analysis of this product was as follows:

| | |
|---|---|
| pH | 5.42 |
| Fat | 24.5% |
| Salt | 3.5% |
| Standard Plate Count | <100 |
| Coli | <10 |
| Yeast/Mold | 0/0 |
| Moisture | 47.5% |
| FDB | 46.6% |

The process cheese spread displayed a short melt and slight string. This style of process in the preferred consumption pattern in the United States. The short body and texture can be accomplished without the flavor destruction that the phosphate salts cause. The use of sodium citrate and sodium aluminum phosphate (KSAL) as melting or emulsifying salts at low levels is accomplished by the addition of the liposomes enveloped microcrystalline cellulose. It is believed that the microcrystalline cellulose absorbs moisture and fat thereby restricts the flow of the melt when heat is applied. The flavor, body, and texture closely resembles a natural pasta filata such as provolone rather than natural cheese.

EXAMPLE 38 IMPROVED PASTEURIZED PROCESSED CHEESE SPREAD

A pasteurized process cheese spread was made from a blend of natural cheeses with liposomes made from lecithin fractions. The processed cheese spread was produced by first comminuting the cheese in a 200 liter capacity open atmosphere chopper manufactured by Maselinenfabrik Seydelmann. The knives used to Comminute the cheese and mix in the dry ingredients were SECURITY-SYSTEM-4-CUT-KNIVES. The comminuted cheese and dry ingredients were transferred via a inclined screw conveyor to the FEPC cooker used in previous examples for the cooking of curd. The drains were replaced by two steam injection nozzles.

The ingredients in Table i were placed in the chopper while in was running on slow speed. The cheeses were added slowly to insure homogeneity. The powder ingredients were added last and mixed in with the chopper in reverse mix mode. The individual chopper batches were made to make up the final cooker batch.

TABLE 1

| INGREDIENT | POUNDS |
|---|---|
| Fresh Hispanic Cheese | 50.0 |
| Manchego Cheese | 75.0 |
| Monterey Jack Cheese | 75.0 |
| Mozzarella | 50.0 |
| Danish Cheese Powder | 15.0 |
| Non Fat milk Powder | 15.0 |
| ALTA 2020 | 3.0 |

TABLE 1-continued

| INGREDIENT | POUNDS |
|---|---|
| TOTAL | 280.0 |

The ingredients in Table 1 were produced in triplicate and conveyed to the cooker. This made a total cooker batch weight was 840 pounds.

The cheese mixture in the cooker was heated via direct steam injection. As the cheese was melting, the ingredients in Table 2 were added in the order of sequence in Table 2.

TABLE 2

| INGREDIENT | POUNDS |
|---|---|
| Butter | 50.0 |
| Enzyme Modified Cheese | 25.0 |
| Liposome Mixture Example No. 40 | 1.0 |
| Lactic Acid | A/R |
| Sodium Citrate | 12.0 |
| Sodium Aluminum Phosphate | 6.0 |
| TOTAL | 94.0 |

When the cheese begins to melt, the butter was added to the cheese mass. The enzyme modified cheese was then added. The mixture from Example 40 containing only liposomes from lecithin fractions was added slowly to the cheese mass. The pH of the cheese was lowered to 5.3 to 5.4 with the addition of lactic acid until tile processed cheese attains the typical stretch and string that was desired. Further heating raised the temperature to 165 degrees F. The sodium citrate and sodium aluminum phosphate were mixed with water and added slowly to the cheese mass. The finished weight of the batch was approximately 973 pounds with the weight of the steam condensation.

The finished cheese was unloaded into kitchen carts and stuffed into casings and cooled as in Example 1. The process cheese cylinders were hung on carts to avoid deformation. The processed cheese was sliced and packed into twelve ounce packages.

The chemical and microbiological analysis of this product was as follows:

| | |
|---|---|
| pH | 5.42 |
| Fat | 24.5% |
| Salt | 3.5% |
| Standard Plate Count | <100 |
| Coli | <10 |
| Yeast/Mold | 0/0 |
| Moisture | 47.5% |
| FDB | 46.6% |

The process cheese spread displayed the same typical melt characteristics that the normal process cheese of this manufacturing formula and processes without the liposomes added. The body of the cheese will string when heated and the texture has the typical chicken breast structure of mozzarella. This style of process matches the preferred consumption pattern of process made for Hispanic cooking. The individual cheese slices did not stick together after packaging for 3 months.

EXAMPLE 39 IMPROVED PASTEURIZED PROCESSED CHEESE SPREAD

A pasteurized process cheese spread was made from a blend of natural cheeses with liposomes made from lecithin fractions enveloping fumed silica. The processed cheese spread was produced by first comminuting the cheese in a 200 liter capacity open atmosphere chopper manufactured by Maselinenfabrik Seydelmann. The knives used to comminute the cheese and mix in the dry ingredients were SECURITY-SYSTEM-4-CUT-KNIVES. The comminuted cheese and dry ingredients were transferred via a inclined screw conveyor to the FEPC cooker used in previous examples for the cooking of curd. The drains were replaced by two steam injection nozzles.

The ingredients in Table 1 were placed in the chopper while in was running on slow speed. The cheese were added slowly to insure homogeneity. The powder ingredients were added last and mixed in with the chopper in reverse mix mode. The individual chopper batches were made to make up the final cooker batch.

TABLE 1

| INGREDIENT | POUNDS |
| --- | --- |
| Fresh Hispanic Cheese | 50.0 |
| Manchego Cheese | 75.0 |
| Monterey Jack Cheese | 75.0 |
| Mozzarella | 50.0 |
| Danish Cheese Powder | 15.0 |
| Non Fat Milk Powder | 15.0 |
| ALTA 2020 | 3.0 |
| TOTAL | 280.0 |

The ingredients in Table 1 were produced in triplicate and conveyed to the cooker. This made a total cooker batch weight was 840 pounds. All of the cheese was manufactured in the CACIQUE plant.

The cheese mixture in the cooker was heated via direct steam injection. As the cheese was melting, the ingredients in Table 2 were added in the order of sequence in Table 2.

TABLE 2

| INGREDIENT | POUNDS |
| --- | --- |
| Butter | 50.0 |
| Enzyme Modified Cheese | 25.0 |
| Liposome Mixture Example No. 41 | 2.0 |
| Lactic Acid | A/R |
| Sodium Citrate | 12.0 |
| Sodium Aluminum Phosphate | 6.0 |
| TOTAL | 95.0 |

When the cheese begins to melt, the butter was added to the cheese mass. The enzyme modified cheese was then added. The mixture from Example 40 containing only liposomes from lecithin fractions enveloping the fumed silica was added slowly to the cheese mass. The pH of the cheese was lowered to 5.3 to 5.4 with the addition of lactic acid until the processed cheese attains the typical stretch and string that is desired. Further heating raised the temperature to 165 degrees F. The sodium citrate and sodium aluminum phosphate were mixed with water and added slowly to the cheese mass. The finished weight of the batch was approximately 975 pounds with the weight of the steam condensation.

The finished cheese was unloaded into kitchen carts and stuffed into casings and cooled as in Example 1. The process cheese cylinders were hung on carts to avoid deformation. The processed cheese was sliced and packed into twelve ounce packages.

The chemical and microbiological analysis of this product was as follows:

| | |
| --- | --- |
| pH | 5.42 |
| Fat | 24.5% |
| Salt | 3.5% |
| Standard Plate Count | <100 |
| Coli | <10 |
| Yeast/Mold | 0/0 |
| Moisture | 47.5% |
| FDB | 46.6% |

The process cheese spread displayed melt characteristics that are typical of high melt, high fat content mozzarella cheese. It is believed that the fumed silica acts like butterfat in furthering the lubricity of the protein strands thereby provides the stretch displayed. The body of the cheese will string exceptionally when heated and the texture has the typical chicken breast structure of natural mozzarella cheese. This style of process matches the preferred consumption pattern of process made for Italian cooking. The individual cheese slices did not stick together after packaging for 3 months.

EXAMPLE 40 LECITHIN BASE FOR FAT FREE CHOLESTEROL FREE FAT SUBSTITUTE PRODUCTS and PROCESS CHEESE PRODUCTS A lecithin base for stabilized fat substitute "SFS" was produced by first dispersing the lecithin fractions in a water-lecithin complex.

The following components were mixed and heated in the STEPHAN cooker.

STEP 1

TABLE 1

| COMPONENTS | QUANTITY/POUND |
| --- | --- |
| Water | 56.0 |
| Alcolec 140 | 14.0 |
| Alcolec SFG | 7.0 |

The liposome premix was heated to 180 degrees F. in the STEPHAN cooker. The premix was transferred a 200 liter capacity vacuum chopper manufactured by Meissner AG. The model number is RSM 200VAC. Experience has shown that optimal liposome formation conditions occur when total weights of about 230 to 260 pounds are processed in choppers of 200 liter capacity. This chopper is equipped with a vacuum hood whereby a vacuum of 28 inches of mercury can be produced. The hood is also equipped with a carbon dioxide injection hood and exhaust exit. The bowl of the chopper can also be heated or cooled with water or steam via sprays underneath the enclosed bowl.

Choppers, long used in the food processing industry for sausage processing, have been found to have utility in producing liposomes formed in accordance with the present invention. In this case, vacuum was employed to reduce the entrapment of air. Air entrapment during the creation of liposomes reduces the efficiency if it done in an open air environment. As air entrapment increases, more air is entrapped at an increasing rate. The small air bubbles act like liposomes and thus, the of the production phase decreases at an increasing rate. Thus, the employment of vacuum reduces the time required for liposome production and the suspension of microcrystalline cellulose.

The following component were mixed and heated in the STEPHAN cooker.

STEP 2

TABLE 2

| COMPONENTS | QUANTITY/POUND |
|---|---|
| Water | 75.0 |

The water was heated to 180 degrees F. by steam injection with high speed agitation. Upon reaching 180 degrees F., the steam flow was terminated, the STEPHAN cooker was opened, and the water was transferred to a clean sterilized bucket and slowly added to the chopper. The pasteurized lecithin-water liposome complex was processed in the chopper for 20 minutes to form liposomes. The same knife pattern was used as in Example 14. Steam was applied to the bottom of the bowl to maintain a temperature of 180 degrees F. Vacuum was applied at 25 inches.

Upon confirming that proper dispersion was achieved, the contents of the chopper was unloaded into 5 gallon pails for use in further processing. This process eliminated the preparation of liposomes in the STEPHAN cooker. The water-lecithin fraction liposome mixture was packed in 5 gallon pails for further use in other products.

EXAMPLE 41 LECITHIN-FUMED SILICA BASE FOR FAT FREE CHOLESTEROL FREE FAT SUBSTITUTE PRODUCTS and PROCESS CHEESE PRODUCTS A lecithin base for stabilized fat substitute "SFS" was produced by first dispersing the lecithin fractions in a water-lecithin complex.

The following components were mixed and heated in the STEPHAN cooker.

STEP 1

TABLE 1

| COMPONENTS | QUANTITY/POUND |
|---|---|
| Water | 56.0 |
| Alcolec 140 | 14.0 |
| Alcolec SFG | 7.0 |

The liposome premix was heated to 180 degrees F. in the STEPHAN cooker. The premix was transferred a 200 liter capacity vacuum chopper manufactured by Meissner AG. The model number is RSM 200VAC. Experience has shown that optimal liposome formation conditions occur when total weights of about 230 to 260 pounds are processed in choppers of 200 liter capacity. This chopper is equipped with a vacuum hood whereby a vacuum of 28 inches of mercury can be produced. The hood is also equipped with a carbon dioxide injection hood and exhaust exit. The bowl of the chopper can also be heated or cooled with water or steam via sprays underneath the enclosed bowl.

Choppers, long used in the food processing industry for sausage processing, have been found to have utility in producing liposomes formed in accordance with the present invention. In this case, vacuum was employed to reduce the entrapment of air. Air entrapment during the creation of liposomes reduces the efficiency if it done in an open air environment. As air entrapment increases, more air is entrapped at an increasing rate. The small air bubbles act like liposomes and thus, the of the production phase decreases at an increasing rate. Thus, the employment of vacuum reduces the time required for liposome production and the suspension of fumed silica.

The following component were mixed and heated in the STEPHAN cooker.

STEP 2

TABLE 2

| COMPONENTS | QUANTITY/POUND |
|---|---|
| Water | 46.0 |

The water was heated to 180 degrees F. by steam injection with high speed agitation. Upon reaching 180 degrees F., the steam flow was terminated, the STEPHAN cooker was opened, and the water was transferred to a clean sterilized bucket and slowly added to the chopper. This step was repeated twice and a total of 92 pounds of water was added to the chopper. The pasteurized lecithin-water liposome complex was processed in the chopper for 20 minutes to form liposomes. The same knife pattern was used as in Example 14. Steam was applied to the bottom of the bowl to maintain a temperature of 180 degrees F. Vacuum was applied at 25 inches.

The following component was incorporated with the liposomes to produce the final lecithin-fumed silica complex.

TABLE 3

| COMPONENTS | QUANTITY/POUND |
|---|---|
| AEROSIL © 200 | 15.0 |

AEROSIL © 200 is a fumed silica product of the Degussa Corporation, 65 Challenger Road, Ridgefield Park, N.J., 07660. The fumed silica was added to the chopper and mixed for approximately 30 minutes maintaining the vacuum at 25 inches and the temperature at 180 degrees F. The chopper was then opened and the liposome mixture was visually examined under a polarized light microscope for proper dispersion. Upon confirming that proper dispersion was achieved, the chopper was unloaded into 5 gallon pails for use in further processing. This eliminated the preparation of liposomes in the STEPHAN cooker.

EXAMPLE 41B

WATER ADDITION

The same procedure was followed as in Example 41, with the exception that an addditional 42 pounds of water was added in an additional step.

HOMOGENIZATION PROCESS

The homogenization process was carried out by using a Moyno pump to force the heavy, viscous lecithin/-fumed silica liposome mixture through the inlet valves of the high pressure homogenizer. The stuffing pressure had to exceed 150 pounds to prevent implosion. A APV RANNIE high pressure homogenizer was used at a first stage pressure of 10,000 pounds per square inch and 1,500 pounds on the second stage.

The fumed silica/lecithin mixture was packed in casings for further use in other products. It resembled a fine cream emulsion after being homogenized.

EXAMPLE 42 FAT FREE CHOLESTEROL FREE SOFT BUTTER SPREAD

A stabilized fat substitute "SFS" soft butter spread was produced by first forming a dispersion of deagglomerated denatured whey protein-caseinate coprecipitate in a continuous phase aqueous medium according to the procedure of Example 1. Ten pounds of sodium caseinate and one and one-half pounds of liposome enveloped fumed silica were added to 120 gallons of whey protein concentrate comprising approximately 14.12% solids and 6.34% protein. The mixture was heated by steam injection to 185 degrees F. and acidified to a pH of 5.6 to 5.65 by the addition of acetic acid in the form of vinegar. This resulted in the formation of a curd coprecipitate of whey protein and casein.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, soft butter spread as described below.

The following components were incorporated with the fat substitute product produced as described above to prepare a soft butter spread.

TABLE 1

| COMPONENTS | QUANTITY/POUND |
| --- | --- |
| Water | 12.0 |
| Alcolec 140 | 5.0 |
| Alcolec SFG | 1.5 |
| Water | 15.0 |
| Avicel RC591 | 5.0 |

STEP 1

The liposome and structure building formation was achieved in a similar manner to that set out in Example 1 or 14 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 14. The STEPHAN cooker was operated for 8 minutes at 120 degrees F. Thereafter, the STEPHAN cooker was opened and the liposomes made from the lecithin-water mixture were visually examined for the presence of undissolved particles and to insure complete dispersion. Upon confirmation that the mixture was uniformly dispersed and that liposomes were formed, a caramel cream-like appearance was observed. An additional 13 pounds of hydration water was added to the liposomes in the STEPHAN cooker together with 5 pounds of microcrystalline cellulose and mixed for approximately 10 minutes. The STEPHAN cooker was then opened and the liposome mixture was visually examined under a polarized light microscope for proper dispersion. Upon confirming that proper dispersion was achieved, the STEPHAN cooker was closed and the temperature raised to 180 degrees F. by steam injection with high speed agitation. Upon reaching 180 degrees F., the steam flow was terminated, the STEPHAN cooker was opened, and the mixture was transferred to a clean sterilized bucket and slowly added to the chopper. The pasteurized lecithin-microcrystalline cellulose complex was processed in the chopper for 10 minutes to form a membrane around the curd particles, to place amphoteric charges on the curd particles, and to create structure in the aqueous phase as described in Example 1.

STEP 2

A second polylayer membrane was produced from the components in Table 2.

TABLE 2

| COMPONENTS | QUANTITY/POUND |
| --- | --- |
| Water | 10.00 |
| Sodium Caseinate | 4.00 |

The water and the sodium caseinate were mixed together in the STEPHAN cooker under high speed for five minutes. The STEPHAN cooker was then opened and the contents subjected to tactile and visual examination as described in Example 1—STEPHAN Cooker Step 2. The temperature was increased to 180 degrees F. and the contents were added to the chopper.

STEP 3

A stabilizer was produced from the components in Table 3.

TABLE 3

| COMPONENTS | QUANTITY/POUND |
| --- | --- |
| Water | 20.00 |
| Slendid Pectin | 3.5 |
| Gelatin 250 Bloom | 1.0 |
| Calcium Chloride Solution | 20 mls. |

The stabilizer from Table 4 was prepared by adding Slendid Pectin to the 26 pounds of water in the STEPHAN cooker. The bottom agitator was set at high speed and the side agitator was turned on for 5 minutes. The STEPHAN cooker was then opened and the pectin dispersion was then inspected for complete dispersion. The 250 Bloom Gelatin was then added to the water-pectin dispersion. The ingredients were mixed in the STEPHAN cooker for 5 minutes at high speed (3,000 rpm) with no steam injection. The STEPHAN cooker was then opened and the calcium chloride solution was added and mixed for 2 minutes. The STEPHAN cooker was then opened and the contents subjected to tactile and visual examination as described in Example 1—Stephan Cooker Step 2.

Additional microbial inhibitors, sugar, and salt were prepared in the STEPHAN cooker using the components from Table 4. These ingredients were added to those made in Step 2 above.

TABLE 4

| COMPONENTS | QUANTITY/POUND |
| --- | --- |
| Salt | 4.5 |
| Alta 2331 | 1.5 |
| Alta 1801 | 1.5 |
| Alta 2001 | 0.5 |
| Alta 1705 | 1.5 |

The ingredients were mixed in the STEPHAN cooker for 2 minutes at high speed (3,000 rpm) The STEPHAN cooker was then opened and the contents subjected to tactile and visual examination as described in Example 1—STEPHAN Cooker Step 2.

STEP 5

The component in Table 5 was added to those in Step 4.

TABLE 5

| COMPONENTS | QUANTITY/POUND |
|---|---|
| Enrich 221 | 6.0 |

The ingredient was mixed in the STEPHAN cooker for 2 minutes at high speed (3,000 rpm) The STEPHAN cooker was then opened and the contents subjected to tactile and visual examination as described in Example 1—STEPHAN Cooker Step 2.

The ingredient was mixed in the STEPHAN cooker for 2 minutes at high speed (3,000 rpm). The STEPHAN cooker was then opened and the contents subjected to tactile and visual examination as described in Example 1—STEPHAN Cooker Step 2.

STEP 6

The components in Table 6 was added to those in Step 5.

TABLE 6

| COMPONENTS | QUANTITY/POUND |
|---|---|
| Parselli SA-2 | 9.0 |

The ingredients were mixed in the STEPHAN cooker for 2 to 3 minutes at high speed (3,000 rpm). The STEPHAN cooker was then opened and the contents subjected to tactile and visual examination as described in Example 1—STEPHAN Cooker Step 2. When satisfactory results were achieved, i.e., even dispersion, the STEPHAN cooker was then closed and the temperature raised to 180 degrees F. by steam injection with high speed agitation. When the temperature reached 180 F., agitation was ceased, steam flow was terminated, and the pressure released. The STEPHAN cooker was then opened and the contents were added slowly to the continually operating chopper.

STEP 7

The components in Table 7 was added to the chopper directly.

TABLE 7

| COMPONENTS | QUANTITY/POUND |
|---|---|
| Liposome Mixture Example 41 | 2.0 |
| Annatto Color(3x) | 200 mls. |
| Butter Flavor (Butr Pow'r LM4) | 1.5 |
| Starter Distillate | 20 mls. |

The annatto color, butter flavor, and starter distillate are all products of Chs. Hansen's Laboratory, Milwaukee, Wis. 53214.

HOMOGENIZATION PROCESS

The homogenization process was carried out by using a Moyno pump to force the heavy, viscous soft butter spread through the inlet valves of the high pressure homogenizer. The stuffing pressure produced by the Moyno pump has to exceed 150 to 200 pounds per square inch to prevent implosion. Since the soft butter spread at this point has a viscosity between 40,000 and 50,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer was used at a first stage pressure of 10,000 pounds per square inch and 1,500 pounds on the second stage.

The soft butter spread was cooled and packaged as described in Example 1.

The chemical and microbiological analysis of this product was as follows:

| | |
|---|---|
| pH | 5.96 |
| Fat | 1.2% |
| Salt | 1.5% |
| Standard Plate Count | <100 |
| Coli | <10 |
| Yeast/Mold | 0/0 |

The Fat Free butter type spread resembled soft spreadable margarine more that it did churned butter. The body and texture were very acceptable. This substitute cannot be used in cooking nor will it melt very well.

EXAMPLE 42 FAT FREE CHOLESTEROL FREE SOFT BUTTER SPREAD

A stabilized fat substitute "SFS" soft butter spread was produced by first forming a dispersion of deagglomerated denatured whey protein-caseinate coprecipitate in a continuous phase aqueous medium according to the procedure of Example 1. Ten pounds of sodium caseinate and one and one-half pounds of liposome enveloped fumed silica were added to 120 gallons of whey protein concentrate comprising approximately 14.12% solids and 6.34% protein. The mixture was heated by steam injection to 185 degrees F. and acidified to a pH of 5.6 to 5.65 by the addition of acetic acid in the form of vinegar. This resulted in the formation of a curd coprecipitate of whey protein and casein.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, soft butter spread as described below.

The following components were incorporated with the fat substitute product produced as described above to prepare a soft butter spread.

TABLE 1

| COMPONENTS | QUANTITY/POUND |
|---|---|
| Water | 12.0 |
| Alcolec 140 | 5.0 |
| Alcolec SFG | 1.5 |
| Water | 15.0 |
| Avicel RC591 | 5.0 |

STEP 1

The liposome and structure building formation was achieved in a similar manner to that set out in Example 1 or 14 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 14. The STEPHAN cooker was operated for 8 minutes at 120 degrees F. Thereafter, the STEPHAN cooker was opened and the liposomes made from the lecithin-water mixture were visually examined for the presence of undissolved particles and to insure complete dispersion. Upon confirmation that the mixture was uniformly dispersed and that liposomes were formed, a caramel cream-like appearance was observed. An additional 13 pounds of hydration water was added to the liposomes in the STEPHAN cooker together with 5 pounds of microcrystalline cellulose and mixed for approximately 10 minutes. The STEPHAN cooker was then opened and the liposome mixture was visually examined under a polarized light microscope for proper dispersion. Upon confirming that proper dispersion was achieved, the STEPHAN cooker was closed and the temperature raised to 180 degrees F. by steam injection with high speed agitation. Upon reaching 180 degrees F., the steam flow was terminated, the STEPHAN cooker was opened, and the mixture was transferred to a clean sterilized bucket and slowly added to the chopper. The pasteurized lecithin-microcrystalline cellulose complex was processed in the chopper for 10 minutes to form a membrane around the curd particles, to place amphoteric charges on the curd particles, and to create structure in the aqueous phase as described in Example 1.

STEP 2

A second polylayer membrane was produced from the components in Table 2.

TABLE 2

| COMPONENTS | QUANTITY/POUND |
|---|---|
| Water | 10.00 |
| Sodium Caseinate | 4.00 |

The water and the sodium caseinate were mixed together in the STEPHAN cooker under high speed for five minutes. The STEPHAN cooker was then opened and the contents subjected to tactile and visual examination as described in Example 1—STEPHAN Cooker Step 2. The temperature was increased to 180 degrees F. and the contents were added to the chopper.

STEP 3

A stabilizer was produced from the components in Table 3.

TABLE 3

| COMPONENTS | QUANTITY/POUND |
|---|---|
| Water | 20.00 |
| Slendid Pectin | 3.5 |
| Gelatin 250 Bloom | 1.0 |
| Calcium Chloride Solution | 20 mls. |

The stabilizer from Table 4 was prepared by adding Slendid Pectin to the 26 pounds of water in the STEPHAN cooker. The bottom agitator was set at high speed and the side agitator was turned on for 5 minutes. The STEPHAN cooker was then opened and the pectin dispersion was then inspected for complete dispersion. The 250 Bloom Gelatin was then added to the water-pectin dispersion. The ingredients were mixed in the STEPHAN cooker for 5 minutes at high speed (3,000 rpm) with no steam injection. The STEPHAN cooker was then opened and the calcium chloride solution was added and mixed for 2 minutes. The STEPHAN cooker was then opened and the contents subjected to tactile and visual examination as described in Example 1—Stephan Cooker Step 2.

STEP 4

Additional microbial inhibitors, sugar, and salt were prepared in the STEPHAN cooker using the components from Table 4. These ingredients were added to those made in Step 2 above.

TABLE 4

| COMPONENTS | QUANTITY/POUND |
|---|---|
| Salt | 4.5 |
| Alta 2331 | 1.5 |
| Alta 1801 | 1.5 |
| Alta 2001 | 0.5 |
| Alta 1705 | 1.5 |

The ingredients were mixed in the STEPHAN cooker for 2 minutes at high speed (3,000 rpm) The STEPHAN cooker was then opened and the contents subjected to tactile and visual examination as described in Example 1—STEPHAN Cooker Step 2.

STEP 5

The component in Table 5 was added to those in Step 4.

TABLE 5

| COMPONENTS | QUANTITY/POUND |
|---|---|
| Enrich 221 | 6.0 |

The ingredient was mixed in the STEPHAN cooker for 2 minutes at high speed (3,000 rpm) The STEPHAN cooker was then opened and the contents subjected to tactile and visual examination as described in Example 1—STEPHAN Cooker Step 2.

The ingredient was mixed in the STEPHAN cooker for 2 minutes at high speed (3,000 rpm). The STEPHAN cooker was then opened and the contents subjected to tactile and visual examination as described in Example 1—STEPHAN Cooker Step 2.

STEP 6

The components in Table 6 was added to those in Step 5.

TABLE 6

| COMPONENTS | QUANTITY/POUND |
|---|---|
| Parselli SA-2 | 9.0 |

The ingredients were mixed in the STEPHAN cooker for 2 to 3 minutes at high speed (3,000 rpm). The STEPHAN cooker was then opened and the contents subjected to tactile and visual examination as described in Example 1—STEPHAN Cooker Step 2. When satisfactory results were achieved, i.e., even dispersion, the STEPHAN cooker was then closed and the temperature raised to 180 degrees F. by steam injection with high speed agitation. When the temperature reached 180 F., agitation was ceased, steam flow was terminated, and the pressure released. The STEPHAN cooker was then opened and the contents were added slowly to the continually operating chopper.

STEP 7

The components in Table 7 was added to the chopper directly.

TABLE 7

| COMPONENTS | QUANTITY/POUND |
|---|---|
| Liposome Mixture Example 41 | 2.0 |
| Annatto Color(3x) | 200 mls. |
| Butter Flavor (Butr Pow'r LM4) | 1.5 |
| Starter Distillate | 20 mls. |

The annatto color, butter flavor, and starter distillate are all products of Chs. Hansen's Laboratory, Milwaukee, Wis. 53214.

HOMOGENIZATION PROCESS

The homogenization process was carried out by using a Moyno pump to force the heavy, viscous soft butter spread through the inlet valves of the high pressure homogenizer. The stuffing pressure produced by the Moyno pump has to exceed 150 to 200 pounds per square inch to prevent implosion. Since the soft butter spread at this point has a viscosity between 40,000 and 50,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer was used at a first stage pressure of 10,000 pounds per square inch and 1,500 pounds on the second stage.

The soft butter spread was cooled and packaged as described in Example 1.

The chemical and microbiological analysis of this product was as follows:

| pH | 5.96 |
|---|---|
| Fat | 1.2% |
| Salt | 1.5% |
| Standard Plate Count | <100 |
| Coli | <10 |
| Yeast/Mold | 0/0 |

The Fat Free butter type spread resembled soft spreadable margarine more that it did churned butter. The body and texture were very acceptable. This substitute cannot be used in cooking nor will it melt very well.

EXAMPLE 43 FAT FREE CHOLESTEROL FREE FAT SUBSTITUTE MADE WITH CORN MICROPARTICULATES

A stabilized fat substitute made from corn microparticulates "SFSCM" is produced by first forming a dispersion of corn microparticulates in water. The corn microparticulates are a commercial product known as STELLAR and produced by the A. E. Staley Company. The corn microparticulates are placed into the dispersed phase by the high sheer of the STEPHAN cooker. The dispersed particles are then enveloped by a lipoprotein bilayer membrane and ultra homogenized.

STEP 1

A STELLAR creme is made at 28% solids according to the following procedures.

TABLE 1

| COMPONENTS | QUANTITY/POUND |
|---|---|
| Stellar | 21.0 |
| Water | 64.0 |

The STELLAR creme is achieved by mixing the corn microparticulates in the water at high speed (3000 RPM) in the STEPHAN cooker for five minutes. The water-STELLAR mixture is checked for dispersion in a similar manner to that set out in Example 1 of the STEPHAN procedures. Upon confirming that proper dispersion is achieved, the STEPHAN cooker is closed and the temperature raised to 140 degrees F. steam injection with high speed agitation. Upon reaching 140 degrees F., the steam flow is terminated, the STEPHAN cooker is opened, and the mixture is transferred to a clean sterilized buckets. The procedure is repeated again to achieve 150 pounds of STELLAR creme. One hundred pounds of the STELLAR creme is transferred to the KRAMER GRABE© research chopper. STELLAR is a product of The A. E. Staley Manufacturing Company, Decater, Ill. 62525.

The process of applying high sheer forces to the creme is achieved by using a KRAMER GRABE© RESEARCH MODEL, 60 liter capacity vacuum chopper (after this, the KRAMER chopper). The KRAMER chopper is equipped with (i) a hood allowing chopping under vacuum, thereby improving high sheer force efficiency, (ii) heating and cooling control components capable of maintaining constant temperature in the substance having the high sheer applied to, and (iii) a knife shaft that can maintain variable speeds from 500 RPM's to 5,000 RPM's, allowing high sheer force rate control.

STEP 2

The creme is high sheer treated for 50 bowl revolutions under 0.6 bar vacuum at 135 degrees F. and a knife speed of 5000 RPM's. The vacuum hood is then opened and ten (10) pounds of the lecithin-microcrystalline premix of Example 26 is added. The hood is closed and the curd is comminuted for another 50 revolutions under 0.6 bar vacuum, a knife speed of 5,000 RPM, and the temperature is maintained at 110 degrees F. The vacuum hood is then opened and the following components are incorporated with the high sheer treated creme to prepare a "SFSCM" for low fat food products.

STEP 3

TABLE 3

| COMPONENTS | QUANTITY/POUND |
|---|---|
| Sodium Caseinate | 4.00 |
| Water | 10.0 |

The water-caseinate mixture is checked for dispersion in a similar manner to that previously done. Upon confirming that proper dispersion is achieved, the STEPHAN cooker is closed and the temperature raised to 180 degrees F. steam injection with high speed agitation. Upon reaching 180 degrees F., the steam flow is terminated. Cooling water is placed on the outside jacket to bring the temperature down to 120 degrees F. The STEPHAN © cooker is opened and the mixture is transferred to a clean sterilized bucket. The casein-water mixture for the creation of the second layer of the bilayer membrane is transferred to the chopper.

The product is high sheared for 50 bowl revolutions with the product temperature maintained at 120 degrees F., vacuum of 0.6 bars, and knife shaft speed of 5,000 RPM's. The knife array is the same as in Example 1 except for the absence of the last two knifes since the KRAMER chopper blade shaft could accommodate only a 10 knife array. The knives are of the same design as in Example 1, but smaller in diameter to fit the smaller bowl of the KRAMER chopper.

STEP 4

After 50 revolutions, the cooling water is applied to the bottom of the bowl. The knife shaft speed is reduced to 500 RPM. When the temperature reaches 60 degrees F., the improved STELLAR creme is unloaded into a kitchen cart.

HOMOGENIZATION PROCESS

The homogenization process is carried out by using a Moyno pump to force the heavy, viscous fat substitute through the inlet valves of the high pressure homogenizer. The stuffing pressure produced by the Moyno pump has to exceed 150 to 200 pounds per square inch to prevent implosion. Since the fat substitute at this point has a viscosity between 35,000 and 45,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer is used at a first stage pressure of 10,000 pounds per square inch and 1,500 pounds on the second stage.

The fat substitute is cooled and packaged as described in Example 1.

The STELLAR improved fat substitute has a greater fat mouthfeel and lubricity than did the STELLAR without the envelopment in the liposome bilayer high density lipoprotein. The long life stability is improved substantially.

EXAMPLE 44 FAT FREE CHOLESTEROL FREE FAT SUBSTITUTE MADE WITH PECTIN MICROPARTICULATES

A stabilized fat substitute made from a specialty pectin "SFSP" is produced by first forming a dispersion of specialty pectins in water. The specialty pectins are commercial products known as SLENDID and GENU and distributed by Hercules, Incorporated. The specialty pectins are placed into the dispersed phase by the high sheer of the STEPHAN cooker. The dispersed pectin particulates are then enveloped by a lipoprotein bilayer membrane and ultra homogenized.

STEP 1

The SLENDID creme is made at 4% solids according to the following procedures.

TABLE 1

| COMPONENTS | QUANTITY/POUND |
| --- | --- |
| Slendid | 2.25 |
| Genu | 0.15 |
| Water | 57.35 |
| Calcium Chloride Solution | 1.0 |

The SLENDID creme is achieved by mixing the SLENDID and GENU in the water at high speed (3000 RPM) in the STEPHAN cooker for three minutes. The water-SLENDID-GENU mixture is checked for dispersion in a similar manner to that set out in Example 1 of the STEPHAN procedures. The calcium chloride is then added with high agitation. Upon confirming that proper dispersion is achieved, the STEPHAN cooker is closed and the temperature raised to 165 degrees F. steam injection with high speed agitation. Upon reaching 165 degrees F., the steam flow is terminated, the STEPHAN cooker is opened, and the mixture is transferred to a clean sterilized buckets. The procedure is repeated again to achieve 120 pounds of SLENDID creme. One hundred pounds of the SLENDID creme is transferred to the KRAMER GRABE research chopper. SLENDID and GENU are products of Hercules Incorporated, Wilmingtion, Del. 19894.

The process of applying further high sheer forces to the creme is achieved by using a KRAMER GRABE RESEARCH MODEL, 60 liter capacity vacuum chopper (after this, the KRAMER chopper). The KRAMER chopper is equipped with (i) a hood allowing chopping under vacuum, thereby improving high sheer force efficiency, (ii) heating and cooling control components capable of maintaining constant temperature in the substance having the high sheer applied to, and (iii) a knife shaft that can maintain variable speeds from 500 RPM's to 5,000 RPM's, allowing high sheer force rate control.

STEP 2

The creme is high sheer treated for 50 bowl revolutions under 0.6 bar vacuum at 135 degrees F. and a knife speed of 5000 RPM's. The vacuum hood is then opened and ten (10) pounds of the lecithin-microcrystalline premix of Example 26 is added. The hood is closed and the curd is comminuted for another 50 revolutions under 0.6 bar vacuum, a knife speed of 5,000 RPM, and the temperature is maintained at 110 degrees F. The vacuum hood is then opened and the following components are incorporated with the high sheer treated creme to prepare a "SFSP" for low fat food products.

STEP 3

TABLE 3

| COMPONENTS | QUANTITY/POUND |
| --- | --- |
| Sodium Caseinate | 4.00 |
| Water | 10.0 |

The water-caseinate mixture is checked for dispersion in a similar manner to that previously done. Upon confirming that proper dispersion is achieved, the STEPHAN cooker is closed and the temperature raised to 180 degrees F. steam injection with high speed agitation. Upon reaching 180 degrees F., the steam flow is terminated. Cooling water is placed on the outside jacket to bring the temperature down to 140 degrees F. The STEPHAN cooker is opened and the mixture is transferred to a clean sterilized bucket. The casein-water mixture for the creation of the second layer of the bilayer membrane is transferred to the chopper.

The product is high sheared for 50 bowl revolutions with the product temperature maintained at 165 degrees F., vacuum of 0.6 bars, and knife shaft speed of 5,000 RPM's. The knife array is the same as in Example 1 except for the absence of the last two knifes since the KRAMER chopper blade shaft could accommodate only a 10 knife array. The knives are of the same design as in Example 1, but smaller in diameter to fit the smaller bowl of the KRAMER chopper.

STEP 4

After 50 revolutions, the cooling water is applied to the bottom of the bowl. The knife shaft speed is reduced to 500 RPM. When the temperature reaches 60 degrees F., the improved SLENDID creme is unloaded into a kitchen cart.

HOMOGENIZATION PROCESS

The homogenization process is carried out by using a Moyno pump to force the heavy, viscous fat substitute through the inlet valves of the high pressure homogenizer. The stuffing pressure produced by the Moyno pump has to exceed 150 to 200 pounds per square inch to prevent implosion. Since the fat substitute at this point has a viscosity between 35,000 and 45,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer is used at a first stage pressure of 10,000 pounds per square inch and 1,500 pounds on the second stage.

The fat substitute is cooled and packaged as described in Example 1.

The SLENDID improved fat substitute has a greater fat mouthfeel and lubricity than did the SLENDID without the envelopment in the liposome bilayer high density lipoprotein. In fact, the best of the two hydrocolloids fat replacers is the Slendid fat replacer made in this manner. The long life stability is improved substantially by enveloping the Slendid in lipoprotein liposomes.

EXAMPLE 45 HOMOGENIZED FAT FREE CHOLESTEROL FREE SOFT FRESH CHEESE

A stabilized fat substitute "SFS" soft fresh cheese was produced by first forming a dispersion of deagglomerated denatured whey protein-casein coprecipitate in a continuous phase aqueous medium according to the procedure of Example 1. Ten pounds of sodium caseinate was added to 120 gallons of whey protein concentrate comprising approximately 14% solids and 9% protein. The mixture was heated by steam injection to 185 degrees F. and acidified to a pH of 5.6 to 5.65 by the addition of acetic acid. This resulted in the formation of a curd precipitate.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, soft fresh cheese as described below.

The following components were incorporated with the fat substitute product produced as described above to prepare a soft fresh cheese.

TABLE 1

| COMPONENTS | QUANTITY/POUND |
|---|---|
| Water | 8.0 |
| Alcolec 140 | 1.0 |
| Alcolec SFG | 1.0 |
| Water | 13.0 |
| Avicel RC591 | 5.0 |

STEP 1

Liposome and structure building formation was achieved in a similar manner to that set out in Example 1 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 1. The STEPHAN cooker was operated for 8 minutes at 120 degrees F. Thereafter, the STEPHAN cooker was opened and the lecithin liposome mixture was visually examined for the presence of undissolved particles to insure complete dispersion. Upon confirmation that the mixture had been uniformly dispersed, a cream-like appearance was observed. An additional 13 pounds of hydration water was added to the liposomes in the STEPHAN cooker with 5 pounds of microcrystalline cellulose and mixed for approximately 10 minutes. The STEPHAN cooker was then opened and visually examined under a polarized light microscope for proper dispersion. Upon confirming that proper dispersion had been achieved, the STEPHAN cooker was closed and the temperature raised to 180 degrees F. by steam injection with mixing. Upon reaching 180 degrees F., the steam flow was terminated, the STEPHAN cooker opened, and the mixture was transferred to a clean sterilized bucket and slowly added to the chopper. The pasteurized lecithin-microcrystalline cellulose complex was processed in the chopper for 10 minutes to form a membrane around the curd particles, to place amphoteric charges on the curd particles, and to create structure in the aqueous phase as described in Example 1.

STEP 2

A stabilizer was produced from the components in Table 2.

TABLE 2

| COMPONENTS | QUANTITY/POUND |
|---|---|
| Water | 26.00 |
| Slendid Pectin | 2.0 |
| Gelatin 250 Bloom | 1.0 |

The stabilizer from Table 2 was prepared by adding SLENDID pectin and the Gelatin 250 Bloom to water in a steam-injected STEPHAN cooker. SLENDID pectin contains a specialty processed pectin distributed by Hercules, Inc., Wilmington, Del. 19894-000 and manufactured by Copenhagen Pectin, DK 4623, Skensved, Denmark. The ingredients were mixed in the STEPHAN cooker for 5 minutes at high speed (3,000 rpm) with no steam injection. The STEPHAN cooker was then opened and the contents subjected to tactile and visual examination as described in Example 1—STEPHAN Cooker Step 2.

STEP 3

Additional microbial inhibitors and salt were prepared in the STEPHAN cooker using the components from Table 3. These ingredients were added to those in Step 2.

TABLE 3

| COMPONENTS | QUANTITY/POUND |
|---|---|
| Salt | 3.0 |
| Alta 2331 | 0.5 |
| Alta 1801 | 0.5 |
| Alta 2001 | 1.5 |
| Alta 1705 | 2.0 |

The ingredients were mixed in the STEPHAN cooker for 5 minutes at high speed (3,000 rpm) The STEPHAN cooker was then opened and the contents subjected to tactile and visual examination as described in Example 1—STEPHAN Cooker Step 2.

STEP 4

The component in Table 4 was added to those in Step 3.

TABLE 4

| COMPONENTS | QUANTITY/POUND |
|---|---|
| Enrich 101 | 5.0 |

The ingredients were mixed in the STEPHAN cooker for 5 minutes at high speed (3,000 rpm) The STEPHAN cooker was then opened and the contents subjected to tactile and visual examination as described in Example 1—STEPHAN Cooker Step 2.

STEP 5

The components in Table 5 was added to those in Step 4.

TABLE 5

| COMPONENTS | QUANTITY/POUND |
|---|---|
| Non Fat Dry Milk Powder | 17.0 |
| Cultured Non Fat Buttermilk* | 5.0 |

*Non Fat Dry Milk powder is a product of Foster Farms Dairy, Modesto, CA 95351 and the Cultured Non Fat Buttermilk is a product of Land 'O Lakes, Arden Hills, MN 55126.

The ingredients were mixed in the STEPHAN cooker for 5 minutes at high speed (3,000 rpm). The STEPHAN cooker was then opened and the contents subjected to tactile and visual examination as described in Example 1—STEPHAN Cooker Step 2.

STEP 6

The components in Table 6 was added to those in Step 5.

TABLE 6

| COMPONENTS | QUANTITY/POUND |
|---|---|
| Parselli SA-2 | 4.0 |
| Cream Cheese Powder | 4.0 |

The ingredients were mixed in the STEPHAN Cooker for 5 minutes at high speed (3,000 rpm) The STEPHAN cooker was then opened and the contents subjected to tactile and visual examination as described in Example 1—STEPHAN Cooker Step 2.

When satisfactory results were achieved, i.e., even dispersion, the STEPHAN cooker was closed and the temperature raised to 180 degrees F. by steam injection with high speed agitation. When the temperature reached 180 F., agitation was ceased, steam flow was terminated, and the pressure released. The STEPHAN cooker was then opened and the contents were added slowly to the continually operating chopper.

ACIDIFICATION PROCESS

The acidification process was carried out according to the procedure outlined in Example 1 in which the mixture was acidified to a pH of 4.9 to 5.0 by adding lactic acid (CCA Biochem b. v. Holland) and 20 ml of starter distillate (Hansen's 15X) to the continually operating chopper and mixing for about one minute.

HOMOGENIZATION PROCESS

The homogenization process was carried out by using a Moyno pump to force the heavy, viscous fat free soft cheese through the inlet valves of the high pressure homogenizer. The stuffing pressure had to exceed 150 pounds to prevent implosion. A APV RANNIE high pressure homogenizer was used at a first stage pressure of 10,000 pounds per square inch and 1,500 pounds on the second stage.

The soft fresh cheese was cooled and packaged as described in Example 1.

The chemical and microbiological analysis of this product is as follows:

| | |
|---|---|
| pH | 5.01 |
| Fat | 0.20% |
| Salt | 2.40% |
| Standard Plate Count | <100 |
| Coli | <10 |
| Yeast/Mold | 0/0 |

The components listed in Table 7, below, were added to the soft fresh cheese produced via the procedures described above. This resulted in garlic and herb flavored soft spreadable cheese.

TABLE 7

| INGREDIENT | WEIGHT PERCENT (%) |
|---|---|
| Soft Fresh Cheese | 99.00 |
| Herb and Garlic C208-B | 1.0 |
| | 100.00 |

The Garlic and Herb Base is a product of Saratoga Specialties, Elmhurst, IL 60126.

The above ingredients were blended for 1 minute in a 5½ qt. KITCHEN AID bowl with a paddle. The resulting spread was evaluated against two commercial low cholesterol spreadable cheeses for spreadable characteristics, texture and smoothness. In comparisons of spreadable characteristics, no significant differences was detected. In comparisons of texture, syneresis was detected in one of the commercial products. However, the product produced via the above described procedures continued to exhibit its creamy texture. The overall smoothness and organoleptic qualities of the product were comparable to that of high fat, spreadable cheese with butterfat ranges of 12% to 30%.

EXAMPLE 46 ENZYME MODIFIED CHEESE MADE WITH LIPOSOME ENVELOPED ENZYMES

A enzyme modified cheese was made from a blend of natural cheeses with liposome enveloped lipolytic and proteolytic enzymes made from lecithin fractions. The enzyme modified cheese was produced by first comminuting the cheese in a 200 liter capacity open atmosphere chopper manufactured by Maselinenfabrik Seydelmann. The knives used to comminute the cheese and mix in the dry ingredients were SECURITY-SYSTEM-4-CUT-KNIVES. The comminuted cheese and dry ingredients were transferred via a inclined screw conveyor to the FEPC cooker used in previous examples for the cooking of curd. The drains were replaced by two steam injection nozzles.

The ingredients in Table 1 were placed in the chopper while in was running on slow speed. The individual cheeses were added slowly to insure homogeneity. The powder ingredients were added last and mixed in with the chopper in reverse mix mode. The individual chopper batches were made to make up the final cooker batch.

TABLE 1

| INGREDIENT | POUNDS |
| --- | --- |
| Fresh Hispanic Cheese | 250.0 |
| Sodium Caseinate | 15.0 |
| Danish Cheese Powder | 10.0 |
| ALTA 2020 | 3.0 |
| TOTAL | 278.0 |

The ingredients in Table 1 were produced in triplicate and Conveyed to the cooker. This made a total cooker cheese batch weight of 834 pounds.

The cheese mixture in the cooker was heated via direct steam injection. As the cheese was melting, the ingredients in Table 2 were added in the order of sequence in Table 2.

TABLE 2

| INGREDIENT | POUNDS |
| --- | --- |
| Butter | 90.0 |
| Liposome Mixture Example No. 41 | 2.0 |
| Lactic Acid | A/R |
| Sodium Citrate | 12.0 |
| Sodium Aluminum Phosphate | 6.0 |
| TOTAL | 110.0 |

When the cheese begins to melt, the butter is added to the cheese mass. The enzyme modified cheese is then added. The mixture from Example 40 containing only liposomes from lecithin fractions enveloping the fumed silica was added slowly to the cheese mass. The pH of the enzymatic modified cheese base cheese is lowered to 5.6 to 5.7 with the addition of lactic acid. Further heating raised the temperature to 195 degrees F. The sodium citrate and sodium aluminum phosphate were mixed with water and added slowly to the cheese mass. The finished weight of the batch was approximately 982 pounds with the weight of the steam condensation.

The finished enzymatic modified cheese base is unloaded into kitchen carts at 200 pounds each.

COOLING, EMULSIFICATION, AND INCORPORATION OF ENZYMES OF THE CHEESE

The enzymatic modified cheese base was transferred to the 200 liter capacity vacuum chopper manufactured by MEISSNER AG. This shopper is equipped with a vacuum hood whereby a vacuum of 28 inches of mercury can be pulled. The hood is also equipped with a carbon dioxide injection hood and exhaust exit. The bowl of the chopper also can be heated or cooled with water or steam via sprays underneath the enclosed bowl.

Choppers, long used in the food processing industry for sausage processing, have been found to have utility in emulsifying enzymatic modified cheese base and incorporating the enzymes into the cheese mass. In this case, vacuum is employed to reduce the entrapment of air. Air entrapment during the emulsification phase creates increased microbiological contamination which, if sufficient, will cause the development of off flavors.

In the process described in the present example, a six knife array is selected for use in the chopper. The knives in this array are SECURITY-SYSTEM-4-CUT-KNIVES used in other examples. The six knife array uses 10 mm. spacers between the knifes to prevent cheese build-up.

The chopper is operated at a high bowl speed of 16 RPM's and a knife shaft speed of 3,000 RPM's with carbon dioxide injection for enough time to cool the enzymatic modified cheese base to 140 degrees F. The vacuum hood was raised and 60 pounds of pasteurized water was added slowly to the revolving cheese mass.

STEPHAN COOKER STEP NUMBER 1

While the chopper is operated to cool the cheese mass described in the preceding paragraph, a vesicle-forming composition is being prepared in the STEPHAN cooker for addition to the cheese mass.

STEP 1

The vesicle or liposome forming are prepared in the STEPHAN cooker using steam-injection and high agitation to form and pasteurize very quickly. The components listed in table one are used for this purpose.

TABLE 1

| Ingredient | Pounds |
| --- | --- |
| Water | 24.0 |
| Alcolec 140 | 6.0 |
| Alcolec SFG | 3.0 |

Forty pounds of water are poured into the STEPHAN cooker to which the following ingredients are added:

(i) Ten pounds of ALCOLEC 140 that contains approximately 40% phosphatidyl choline by weight;

(ii) Five pounds ALCOLEC SFG which is high in inositol and glycolipids content.

These contents are processed in the STEPHAN cooker for 8 minutes at 120 degrees F. with the lower knife blade operating at 3,000 RPM and the side scraper blade on high speed in order to form liposomes. At the end of 8 minutes, the blade/scraper action is interrupted and the STEPHAN cooker opened to visually examine the contents for even dispersion. The contents of the STEPHAN cooker were increased to 180 degrees F. and then cooled to 80 degrees F.

STEP 2

TABLE 1

| Ingredient | Pounds |
| --- | --- |
| Pasteurized Water | 30.0 |
| Hansen's Calf Lipase | 75 grams |
| Hansen's Lamb Lipase | 75 grams |
| IBT Protease RST-30 | 300 grams |

The enzymes were mixed with pasteurized water approximately twenty minutes before the addition to the liposomes. They were mixed vigorously and allowed to stand to leach out the enzymes from the animal tissue. The temperature of the water should not exceed 90 degrees F. The lipases are products of Chs. Hansen's Laboratory, Milwaukee, Wis. 53214. IBT Protease is a product of Imperial Biotechnology, London, England, SW7 2BT.

Once even dispersion is confirmed, the enzyme containing water was added to the STEPHAN cooker and high speed agitation is again applied for 10 minutes making sure the temperature never exceeds 90 degrees F. The STEPHAN cooker now contains enough liposome enveloped enzymes to do 3 batches of enzymatic modified cheese.

The chopper continues operation until the cheese base and added water has cooled to 35 to 40 degrees F. Twenty pounds of the liposome enveloped enzymes were added to the enzyme modified cheese base and the chopper continues operation until the liposomes are adequately mixed to insure homogeneity. In not case, however, should the temperature exceed 65 degrees F. as this will begin to melt the butterfat sufficiently to coat the liposomes and thus, the enzymes will not penetrate the cheese mass.

The enzyme modified cheese is removed from the chopper and stuffed into casings with the RISCO stuffer. The enzyme modified cheese is stored at 58 to 60 degrees F. for ten to thirty days or until the proper intense flavor and essence has developed.

When the intense flavor has developed, the enzyme modified cheese is pasteurized at 195 degrees F. in the FPEC cooker and packed in 5 gallon pails. The use of the liposome envelopment has made the efficiency of the enzyme double approximately. In other words, the cost of the enzyme to produce enzyme modified cheese has been reduced by fifty percent.

The chemical and microbiological analysis of this product was as follows:

| | |
|---|---|
| pH | 5.42 |
| Fat | 21.2% |
| Salt | 3.5% |
| Standard Plate Count | <100 |
| Coli | <10 |
| Yeast/Mold | 0/0 |
| Moisture | 59.5% |
| FDB | 51.6% |

EXAMPLE 47 FAT FREE CHOLESTEROL FREE FAT SUBSTITUTE

A stabilized fat substitute "SFS" was produced by first forming a dispersion of deagglomerated denatured whey protein-casein coprecipitate in a continuous phase aqueous medium according to the procedure of Example 1. Ten pounds of sodium caseinate were added to 120 gallons of whey protein concentrate comprising approximately 14.45% solids and 6.64% protein. The mixture was heated by steam injection to 185 degrees F. and acidified to a pH of 5.6 to 5.65 by the addition of acetic acid in the form of vinegar. This resulted in the formation of a curd coprecipitate of whey protein and casein.

Two hundred pounds of curd were transferred from the FPEC cooker to the bowl chopper using a false bottom kitchen cart. Comminution/deagglomeration of the curd was achieved according to the procedure described in Example 1. The resulting fat substitute product was further processed into fat free, cholesterol free, fat substitute as described below.

The following components were incorporated with the fat substitute product produced as described above to prepare a fat substitute.

TABLE 1

| COMPONENTS | QUANTITY/POUND |
|---|---|
| Water | 8.0 |
| Alcolec 140 | 2.0 |
| Alcolec SFG | 1.0 |
| Water | 13.0 |
| Avicel RC591 | 5.0 |

STEP 1

The liposome and structure building formation was achieved in a similar manner to that set out in Example 1 in which the membrane-forming, surface active, and structure building agents were prepared in the STEPHAN cooker. The lecithin fractions (American Lecithin Company, Danbury, Conn. 06813-1908) were added to water in the STEPHAN cooker to form liposomes as described in Example 1. The STEPHAN cooker was operated for 8 minutes at 120 degrees F. Thereafter, the STEPHAN cooker was opened and the liposomes made from the lecithin-water mixture were visually examined for the presence of undissolved particles and to insure complete dispersion. Upon confirmation that the mixture was uniformly dispersed and that liposomes were formed, a caramel cream-like appearance was observed. An additional 13 pounds of hydration water was added to the liposomes in the STEPHAN cooker together with 5 pounds of microcrystalline cellulose and mixed for approximately 10 minutes. The STEPHAN cooker was then opened and the liposome mixture was visually examined under a polarized light microscope for proper dispersion. Upon confirming that proper dispersion was achieved, the STEPHAN cooker was closed and the temperature raised to 180 degrees F. by steam injection with high speed agitation. Upon reaching 180 degrees F., the steam flow was terminated, the STEPHAN cooker was opened, and the mixture was transferred to a clean sterilized bucket and slowly added to the chopper. The pasteurized lecithin-microcrystalline cellulose complex was processed in the chopper for 10 minutes to form a membrane around the curd particles, to place amphoteric charges on the curd particles, and to create structure in the aqueous phase as described in Example 1.

STEP 2

A stabilizer was produced from the components in Table 2.

TABLE 2

| COMPONENTS | QUANTITY/POUND |
|---|---|
| Water | 20.00 |
| Slendid Pectin | 2.0 |
| Genu Pectin | 0.5 |
| Calcium Chloride Solution | 20 mls. |

The stabilizer from Table 2 was prepared by adding SLENDID pectin and the GENU pectin to the 20 pounds of water in the STEPHAN cooker. The bottom agitator was set at high speed and the side agitator was turned on for 5 minutes. The STEPHAN cooker was then opened and the pectin dispersion was then inspected for complete dispersion. The ingredients were mixed in the STEPHAN cooker for 5 minutes at high speed (3,000 rpm) with no steam injection. The STEPHAN cooker was then opened and the calcium chloride solution was added and mixed for 2 minutes. The STEPHAN cooker was then opened and the contents subjected to tactile and visual examination as described in Example 1—STEPHAN Cooker Step 2. SLENDID and GENU pectins are specialty processed pectins distributed by Hercules, Inc., Wilmington, Del. 19894-000.

STEP 3

Additional microbial inhibitors were prepared in the STEPHAN cooker using the components from Table 3.

These ingredients were added to those made in Step 2 above.

TABLE 3

| COMPONENTS | QUANTITY/POUND |
|---|---|
| Alta 2331 | 0.5 |
| Alta 1801 | 0.5 |
| Alta 2001 | 0.5 |
| Alta 1705 | 0.5 |

The ingredients were mixed in the STEPHAN cooker for 2 minutes at high speed (3,000 rpm). The STEPHAN cooker was then opened and the contents subjected to tactile and visual examination as described in Example 1—STEPHAN Cooker Step 2.

STEP 4

The component in Table 4 was added to those in Step 3.

TABLE 4

| COMPONENT | QUANTITY/POUND |
|---|---|
| Enrich 221 | 2.0 |

The ingredients were mixed in the STEPHAN cooker for 2 minutes at high speed (3,000 rpm). The STEPHAN cooker was then opened and the contents subjected to tactile and visual examination as described in Example 1—STEPHAN Cooker Step 2. The Enrich 221 is a natural microbial stabilizer available from Quest-Microlife Technics, Inc. of Sarasota, Fla., 34230.

STEP 5

The component in Table 5 was added to those in Step 4.

TABLE 5

| COMPONENT | QUANTITY/POUND |
|---|---|
| Cal Pro 50 Whey Protein | 2.0 |

The ingredient was mixed in the STEPHAN cooker for 2 minutes at high speed (3,000 rpm). The STEPHAN cooker was then opened and the contents subjected to tactile and visual examination as described in Example 1—STEPHAN Cooker Step 2. Non Fat Dry Milk powder is a product of Cal Pro Proteins, Corona, Calif. 91720.

STEP 6

The components in Table 6 was added to those in Step 5.

TABLE 6

| COMPONENTS | QUANTITY/POUND |
|---|---|
| Parselli SA-2 | 2.0 |
| GP Maltodextrin 040 | 2.0 |

The ingredients were mixed in the STEPHAN cooker for 2 to 3 minutes at high speed (3,000 rpm). The STEPHAN cooker was then opened and the contents subjected to tactile and visual examination as described in Example 1—STEPHAN cooker Step 2. When satisfactory results were achieved, i.e., even dispersion, the STEPHAN cooker was then closed and the temperature raised to 180 degrees F. by steam injection with high speed agitation. When the temperature reached 180 F., agitation was ceased, steam flow was terminated, and the pressure released. The STEPHAN cooker was then opened and the contents were added slowly to the continually operating chopper.

HOMOGENIZATION PROCESS

The homogenization process was carried out by using a Moyno pump to force the heavy, viscous fat substitute through the inlet valves of the high pressure homogenizer. The stuffing pressure produced by the Moyno pump has to exceed 150 to 200 pounds per square inch to prevent implosion. Since the fat substitute at this point has a viscosity between 35,000 and 45,000 CPS, it will not flow readily into the homogenizer cylinder when the piston makes the inlet stroke. A void is created that will cause implosion on the forward motion of the piston when the pressure begins to exceed 8,000 pounds or greater. A APV RANNIE high pressure homogenizer was used at a first stage pressure of 10,000 pounds per square inch and 1,500 pounds on the second stage.

The fat substitute was cooled and packaged as described in Example 1.

The chemical and microbiological analysis of this product was as follows:

| | |
|---|---|
| pH | 5.82 |
| Fat | 0.81% |
| Salt | 1.55% |
| Standard Plate Count | <100 |
| Coli | <10 |
| Yeast/Mold | 0/0 |

The fat substitute was held for 90 days at refrigerated temperatures and analysis was preformed for Standard Plate Count and for the appearance of grainy or rough mouthfeel or chalkiness. The SPC had increased to less than 1,000 CFU and the fat substitute did not have any indication of degradation of the fat-like mouthfeel. This fat substitute would be applicable where pH is a factor in stability. Since casein is a factor in the formulation of Example 19 as a component of the non fat milk solids in Step No. 5, whey protein was substituted in place of the non fat solids. Casein will precipitate at pH 4.6, whereas whey protein will not until the pH of 3.3 is reached. Thus, the fat substitute in this example will remain acid pH stable.

The descriptive portions of this specification discuss dairy whey as the source of whey protein curd, but the general principles of this invention are to be understood to be applicable to other protein sources. The descriptive portions also discuss the presently available lecithin fractions which enable formation of the liposomes useful in the present invention. As additional formulations of lecithin fractions become available, such fractions and/or derivatives are contemplated for use in connection with the present invention.

The descriptive portions of this specification also discuss enrobement of specific proteins and carbohydrates, but the general principles of this invention are to be understood to be applicable to other protein sources.

Modifications and variations in practice of the invention are expected to occur to those of ordinary skill in the art upon consideration of the foregoing description of the invention and, consequently, only such limitations as appear in the appended claims should be placed thereon.

I claim:

1. A method of forming a fat-replicating dispersion of protein particles in a continuous aqueous phase which comprises:
   (a) heating and acidifying whey to form (i) a hard curd comprised of agglomerated denatured protein and an aqueous component retained in the curd and (ii) second whey;
   (b) separating said hard curd from said second whey;
   (c) deagglomerating the hard curd to form a fat-replicating dispersion having a substantially smooth emulsion like organoleptic character comprised of (i) a continuous aqueous phase of aqueous component released by said curd during deagglomeration and (ii) said denatured whey proteinaceous particles; and
   (d) encapsulating said particles with liposomes to form a membrane on said particles.

2. The method of claim 1 wherein said whey is heated by steam introduced directly into the whey and at least a portion of said steam is entrained in said whey.

3. The method of claim 1 wherein said whey is a dairy whey.

4. The method of claim 3 wherein said dairy whey is a whey protein concentrate.

5. The method of claim 4 where in the dairy whey protein concentrate contains a protein additive.

6. The method of claim 5 wherein the additive is a caseinate.

7. The method of claim 2 wherein said whey is a dairy whey.

8. The method of claim 2 wherein said dairy whey is a whey protein concentrate.

9. The method of claim 2 wherein the dairy whey protein concentrate contains a protein additive.

10. The method of claim 2 wherein the additive is a caseinate.

11. The method of claim 10 wherein the curd contains, as a major component thereof, said aqueous component retained in the curd.

12. The method of claim 9 wherein the curd contains, as a major component thereof, said aqueous component retained in the curd.

13. The method of claim 8 wherein the curd contains, as a major component thereof, said aqueous component retained in the curd.

14. The method of claim 7 wherein the curd contains, as a major component thereof, said aqueous component retained in the curd.

15. A method of forming liposome-membrane encased hydrocolloid dispersoids which comprises:
   (a) forming a dispersion of said hydrocolloid dispersoids in a continuous aqueous phase; and
   (b) encapsulating said hydrocolloid dispersoids selected from the group consisting of xanthan gum, carrageenan, carboxymethyl cellulose, methylcellulose, oat fiber, microcrystalline cellulose, fused silica, alginate, konjac flour, pectin, agar, gum arabic, flocced cellulose and mixtures thereof in phospholipid liposomes to form phospholipid liposome-encapsulated hydrocolloid dispersoids dispersed in said continuous aqueous phase; and
   (c) drying said phospholipid liposome-encapsulated hydrocolloid dispersoids.

16. The method of claim 15 wherein the drying is effected by low temperature or freeze drying.

17. The method of claim 16 wherein the dispersion of phospholipid liposome-encapsulated hydrocolloids formed in step (b) of claim 15 is homogenized and then dried by low temperature or freeze drying.

18. In a method of forming a dispersion of solid denatured protein particles from heat denatured whey proteins, said dispersion having a substantially smooth, emulsion like organoleptic character, the improvement which comprises:
   (a) heating whey to denature the whey protein therein;
   (b) acidifying the heated whey to form: i) a curd comprised of an agglomerated denatured whey protein component and an aqueous component retained in the curd and ii) a second whey;
   (c) separating said curd from said second whey; and
   (d) subjecting the separated curd to deagglomerating shear forces to deagglomerate the agglomerated denatured whey protein to form a dispersion of denatured whey protein particles in a continuous aqueous phase of aqueous component released by said curd during deagglomeration, said dispersion having a substantially smooth, emulsion like organoleptic character.

19. The method of claim 18 wherein the whey is a dairy whey.

20. The method of claim 19 wherein steam is introduced into a dairy whey and to entrain at least a portion of said steam in said dairy whey to form a steam-entrained dairy whey.

21. The method of claim 20 wherein the dairy whey is a whey protein concentrate.

22. The method of claim 21 wherein the dairy whey is a whey protein concentrate containing a protein additive.

23. The method of claim 22 wherein the additive is caseinate.

24. The method of claim 18 wherein the curd contains, as a major component thereof, said aqueous component retained in the curd during curd formation.

25. The method of claim 24 wherein said curd has a density less than density of said second whey; and said aqueous component of said curd contains water present in an amount of from about 60 percent by weight to about so percent by weight based on curd weight after the curd is separated from the second whey.

26. The method of claim 22 wherein the curd contains, as a major component thereof, said aqueous component retained in the curd during curd formation.

27. The method of claim 26 wherein said curd has a density less than density of said second whey; and said aqueous component of said curd contains water present in an amount of from about 60 percent by weight to about 80 percent by weight based on curd weight after the curd is separated from the second whey.

28. The method of claim 20 wherein the volume of dairy whey after steam entrainment is greater than the volume of dairy whey prior to steam entrainment, 29. The method of claim 28 wherein the volume of the steam entrained whey is at least about 10 percent greater than the volume of the dairy whey prior to steam entrainment.

30. The method of claim 29 wherein the volume of the steam entrained whey is from about 15 percent to about 20 percent greater than the Volume of the dairy whey prior to steam entrainment.

31. The method of claim 21 wherein the curd contains, as a major component thereof, said aqueous component retained in the curd during curd formation.

32. The method of claim 31 wherein said curd has a density less than density of said second whey; and said aqueous component of said curd contains water present in an amount of from about 60 percent by weight to about 80 percent by weight based on curd weight after the curd is separated from the second whey.

33. The method of claim 20 wherein the curd contains, as a major component thereof, said aqueous component retained in the curd during curd formation.

34. The method of claim 33 wherein said curd has a density less than density of said second whey; and said aqueous component of said curd contains water present in an amount of from about 60 percent by weight to about 80 percent by weight based on curd weight after the curd is separated from the second whey.

35. In a fat-containing food product, the improvement which comprises partial or total replacement of fat in said product by a substantially fat-free comminuted whey curd having a substantially smooth emulsion-like organoleptic character, said whey curd being comprised of liposome encapsulated whey curd particles.

36. The improved product of claim 35 wherein the liposome is comprised of liposomal phospholipid.

37. The improved product of claim 36 wherein the whey curd particles are encapsulated in a lipoprotein membrane.

38. The improved product of claim 36 wherein the food product is selected from the group consisting of cheese, cream-style dressing, mayonnaise, sour cream batter and ice cream.

39. The ice cream of claim 38 wherein the whey curd is a comminuted denatured whey protein-caseinate coagglomerate and the whey protein component of the comminuted denatured whey protein-caseinate coagglomerate is derived from dairy whey and the ice cream also contains nonfat milk solids.

40. The improved product of claim 39 further comprising a monoglyceride.

41. The ice cream of claim 40 further comprising gelatin.

42. The improved product of claim 35 wherein the whey curd particles are encapsulated in a lipoprotein membrane.

43. In a fat-containing food base, the improvement which comprises partial or total replacement of fat in said base by a substantially fat-free comminuted whey curd having a substantially smooth, emulsion-like organoleptic character, said whey curd being comprised of liposome encapsulated whey curd particles.

44. The improved product of claim 43 wherein the liposome is comprised of liposomal phospholipid.

45. The improved base of claim 44 wherein the food base is cheesecake base.

46. The improved product of claim 43 wherein the whey curd particles are encapsulated in a lipoprotein membrane.

47. The improved product of claim 43 wherein the whey curd particles are encapsulated in a lipoprotein membrane.

48. A substantially fat-free light cream comprised of deagglomerated washed whey curd having a substantially smooth, emulsion-like organoleptic character, said whey curd being comprised of liposome encapsulated whey curd particles.

49. In a fat-replicating or fat-based food product, the improvement which comprises dispersing therein microcrystalline cellulose enrobed in a liposome.

50. In a presliced cheese block, the improvement which comprises phospholipid encapsulated microcrystalline cellulose dispersed therein.

51. A method of making a meat-fat replicating composition which comprises:
 (a) forming a dispersion of particles comprised of denatured coprecipitate of whey protein and caseinate having a substantially smooth, emulsion-like organoleptic character;
 (b) forming a liposome dispersion comprised of liposome encapsulated crystals of a microcrystalline edible food additive;
 (c) admixing the dispersions formed in steps (a) and (b); and
 (d) forming a hydrocolloid and incorporating said hydrocolloid into the admixture of step (c) to form a solid meat-fat substitute.

52. The method of claim 51 further comprising mixing liposomes or the combination of fumed silica and liposomes with the solid fat substitute formed in step (c) to form pieces of a solid meat-fat substitute having a deposit of liposomes or fumed silica and liposomes on the surface thereof.

53. The method of claim 52 further comprising combining a lean meat with the coated pieces of meat-fat substitute of claim 52 to form an emulsified low fat meat product.

54. The method of claim 53 further comprising adding liposome dispersion comprised of liposome encapsulated crystals of an edible microcrystalline additive to the emulsified low fat meat product and dispersing said crystals in said emulsified low fat meat product.

55. The method of claim 54 wherein the microcrystalline food additive is microcrystalline cellulose.

56. The method of claim 51 wherein the microcrystalline food additive is microcrystalline cellulose.

57. The method of claim 56 wherein the hydrocolloid is comprised of hydrocolloid formed from konjac flour and/or carrageenan.

58. The method of claim 51 wherein the hydrocolloid is comprised of hydrocolloid formed from konjac flour and/or carrageenan.

59. A method of making a fat substitute from corn microparticulates which comprises encapsulating said particles in a lipoprotein membrane and then homogenizing the encapsulated particles.

60. The method of claim 59 wherein a liposome dispersion comprised of liposome encapsulated microcrystalline cellulose is used to form liposome encapsulated corn microparticles; and protein is deposited on said encapsulated corn particles to form a lipoprotein membrane having an outer layer comprised of protein.

61. The method of claim 59 wherein the corn microparticle membrane is comprised of a lipid and caseinate.

62. The method of claim 61 wherein the lipid is a phospholipid.

63. The method of claim 62 wherein a liposome dispersion comprised of liposome encapsulated microcrystalline cellulose is used to form the liposome encapsulated whey curd particles.

64. The method of claim 63 wherein protein is deposited on the liposome encapsulated denatured whey curd particles to form lipoprotein membrane encapsulated denatured whey curd particles, hydrocolloid is added to the dispersion and the hydrocolloid-containing dispersion is acidified and homogenized.

65. The method of claim 64 wherein the protein additive is caseinate and the hydrocolloid is comprised of pectin.

66. A method of forming a stabilized fat substitute which comprises:
   (a) heating a whey protein concentrate containing egg white and adjusting the pH above 6 and below 8;
   (b) forming a whey curd from said whey protein concentrate containing egg white;
   (c) deagglomerating the whey curd to form a dispersion of denatured whey curd particles, said dispersion having a substantially smooth emulsion-like organoleptic character; and
   (d) encapsulating whey curd particles formed in step (c) with a liposome to form liposome encapsulated whey curd particles.

67. The method of claim 66 wherein the whey protein concentrate also contains caseinate.

68. A method of improving the resistance to deformity of a proteinaceous particle in a fat-replicating dispersion having a substantially smooth emulsion like organoleptic character wherein said particle is dispersed in a continuous aqueous phase which comprises introducing microcrystals of an edible microcrystalline food additive into said particle.

69. The method of claim 68 wherein the microcrystalline food additive is microcrystalline cellulose.

70. The method of claim 68 further comprising heating said particle in said continuous aqueous phase, said continuous aqueous phase having at a pH above about 6.0.

71. The method of claim 68 wherein the dispersion further contains hydrocolloid and protein additive and the dispersion is cooked to form a complex between at least a portion of the protein additive and hydrocolloid.

72. A method of adjusting the body, texture and moisture content of a fat substitute comprised of a dispersion of liposome encased proteinaceous particles, which method comprises forming a whey curd which is deagglomerated to form said proteinaceous particles from a whey or whey protein concentrate, optionally containing caseinate, which comprises adjusting one or more of the following variables:
   (a) the pH of the whey or whey protein concentrate feedstock;
   (b) the degree of protein hydrolysis of said feedstock;
   (c) the ratio of casein to whey protein in the feedstock;
   (d) the addition of hydrocolloid to the feedstock;
   (e) the pH of the whey protein feedstock during cooking;
   (f) the cooking temperature and the length of cooking time;
   (g) the length of time between cooking and deagglomeration;
   (h) the use of a vacuum and the level of vacuum used during agglomeration; and
   (i) the product temperature of the deagglomerated particles during processing after deagglomeration.

73. A fat-replicating dispersion having a substantially smooth emulsion like organoleptic character comprised of:
   (a) liposome encapsulated particles comprised of:
      (i) a proteinaceous core; encapsulated in
      (ii) a liposome membrane, said membrane or core containing microcrystalline cellulose,
   dispersed in:
   (b) a continuous aqueous phase.

74. The fat-replicating dispersion of claim 73 wherein the membrane and core contain microcrystalline cellulose.

75. The dispersion of claim 74 wherein the core is proteinaceous and comprised of (i) a hardened whey curd component of sponge-like architecture with openings therein and (ii) an aqueous component in said openings.

76. The dispersion of claim 75 wherein the continuous aqueous phase has phospholipid coated cellulose microcrystals dispersed therein, the aqueous component in the openings of the hardened whey curd contains cellulose microcrystals; and, the phospholipid membrane enrobing the particle has cellulose microcrystals embedded therein.

77. The dispersion of claim 73 wherein the core is proteinaceous and comprised of (i) a hardened whey curd component of sponge-like architecture with openings therein and (ii) an aqueous component in said openings.

78. The dispersion of claim 77 wherein the continuous aqueous phase has phospholipid coated cellulose microcrystals dispersed therein, the aqueous component in the openings of the hardened whey curd contains cellulose microcrystals; and, the phospholipid membrane enrobing the particle has cellulose microcrystals embedded therein.

79. A fat-replicating dispersion having a substantially smooth emulsion like organoleptic character comprised of:
   (a) liposome encapsulated particles comprised of:
      (i) a core of hardened whey curd component of sponge-like architecture with openings therein and an aqueous component in said openings; encapsulated in
      (ii) a liposome membrane,
   dispersed in:
   (b) a continuous aqueous phase.

80. The dispersion of claim 79 further comprising a thixotropic agent or hydrocolloid stabilizer in the continuous aqueous phase.

81. The dispersion of claim 80 wherein said hydrocolloid is selected from the group consisting of konjac flour, carrageenan, xanthan gum, pectin, carboxy methyl cellulose, fermented dairy products and combinations thereof.

82. The dispersion of claim 79 further comprising a structure builder in the continuous aqueous phase selected from the group consisting of microcrystalline cellulose, powdered cellulose, fumed silica and combinations thereof.

83. A fat-replicating dispersion having a substantially smooth emulsion like organoleptic character comprised of:
   (a) liposome encapsulated particles comprised of:
      (i) a proteinaceous core; encapsulated in
      (ii) a liposome membrane; and
   (b) phospholipid coated cellulose microcrystals dispersed in:
   (c) a continuous aqueous phase.

84. A fat-replicating dispersion having a substantially smooth emulsion like organoleptic character comprised of:
   (a) liposome encapsulated particles comprised of:
      (i) a proteinaceous core; encapsulated in
      (ii) a liposome membrane and
   (b) a thixotropic agent or hydrocolloid stabilizer, dispersed in:
(c) a continuous aqueous phase.

85. The dispersion of claim 84 wherein said hydrocolloid is selected from the group consisting of konjac flour, carrageenan, xanthan gum, pectin, carboxy methyl cellulose, fermented dairy products and combinations thereof.

86. The dispersion of claim 85 wherein said hydrocolloid is xanthan gum or pectin.

87. A fat-replicating dispersion having a substantially smooth emulsion like organoleptic character comprised of:
(a) liposome encapsulated particles comprised of:
(i) a proteinaceous core; encapsulated in
(ii) a liposome membrane and
(b) a structure builder selected from the group consisting of microcrystalline cellulose, powdered cellulose, fumed silica and combinations thereof, dispersed in:
(c) a continuous aqueous phase.

88. A fat-replicating dispersion having a substantially smooth emulsion like organoleptic character comprised of:
(a) a continuous aqueous phase;
(b) liposome encapsulated particles comprised of:
(i) a proteinaceous core; encapsulated in
(ii) a liposome membrane, said liposome encapsulated particles being dispersed in said continuous aqueous phase, and
(c) edible microcrystals in the continuous aqueous phase or liposome encapsulated particle.

89. The dispersion of claim 88 wherein the edible microcrystals are crystals of microcrystalline cellulose.

90. The dispersion of claim 89 wherein the microcrystalline cellulose is liposome encapsulated.

91. The dispersion of claim 88 wherein the edible microcrystals are liposome encapsulated.

92. A method of forming a fat-replicating dispersion of protein particles in a continuous aqueous phase which comprises:
(a) encapsulating said particles with liposomal phospholipids to form a membrane on said particles and
(b) dispersing phospholipid encapsulated edible microcrystals in said fat-replicating dispersion.

93. The method of claim 92 wherein said edible microcrystals are comprised of microcrystalline cellulose.

94. The method of claim 93 wherein the liposomes encapsulating the crystals of microcrystalline cellulose are formed in an aqueous medium containing liposomal phospholipid.

95. The method of claim 93 further comprising entraining said encapsulated cellulose microcrystals in the phospholipid membrane.

96. The method of claim 92 further comprising entraining said encapsulated edible microcrystals in the phospholipid membrane.

97. A method of forming a fat-replicating dispersion of protein in a continuous aqueous phase which comprises:
(a) encapsulating said particles with liposomal phospholipids to form a membrane on said particles and
(b) incorporating a proteinaceous micelle or fibril forming component in the membrane to form an exposed protein-containing membrane layer contiguous with the continuous aqueous phase.

98. The method of claim 97 further comprising incorporating caseinate in the membrane to form an exposed caseinate-containing membrane layer contiguous with the continuous aqueous phase.

99. The method of claim 98 further comprising forming hairy fibrils on the exposed caseinate-containing surface of the membrane encapsulated particle produced according to the method of claim 98.

100. The method of claim 99 wherein said hairy fibrils are formed by homogenization.

101. The method of claim 100 wherein said hairy fibrils are formed by high pressure homogenization.

102. A method of forming a fat-replicating dispersion of protein particles in a continuous aqueous phase which comprises:
(a) forming protein particles comprised of (i) a proteinaceous hardened whey curd component of sponge-like architecture with openings therein and (ii) an aqueous component in said openings; and
(b) encapsulating said particles with liposomes to form a membrane on said particles.

103. A method of forming a fat-replicating dispersion of protein particles in a continuous aqueous phase which comprises:
(a) forming liposomes in an aqueous medium containing liposomal phospholipids;
(b) encapsulating protein particles dispersed in a continuous aqueous phase with said liposomes to form a membrane on said particles; and
(c) incorporating a thixotropic agent or hydrocolloid stabilizer into the continuous aqueous phase.

104. The method of claim 103 wherein said hydrocolloid is selected from the group consisting of konjac flour, carrageenan, xanthan gum, pectin, carboxy methyl cellulose, fermented dairy products and combinations thereof.

105. The method of claim 103 wherein the hydrocolloid is pectin.

106. The method of claim 103 wherein the hydrocolloid is xanthan gum.

107. In a fat-replicating dispersion comprised of proteinaceous or carbohydrate particles, the improvement which comprises using, as said particles, liposome encapsulated particles comprised of:
(a) a proteinaceous or carbohydrate core; encapsulated in
(b) a polylayered liposomal phospholipid membrane, said membrane comprised of an exposed protein-containing membrane layer.

108. The particles of claim 107 wherein the core is comprised of hydrocolloid.

109. The particles of claim 108 wherein the hydrocolloid is pectin.

110. Tho particle of claim 107 wherein the proteinaceous material is selected from the group consisting of whey protein, caseinate end egg protein and combinations thereof.

111. The particles of claim 110 wherein the membrane surface has protein micelles and/or fibrils extending outwardly therefrom.

112. The particles of claim 107 wherein the core component is selected from the group consisting of whey protein, caseinate egg protein, hydrocolloids, maltodextrin, konjac, pectin, corn microparticulates, microcrystalline cellulose, and powdered cellulose and combinations thereof.

113. The particles of claim 107 wherein the membrane surface has protein micelles and/or fibrils extending outwardly therefrom.

114. The particles of claim 107 wherein the membrane is further comprised of microcrystals of an edible microcrystalline composition.

115. The particles of claim 114 wherein the composition is microcrystalline cellulose.

116. The particles of claim 107 wherein the membrane is further comprised of microcrystals of an edible microcrystalline composition.

117. The particles of claim 107 wherein the composition is microcrystalline cellulose.

118. The particles of claim 107 wherein the origin of the proteinaceous material is whey protein and/or caseinate.

119. The dispersion or claim 118 wherein the source of protein of the proteinaceous component is calcium caseinate.

120. The dispersion of claim 118 wherein the dispersed particles are homogenized particles.

121. A method of increasing the stability of a fat-replicating dispersion having a substantially smooth emulsion like organoleptic character containing particles comprised of a proteinaceous core, a liposome membrane encapsulating said core and an aqueous dispersant which comprises preparing the dispersion by one or more of the following steps:

(a) forming the core;

(b) encapsulating the core with liposomal phospholipid;

(c) introducing microcrystalline cellulose into the dispersant;

(d) forming a membrane surface layer comprised of protein;

(e) adding one or more ingredients to the dispersion; and then homogenizing the dispersion after one or more of said steps.

122. The method of claim 121 wherein homogenization is effected using one or more stages and/or making one or more passes through one or more or said stages.

123. The method of claim 122 wherein a plurality stages and/or a plurality of homogenization pressures are employed.

124. In the method of dispersing microcrystalline cellulose in a food precursor, base or product comprised of fat, protein or carbohydrate dispersed in an aqueous phase, the improvement which comprises (a) forming liposomes in an aqueous medium; (b) encapsulating said microcrystalline cellulose with said liposomes to form a membrane on said microcrystalline cellulose and then adding said microcrystalline cellulose in liposome encapsulated form to said food precursor, base or product.

* * * * *